(12) United States Patent
Wang et al.

(10) Patent No.: US 8,518,933 B2
(45) Date of Patent: Aug. 27, 2013

(54) MODULATORS OF 5-HT RECEPTORS AND METHODS OF USE THEREOF

(75) Inventors: Ying Wang, Lake Villa, IL (US); Jason T. Brewer, Zion, IL (US); Irini Akritopoulou-Zanze, Libertyville, IL (US); Stevan W. Djuric, Libertyville, IL (US); Bhadra Shelat, Lake Forest, IL (US); Frauke Pohlki, Mutterstadt (DE); Wilfried Braje, Mannhaim (DE); Ana-Lucia Relo, Gonnheim (DE)

(73) Assignees: AbbVie Inc., North Chicago, IL (US); AbbVie Deutschland GmbH & Co. KG, Wiesbaden (DE)

( * ) Notice: Subject to any disclaimer, the term of this patent is extended or adjusted under 35 U.S.C. 154(b) by 195 days.

(21) Appl. No.: 12/765,034

(22) Filed: Apr. 22, 2010

(65) Prior Publication Data
US 2010/0273767 A1    Oct. 28, 2010

Related U.S. Application Data

(60) Provisional application No. 61/171,912, filed on Apr. 23, 2009.

(51) Int. Cl.
*C07D 515/00*    (2006.01)
*A61K 31/553*    (2006.01)
*A61P 25/00*    (2006.01)

(52) U.S. Cl.
USPC ........................ 514/211.1; 540/548

(58) Field of Classification Search
USPC ........................ 540/548; 514/211.1
See application file for complete search history.

(56) References Cited

U.S. PATENT DOCUMENTS

| | | |
|---|---|---|
| 3,328,390 A | 6/1967 | Grogan |
| 4,082,773 A | 4/1978 | Hauck |
| 4,213,983 A | 7/1980 | Hadley et al. |
| 4,740,602 A | 4/1988 | Bottcher et al. |
| 5,049,564 A | 9/1991 | DeBernardis et al. |
| 5,244,888 A | 9/1993 | DeBernardis et al. |
| 5,254,561 A | 10/1993 | Billington et al. |
| 5,432,177 A | 7/1995 | Baker et al. |
| 5,486,513 A | 1/1996 | Warshawsky et al. |
| 5,529,996 A | 6/1996 | Warshawsky et al. |
| 5,597,922 A | 1/1997 | Cai et al. |
| 5,622,950 A | 4/1997 | Baker et al. |
| 5,712,285 A | 1/1998 | Curtis et al. |
| 6,057,329 A | 5/2000 | Davis et al. |
| 2005/0256102 A1 | 11/2005 | Claiborne et al. |
| 2007/0197594 A1 | 8/2007 | Hayashibe et al. |
| 2007/0225274 A1 | 9/2007 | Jacobson et al. |
| 2007/0225277 A1 | 9/2007 | Rosenzweig-Lipson et al. |
| 2008/0045501 A1 | 2/2008 | Claiborne et al. |
| 2008/0146583 A1 | 6/2008 | McMurray et al. |
| 2008/0188460 A1 | 8/2008 | Casara et al. |
| 2008/0214597 A1 | 9/2008 | Jaraskova et al. |
| 2009/0203688 A1 | 8/2009 | Gaul et al. |
| 2010/0210680 A1 | 8/2010 | Grove et al. |

FOREIGN PATENT DOCUMENTS

| | | |
|---|---|---|
| EP | 126343 A1 | 11/1984 |
| EP | 0206225 A2 | 12/1986 |
| EP | 388977 A2 | 9/1990 |
| EP | 389189 A2 | 9/1990 |
| EP | 0463691 A2 | 1/1992 |
| EP | 534363 A2 | 3/1993 |
| EP | 534396 A2 | 3/1993 |
| JP | 9249570 A | 9/1997 |
| WO | 8807997 A1 | 10/1988 |
| WO | 9006927 A1 | 6/1990 |
| WO | 9308166 A1 | 4/1993 |
| WO | 9604288 A1 | 2/1996 |
| WO | 9828281 A1 | 7/1998 |
| WO | 0147510 A2 | 7/2001 |
| WO | 02100350 A2 | 12/2002 |
| WO | 2005087775 A1 | 9/2005 |
| WO | 2005118591 A1 | 12/2005 |
| WO | 2006024628 A1 | 3/2006 |
| WO | 2006028961 A2 | 3/2006 |
| WO | 2006033318 A1 | 3/2006 |
| WO | 2006125179 A1 | 11/2006 |
| WO | 2007023273 A1 | 3/2007 |
| WO | 2007115232 A2 | 10/2007 |

Example 42

| WO | 2007117180 A1 | 10/2007 |
| WO | 2008007661 A1 | 1/2008 |
| WO | 2008040332 A1 | 4/2008 |
| WO | 2009037220 A1 | 3/2009 |
| WO | 2009098236 A1 | 8/2009 |

OTHER PUBLICATIONS

Arjona A.A., et al., "Effect of a 5-Ht(2C) Serotonin Agonist, Dexnorfenfluramine, on Amyloid Precursor Protein Metabolism in Guinea Pigs," Brain Research, 2002, vol. 951 (1), pp. 135-140.

Banzatti C., et al., "Derivatives of Imidazo (5,1-c) (1,4) benzoxazin-1-ones and Related Analogs—Part I," Journal of Heterocyclic Chemistry, 1983, vol. 20, pp. 139-144.

Barr A.M., et al., "The Selective Serotonin-2A Receptor Antagonist M100907 Reverses Behavioral Deficits in Dopamine Transporter Knockout Mice," Neuropsychopharmacology, 2004, vol. 29 (2), pp. 221-228.

Berge, S. M. et al., "Pharmaceutical Salts," Journal of Pharmaceutical Sciences, 1977, vol. 66 (1), pp. 1-19.

Bhandari K., et al., "Agents Acting on Central Nervous System. Part XXXIV-1,2,3,4,4A,5,6,7-Octahydropyrazino[1,2-a]-1-Benzazepines," Indian Journal of Chemistry, 1986, vol. 25B (12), pp. 1231-1233.

Brennan P.E., et al., "Discovery of a Novel Azepine Series of Potent and Selective 5-Ht2C Agonists as Potential Treatments for Urinary Incontinence," Bioorganic * Medicinal Chemistry Letters, 2009, vol. 19 (17), pp. 4999-5003.

Brus R., et al., "Influence of 5,7-Dihydroxytryptamine (5,7-DHT) on the Antinociceptive Effect of Serotonine (5-HT) 5-HT 2C Receptor Agonist in Male and Female Rats," Medical Science & Monitoring, 1997, vol. 3 (5), pp. 654-656.

Bryant H.U., et al., "A Novel Class of 5-HT2A Receptor Antagonists: Aryl Aminoguanidines," Life Sciences, 1996, vol. 59 (15), pp. 1259-1268.

Bubar M.J., et al., "Prospects for Serotonin 5-HT2R Pharmacotherapy in Psychostimulant Abuse," Progress in Brain Research, 2008, vol. 172, pp. 319-346.

Cheng Y., et al., "Relationship Between the Inhibition Constant (KI) and the Concentration of Inhibitor Which Causes 50 Per Cent Inhibition (I.sub.50) of an Enzymatic Reaction ," Biochemical Pharmacology, 1973, vol. 22 , pp. 3099-3108.

Chou-Green J.M., et al., "Compulsive Behavior in the 5-HT2C Receptor Knockout Mouse," Physiology & Behavior, 2003, vol. 78 (4-5), pp. 641-649.

Chou-Green J.M., et al., "Repeated Stress in Young and Old 5-HT(2C) Receptor Knockout Mice," Physiology & Behavior, 2003, vol. 79 (2), pp. 217-226.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 13-30.

Cryan J.F., et al., "Antidepressant-Like Behavioral Effects Mediated by 5-Hydroxytryptamine(2C) Receptors," The Journal of Pharmacology and Experimental Therapeutics, 2000, vol. 295 (3), pp. 1120-1126.

Davis K.L., et al., "Dopamine in Schizophrenia: A Review and Reconceptualization," The American Journal of Psychiatry, 1991, vol. 148 (11), pp. 1474-1486.

Dekeyne A., et al., "S32006, A Novel 5-HT2C Receptor Antagonist Displaying Broad-Based Antidepressant and Anxiolytic Properties in Rodent Models," Psychopharmacology, 2008, pp. 199 (4), pp. 549-568.

Di Giovanni G., et al., "Preferential Modulation of Mesolimbic vs. Nigrostriatal Dopaminergic Function by Serotonin(2C/2B) Receptor Agonists: A Combined in Vivo Electrophysiological and Microdialysis Study," Synapse, 2000, vol. 35 (1), pp. 53-61.

Di Matteo V., et al., "SB 242084, A Selective Serotonin2C Receptor Antagonist, Increases Dopaminergic Transmission in the Mesolimbic System," Neuropharmacology, 1999, vol. 38 (8), pp. 1195-1205.

Du Y., et al., "Editing of the Serotonin 2C Receptor Pre-mRNA: Effects of the Morris Water Maze," Gene, 2007, vol. 391 (1-2), pp. 186-197.

Dunlop J., et al., "Pharmacological Profile of the 5-HT2C Receptor Agonist Way-163909; Therapeutic Potential in Multiple Indications," CNS Drug Reviews, 2006, vol. 12 (3-4), pp. 167-177.

Dunlop J., et al., "Way-163909 [(7bR,10aR)-1,2,3,4,8,9,10,10a-Octahydro-7bHcyclopenta-[b][1,4]Diazepino[6,7,1Hi]Indole], A Novel 5-Hydroxytryptamine 2C Receptor-Selective Agonist with Anorectic Activity," The Journal of Pharmacology and Experimental Therapeutics, 2005, vol. 313 (2), pp. 862-869.

Esposito E., et al., "Role of central 5-HT2C receptor in the control of basal ganglia functions," The Basal Ganglia Pathophysiology, 2007, pp. 97-127.

Feldman H.A., "Mathematical Theory of Complex Ligand-Binding Systems at Equilibrium," Analytical Biochemistry, 1972, vol. 48 (2), pp. 317-338.

Fletcher P.J., et al., "Serotonin Receptors as Potential Targets for Modulation of Nicotine Use and Dependence," Progress in Brain Research, 2008, vol. 172, pp. 361-383.

Frank M.G., et al., "Sleep and Sleep Homeostasis in Mice Lacking the 5-HT2C Receptor," Neuropsychopharmacology, 2002, vol. 27 (5), pp. 869-873.

Greene T.W., et al., "Protection for the Amino group," Protective Groups in Organic Synthesis, 1999, Third Edition, pp. 494-653.

International Preliminary Report on Patentability and Written Opinion for Application No. PCT/US2010/031974, mailed on Oct. 25, 2011, 11 pages.

International Search Report for Application No. PCT/US2010/031974, mailed on Dec. 22, 2010, 7 pages.

Isaac M., "Serotonergic 5-HT2C Receptors as a Potential Therapeutic Target for the Design Antiepileptic Drugs," Current Topic in Medicinal Chemistry, 2005, vol. 5 (1), pp. 59-67.

Iwamoto K., et al., "Altered RNA Editing of Serotonin 2C Receptor in a Rat Model of Depression," Neuroscience Search, 2005, vol. 53 (1), pp. 69-76.

Iwamoto K., et al., "RNA Editing of Serotonin 2C Receptor in Human Postmortem Brains of Major Mental Disorders," Neuroscience Letters, 2003, vol. 346 (3), pp. 169-172.

Kao T., et al., "Role of the 5-HT2C Receptor in Improving Weight-Supported Stepping in Adult Rats Spinalized as Neonates," Brain Research, 2006, vol. 1112 (1), pp. 159-168.

Kaufman M.J., et al., "Cyclic Gmp Inhibits Phosphoinositide Turnover in Choroid Plexus: Evidence for Interactions between Second Messengers Concurrently Triggered by 5-HT2C Receptors," Neuroscience Letters, 1996, vol. 206 (2-3), pp. 153-156.

Leone M., et al., "The Serotonergic System in Migraine," Journal of Headache Pain, 2001, vol. 2, pp. S43-S46.

Lopez-Gimenez J.F., et al., "Regional Distribution and Cellular Localization of 5-HT2C Receptor MRNA in Monkey Brain: Comparison with [3H]Mesulergine Binding Sites and Choline Acetyltransferase MRNA," Synapse, 2001, vol. 42 , pp. 2010-12-2010-26.

Marquis K.L., et al., "Way-163909 [(7bR,10aR)-1,2,3,4,8,9,10,10a-Octahydro-7bH-Cyclopenta-[b][1,4]Diazepino[6,7,1Hi]Indole]: A Novel 5-Hydroxytryptamine 2C Receptor-Selective Agonist with Preclinical Antipsychotic-Like Activity," The Journal of Pharmacology and Experimental Therapeutics, 2007, vol. 320 (1), pp. 486-496.

Mbaki Y., et al., "Investigation of the Role of 5-HT2 Receptor Subtypes in the Control of the Bladder and the Urethra in the Anaesthetized Female Rat," British Journal of Pharmacology, 2008, vol. 155 (3), pp. 343-356.

Motofei I.G., "A Dual Physiological Character for Sexual Function: The Role of Serotonergic Receptors," BJU International, 2008, vol. 101 (5), pp. 531-534.

Muller W., et al., "Synthese von 1, 2-annelierten 1, 4-Benzodiazepinen und 4, 1-Benzoxazepinen," Helvetica Chimica Acta, 1982, vol. 65 (7), pp. 2118-2132.

Munson P.J., et al., "Ligand: A Versatile Computerized Approach for Characterization of Ligand-Binding Systems," Analytical Biochemistry , 1980, vol. 107 (1), pp. 220-239.

Nakae A., et al., "Serotonin2C Receptor MRNA Editing in Neuropathic Pain Model," Neuroscience Research, 2008, vol. 60 (2), pp. 228-231.

Nakae A., et al., "The Role of RNA Editing of the Serotonin 2C Receptor in a Rat Model of Oro-Facial Neuropathic Pain," The European Journal of Neuroscience, 2008, vol. 27 (9), pp. 2373-2379.

Niswender C.M., et al., "RNA Editing of the Human Serotonin 5-HT2C Receptor. Alterations in Suicide and Implications for Serotonergic Pharmacotherapy," Neuropsychopharmacology, 2001, vol. 24 (5), pp. 478-491.

Nunes-De-Souza V., et al., "5-HT2 Receptor Activation in the Midbrain Periaqueductal Grey (PAG) Reduces Anxiety-Like Behaviour in Mice," Behavioural Brain Research, 2008, vol. 187 (1), pp. 72-79.

Obata H., et al., "Antiallodynic Effects of Intrathecally Administered 5-HT(2C) Receptor Agonists in Rats with Nerve Injury," Pain, 2004, vol. 108 (1-2), pp. 163-169.

Obata H., et al., "Possible Involvement of Spinal Noradrenergic Mechanisms in the Antiallodynic Effect of Intrathecally Administered 5-HT2C Receptor Agonists in the Rats with Peripheral Nerve Injury," European Journal of Pharmacology, 2007, vol. 567 (1-2), pp. 89-94.

Pompeiano M., et al., "Distribution of the Serotonin 5-HT2 Receptor Family mRNAs: Comparison between 5-HT2A and 5-HT2C Receptors," Molecular Brain Research, 1994, vol. 23 (1-2), pp. 163-178.

Poste G. et al., "Lipid Vesicles as Carriers for Introducing Biologically Active Materials into Cells," Methods in Cell Biology, 1976, vol. 14, pp. 33-71.

Remington G., et al., "Atypical antipsychotics: are some more atypical than others", Psychopharmacology, 2000, vol. 148, pp. 3-15.

Rocha B.A., et al., "Enhanced Locomotor, Reinforcing, and Neurochemical Effects of Cocaine in Serotonin 5-Hydroxytryptamine 2C Receptor Mutant Mice," The Journal of Neuroscience, 2002, vol. 22 (22), pp. 10039-10045.

Rosenzweig-Lipson S., et al., "5-HT2C Receptor Agonists as an Innovative Approach for Psychiatric Disorders," Drug News & Perspectives, 2007, vol. 20 (9), pp. 565-571.

Rosenzweig-Lipson S., et al., "Antidepressant-Like Effects of the Novel, Selective, 5-HT2C Receptor Agonist Way-163909 in Rodents," Psychopharmacology, 2007, vol. 192 (2), pp. 159-170.

Rosenzweig-Lipson S., et al., "Antiobesity-Like Effects of the 5-HT2C Receptor Agonist Way-161503," Brain Research, 2006, vol. 1073-1074, pp. 240-251.

Russell M.G., et al.. "Benz[f]isoquinoline Analogues as High-Affinity Sigma Ligands," Journal of Medicinal Chemistry, 1992, vol. 35 (11), pp. 2025-2033.

Schmauss C., "Serotonin 2C Receptors: Suicide, Serotonin, and Runaway RNA Editing," The Neuroscientist, 2003, vol. 9 (4), pp. 237-242.

Sharif N.A., et al., "AL-34662: A Potent, Selective, and Efficacious Ocular Hypotensive Serotonin-2 Receptor Agonist," Journal of Ocular Pharmacology and Therapeutics, 2007, vol. 23 (1), pp. 1-13.

Shimada I., et al., "Synthesis and Structure-Activity Relationships of a Series of Benzazepine Derivatives as 5-HT2C Receptor Agonists," Bioorganic & Medicinal Chemistry , 2008, vol. 16 (6), pp. 3309-3320.

Siuciak J.A., et al., "CP-809,101, A Selective 5-HT2C Agonist, Shows Activity in Animal Models of Antipsychotic Activity," Neuropharmacology, 2007, vol. 52 (2), pp. 279-290.

Smith B.M., et al., "Discovery and Structure-Activity Relationship of (1R)-8-Chloro-2,3,4,5-Tetrahydro-1-Methyl-1H-3-Benzazepine (Lorcaserin), A Selective Serotonin 5-HT2C Receptor Agonist for the Treatment of Obesity," Journal of Medicinal Chemistry, 2008, vol. 51 (2), pp. 305-313.

Smith R.G., et al., "Synthesis and Anxiolytic Activity of a Series of Pyrazino[1,2-a][1,4]benzodiazepine Derivatives," Journal of Medicinal Chemistry, 1980, vol. 23 (8), pp. 952-955.

Tecott L.H., et al., "Eating Disorder and Epilepsy in Mice Lacking 5-HT2C Serotonin Receptors," Nature, 1995, vol. 374 (6522), pp. 542-546.

Thomsen W.J., et al., "Lorcaserin, A Novel Selective Human 5-Hydroxytryptamine2C Agonist: In Vitro and In Vivo Pharmacological Characterization," The Journal of Pharmacology and Experimental Therapeutics, 2008, vol. 325 (2), pp. 577-587.

Thorslund K., et al., "Serotonergic Drugs—A Possible Role in the Treatment of Psoriasis", Drug News & Perspectives, 2007, vol. 20 (8), pp. 521-525.

Weinberger D.R., et al., "Prefrontal Function in Schizophrenia: Confounds and Controversies," Philosophical Transactions of the Royal Society of London, 1996, vol. 351 (1346), pp. 1495-1503.

Werry T.D., et al., "RNA Editing of the Serotonin 5HT2C Receptor and its Effects on Cell Signalling, Pharmacology and Brain Function," Pharmacology & Therapeutics, 2008, vol. 119 (1), pp. 7-23.

*Primary Examiner* — Bruck Kifle

(74) *Attorney, Agent, or Firm* — Lisa V. Mueller; Michael Best & Friedrich LLP

(57) ABSTRACT

The present application relates to 1,2,3,4,4a,5,6,7-octahydropyrazino[1,2 -a][1,4]benzodiazepine, 1,2,3,4,4a,5,6,7-octahydropyrazino[1,2-a][1,5]benzodiazepine, 2,3,4,4a,5,6,7,11b-octahydro-1H-pyrido[3,4-d][2]benzazepine, 1,2,3,4,4a,5,6,7 -octahydropyrazino[1,2-a][1]benzazepine, 1,2,3,4,4a,5-hexahydro-7H-pyrazino[1,2 -a][4,1]benzoxazepine, and 2,3,4,4a,5,6-hexahydro-1H-pyrazino[2,1-d][1,5]benzoxazepine, and 5,6,7,7a,8,9,10,11-octahydropyrazino[1,2-d]pyrido[3,2-b][1,4]diazepine derivatives of formula (I)

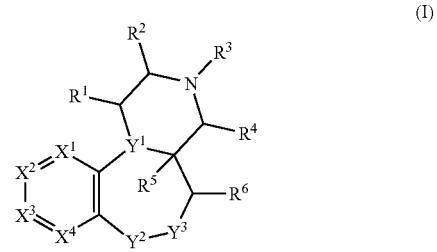

wherein $R^1$, $R^2$, $R^3$, $R^4$, $R^5$, $R^6$, $X^1$, $X^2$, $X^3$, $X^4$, $Y^1$, $Y^2$, and $Y^3$ are as defined in the specification. The present application also relates to compositions comprising such compounds, and methods of treating disease conditions using such compounds and compositions, and methods for identifying such compounds.

9 Claims, 6 Drawing Sheets

MODULATORS OF 5-HT RECEPTORS AND METHODS OF USE THEREOF

CROSS-REFERENCE TO RELATED APPLICATIONS

This patent application claims priority to U.S. Provisional Patent Application No. 61/171,912, filed on Apr. 23, 2009, the entirety of which is incorporated herein by reference.

FIELD OF THE INVENTION

The present invention relates to 1,2,3,4,4a,5,6,7-octahydropyrazino[1,2-a][1,4]benzodiazepine, 1,2,3,4,4a,5,6,7-octahydropyrazino[1,2-a][1,5]benzodiazepine, 2,3,4,4a,5,6,7,11b-octahydro-1H-pyrido[3,4-d][2]benzazepine, 1,2,3,4,4a,5,6,7-octahydropyrazino[1,2-a][1]benzazepine, 1,2,3,4,4a,5-hexahydro-7H-pyrazino[1,2-a][4,1]benzoxazepine, and 2,3,4,4a,5,6-hexahydro-1H-pyrazino[2,1-d][1,5]benzoxazepine, and 5,6,7,7a,8,9,10,11-octahydropyrazino[1,2-d]pyrido[3,2-b][1,4]diazepine derivatives, compositions comprising these 1,2,3,4,4a,5,6,7-octahydropyrazino[1,2-a][1,4]benzodiazepine, 1,2,3,4,4a,5,6,7-octahydropyrazino[1,2-a][1,5]benzodiazepine, 2,3,4,4a,5,6,7,11b-octahydro-1H-pyrido[3,4-d][2]benzazepine, 1,2,3,4,4a,5,6,7-octahydropyrazino[1,2-a][1]benzazepine, 1,2,3,4,4a,5-hexahydro-7H-pyrazino[1,2-a][4,1]benzoxazepine, 2,3,4,4a,5,6-hexahydro-1H-pyrazino[2,1-d][1,5]benzoxazepine, and 5,6,7,7a,8,9,10,11-octahydropyrazino[1,2-d]pyrido[3,2-b][1,4]diazepine derivatives, methods of modulating the $5\text{-HT}_{2C}$ receptor, the $5\text{-HT}_6$ receptor or both the $5\text{-HT}_{2C}$ and $5\text{-HT}_6$ receptor in the prevention or treatment of serotonin-related conditions and disorders using such compounds or compositions containing such compounds, and processes for preparing such compounds and compositions.

BACKGROUND OF THE INVENTION

The present invention relates to compounds and pharmaceutical compositions containing the compounds useful as $5\text{-HT}_{2C}$ receptor agonists or partial agonists, $5\text{-HT}_6$ antagonists or both $5\text{-HT}_{2C}$ receptor agonists or partial agonists and $5\text{-HT}_6$ antagonists for the treatment of diseases, disorders and conditions where $5\text{-HT}_{2C}$ or $5\text{-HT}_6$ modulation is desired such as depression, anxiety, schizophrenia, bipolar disorder, obsessive compulsive disorder, migraine, pain, epilepsy, substance abuse, eating disorders, obesity, diabetes, erectile dysfunction and others.

Serotonin (5-hydroxytryptamine, 5-HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5-HT is implicated in a vast array of physiological and pathophysiological pathways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5-HT are termed serotonergic. The function of 5-HT is exerted upon its interaction with specific (serotonergic) neurons. Seven types of 5-HT receptors have been identified: $5\text{-HT}_1$ (with subtypes $5\text{-HT}_{1A}$, $5\text{-HT}_{1B}$, $5\text{-HT}_{1D}$, $5\text{-HT}_{1E}$ and $5\text{-HT}_{1F}$), $5\text{-HT}_2$ (with subtypes $5\text{-HT}_{2A}$, $5\text{-HT}_{2B}$ and $5\text{-HT}_{2C}$), $5\text{-HT}_3$, $5\text{-HT}_4$, $5\text{-HT}_5$ (with subtypes $5\text{-HT}_{5A}$ and $5\text{-HT}_{5B}$), $5\text{-HT}_6$ and $5\text{-HT}_7$. Most of these receptors are coupled to G-proteins that affect the activities of adenylate cyclase or phospholipase Cγ.

Alterations in the activity of multiple neurotransmitter receptor systems (dopamine, serotonin, glutamate, GABA, acetylcholine) have been implicated in the manifestation of the symptoms of schizophrenia. The most widely accepted "Dopamine Hypothesis of Schizophrenia" in its simplest form states that the positive symptoms of this pathology relate to a functional hyperactivity of the mesolimbic dopaminergic system, while the negative and cognitive aspects can be traced to a functional hypoactivity of the mesocortical dopaminergic projections. Atypical antipsychotics block the mesolimbic dopaminergic neurotransmission, thereby controlling positive symptoms, with little or no effect on the nigrostriatal system, leading to less induction of extrapyramidal side effects (EPS).

Primary negative and cognitive symptoms of schizophrenia reflect a dysfunction of the frontal cortex ("hypofrontality"), which is thought to be induced by a decreased tone in the mesocortical dopaminergic projection field [Davis K L, Kahn R S, Ko G and Davidson M (1991). Dopamine in schizophrenia: a review and re-conceptualization. *Am J Psychiatry* 148: 1474-86. Weinberger D R and Berman K F (1996). Prefrontal function in schizophrenia: confounds and controversies. *Philos Trans R Soc Lond B Biol Sci* 351: 1495-503]. Agents that selectively enhance dopamine levels in the cortex have the potential to address the negative symptoms of this disorder. Atypical antipsychotics lack robust efficacy against negative and cognitive components of the schizophrenic syndrome.

The schizophrenic symptomatology is further complicated by the occurrence of drug-induced so-called secondary negative symptoms and cognitive impairment, which are difficult to distinguish from primary negative and cognitive symptoms [Remington G and Kapur S (2000). Atypical antipsychotics: are some more atypical than others? *Psychopharmacol* 148: 3-15]. The occurrence of secondary negative symptoms not only limits therapeutic efficacy but also, together with these side effects, negatively affects patient compliance.

It may thus be hypothesized that a novel mechanistic approach that blocks dopaminergic neurotransmission in the limbic system but does not affect the striatal and pituitary projection fields, and stimulates frontocortical projection fields, would provide an efficacious treatment for all parts of the schizophrenic pathology, including its positive, negative and cognitive symptoms. Moreover, a selective compound that is substantially free of the ancillary pharmacology that characterizes current agents would be expected to avoid a variety of off-target side effects that plague current treatments such as extrapyramidal side effects (EPS) and weight gain.

The $5\text{-HT}_{2C}$ receptor, previously named 5-HT1C, is a G-protein-coupled receptor, which couples to multiple cellular effector systems including the phospholipase C, A and D pathways. It is found primarily in the brain and its distribution is particularly high in the plexus choroideus, where it is assumed to control cerebrospinal fluid production [Kaufman M J, Hirata F (1996) Cyclic GMP inhibits phosphoinositide turnover in choroid plexus: evidence for interactions between second messengers concurrently triggered by $5\text{-HT}_{2C}$ receptors. *Neurosci Lett* 206:153-156]. Very high levels were also found in the retrosplenial, piriform and entorhinal cortex, anterior olfactory nucleus, lateral septal nucleus, subthalamic nucleus, amygdala, subiculum and ventral part of CA3, lateral habenula, substantia nigra pars compacta, several brainstem nuclei and the whole grey matter of the spinal cord [Pompeiano M, Palacios J M, Mengod G (1994). Distribution of the serotonin 5-HT2 receptor family mRNAs: comparison between 5-HT$_{2A}$ and 5-HT$_{2C}$ receptors. *Brain Res Mol Brain Res* 23:163-178]. A comparison of the distribution of 5-HT$_{2C}$ mRNA with that of 5-HT$_{2C}$ protein in monkey and human brains has revealed both pre- and postsynaptic localization [Lopez-Gimenez J F, Mengod G, Palacios J M, Vilaro M T (2001) Regional distribution and cellular localization of 5-HT$_{2C}$ receptor mRNA in monkey brain: comparison with [$^3$H]mesulergine binding sites and choline acetyltransferase mRNA. *Synapse* 42:12-26].

It is anticipated that modulation of the 5-HT$_{2C}$ receptor will improve disorders such as depression, anxiety, schizophrenia, cognitive deficits of schizophrenia, obsessive compulsive disorder, bipolar disorder, migraine, epilepsy, substance abuse, eating disorders, obesity, diabetes, sexual dysfunction/erectile dysfunction, sleep disorders, psoriasis, Parkinson's disease, pain conditions and disorders, and spinal cord injury, smoking cessation, ocular hypertension and Alzheimer's disease. Modulators of the 5-HT$_{2C}$ receptor are also shown to be useful in the modulation of bladder function, including the prevention or treatment of urinary incontinence.

The modulation of the 5-HT$_6$ receptor by suitable substances is expected to improve certain disorders including cognitive dysfunctions, such as a deficit in memory, cognition and learning associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, drug addiction and obesity.

There is still an ongoing need for providing compounds having high affinity and selectivity for the 5-HT$_6$ receptor. In particular the compounds should have low affinity to adrenergic receptors, such as the α$_1$-adrenergic receptor, histamine receptors, such as the H$_1$-receptor, and dopaminergic receptors, such as the D$_2$-receptor, in order to avoid or reduce side effects associated with modulation of these receptors, such as postural hypotension, reflex tachycardia, potentiation of the antihypertensive effect of prazosin, terazosin, doxazosin and labetalol or dizziness associated with the blockade of the α$_1$-adrenergic receptor, weight gain, sedation, drowsiness or potentiation of central depressant drugs associated with the blockade of the H$_1$-receptor, or extrapyramidal movement disorder, such as dystonia, parkinsonism, akathisia, tardive dyskinesia or rabbit syndrome, or endocrine effects, such as prolactin elevation (galactorrhea, gynecomastia, menstrual changes, sexual dysfunction in males), associated with the blockade of the D$_2$-receptor.

The present invention provides compounds which have an affinity for the 5-HT$_{2C}$ or 5-HT$_6$ receptor or both the 5-HT$_{2C}$ and 5-HT$_6$ receptors, thus allowing the treatment of disorders related to or affected by the 5-HT$_{2C}$ or 5-HT$_6$ receptors or both the 5-HT$_{2C}$ and 5-HT$_6$ receptors.

SUMMARY OF THE INVENTION

The invention is directed to 1,2,3,4,4a,5,6,7-octahydropyrazino[1,2-a][1,4]benzodiazepine, 1,2,3,4,4a,5,6,7-octahydropyrazino[1,2-a][1,5]benzodiazepine, 2,3,4,4a,5,6,7,11b-octahydro-1H-pyrido[3,4-d][2]benzazepine, 1,2,3,4,4a,5,6,7-octahydropyrazino[1,2-a][1]benzazepine, 2,3,4,4a,5,6-hexahydro-1H-pyrazino[2,1-d][1,5]benzoxazepine, 1,2,3,4,4a,5-hexahydro-7H-pyrazino[1,2-a][4,1]benzoxazepine and 5,6,7,7a,8,9,10,11-octahydropyrazino[1,2-d]pyrido[3,2-b][1,4]diazepine derivatives, compositions comprising such compounds, and methods of using such compounds and compositions.

In one aspect, the present invention relates to compounds of having a formula of (I):

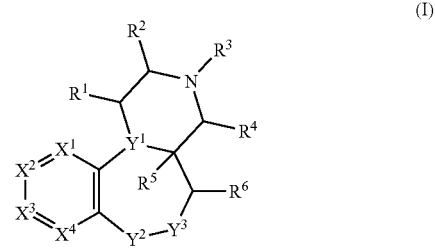

or a pharmaceutically acceptable salt or prodrug thereof, wherein

R$^1$, R$^2$, R$^4$, R$^5$ and R$^6$ are independently selected from the group consisting of hydrogen, alkenyl, alkyl, haloalkyl, G$^1$, and —(CR$^{4a}$R$^{5a}$)$_m$-G$^1$;

R$^{4a}$ and R$^{5a}$, at each occurrence, are each independently hydrogen, halogen, alkyl, or haloalkyl;

G$^1$, at each occurrence, is independently aryl or heteroaryl, wherein each G$^1$ is independently unsubstituted or substituted with 1, 2, 3, 4, or 5 substituents selected from the group consisting of alkyl, alkenyl, alkynyl, halogen, cyano, -G$^3$, —NO$_2$, —OR$^{1b}$, —O—(CR$^{4b}$R$^{5b}$)$_m$-G$^3$, —OC(O)R$^{1b}$, —OC(O)N(R$^b$)(R$^{3b}$), —SR$^{1b}$, —S(O)R$^{2b}$, —S(O)$_2$R$^{2b}$, —S(O)$_2$N(R$^b$)(R$^{3b}$), —C(O)R$^{1b}$, —C(O)OR$^{1b}$, —C(O)N(R$^b$)(R$^{3b}$), —C(OH)[(CR$^{4b}$R$^{5b}$)$_m$—R$^{4b}$]$_2$, —N(R$^b$)(R$^{3b}$), —N(R$^a$)C(O)R$^{1b}$, —N(R$^a$)C(O)O(R$^{1b}$), —N(R$^a$)C(O)N(R$^b$)(R$^{3b}$), —(CR$^{4b}$R$^{5b}$)$_m$-G$^3$, —(CR$^{4b}$R$^{5b}$)$_m$—NO$_2$, —(CR$^{4b}$R$^{5b}$)$_m$—OR$^{1b}$, —(CR$^{4b}$R$^{5b}$)$_m$—OC(O)R$^{1b}$, —(CR$^{4b}$R$^{5b}$)$_m$—OC(O)N(R$^b$)(R$^{3b}$), (CR$^{4b}$R$^{5b}$)$_m$SR$^{1b}$, —(CR$^{4b}$R$^{5b}$)$_m$S(O)$_2$R$^{2b}$, —(CR$^{4b}$R$^{5b}$)$_m$S(O)$_2$N(R$^b$)(R$^{3b}$), —(CR$^{4b}$R$^{5b}$)$_m$—C(O)R$^{1b}$, —(CR$^{4b}$R$^{5b}$)$_m$—C(O)OR$^{1b}$, —(CR$^{4b}$R$^{5b}$)$_m$—C(O)N(R$^b$)(R$^{3b}$), —(CR$^{4b}$R$^{5b}$)$_m$—N(R$^b$)(R$^{3b}$), —(CR$^{4b}$R$^{5b}$)$_m$—N(R$^a$)C(O)R$^{1b}$, —(CR$^{4b}$R$^{5b}$)$_m$—N(R$^a$)C(O)O(R$^{1b}$), —(CR$^{4b}$R$^{5b}$)$_m$—N(R$^a$)C(O)N(R$^b$)(R$^{3b}$), cyanoalkyl, and haloalkyl;

R$^a$ and R$^b$, at each occurrence, are each independently hydrogen, alkyl, or haloalkyl;

R$^{1b}$ and R$^{3b}$, at each occurrence, are each independently hydrogen, alkyl, or haloalkyl;

R$^{2b}$, at each occurrence, is independently alkyl or haloalkyl;

R$^{4b}$ and R$^{5b}$, at each occurrence, are each independently hydrogen, halogen, alkyl, or haloalkyl;

m, at each occurrence, is independently 1, 2, 3, 4, or 5;

G$^3$, at each occurrence, is independently aryl or heteroaryl, wherein each G$^3$ is independently unsubstituted or substituted with 1, 2, 3, 4, or 5 substituents selected from the group consisting of alkyl, alkenyl, alkynyl, halogen, cyano, —NO$_2$, —OR$^{1b}$, —OC(O)R$^{1b}$, —OC(O)N(R$^b$)(R$^{3b}$), —SR$^{1b}$, —S(O)R$^{2b}$, —S(O)$_2$R$^{2b}$, —S(O)$_2$N(R$^b$)(R$^{3b}$), —C(O)R$^{1b}$, —C(O)OR$^{1b}$, —C(O)N(R$^b$)(R$^{3b}$), —N(R$^b$)(R$^{3b}$), —N(R$^a$)C(O)R$^{1b}$, —N(R$^a$)C(O)O(R$^{1b}$), —N(R$^a$)C(O)N(R$^b$)(R$^{3b}$), —(CR$^{4b}$R$^{5b}$)$_m$—NO$_2$, —(CR$^{4b}$R$^{5b}$)$_m$—OR$^{1b}$, —(CR$^{4b}$R$^{5b}$)$_m$—OC(O)R$^{1b}$, —(CR$^{4b}$R$^{5b}$)$_m$—OC(O)N(R$^b$)(R$^{3b}$), —(CR$^{4b}$R$^{5b}$)$_m$—SR$^{1b}$, —(CR$^{4b}$R$^{5b}$)$_m$—S(O)$_2$R$^{2b}$, —(CR$^{4b}$R$^{5b}$)S(O)$_2$N(R$^b$)(R$^{3b}$), —(CR$^{4b}$R$^{5b}$)$_m$—C(O)R$^{1b}$, —(CR$^{4b}$R$^{5b}$)$_m$—C(O)OR$^{1b}$, —(CR$^{4b}$R$^{5b}$)$_m$—C(O)N(R$^b$)(R$^{3b}$), —(CR$^{4b}$R$^{5b}$)$_m$—N(R$^b$)(R$^{3b}$), —(CR$^{4b}$R$^{5b}$)$_m$—N(R$^a$)C(O)R$^{1b}$, —(CR$^{4b}$R$^{5b}$)$_m$—N(R$^a$)C(O)O(R$^{1b}$), —(CR$^{4b}$R$^{5b}$)$_m$—N(R$^a$)C(O)N(R$^b$)(R$^{3b}$), cyanoalkyl, and haloalkyl;

R$^3$ is selected from the group consisting of hydrogen, alkyl, alkylcarbonyl, haloalkyl, (CR$^{4a}$R$^{5a}$)$_m$-G$^1$, —C(O)-G$^1$, —S(O)$_2$R$^7$, and —C(O)NR$^8$R$^9$;

R$^7$ and R$^8$ are independently selected from the group consisting of alkyl, haloalkyl, G$^1$ and —(CR$^{4a}$R$^{5a}$)$_m$-G$^1$;

R$^9$ is selected from the group consisting of hydrogen, alkyl, and haloalkyl;

X$^1$ is N or CR$^{10}$;
X$^2$ is N or CR$^{11}$;
X$^3$ is N or CR$^{12}$;
X$^4$ is N or CR$^{13}$;

with the proviso that only one or two of X$^1$, X$^2$, X$^3$, or X$^4$ can be N;

R$^{10}$R$^{11}$, R$^{12}$, and R$^{13}$ are each independently hydrogen, alkyl, alkenyl, alkynyl, halogen, cyano, -G$^1$, -G$^2$, —NO$_2$, —OR$^{1a}$, —O—(CR$^{4a}$R$^{5a}$)$_m$-G$^1$, —O—(CR$^{4a}$R$^{5a}$)$_m$-G$^2$, —OC(O)R$^{1a}$, —OC(O)N(R$^b$)(R$^{3a}$), —SR$^{1a}$, —S(O)R$^{2a}$, —S(O)$_2$R$^{2a}$, —S(O)$_2$N(R$^b$)(R$^{3a}$), —C(O)R$^{1a}$, —C(O)OR$^{1a}$, —C(O)N(R$^b$)(R$^{3a}$), —N(R$^b$)(R$^{3a}$), —N(R$^a$)C(O)R$^{1a}$, —N(R$^a$)C(O)O(R$^{1a}$), —N(R$^a$)C(O)N(R$^b$)(R$^{3a}$), —N(R$^a$)S(O)$_2$(R$^{2a}$), —(CR$^{4a}$R$^{5a}$)$_m$—NO$_2$, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)$_m$—OC(O)N(R$^b$)(R$^{3a}$), —(CR$^{4a}$R$^{5a}$)$_m$—SR$^{1a}$, —(CR$^{4a}$R$^{5a}$)$_m$—S(O)R$^{2a}$, —(CR$^{4a}$R$^{5a}$)$_m$—S(O)$_2$R$^{2a}$, —(CR$^{4a}$R$^{5a}$)$_m$—S(O)$_2$N(R$^b$)(R$^{3a}$), —(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R$^{1a}$, —(CR$^{4a}$R$^{5a}$)$_m$—N(R$^a$)C(O)O(R$^{1a}$), —(CR$^{4a}$R$^{5a}$)$_m$—N(R$^a$)C(O)N(R$^b$)(R$^{3a}$), —(CR$^{4a}$R$^{5a}$)$_m$-G$^1$, —CR$^{4a}$=CR$^{5a}$-G$^1$, cyanolkyl, or haloalkyl; wherein R$^{1a}$ and R$^{3a}$, at each occurrence, are each independently hydrogen, alkyl, haloalkyl, G$^1$, or —(CR$^{4a}$R$^{5a}$)$_m$-G$^1$;

R$^{2a}$, at each occurrence, is independently alkyl, haloalkyl, G$^1$, or —(CR$^{4a}$R$^{5a}$)$_m$-G$^1$;

G$^2$, at each occurrence, is independently cycloalkyl, cycloalkenyl or heterocycle, wherein each G$^2$ is independently unsubstituted or substituted with 1, 2, 3, 4, or 5 substituents selected from the group consisting of alkyl, alkenyl, halogen, cyano, —NO$_2$, —OR$^{1b}$, —S(O)$_2$R$^{2b}$, —C(O)OR$^{1b}$, haloalkyl, and oxo; or R$^{10}$ and R$^{11}$, or R$^{11}$ and R$^{12}$, or R$^{12}$ and R$^{13}$ taken together with the carbon atoms to which they are attached form a substituted or unsubstituted phenyl ring, substituted or unsubstituted cycloalkyl, substituted or unsubstituted heterocycle, or substituted or unsubstituted heteroaryl;

Y$^1$ is N or CH;

Y$^2$ is NR$^{14}$, CR$^{15}$R$^{16}$, C(O), or O;

Y$^3$ is NR$^{14}$, CR$^{15}$R$^{16}$, C(O), or O with the provisos that Y$^2$ and Y$^3$ are not simultaneously NR$^{14}$, C(O), or O and Y$^2$ and Y$^3$ taken together are other than C(O)O, OC(O), ONR$^{14}$, or NR$^{14}$O;

R$^{14}$ is selected from the group consisting of hydrogen, alkyl, alkylcarbonyl, haloalkyl, —C(O)-G$^1$, and —(CR$^{4a}$R$^{5a}$)$_m$-G$^1$;

R$^{15}$ and R$^{16}$ are independently selected from the group consisting of hydrogen, alkyl, and haloalkyl; and provided that the compound of formula (I) is other than 3-methyl-2,3,4,4a,5,6-hexahydropyrazino[1,2-a][1,4]benzodiazepin-7(1H)-one, 3-methyl-9-nitro-2,3,4,4a,5,6-hexahydropyrazino[1,2-a][1,4]benzodiazepin-7(1H)-one, 9-amino-3-methyl-2,3,4,4a,5,6-hexahydropyrazino[1,2-a][1,4]benzodiazepin-7(1H)-one, 1,2,3,4,4a,5,6,7-octahydropyrazino[1,2-a][1]benzazepine, 3-methyl-1,2,3,4,4a,5,6,7-octahydropyrazino[1,2-a][1]benzazepine, 3-(2-pyridin-4-ylethyl)-1,2,3,4,4a,5,6,7-octahydropyrazino[1,2-a][1]benzazepine, 3-methyl-9-nitro-1,2,3,4,4a,5-hexahydro-7H-pyrazino[1,2-a][4,1]benzoxazepine, 3-methyl-1,2,3,4,4a,5-hexahydro-7H-pyrazino[1,2-a][4,1]benzoxazepin-9-amine, 9-chloro-3-methyl-1,2,3,4,4a,5-hexahydro-7H-pyrazino[1,2-a][4,1]benzoxazepine, 3-methyl-1,2,3,4,4a,5-hexahydro-7H-pyrazino[1,2-a][4,1]benzoxazepine, or 3,7,7-trimethyl-1,2,3,4,4a,5-hexahydro-7H-pyrazino[1,2-a][4,1]benzoxazepine.

In another aspect, the present invention relates to pharmaceutical compositions comprising a therapeutically effective amount of at least one compound having a formula of (I) described above or pharmaceutically acceptable salts thereof, in combination with at least one pharmaceutically acceptable carrier.

Another aspect of the invention relates to pharmaceutical compositions comprising compounds of the invention. Such compositions can be administered in accordance with a method of the invention, typically as part of a therapeutic regimen for treatment or prevention of conditions and disorders related to 5-HT activity, and more particularly 5-HT$_2$, activity, 5-HT$_6$ activity, or both 5-HT$_2$, activity and 5-HT$_6$ activity.

In yet another aspect, the present invention relates to a method of preventing or treating a cognitive dysfunction, attention deficit/hyperactivity syndrome, personality disorders, affective disorders, motion or motor disorders, migraine, pain, urinary incontinence, sleep disorders, feeding disorders, gastrointestinal disorders, diseases associated with neurodegeneration, addiction diseases, obesity, diabetes, psoriasis, or ocular hypertension disorder using a compound of formula (I). Such methods involve administering a therapeutically effective amount of at least one compound of formula (I) to a subject in need of treatment thereof. Examples of cognitive dysfunction are deficits in memory, cognition, and learning, Alzheimer's disease, age-related cognitive decline, and mild cognitive impairment, or any combinations thereof. Examples of personality disorders are schizophrenia and cognitive deficits related to schizophrenia. Examples of affective disorders are depression, anxiety, bipolar disorder and obsessive compulsive disorders, or any combination thereof. Examples of motion or motor disorders are Parkinson's disease and epilepsy. Examples of feeding disorders are anorexia and bulimia. Examples of gastrointestinal disorders are irritable bowel syndrome. Examples of diseases associated with neurodegeneration are stroke, spinal or head trauma, and head injuries.

In one embodiment of the present invention, a method of treating a mammal suffering from schizophrenia and/or cognitive deficits related to schizophrenia is provided that includes administering to the mammal at least one compound of formula (I) or a pharmaceutically acceptable salt thereof.

In still yet another aspect, the present invention relates to the use of a compound of formula (I) or a pharmaceutically acceptable salt thereof in the manufacture of a medicament for the prevention or treatment of the disorders described above, alone or in combination with at least one pharmaceutically acceptable carrier.

The compounds of formula (I), compositions comprising these compounds, and methods for preventing or treating cognitive dysfunction, attention deficit/hyperactivity syndrome, personality disorders, affective disorders, motion or motor disorders, migraine, sleep disorders, feeding disorders, gastrointestinal disorders, diseases associated with neurodegeneration, addiction diseases, obesity, diabetes, psoriasis, or ocular hypertension disorders by administering these compounds or pharmaceutical compositions are further described herein.

The compounds, compositions comprising the compounds, methods for using the compounds, and processes for preparing the compounds, as well as intermediates obtained in such processes, are further described herein.

These and other objects of the invention are described in the following paragraphs. These objects should not be deemed to narrow the scope of the invention.

DETAILED DESCRIPTION

Figure 1:
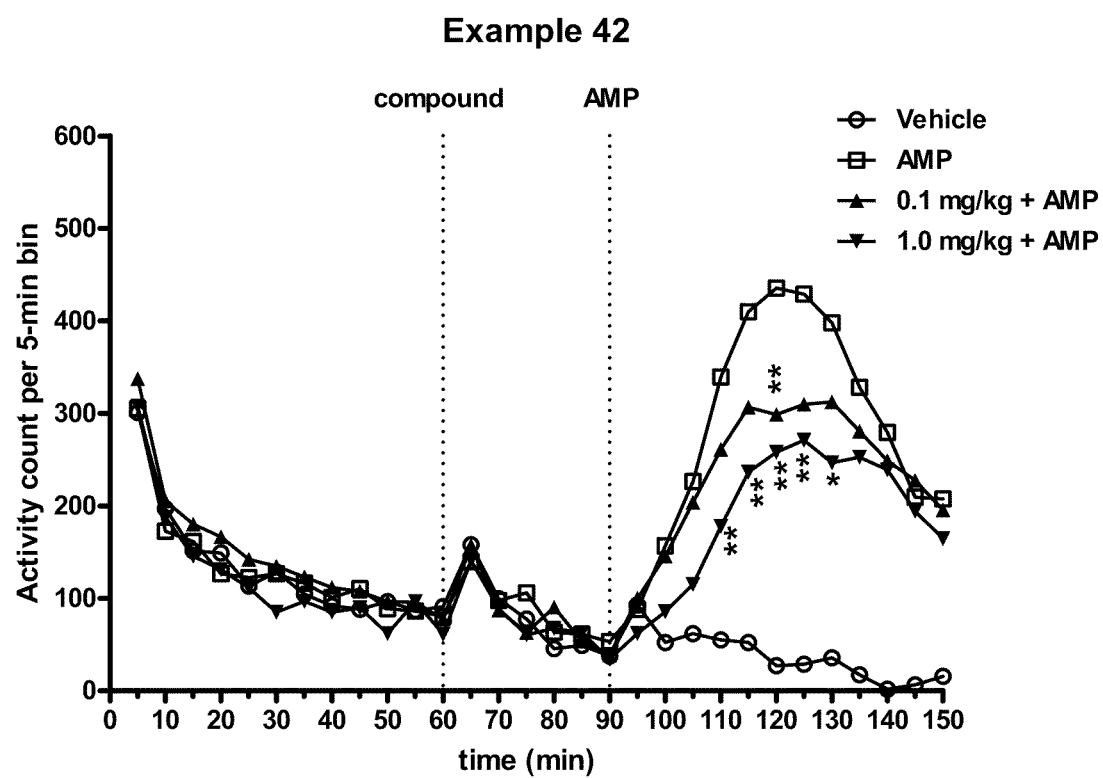
FIG. 1 shows a graphical representation of the concentration-dependent effects of Example 42 attenuating the affect of d-amphetamine. Animals were treated with vehicle, d-amphetamine or a dose of Example 42 followed by d-amphetamine. The X-axis represents time (minutes), and the Y-axis represents activity counts per 5 minute time period.

In one aspect, the present invention relates to compounds having a formula (I) as shown below:

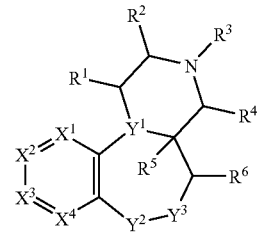

wherein $R^1$, $R^2$, $R^3$, $R^4$, $R^5$, $R^6$, $X^1$, $X^2$, $X^3$, $X^4$, $Y^1$, $Y^2$ and $Y^3$ are as defined above in the Summary of the Invention.

In another aspect, the present invention relates to compositions comprising compounds having a formula (I) as described above and at least one pharmaceutically acceptable carrier.

In still yet another aspect, the present invention relates to methods for preventing and treating disease conditions, such as treating cognitive dysfunction, attention deficit/hyperactivity syndrome, personality disorders, affective disorders, motion or motor disorders, migraine, sleep disorders, feeding disorders, gastrointestinal disorders, diseases associated with neurodegeneration, addiction diseases, obesity, diabetes, psoriasis, or ocular hypertension disorders, using compounds having a formula of formula (I) as described above.

In still yet another aspect, the present invention relates to the use of compounds having a formula (I) in the manufacture of a medicament for the prevention or treatment of the disease conditions, such as treating cognitive dysfunction, attention deficit/hyperactivity syndrome, personality disorders, affective disorders, motion or motor disorders, migraine, sleep disorders, feeding disorders, gastrointestinal disorders, diseases associated with neurodegeneration, addiction diseases, obesity, diabetes, psoriasis, or ocular hypertension disorders, described above, alone or in combination with at least one pharmaceutically acceptable carrier.

In various embodiments, the present invention provides at least one variable that occurs more than one time in any substituent or in the compound of the present invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. DEFINITIONS

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH=CH—, —CH=CH$_2$CH$_2$—, and —CH=C(CH$_3$)CH$_2$—.

The term "alkyl" as used herein, means a straight or branched, saturated hydrocarbon chain containing from 1 to 10 carbon atoms. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylene" means a divalent group derived from a straight or branched chain hydrocarbon of from 1 to 10 carbon atoms. Representative examples of alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indanyl, 1-indanonyl, 2-indanoneyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "carbonyl" as used herein means a —C(=O)— group.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein means a cyclic hydrocarbon group containing from 3 to 10 carbons, containing 1 or 2 carbon-carbon double bonds. Examples of cycloalkenyl include cyclopropenyl, cyclobutenyl, cyclopentenyl, cyclohexenyl, cycloheptentyl, and cyclooctenyl.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, fluoromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-c]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroatom" as used herein, means a nitrogen, oxygen, or sulfur atom.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "oxo" as used herein, means a=O moiety.

b. COMPOUNDS

Compounds of the present invention have the formula (I) as described above.

Particular values of variable groups in compounds of formula (I) are as follows. Such values may be used where appropriate with any of the other values, definitions, claims or embodiments defined hereinbefore or hereinafter.

In one embodiment, $Y^1$ is CH.

In another embodiment, $Y^1$ is N.

In one embodiment, $Y^2$ and $Y^3$ taken together are —C(O)NR$^{14}$—, wherein R$^{14}$ is hydrogen, alkyl, alkylcarbonyl, haloalkyl, —C(O)-G$^1$, or —(CR$^{4a}$R$^{5a}$)$_m$-G$^1$. In another embodiment, R$^{14}$ is hydrogen.

In one embodiment, $Y^2$ and $Y^3$ taken together are —R$^{14}$NC(O)—, wherein R$^{14}$ is hydrogen, alkyl, alkylcarbonyl, haloalkyl, —C(O)-G$^1$, or —(CR$^{4a}$R$^{5a}$)$_m$-G$^1$. In another embodiment, R$^{14}$ is hydrogen or alkyl.

In one embodiment, $Y^2$ and $Y^3$ taken together are —(CR$^{15}$R$^{16}$)(CR$^{15}$R$^{16}$)—, wherein R$^{15}$ and R$^{16}$ are independently hydrogen, alkyl, or haloalkyl. In another embodiment, R$^{15}$ and R$^{16}$ are each hydrogen.

In one embodiment, $Y^2$ and $Y^3$ taken together are —N(R$^{14}$)CR$^{15}$R$^{16}$—, wherein R$^{14}$ is hydrogen, alkyl, alkylcarbonyl, haloalkyl, —C(O)-G$^1$, or —(CR$^{4a}$R$^{5a}$)$_m$-G$^1$, and R$^{15}$ and R$^{16}$ are independently hydrogen, alkyl, or haloalkyl. In another embodiment R$^{14}$ is hydrogen, alkyl or —(CR$^{4a}$R$^{5a}$)$_m$-G$^1$, and R$^{15}$ and R$^{16}$ are independently hydrogen.

In one embodiment, $Y^2$ and $Y^3$ taken together are —(CR$^{15}$R$^{16}$)N(R$^{14}$)—, wherein R$^{14}$ is hydrogen, alkyl, alkylcarbonyl, haloalkyl, —C(O)-G$^1$, or —(CR$^{4a}$R$^{5a}$)$_m$-G$^1$, and R$^{15}$ and R$^{16}$ are independently hydrogen or alkyl. In another embodiment R$^{14}$ is hydrogen, alkyl or —(CR$^{4a}$R$^{5a}$)$_m$-G$^1$, and R$^{15}$ and R$^{16}$ are independently hydrogen.

In one embodiment, $Y^2$ and $Y^3$ taken together are —OCR$^{15}$R$^{16}$—, wherein R$^{15}$ and R$^{16}$ are independently hydrogen, alkyl, or haloalkyl. In another embodiment R$^{15}$ and R$^{16}$ are independently hydrogen.

In one embodiment, $Y^2$ and $Y^3$ taken together are —(CR$^{15}$R$^{16}$)O—, wherein R$^{15}$ and R$^{16}$ are independently hydrogen, alkyl, or haloalkyl. In another embodiment R$^{15}$ and R$^{16}$ are independently hydrogen.

In one embodiment, R$^1$, R$^2$, R$^4$, R$^5$ and R$^6$ are independently hydrogen, alkenyl, alkyl, haloalkyl, G$^1$, or —(CR$^{4a}$R$^{5a}$)$_m$-G$^1$. In another embodiment, R$^1$, R$^2$, R$^4$, R$^5$ and R$^6$ are each hydrogen.

In one embodiment, R$^3$ is hydrogen, alkyl, alkylcarbonyl, haloalkyl, —(CR$^{4a}$R$^{5a}$)$_m$-G$^1$, —C(O)-G$^1$, —S(O)$_2$R$^7$, or —C(O)NR$^8$R$^9$. In another embodiment, R$^3$ is hydrogen, alkyl, or —(CR$^{4a}$R$^{5a}$)$_m$-G$^1$, wherein R$^{4a}$ and R$^{5a}$ are each hydrogen, m is 1, and G$^1$ is optionally substituted aryl.

In one embodiment, X$^1$, X$^2$, X$^3$ and X$^4$ are N or CR$^{10}$, CR$^{11}$, CR$^{12}$, or CR$^{13}$, respectively, provided only one or two of X$^1$, X$^2$, X$^3$ or X$^4$ is N. In another embodiment, X$^1$, X$^2$, X$^3$ and X$^4$ are CR$^{10}$, CR$^{11}$, CR$^{12}$, or CR$^{13}$, respectively. In another embodiment, X$^1$ is N, and X$^2$, X$^3$ and X$^4$ are CR$^{11}$, CR$^{12}$, or CR$^{13}$, respectively.

In one embodiment, R$^{10}$, R$^{11}$, R$^{12}$, and R$^{13}$ are each independently hydrogen, alkyl, alkenyl, alkynyl, halogen, cyano, -G$^1$, -G$^2$, —NO$_2$, —OR$^{1a}$, —O—(CR$^{4a}$R$^{5a}$)$_m$-G$^1$, —O—(CR$^{4a}$R$^{5a}$)$_m$-G$^2$, —OC(O)R$^{1a}$, —OC(O)N(R$^b$)(R$^{3a}$), —SR$^{1a}$, —S(O)R$^{2a}$, —S(O)$_2$R$^{2a}$, —S(O)$_2$N(R$^b$)(R$^{3a}$), —C(O)R$^{1a}$, —C(O)OR$^{1a}$, —C(O)N(R$^b$)(R$^{3a}$), —N(R$^b$)(R$^{3a}$), —N(R$^a$)C(O)R$^{1a}$, —N(R$^a$)C(O)O(R$^{1a}$), —N(R$^a$)C(O)N(R$^b$)(R$^{3a}$), —N(R$^a$)S(O)$_2$(R$^{2a}$), —(CR$^{4a}$R$^{5a}$)$_m$—NO$_2$, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)OC(O)N(R$^b$)(R$^{3a}$), —(CR$^{4a}$R$^{5a}$)$_m$—SR$^{1a}$, —(CR$^{4a}$R$^{5a}$)$_m$—S(O)R$^{2a}$, —(CR$^{4a}$R$^{5a}$)$_m$—S(O)$_2$R$^{2a}$, —(CR$^{4a}$R$^{5a}$)S(O)$_2$N(R$^b$)(R$^{3a}$), —(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R$^{1a}$, —(CR$^{4a}$R$^{5a}$)$_m$—N(R$^a$)C(O)O(R$^{1a}$), —(CR$^{4a}$R$^{5a}$)$_m$—N(R$^a$)C(O)N(R$^b$)(R$^{3a}$), —(CR$^{4a}$R$^{5a}$)$_m$-G$^1$, —CR$^{4a}$=CR$^{5a}$-G$^1$, cyanoalkyl, or haloalkyl; wherein R$^a$ and R$^b$, at each occurrence, are each independently hydrogen, alkyl, or haloalkyl; R$^{1a}$ and R$^{1a}$, at each occurrence, are each independently hydrogen, alkyl, haloalkyl, G$^1$, or —(CR$^{4a}$R$^{5a}$)$_m$-G$^1$; R$^{2a}$, at each occurrence, is independently alkyl, haloalkyl, G$^1$, or —(CR$^{4a}$R$^{5a}$)$_m$-G$^1$; and R$^{4a}$ and R$^{5a}$, at each occurrence, are each independently hydrogen, halogen, alkyl, or haloalkyl. In another embodiment, R$^{10}$, R$^{11}$, R$^{12}$, and R$^{13}$ are each independently hydrogen, alkyl, halogen, cyano, -G$^1$, -G$^2$-O—(CR$^{4a}$R$^{5a}$)$_m$-G$^1$, —O—(CR$^{4a}$R$^{5a}$)$_m$-G$^2$, —N(R$^b$)(R$^{3a}$), —N(R$^a$)S(O)$_2$(R$^{2a}$), —(CR$^{4a}$R$^{5a}$)$_m$-G$^1$, —(CR$^{4a}$R$^{5a}$)$_m$—OR$^{1a}$, —CR$^{4a}$=CR$^{5a}$-G$^1$, —C(O)OR$^{1a}$, —S(O)$_2$R$^{2a}$, or haloalkyl, wherein R$^a$, R$^{4a}$ and R$^{5a}$ are hydrogen; R$^{2a}$ is G$^1$; m is 1 or 2; and G$^1$ is optionally substituted aryl or heteroaryl.

In one embodiment, R$^{10}$ and R$^{11}$, or R$^{11}$ and R$^{12}$, or R$^{12}$ and R$^{13}$ taken together with the carbon atoms to which they are attached form a substituted or unsubstituted phenyl ring.

In another embodiment, R$^{10}$ and R$^{11}$ are each hydrogen, and R$^{12}$ and R$^{13}$ taken together with the carbon atoms to which they are attached form a substituted or unsubstituted phenyl ring.

In another embodiment, R$^{10}$ and R$^{11}$, or R$^{11}$ and R$^{12}$, or R$^{12}$ and R$^{13}$ taken together with the carbon atoms to which they are attached form a substituted or unsubstituted cycloalkyl ring. In another embodiment, R$^{10}$ and R$^{11}$ are each hydrogen, and R$^{12}$ and R$^{13}$ taken together with the carbon atoms to which they are attached form a substituted or unsubstituted cycloalkyl ring.

In another embodiment, R$^{10}$ and R$^{11}$, or R$^{11}$ and R$^{12}$, or R$^{12}$ and R$^{13}$ taken together with the carbon atoms to which they are attached form a substituted or unsubstituted heterocycle ring. In another embodiment, R$^{10}$ and R$^{11}$ are each hydrogen, and R$^{12}$ and R$^{13}$ taken together with the carbon atoms to which they are attached form a substituted or unsubstituted heterocycle ring.

In another embodiment, R$^{10}$ and R$^{11}$, or R$^{11}$ and R$^{12}$, or R$^{12}$ and R$^{13}$ taken together with the carbon atoms to which they are attached form a substituted or unsubstituted heteroaryl ring. In another embodiment, R$^{10}$ and R$^{11}$ are each hydrogen, and R$^{12}$ and R$^{13}$ taken together with the carbon atoms to which they are attached form a substituted or unsubstituted heteroaryl ring.

In a further embodiment, R$^{10}$ and R$^{11}$, or R$^{11}$ and R$^{12}$, or R$^{12}$ and R$^{13}$ taken together with the carbon atoms to which they are attached form a substituted phenyl ring, a substituted cycloalkyl ring, a substituted heterocycle ring, or a substituted heteroaryl ring wherein the phenyl ring, cycloalkyl ring, heterocycle ring or heteroaryl ring are substituted with 1, 2, 3, 4, or 5 substitutents selected from the group consisting of alkyl, alkenyl, alkynyl, halogen, cyano, -G$^1$, -G$^2$, —NO$_2$, —OR$^{1a}$, —O—(CR$^{4a}$R$^{5a}$)$_m$-G$^1$, —O—(CR$^{4a}$R$^{5a}$)$_m$-G$^2$, —OC(O)R$^{1a}$, —OC(O)N(R$^b$)(R$^{3a}$), —SR$^{1a}$—S(O)R$^{2a}$, —S(O)$_2$R$^{2a}$, —S(O)$_2$N(R$^b$)(R$^{3a}$), —C(O)R$^{1a}$, —C(O)OR$^{1a}$, —C(O)N(R$^b$)(R$^{3a}$), —N(R$^b$)(R$^{3a}$), —N(R$^a$)C(O)R$^{1a}$, —N(R$^a$)C(O)O(R$^{1a}$), —N(R$^a$)C(O)N(R$^b$)(R$^{3a}$), —N(R$^a$)S(O)$_2$(R$^{2a}$), —(CR$^{4a}$R$^{5a}$)$_m$—NO$_2$, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)$_m$—OC(O)N(R$^b$)(R$^{3a}$)$_m$—(CR$^{4a}$R$^{5a}$)$_m$—SR$^{1a}$, —(CR$^{4a}$R$^{5a}$)$_m$—S(O)R$^{2a}$, —(CR$^{4a}$R$^{5a}$)$_m$—S(O)$_2$R$^{2a}$, —(CR$^{4a}$R$^{5a}$)$_m$—S(O)$_2$N(R$^b$)(R$^{3a}$), —(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R$^{1a}$, —(CR$^{4a}$R$^{5a}$)$_m$—N(R$^a$)C(O)O(R$^{1a}$), —(CR$^{4a}$R$^{5a}$)$_m$—N(R$^a$)C(O)N(R$^b$)(R$^{3a}$), —(CR$^{4a}$R$^{5a}$)$_m$-G$^1$, —CR$^{4a}$=CR$^{5a}$-G$^1$, cyanoalkyl, or haloalkyl; wherein R$^a$ and R$^b$, at each occurrence, are each independently hydrogen, alkyl, or haloalkyl; R$^{1a}$ and R$^{1a}$, at each occurrence, are each independently hydrogen, alkyl, haloalkyl, G$^1$, or —(CR$^{4a}$R$^{5a}$)$_m$-G$^1$; R$^{2a}$, at each occurrence, is independently alkyl, haloalkyl, G$^1$, or —(CR$^{4a}$R$^{5a}$)$_m$-G$^1$; and R$^{4a}$ and R$^{5a}$, at each occurrence, are each independently hydrogen, halogen, alkyl, or haloalkyl.

In one embodiment, compounds of formula (I) can include compounds of formula (Ia):

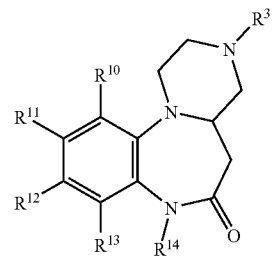

(Ia)

wherein R$^3$, R$^{10}$, R$^{11}$, R$^{12}$, R$^{13}$, and R$^{14}$ are as described above.

In another embodiment of the present invention, compounds of formula (Ia) are disclosed wherein R$^3$ is hydrogen or alkyl and R$^{14}$ is hydrogen or alkyl.

Representative examples of formula (Ia) include, but are not limited to:

1,2,3,4,4a,5-hexahydropyrazino[1,2-a][1,5]benzodiazepin-6(7H)-one;

(4aS)-1,2,3,4,4a,5-hexahydropyrazino[1,2-a][1,5]benzodiazepin-6(7H)-one;

10-chloro-1,2,3,4,4a,5-hexahydropyrazino[1,2-a][1,5]benzodiazepin-6(7H)-one;

10-bromo-1,2,3,4,4a,5-hexahydropyrazino[1,2-a][1,5]benzodiazepin-6(7H)-one;

10-phenyl-1,2,3,4,4a,5-hexahydropyrazino[1,2-a][1,5]benzodiazepin-6(7H)-one;

10-[(E)-2-phenylvinyl]-1,2,3,4,4a,5-hexahydropyrazino[1,2-a][1,5]benzodiazepin-6(7H)-one;

10-(3-chlorophenyl)-1,2,3,4,4a,5-hexahydropyrazino[1,2-a][1,5]benzodiazepin-6(7H)-one;

10-(2-chlorophenyl)-1,2,3,4,4a,5-hexahydropyrazino[1,2-a][1,5]benzodiazepin-6(7H)-one;

10-[(E)-2-(3-fluorophenyl)vinyl]-1,2,3,4,4a,5-hexahydropyrazino[1,2-a][1,5]benzodiazepin-6(7H)-one;

10-methyl-1,2,3,4,4a,5-hexahydropyrazino[1,2-a][1,5]benzodiazepin-6(7H)-one;

6-oxo-1,2,3,4,4a,5,6,7-octahydropyrazino [1,2-a][1,5]benzodiazepine-10-carbonitrile;

10-methoxy-1,2,3,4,4a,5-hexahydropyrazino[1,2-a][1,5]benzodiazepin-6(7H)-one;

9-bromo-1,2,3,4,4a,5-hexahydropyrazino[1,2-a][1,5]benzodiazepin-6(7H)-one;

9-(4-chlorophenyl)-1,2,3,4,4a,5-hexahydropyrazino[1,2-a][1,5]benzodiazepin-6(7H)-one;

9,10-dichloro-1,2,3,4,4a,5-hexahydropyrazino[1,2-a][1,5]benzodiazepin-6(7H)-one;

7-methyl-1,2,3,4,4a,5-hexahydropyrazino[1,2-a][1,5]benzodiazepin-6(7H)-one;

3-ethyl-1,2,3,4,4a,5-hexahydropyrazino[1,2-a][1,5]benzodiazepin-6(7H)-one;

3-benzyl-10-chloro-1,2,3,4,4a,5-hexahydropyrazino[1,2-a][1,5]benzodiazepin-6(7H)-one;

10-[(E)-2-(3-chlorophenyl)vinyl]-1,2,3,4,4a,5-hexahydropyrazino[1,2-a][1,5]benzodiazepin-6(7H)-one;

10-[(E)-2-(4-fluorophenyl)vinyl]-1,2,3,4,4a,5-hexahydropyrazino[1,2-a][1,5]benzodiazepin-6(7H)-one;

10-[(E)-2-(4-chlorophenyl)vinyl]-1,2,3,4,4a,5-hexahydropyrazino[1,2-a][1,5]benzodiazepin-6(7H)-one;

10-[(E)-2-(2,4-difluorophenyl)vinyl]-1,2,3,4,4a,5-hexahydropyrazino[1,2-a][1,5]benzodiazepin-6(7H)-one;

10-(2-phenylethyl)-1,2,3,4,4a,5-hexahydropyrazino[1,2-a][1,5]benzodiazepin-6(7H)-one;

11-bromo-1,2,3,4,4a,5-hexahydropyrazino[1,2-a][1,5]benzodiazepin-6(7H)-one;
10-(trifluoromethyl)-1,2,3,4,4a,5-hexahydropyrazino[1,2-a][1,5]benzodiazepin-6(7H)-one;
8-fluoro-1,2,3,4,4a,5-hexahydropyrazino[1,2-a][1,5]benzodiazepin-6(7H)-one;
11-fluoro-1,2,3,4,4a,5-hexahydropyrazino[1,2-a][1,5]benzodiazepin-6(7H)-one;
9-fluoro-1,2,3,4,4a,5-hexahydropyrazino[1,2-a][1,5]benzodiazepin-6(7H)-one;
10-fluoro-1,2,3,4,4a,5-hexahydropyrazino[1,2-a][1,5]benzodiazepin-6(7H)-one;
(4aS)-10-methyl-1,2,3,4,4a,5-hexahydropyrazino[1,2-a][1,5]benzodiazepin-6(7H)-one;
(4aS)-9,10-dichloro-1,2,3,4,4a,5-hexahydropyrazino[1,2-a][1,5]benzodiazepin-6(7H)-one;
3-methyl-1,2,3,4,4a,5-hexahydropyrazino[1,2-a][1,5]benzodiazepin-6(7H)-one;
3,3a,4,5,6,7-hexahydronaphtho[1,2-b]pyrazino[1,2-d][1,4]diazepin-2(1H)-one;
8-methyl-1,2,3,4,4a,5-hexahydropyrazino[1,2-a][1,5]benzodiazepin-6(7H)-one;
(4aS)-10-chloro-1,2,3,4,4a,5-hexahydropyrazino[1,2-a][1,5]benzodiazepin-6(7H)-one;
(4aS)-10-(2-phenylethyl)-1,2,3,4,4a,5-hexahydropyrazino[1,2-a][1,5]benzodiazepin-6(7H)-one;
(4aS)-10-methoxy-1,2,3,4,4a,5-hexahydropyrazino[1,2-a][1,5]benzodiazepin-6(7H)-one;
10-ethoxy-1,2,3,4,4a,5-hexahydropyrazino[1,2-a][1,5]benzodiazepin-6(7H)-one;
9-methyl-1,2,3,4,4a,5-hexahydropyrazino[1,2-a][1,5]benzodiazepin-6(7H)-on;
ethyl 6-oxo-1,2,3,4,4a,5,6,7-octahydropyrazino [1,2-a][1,5]benzodiazepine-10-carboxylate;
9-chloro-1,2,3,4,4a,5-hexahydropyrazino[1,2-a][1,5]benzodiazepin-6(7H)-one;
10-cyclopropyl-1,2,3,4,4a,5-hexahydropyrazino[1,2-a][1,5]benzodiazepin-6(7H)-one;
11-methyl-1,2,3,4,4a,5-hexahydropyrazino[1,2-a][1,5]benzodiazepin-6(7H)-one;
(4aS)-9-chloro-1,2,3,4,4a,5-hexahydropyrazino[1,2-a][1,5]benzodiazepin-6(7H)-one;
10-(1-benzyl-1H-pyrazol-4-yl)-1,2,3,4,4a,5-hexahydropyrazino[1,2-a][1,5]benzodiazepin-6(7H)-one;
10-(2-naphthyl)-1,2,3,4,4a,5-hexahydropyrazino[1,2-a][1,5]benzodiazepin-6(7H)-one;
10-(4-methoxyphenyl)-1,2,3,4,4a,5-hexahydropyrazino[1,2-a][1,5]benzodiazepin-6(7H)-one;
10-(biphenyl-3-yl)-1,2,3,4,4a,5-hexahydropyrazino[1,2-a][1,5]benzodiazepin-6(7H)-one;
10-(1-methyl-1H-pyrazol-4-yl)-1,2,3,4,4a,5-hexahydropyrazino[1,2-a][1,5]benzodiazepin-6(7H)-one;
10-(3-fluorophenyl)-1,2,3,4,4a,5-hexahydropyrazino[1,2-a][1,5]benzodiazepin-6(7H)-one;
10-(quinolin-3-yl)-1,2,3,4,4a,5-hexahydropyrazino[1,2-a][1,5]benzodiazepin-6(7H)-one;
10-(2-methoxyphenyl)-1,2,3,4,4a,5-hexahydropyrazino[1,2-a][1,5]benzodiazepin-6(7H)-one;
10-(biphenyl-2-yl)-1,2,3,4,4a,5-hexahydropyrazino[1,2-a][1,5]benzodiazepin-6(7H)-one;
10-(3-methoxyphenyl)-1,2,3,4,4a,5-hexahydropyrazino[1,2-a][1,5]benzodiazepin-6(7H)-one;
10-(1-benzothiophen-3-yl)-1,2,3,4,4a,5-hexahydropyrazino[1,2-a][1,5]benzodiazepin-6(7H)-one;
10-(1-naphthyl)-1,2,3,4,4a,5-hexahydropyrazino[1,2-a][1,5]benzodiazepin-6(7H)-one;
10-(1H-indol-4-yl)-1,2,3,4,4a,5-hexahydropyrazino[1,2-a][1,5]benzodiazepin-6(7H)-one;
10-(3-furyl)-1,2,3,4,4a,5-hexahydropyrazino[1,2-a][1,5]benzodiazepin-6(7H)-one;
10-(2-fluorophenyl)-1,2,3,4,4a,5-hexahydropyrazino[1,2-a][1,5]benzodiazepin-6(7H)-one;
10-(pyridin-2-yl)-1,2,3,4,4a,5-hexahydropyrazino[1,2-a][1,5]benzodiazepin-6(7H)-one;
10-(3-thienyl)-1,2,3,4,4a,5-hexahydropyrazino[1,2-a][1,5]benzodiazepin-6(7H)-one;
10-[3-(1H-pyrazol-1-yl)phenyl]-1,2,3,4,4a,5-hexahydropyrazino[1,2-a][1,5]benzodiazepin-6(7H)-one;
10-(4-fluorophenyl)-1,2,3,4,4a,5-hexahydropyrazino[1,2-a][1,5]benzodiazepin-6(7H)-one;
10-(1-benzothiophen-2-yl)-1,2,3,4,4a,5-hexahydropyrazino[1,2-a][1,5]benzodiazepin-6(7H)-one;
N-(6-oxo-1,2,3,4,4a,5,6,7-octahydropyrazino [1,2-a][1,5]benzodiazepin-9-yl)benzenesulfonamide;
9-chloro-7-ethyl-1,2,3,4,4a,5-hexahydropyrazino[1,2-a][1,5]benzodiazepin-6(7H)-one;
9-chloro-7-ethyl-3-methyl-1,2,3,4,4a,5-hexahydropyrazino[1,2-a][1,5]benzodiazepin-6(7H)-one;
8-fluoro-3-methyl-1,2,3,4,4a,5-hexahydropyrazino[1,2-a][1,5]benzodiazepin-6(7H)-one;
9-chloro-7-methyl-1,2,3,4,4a,5-hexahydropyrazino[1,2-a][1,5]benzodiazepin-6(7H)-one;
(4aR)-8-fluoro-1,2,3,4,4a,5-hexahydropyrazino[1,2-a][1,5]benzodiazepain-6(7H)-one;
(4aS)-10-chloro-3-methyl-1,2,3,4,4a,5-hexahydropyrazino[1,2-a][1,5]benzodiazepin-6(7H)-one;
(4aS)-8-fluoro-1,2,3,4,4a,5-hexahydropyrazino[1,2-a][1,5]benzodiazepin-6(7H)-one;
(4aS)-11-fluoro-1,2,3,4,4a,5-hexahydropyrazino[1,2-a][1,5]benzodiazepain-6(7H)-one;
(4aR)-11-fluoro-1,2,3,4,4a,5-hexahydropyrazino[1,2-a][1,5]benzodiazepin-6(7H)-one;
(4aS)-8-fluoro-3-methyl-1,2,3,4,4a,5-hexahydropyrazino[1,2-a][1,5]benzodiazepin-6(7H)-one;
10-(3-methylphenyl)-1,2,3,4,4a,5-hexahydropyrazino[1,2-a][1,5]benzodiazepin-6(7H)-one;
10-[3-(trifluoromethyl)phenyl]-1,2,3,4,4a,5-hexahydropyrazino[1,2-a][1,5]benzodiazepin-6(7H)-one;
10-(3-ethylphenyl)-1,2,3,4,4a,5-hexahydropyrazino[1,2-a][1,5]benzodiazepin-6(7H)-one;
10-(3-isopropylphenyl)-1,2,3,4,4a,5-hexahydropyrazino[1,2-a][1,5]benzodiazepin-6(7H)-one;
10-[3-(trifluoromethoxy)phenyl]-1,2,3,4,4a,5-hexahydropyrazino[1,2-a][1,5]benzodiazepin-6(7H)-one;
10-(3-isopropoxyphenyl)-1,2,3,4,4a,5-hexahydropyrazino[1,2-a][1,5]benzodiazepin-6(7H)-one;
10-[3-(benzyloxy)phenyl]-1,2,3,4,4a,5-hexahydropyrazino[1,2-a][1,5]benzodiazepain-6(7H)-one;
10-(3-isobutoxyphenyl)-1,2,3,4,4a,5-hexahydropyrazino[1,2-a][1,5]benzodiazepin-6(7H)-one;
N-(6-oxo-1,2,3,4,4a,5,6,7-octahydropyrazino [1,2-a][1,5]benzodiazepin-9-yl)biphenyl-2-sulfonamide;
2-methyl-N-(6-oxo-1,2,3,4,4a,5,6,7-octahydropyrazino[1,2-a][1,5]benzodiazepin-9-yl)benzenesulfonamide;
4-methyl-N-(6-oxo-1,2,3,4,4a,5,6,7-octahydropyrazino[1,2-a][1,5]benzodiazepin-9-yl)benzenesulfonamide;
3-methyl-N-(6-oxo-1,2,3,4,4a,5,6,7-octahydropyrazino[1,2-a][1,5]benzodiazepin-9-yl)benzenesulfonamide;
3-chloro-N-(6-oxo-1,2,3,4,4a,5,6,7-octahydropyrazino[1,2-a][1,5]benzodiazepin-9-yl)benzenesulfonamide;
4-chloro-N-(6-oxo-1,2,3,4,4a,5,6,7-octahydropyrazino[1,2-a][1,5]benzodiazepin-9-yl)benzenesulfonamide;

2-fluoro-N-(6-oxo-1,2,3,4,4a,5,6,7-octahydropyrazino[1,2-a][1,5]benzodiazepin-9-yl)benzenesulfonamide;
3-fluoro-N-(6-oxo-1,2,3,4,4a,5,6,7-octahydropyrazino[1,2-a][1,5]benzodiazepin-9-yl)benzenesulfonamide;
4-fluoro-N-(6-oxo-1,2,3,4,4a,5,6,7-octahydropyrazino[1,2-a][1,5]benzodiazepin-9-yl)benzenesulfonamide;
2-methoxy-N-(6-oxo-1,2,3,4,4a,5,6,7-octahydropyrazino[1,2-a][1,5]benzodiazepin-9-yl)benzenesulfonamide;
3-methoxy-N-(6-oxo-1,2,3,4,4a,5,6,7-octahydropyrazino[1,2-a][1,5]benzodiazepin-9-yl)benzenesulfonamide;
4-methoxy-N-(6-oxo-1,2,3,4,4a,5,6,7-octahydropyrazino[1,2-a][1,5]benzodiazepin-9-yl)benzenesulfonamide;
N-(6-oxo-1,2,3,4,4a,5,6,7-octahydropyrazino[1,2-a][1,5]benzodiazepin-9-yl)thiophene-2-sulfonamide;
8-chloro-1,2,3,4,4a,5-hexahydropyrazino[1,2-a][1,5]benzodiazepin-6(7H)-one;
10-(phenoxymethyl)-1,2,3,4,4a,5-hexahydropyrazino[1,2-a][1,5]benzodiazepin-6(7H)-one;
9-(phenylsulfonyl)-1,2,3,4,4a,5-hexahydropyrazino[1,2-a][1,5]benzodiazepin-6(7H)-one;
10-[(2-fluorophenoxy)methyl]-1,2,3,4,4a,5-hexahydropyrazino[1,2-a][1,5]benzodiazepin-6(7H)-one;
10-[(3-fluorophenoxy)methyl]-1,2,3,4,4a,5-hexahydropyrazino[1,2-a][1,5]benzodiazepin-6(7H)-one;
10-[(4-fluorophenoxy)methyl]-1,2,3,4,4a,5-hexahydropyrazino[1,2-a][1,5]benzodiazepin-6(7H)-one;
(4aS)-10-(2-fluorophenyl)-1,2,3,4,4a,5-hexahydropyrazino[1,2-a][1,5]benzodiazepin-6(7H)-one;
(4aS)-10-(3-isopropoxyphenyl)-1,2,3,4,4a,5-hexahydropyrazino[1,2-a][1,5]benzodiazepin-6(7H)-one;
(4aS)-10-[2-(2-fluorophenyl)ethoxy]-1,2,3,4,4a,5-hexahydropyrazino[1,2-a][1,5]benzodiazepin-6(7H)-one;
2,6-dichloro-N-(6-oxo-1,2,3,4,4a,5,6,7-octahydropyrazino[1,2-a][1,5]benzodiazepin-9-yl)benzenesulfonamide;
N-(6-oxo-1,2,3,4,4a,5,6,7-octahydropyrazino [1,2-a][1,5]benzodiazepin-9-yl)-3-(trifluoromethoxy)benzenesulfonamide;
4-cyano-N-(6-oxo-1,2,3,4,4a,5,6,7-octahydropyrazino [1,2-a][1,5]benzodiazepin-9-yl)benzenesulfonamide;
3-cyano-N-(6-oxo-1,2,3,4,4a,5,6,7-octahydropyrazino [1,2-a][1,5]benzodiazepin-9-yl)benzenesulfonamide;
2,6-difluoro-N-(6-oxo-1,2,3,4,4a,5,6,7-octahydropyrazino [1,2-a][1,5]benzodiazepin-9-yl)benzenesulfonamide;
N-(6-oxo-1,2,3,4,4a,5,6,7-octahydropyrazino [1,2-a][1,5]benzodiazepin-9-yl)naphthalene-1-sulfonamide;
2,5-dimethyl-N-(6-oxo-1,2,3,4,4a,5,6,7-octahydropyrazino [1,2-a][1,5]benzodiazepin-9-yl)benzenesulfonamide;
N-(6-oxo-1,2,3,4,4a,5,6,7-octahydropyrazino [1,2-a][1,5]benzodiazepin-9-yl)-2-(trifluoromethyl)benzenesulfonamide;
5-chloro-N-(6-oxo-1,2,3,4,4a,5,6,7-octahydropyrazino [1,2-a][1,5]benzodiazepin-9-yl)thiophene-2-sulfonamide;
N-(6-oxo-1,2,3,4,4a,5,6,7-octahydropyrazino [1,2-a][1,5]benzodiazepin-9-yl)naphthalene-2-sulfonamide;
3,5-dimethyl-N-(6-oxo-1,2,3,4,4a,5,6,7-octahydropyrazino [1,2-a][1,5]benzodiazepin-9-yl)benzenesulfonamide;
N-(6-oxo-1,2,3,4,4a,5,6,7-octahydropyrazino [1,2-a][1,5]benzodiazepin-9-yl)-2-(trifluoromethoxy)benzenesulfonamide;
(4aS)-10-(difluoromethoxy)-1,2,3,4,4a,5-hexahydropyrazino[1,2-a][1,5]benzodiazepin-6(7H)-one;
10-[(E)-2-(2-fluorophenyl)vinyl]-1,2,3,4,4a,5-hexahydropyrazino[1,2-a][1,5]benzodiazepin-6(7H)-one;
10-{(E)-2-[2-(trifluoromethyl)phenyl]vinyl}-1,2,3,4,4a,5-hexahydropyrazino[1,2-a][1,5]benzodiazepin-6(7H)-one;
10-[(E)-2-(3,5-difluorophenyl)vinyl]-1,2,3,4,4a,5-hexahydropyrazino[1,2-a][1,5]benzodiazepin-6(7H)-one;
10-[2-(2-fluorophenyl)ethyl]-1,2,3,4,4a,5-hexahydropyrazino[1,2-a][1,5]benzodiazepin-6(7H)-one;
10-[2-(3-fluorophenyl)ethyl]-1,2,3,4,4a,5-hexahydropyrazino[1,2-a][1,5]benzodiazepin-6(7H)-one;
10-{2-[2-(trifluoromethyl)phenyl]ethyl}-1,2,3,4,4a,5-hexahydropyrazino[1,2-a][1,5]benzodiazepin-6(7H)-one;
10-[2-(3,5-difluorophenyl)ethyl]-1,2,3,4,4a,5-hexahydropyrazino[1,2-a][1,5]benzodiazepin-6(7H)-one;
(4aS)-8-chloro-1,2,3,4,4a,5-hexahydropyrazino[1,2-a][1,5]benzodiazepin-6(7H)-one;
10-(benzyloxy)-1,2,3,4,4a,5-hexahydropyrazino[1,2-a][1,5]benzodiazepin-6(7H)-one;
7-methyl-10-(2-phenylethyl)-1,2,3,4,4a,5-hexahydropyrazino[1,2-a][1,5]benzodiazepin-6(7H)-one;
10-[2-(3-fluorophenyl)ethoxy]-1,2,3,4,4a,5-hexahydropyrazino[1,2-a][1,5]benzodiazepin-6(7H)-one;
10-[(1R)-1-phenylethoxy]-1,2,3,4,4a,5-hexahydropyrazino[1,2-a][1,5]benzodiazepin-6(7H)-one;
10-[(1S)-1-phenylethoxy]-1,2,3,4,4a,5-hexahydropyrazino[1,2-a][1,5]benzodiazepin-6(7H)-one;
10-[(2-fluorobenzyl)oxy]-1,2,3,4,4a,5-hexahydropyrazino[1,2-a][1,5]benzodiazepin-6(7H)-one;
10-[(3-fluorobenzyl)oxy]-1,2,3,4,4a,5-hexahydropyrazino[1,2-a][1,5]benzodiazepin-6(7H)-one;
10-{[2-(trifluoromethyl)benzyl]oxy}-1,2,3,4,4a,5-hexahydropyrazino[1,2-a][1,5]benzodiazepin-6(7H)-one;
10-(2-phenylethoxy)-1,2,3,4,4a,5-hexahydropyrazino[1,2-a][1,5]benzodiazepin-6(7H)-one;
10-{[(2R)-1-phenylpropan-2-yl]oxy}-1,2,3,4,4a,5-hexahydropyrazino[1,2-a][1,5]benzodiazepin-6(7H)-one;
10-{[(2S)-1-phenylpropan-2-yl]oxy}-1,2,3,4,4a,5-hexahydropyrazino[1,2-a][1,5]benzodiazepin-6(7H)-one;
10-[(1R)-1-(2-fluorophenyl)ethoxy]-1,2,3,4,4a,5-hexahydropyrazino[1,2-a][1,5]benzodiazepin-6(7H)-one;
10-[(1S)-1-(2-fluorophenyl)ethoxy]-1,2,3,4,4a,5-hexahydropyrazino[1,2-a][1,5]benzodiazepin-6(7H)-one;
(4aS)-10-{[(2S-1-phenylpropan-2-yl]oxy}-1,2,3,4,4a,5-hexahydropyrazino[1,2-a][1,5]benzodiazepin-6(7H)-one;
(4aS)-10-[2-(3-fluorophenyl)ethoxy]-1,2,3,4,4a,5-hexahydropyrazino[1,2-a][1,5]benzodiazepin-6(7H)-one;
(4aS)-10-{[(2R)-1-phenylpropan-2-yl]oxy}-1,2,3,4,4a,5-hexahydropyrazino[1,2-a][1,5]benzodiazepin-6(7H)-one;
(4aR)-10-{[(2R)-1-phenylpropan-2-yl]oxy}-1,2,3,4,4a,5-hexahydropyrazino[1,2-a][1,5]benzodiazepin-6(7H)-one;
(4aR)-10-{[(2S-1-phenylpropan-2-yl]oxy}-1,2,3,4,4a,5-hexahydropyrazino[1,2-a][1,5]benzodiazepin-6(7H)-one;
(4aS)-10-(cyclopropylmethoxy)-1,2,3,4,4a,5-hexahydropyrazino[1,2-a][1,5]benzodiazepin-6(7H)-one;
(4aS)-10-[2-(pyridin-2-yl)ethoxy]-1,2,3,4,4a,5-hexahydropyrazino[1,2-a][1,5]benzodiazepin-6(7H)-one;
(4aS)-10-[2-(2-chlorophenyl)ethoxy]-1,2,3,4,4a,5-hexahydropyrazino[1,2-a][1,5]benzodiazepin-6(7H)-one;
(4aS)-10-{2-[3-(trifluoromethyl)phenyl]ethoxy}-1,2,3,4,4a,5-hexahydropyrazino[1,2-a][1,5]benzodiazepin-6(7H)-one;
(4aS)-10-sec-butoxy-1,2,3,4,4a,5-hexahydropyrazino[1,2-a][1,5]benzodiazepin-6(7H)-one;
(4aS)-10-[2-(3-chlorophenyl)ethoxy]-1,2,3,4,4a,5-hexahydropyrazino[1,2-a][1,5]benzodiazepin-6(7H)-one;
(4aS)-10-[2-(3-methylphenyl)ethoxy]-1,2,3,4,4a,5-hexahydropyrazino[1,2-a][1,5]benzodiazepin-6(7H)-one;
(4aS)-10-(1-phenylpropoxy)-1,2,3,4,4a,5-hexahydropyrazino[1,2-a][1,5]benzodiazepin-6(7H)-one;
(4aS)-10-[(1R)-1-(2,5-difluorophenyl)ethoxy]-1,2,3,4,4a,5-hexahydropyrazino[1,2-a][1,5]benzodiazepin-6(7H)-one;
(4aS)-10-ethoxy-1,2,3,4,4a,5-hexahydropyrazino[1,2-a][1,5]benzodiazepin-6(7H)-one;

N-(7-oxo-1,2,3,4,4a,5,6,7-octahydropyrazino [1,2-a][1,4] benzodiazepin-9-yl)-3-(trifluoromethyl)benzenesulfonamide; or 10-benzyl-1,2,3,4,4a,5-hexahydropyrazino[1,2-a][1,5]benzodiazepin-6(7H)-one.

In one embodiment, compounds of formula (I) can include compounds of formula (Ib):

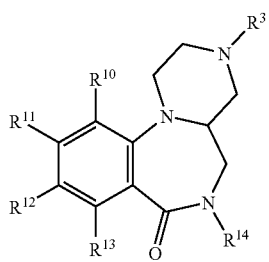

(Ib)

wherein $R^3$ is selected from the group consisting of hydrogen, alkylcarbonyl, haloalkyl, —$(CR^{4a}R^{5a})_m$-$G^1$, —C(O)-$G^1$, —S(O)$_2R^7$, and —C(O)NR$^8$R$^9$, and wherein $R^{10}$, $R^{11}$, $R^{12}$, $R^{13}$ and $R^{14}$ are as described above.

In another embodiment of the present invention, compounds of formula (Ib) are disclosed wherein $R^3$ is hydrogen or —$(CR^{4a}R^{5a})_m$-$G^1$ and $R^{14}$ is hydrogen.

Representative examples of formula (Ib) include, but are not limited to:

3-benzyl-2,3,4,4a,5,6-hexahydropyrazino[1,2-a][1,4]benzodiazepin-7(1H)-one;

2,3,4,4a,5,6-hexahydropyrazino[1,2-a][1,4]benzodiazepin-7(1H)-one;

N-(3-benzyl-7-oxo-1,2,3,4,4a,5,6,7-octahydropyrazino[1,2-a][1,4]benzodiazepin-9-yl)benzenesulfonamide; or N-(7-oxo-1,2,3,4,4a,5,6,7-octahydropyrazino[1,2-a][1,4]benzodiazepin-9-yl)benzenesulfonamide.

In one embodiment, compounds of formula (I) can include compounds of formula (Ic):

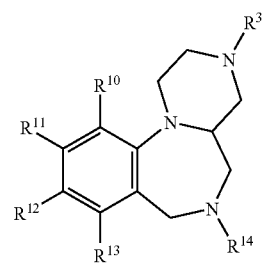

(Ic)

wherein $R^3$, $R^{10}$, $R^{11}$, $R^{12}$, $R^{13}$, and $R^{14}$ are as described above.

In another embodiment, compounds of formula (Ic) are disclosed wherein $R^3$ is selected from the group consisting of hydrogen, alkyl, alkylcarbonyl, haloalkyl, —S(O)$_2R^2$, and —C(O)NR$^8$R$^9$ and $R^{14}$ is preferably hydrogen.

In one embodiment, compounds of formula (I) can include compounds of formula (Id):

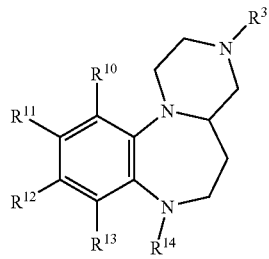

(Id)

wherein $R^3$, $R^{10}$, $R^{11}$, $R^{12}$, $R^{13}$, and $R^{14}$ are as described above.

In another embodiment, compounds of formula (Id) are disclosed wherein $R^3$ is selected from the group consisting of hydrogen or alkyl, and $R^{14}$ is preferably hydrogen.

Representative examples of formula (Id) include, but are not limited to:

9,10-dichloro-1,2,3,4,4a,5,6,7-octahydropyrazino[1,2-a][1,5]benzodiazepine;

1,2,3,4,4a,5,6,7-octahydropyrazino[1,2-a][1,5]benzodiazepine;

10-chloro-1,2,3,4,4a,5,6,7-octahydropyrazino[1,2-a][1,5]benzodiazepine;

9-bromo-1,2,3,4,4a,5,6,7-octahydropyrazino[1,2-a][1,5]benzodiazepine;

7-(2-chlorobenzyl)-1,2,3,4,4a,5,6,7-octahydropyrazino[1,2-a][1,5]benzodiazepine;

7-(3-chlorobenzyl)-1,2,3,4,4a,5,6,7-octahydropyrazino[1,2-a][1,5]benzodiazepine;

(4aS)-9-bromo-1,2,3,4,4a,5,6,7-octahydropyrazino[1,2-a][1,5]benzodiazepine;

9-chloro-7-methyl-1,2,3,4,4a,5,6,7-octahydropyrazino[1,2-a][1,5]benzodiazepine; or 9-chloro-7-ethyl-3-methyl-1,2,3,4,4a,5,6,7-octahydropyrazino[1,2-a][1,5]benzodiazepine.

In one embodiment, compounds of formula (I) can include compounds of formula (Ie):

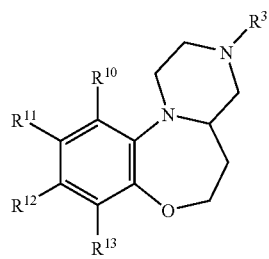

(Ie)

wherein $R^3$, $R^{10}$, $R^{11}$, $R^{12}$, and $R^{13}$ are as described above.

In another embodiment, compounds of formula (Ie) are disclosed wherein $R^3$ is selected from the group consisting of hydrogen, alkyl, alkylcarbonyl, haloalkyl, —$(CR^{4a}R^{5a})_m$-$G^1$, —C(O)-$G^1$, —S(O)$_2R^7$, or —C(O)NR$^8$R$^9$.

In another embodiment of the present invention, compounds of formula (Ie) are disclosed wherein $R^3$ is hydrogen or alkyl.

Representative examples of formula (Ie) include, but are not limited to:

(4aS)-3-methyl-2,3,4,4a,5,6-hexahydro-1H-pyrazino[2,1-d][1,5]benzoxazepine;

(4aS)-10-methyl-2,3,4,4a,5,6-hexahydro-1H-pyrazino[2,1-d][1,5]benzoxazepine;
(4aS)-10-methoxy-2,3,4,4a,5,6-hexahydro-1H-pyrazino[2,1-d][1,5]benzoxazepine;
(4aS)-2,3,4,4a,5,6-hexahydro-1H-pyrazino[2,1-d][1,5]benzoxazepin-10-amine;
(4aS)-10-fluoro-2,3,4,4a,5,6-hexahydro-1H-pyrazino[2,1-d][1,5]benzoxazepine;
(4aS)-9-methyl-2,3,4,4a,5,6-hexahydro-1H-pyrazino[2,1-d][1,5]benzoxazepine;
(4aS)-11-chloro-2,3,4,4a,5,6-hexahydro-1H-pyrazino [2,1-d][1,5]benzoxazepine;
(4aS)-11-fluoro-2,3,4,4a,5,6-hexahydro-1H-pyrazino [2,1-d][1,5]benzoxazepine;
(4aS)-9-chloro-2,3,4,4a,5,6-hexahydro-1H-pyrazino[2,1-d][1,5]benzoxazepine;
(4aS)-3-benzyl-2,3,4,4a,5,6-hexahydro-1H-pyrazino[2,1-d][1,5]benzoxazepine;
(4aS)-2,3,4,4a,5,6-hexahydro-1H-pyrazino[2,1-d][1,5]benzoxazepine;
(4aS)-10-chloro-2,3,4,4a,5,6-hexahydro-1H-pyrazino[2,1-d][1,5]benzoxazepine;
(4aS)-3-benzyl-9-chloro-2,3,4,4a,5,6-hexahydro-1H-pyrazino[2,1-d][1,5]benzoxazepine;
(4aS)-9-phenyl-2,3,4,4a,5,6-hexahydro-1H-pyrazino[2,1-d][1,5]benzoxazepine;
(4aS)-9-chloro-3-methyl-2,3,4,4a,5,6-hexahydro-1H-pyrazino[2,1-d][1,5]benzoxazepine;
(4aS)-9-(2-methylphenyl)-2,3,4,4a,5,6-hexahydro-1H-pyrazino[2,1-d][1,5]benzoxazepine;
(4aS)-9-(3-methylphenyl)-2,3,4,4a,5,6-hexahydro-1H-pyrazino [2,1-d][1,5]benzoxazepine;
(4aS)-9-(4-methylphenyl)-2,3,4,4a,5,6-hexahydro-1H-pyrazino [2,1-d][1,5]benzoxazepine;
(4aS)-9-(2-methoxyphenyl)-2,3,4,4a,5,6-hexahydro-1H-pyrazino [2,1-d][1,5]benzoxazepine;
(4aS)-9-(3-methoxyphenyl)-2,3,4,4a,5,6-hexahydro-1H-pyrazino [2,1-d][1,5]benzoxazepine;
(4aS)-9-(4-methoxyphenyl)-2,3,4,4a,5,6-hexahydro-1H-pyrazino [2,1-d][1,5]benzoxazepine;
(4aS)-9-[2-(methylsulfonyl)phenyl]-2,3,4,4a,5,6-hexahydro-1H-pyrazino [2,1-d][1,5]benzoxazepine;
(4aS)-9-[3-(methylsulfonyl)phenyl]-2,3,4,4a,5,6-hexahydro-1H-pyrazino [2,1-d][1,5]benzoxazepine;
1-{2-[(4aS)-2,3,4,4a,5,6-hexahydro-1H-pyrazino [2,1-d][1,5]benzoxazepin-9-yl]phenyl}ethanone;
1-{3-[(4aS)-2,3,4,4a,5,6-hexahydro-1H-pyrazino [2,1-d][1,5]benzoxazepin-9-yl]phenyl}ethanone;
1-{4-[(4aS)-2,3,4,4a,5,6-hexahydro-1H-pyrazino [2,1-d][1,5]benzoxazepin-9-yl]phenyl}ethanone;
2-[(4aS)-2,3,4,4a,5,6-hexahydro-1H-pyrazino[2,1-d][1,5]benzoxazepin-9-yl]phenol;
3-[(4aS)-2,3,4,4a,5,6-hexahydro-1H-pyrazino[2,1-d][1,5]benzoxazepin-9-yl]phenol;
4-[(4aS)-2,3,4,4a,5,6-hexahydro-1H-pyrazino[2,1-d][1,5]benzoxazepin-9-yl]phenol;
(4aS)-9-(2-fluorophenyl)-2,3,4,4a,5,6-hexahydro-1H-pyrazino [2,1-d][1,5]benzoxazepine;
(4aS)-9-(3-fluorophenyl)-2,3,4,4a,5,6-hexahydro-1H-pyrazino [2,1-d][1,5]benzoxazepine;
(4aS)-9-(4-fluorophenyl)-2,3,4,4a,5,6-hexahydro-1H-pyrazino [2,1-d][1,5]benzoxazepine;
(4aS)-9-(pyridin-3-yl)-2,3,4,4a,5,6-hexahydro-1H-pyrazino [2,1-d][1,5]benzoxazepine; or
(4aS)-9-(pyridin-4-yl)-2,3,4,4a,5,6-hexahydro-1H-pyrazino [2,1-d][1,5]benzoxazepine.

In one embodiment, compounds of formula (I) can include compounds of formula (If):

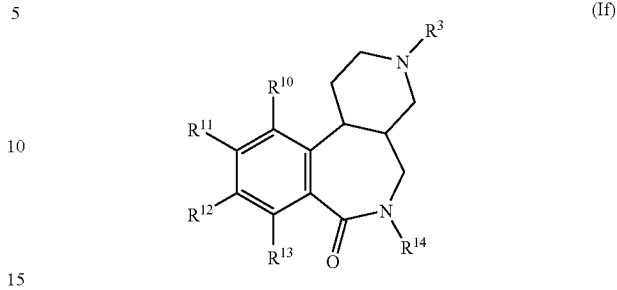

wherein $R^{10}$, $R^{11}$, $R^{12}$, $R^{13}$, and $R^{14}$ are as described above; and $R^3$ is hydrogen.

In another embodiment, compounds of formula (If) are disclosed wherein $R^3$ and $R^{14}$ are independently hydrogen or alkyl.

Representative examples of formula (Ie) include, but are not limited to:
cis-1,2,3,4,4a,5,6,11b-octahydro-7H-pyrido[3,4-d][2]benzazepin-7-one.

In one embodiment, compounds of formula (I) can include compounds of formula (Ig):

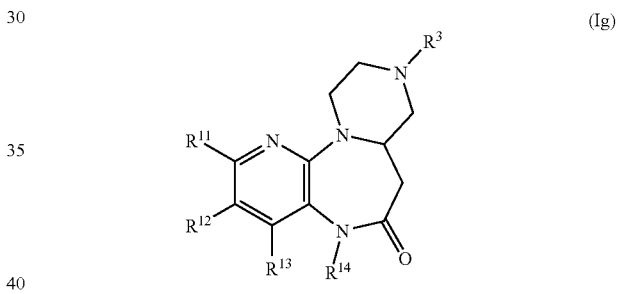

wherein $R^{11}$, $R^{12}$, $R^{13}$, and $R^{14}$ are as described above; and $R^3$ is hydrogen.

In another embodiment, compounds of formula (Ig) are disclosed wherein $R^3$ and $R^{14}$ are independently hydrogen or alkyl.

Representative examples of formula (Ie) include, but are not limited to:
7,7a,8,9,10,11-hexahydropyrazino[1,2-d]pyrido[3,2-b][1,4]diazepin-6(5H)-one.

Specific embodiments of compounds contemplated as part of the invention include, but are not limited to:
1,2,3,4,4a,5-hexahydropyrazino[1,2-a][1,5]benzodiazepin-6(7H)-one;
(4aS)-1,2,3,4,4a,5-hexahydropyrazino[1,2-a][1,5]benzodiazepin-6(7H)-one;
10-chloro-1,2,3,4,4a,5-hexahydropyrazino[1,2-a][1,5]benzodiazepin-6(7H)-one;
10-bromo-1,2,3,4,4a,5-hexahydropyrazino[1,2-a][1,5]benzodiazepin-6(7H)-one;
10-phenyl-1,2,3,4,4a,5-hexahydropyrazino[1,2-a][1,5]benzodiazepin-6(7H)-one;
10-[(E)-2-phenylvinyl]-1,2,3,4,4a,5-hexahydropyrazino[1,2-a][1,5]benzodiazepin-6(7H)-one;
10-(3-chlorophenyl)-1,2,3,4,4a,5-hexahydropyrazino[1,2-a][1,5]benzodiazepin-6(7H)-one;

10-(2-chlorophenyl)-1,2,3,4,4a,5-hexahydropyrazino[1,2-a][1,5]benzodiazepin-6(7H)-one;
10-[(E)-2-(3-fluorophenyl)vinyl]-1,2,3,4,4a,5-hexahydropyrazino[1,2-a][1,5]benzodiazepin-6(7H)-one;
10-methyl-1,2,3,4,4a,5-hexahydropyrazino[1,2-a][1,5]benzodiazepin-6(7H)-one;
6-oxo-1,2,3,4,4a,5,6,7-octahydropyrazino[1,2-a][1,5]benzodiazepine-10-carbonitrile;
10-methoxy-1,2,3,4,4a,5-hexahydropyrazino[1,2-a][1,5]benzodiazepin-6(7H)-one;
9-bromo-1,2,3,4,4a,5-hexahydropyrazino[1,2-a][1,5]benzodiazepin-6(7H)-one;
9-(4-chlorophenyl)-1,2,3,4,4a,5-hexahydropyrazino[1,2-a][1,5]benzodiazepin-6(7H)-one;
9,10-dichloro-1,2,3,4,4a,5-hexahydropyrazino[1,2-a][1,5]benzodiazepin-6(7H)-one;
9,10-dichloro-1,2,3,4,4a,5,6,7-octahydropyrazino[1,2-a][1,5]benzodiazepine;
1,2,3,4,4a,5,6,7-octahydropyrazino[1,2-a][1,5]benzodiazepine;
10-chloro-1,2,3,4,4a,5,6,7-octahydropyrazino[1,2-a][1,5]benzodiazepine;
9-bromo-1,2,3,4,4a,5,6,7-octahydropyrazino[1,2-a][1,5]benzodiazepine;
7-methyl-1,2,3,4,4a,5-hexahydropyrazino[1,2-a][1,5]benzodiazepin-6(7H)-one;
7-(2-chlorobenzyl)-1,2,3,4,4a,5,6,7-octahydropyrazino[1,2-a][1,5]benzodiazepine;
7-(3-chlorobenzyl)-1,2,3,4,4a,5,6,7-octahydropyrazino[1,2-a][1,5]benzodiazepine;
3-ethyl-1,2,3,4,4a,5-hexahydropyrazino[1,2-a][1,5]benzodiazepin-6(7H)-one;
3-benzyl-10-chloro-1,2,3,4,4a,5-hexahydropyrazino[1,2-a][1,5]benzodiazepin-6(7H)-one;
10-[(E)-2-(3-chlorophenyl)vinyl]-1,2,3,4,4a,5-hexahydropyrazino[1,2-a][1,5]benzodiazepin-6(7H)-one;
10-[(E)-2-(4-fluorophenyl)vinyl]-1,2,3,4,4a,5-hexahydropyrazino[1,2-a][1,5]benzodiazepin-6(7H)-one;
10-[(E)-2-(4-chlorophenyl)vinyl]-1,2,3,4,4a,5-hexahydropyrazino[1,2-a][1,5]benzodiazepin-6(7H)-one;
10-[(E)-2-(2,4-difluorophenyl)vinyl]-1,2,3,4,4a,5-hexahydropyrazino[1,2-a][1,5]benzodiazepin-6(7H)-one;
10-(2-phenylethyl)-1,2,3,4,4a,5-hexahydropyrazino[1,2-a][1,5]benzodiazepin-6(7H)-one;
11-bromo-1,2,3,4,4a,5-hexahydropyrazino[1,2-a][1,5]benzodiazepin-6(7H)-one;
10-(trifluoromethyl)-1,2,3,4,4a,5-hexahydropyrazino[1,2-a][1,5]benzodiazepin-6(7H)-one;
8-fluoro-1,2,3,4,4a,5-hexahydropyrazino[1,2-a][1,5]benzodiazepin-6(7H)-one;
11-fluoro-1,2,3,4,4a,5-hexahydropyrazino[1,2-a][1,5]benzodiazepin-6(7H)-one;
9-fluoro-1,2,3,4,4a,5-hexahydropyrazino[1,2-a][1,5]benzodiazepin-6(7H)-one;
10-fluoro-1,2,3,4,4a,5-hexahydropyrazino[1,2-a][1,5]benzodiazepin-6(7H)-one;
(4aS)-10-methyl-1,2,3,4,4a,5-hexahydropyrazino[1,2-a][1,5]benzodiazepin-6(7H)-one;
(4aS)-9,10-dichloro-1,2,3,4,4a,5-hexahydropyrazino[1,2-a][1,5]benzodiazepin-6(7H)-one;
3-methyl-1,2,3,4,4a,5-hexahydropyrazino[1,2-a][1,5]benzodiazepin-6(7H)-one;
3,3a,4,5,6,7-hexahydronaphtho[1,2-b]pyrazino[1,2-d][1,4]diazepin-2(1H)-one;
8-methyl-1,2,3,4,4a,5-hexahydropyrazino[1,2-a][1,5]benzodiazepin-6(7H)-one;
(4aS)-10-chloro-1,2,3,4,4a,5-hexahydropyrazino[1,2-a][1,5]benzodiazepin-6(7H)-one;
(4aS)-10-(2-phenylethyl)-1,2,3,4,4a,5-hexahydropyrazino[1,2-a][1,5]benzodiazepin-6(7H)-one;
(4aS)-10-methoxy-1,2,3,4,4a,5-hexahydropyrazino[1,2-a][1,5]benzodiazepin-6(7H)-one;
10-ethoxy-1,2,3,4,4a,5-hexahydropyrazino[1,2-a][1,5]benzodiazepin-6(7H)-one;
3-benzyl-2,3,4,4a,5,6-hexahydropyrazino[1,2-a][1,4]benzodiazepin-7(1H)-one;
2,3,4,4a,5,6-hexahydropyrazino[1,2-a][1,4]benzodiazepin-7(1H)-one;
N-(3-benzyl-7-oxo-1,2,3,4,4a,5,6,7-octahydropyrazino[1,2-a][1,4]benzodiazepin-9-yl)benzenesulfonamide;
N-(7-oxo-1,2,3,4,4a,5,6,7-octahydropyrazino[1,2-a][1,4]benzodiazepin-9-yl)benzenesulfonamide;
9-methyl-1,2,3,4,4a,5-hexahydropyrazino[1,2-a][1,5]benzodiazepin-6(7H)-on;
ethyl 6-oxo-1,2,3,4,4a,5,6,7-octahydropyrazino[1,2-a][1,5]benzodiazepine-10-carboxylate;
9-chloro-1,2,3,4,4a,5-hexahydropyrazino[1,2-a][1,5]benzodiazepin-6(7H)-one;
10-cyclopropyl-1,2,3,4,4a,5-hexahydropyrazino[1,2-a][1,5]benzodiazepin-6(7H)-one;
11-methyl-1,2,3,4,4a,5-hexahydropyrazino[1,2-a][1,5]benzodiazepin-6(7H)-one;
(4aS)-9-bromo-1,2,3,4,4a,5,6,7-octahydropyrazino[1,2-a][1,5]benzodiazepine;
(4aS)-9-chloro-1,2,3,4,4a,5-hexahydropyrazino[1,2-a][1,5]benzodiazepin-6(7H)-one;
10-(1-benzyl-1H-pyrazol-4-yl)-1,2,3,4,4a,5-hexahydropyrazino[1,2-a][1,5]benzodiazepin-6(7H)-one;
10-(2-naphthyl)-1,2,3,4,4a,5-hexahydropyrazino[1,2-a][1,5]benzodiazepin-6(7H)-one;
10-(4-methoxyphenyl)-1,2,3,4,4a,5-hexahydropyrazino[1,2-a][1,5]benzodiazepin-6(7H)-one;
10-(biphenyl-3-yl)-1,2,3,4,4a,5-hexahydropyrazino[1,2-a][1,5]benzodiazepin-6(7H)-one;
10-(1-methyl-1H-pyrazol-4-yl)-1,2,3,4,4a,5-hexahydropyrazino[1,2-a][1,5]benzodiazepin-6(7H)-one;
10-(3-fluorophenyl)-1,2,3,4,4a,5-hexahydropyrazino[1,2-a][1,5]benzodiazepin-6(7H)-one;
10-(quinolin-3-yl)-1,2,3,4,4a,5-hexahydropyrazino[1,2-a][1,5]benzodiazepin-6(7H)-one;
10-(2-methoxyphenyl)-1,2,3,4,4a,5-hexahydropyrazino[1,2-a][1,5]benzodiazepin-6(7H)-one;
10-(biphenyl-2-yl)-1,2,3,4,4a,5-hexahydropyrazino[1,2-a][1,5]benzodiazepin-6(7H)-one;
10-(3-methoxyphenyl)-1,2,3,4,4a,5-hexahydropyrazino[1,2-a][1,5]benzodiazepin-6(7H)-one;
10-(1-benzothiophen-3-yl)-1,2,3,4,4a,5-hexahydropyrazino[1,2-a][1,5]benzodiazepin-6(7H)-one;
10-(1-naphthyl)-1,2,3,4,4a,5-hexahydropyrazino[1,2-a][1,5]benzodiazepin-6(7H)-one;
10-(1H-indol-4-yl)-1,2,3,4,4a,5-hexahydropyrazino[1,2-a][1,5]benzodiazepin-6(7H)-one;
10-(3-furyl)-1,2,3,4,4a,5-hexahydropyrazino[1,2-a][1,5]benzodiazepin-6(7H)-one;
10-(2-fluorophenyl)-1,2,3,4,4a,5-hexahydropyrazino[1,2-a][1,5]benzodiazepin-6(7H)-one;
10-(pyridin-2-yl)-1,2,3,4,4a,5-hexahydropyrazino[1,2-a][1,5]benzodiazepin-6(7H)-one;
10-(3-thienyl)-1,2,3,4,4a,5-hexahydropyrazino[1,2-a][1,5]benzodiazepin-6(7H)-one;
10-[3-(1H-pyrazol-1-yl)phenyl]-1,2,3,4,4a,5-hexahydropyrazino[1,2-a][1,5]benzodiazepin-6(7H)-one;

10-(4-fluorophenyl)-1,2,3,4,4a,5-hexahydropyrazino[1,2-a]
[1,5]benzodiazepin-6(7H)-one;
10-(1-benzothiophen-2-yl)-1,2,3,4,4a,5-hexahydropyrazino
[1,2-a][1,5]benzodiazepain-6(7H)-one;
N-(6-oxo-1,2,3,4,4a,5,6,7-octahydropyrazino [1,2-a][1,5]
benzodiazepin-9-yl)benzenesulfonamide;
9-chloro-7-ethyl-1,2,3,4,4a,5-hexahydropyrazino[1,2-a][1,
5]benzodiazepin-6(7H)-one;
9-chloro-7-ethyl-3-methyl-1,2,3,4,4a,5-hexahydropyrazino
[1,2-a][1,5]benzodiazepin-6(7H)-one;
8-fluoro-3-methyl-1,2,3,4,4a,5-hexahydropyrazino[1,2-a]
[1,5]benzodiazepin-6(7H)-one;
9-chloro-7-methyl-1,2,3,4,4a,5-hexahydropyrazino[1,2-a]
[1,5]benzodiazepin-6(7H)-one;
9-chloro-7-methyl-1,2,3,4,4a,5,6,7-octahydropyrazino [1,2-
a][1,5]benzodiazepine;
9-chloro-7-ethyl-3-methyl-1,2,3,4,4a,5,6,7-octahydropyrazino [1,2-a][1,5]benzodiazepine;
(4aR)-8-fluoro-1,2,3,4,4a,5-hexahydropyrazino[1,2-a][1,5]
benzodiazepain-6(7H)-one;
(4aS)-10-chloro-3-methyl-1,2,3,4,4a,5-hexahydropyrazino
[1,2-a][1,5]benzodiazepin-6(7H)-one;
(4aS)-8-fluoro-1,2,3,4,4a,5-hexahydropyrazino[1,2-a][1,5]
benzodiazepin-6(7H)-one;
(4aS)-11-fluoro-1,2,3,4,4a,5-hexahydropyrazino[1,2-a][1,5]
benzodiazepain-6(7H)-one;
(4aR)-11-fluoro-1,2,3,4,4a,5-hexahydropyrazino[1,2-a][1,
5]benzodiazepin-6(7H)-one;
(4aS)-8-fluoro-3-methyl-1,2,3,4,4a,5-hexahydropyrazino[1,
2-a][1,5]benzodiazepin-6(7H)-one;
10-(3-methylphenyl)-1,2,3,4,4a,5-hexahydropyrazino[1,2-
a][1,5]benzodiazepin-6(7H)-one;
10-[3-(trifluoromethyl)phenyl]-1,2,3,4,4a,5-hexahydropyrazino[1,2-a][1,5]benzodiazepin-6(7H)-one;
10-(3-ethylphenyl)-1,2,3,4,4a,5-hexahydropyrazino[1,2-a]
[1,5]benzodiazepin-6(7H)-one;
10-(3-isopropylphenyl)-1,2,3,4,4a,5-hexahydropyrazino[1,
2-a][1,5]benzodiazepin-6(7H)-one;
10-[3-(trifluoromethoxy)phenyl]-1,2,3,4,4a,5-hexahydropyrazino[1,2-a][1,5]benzodiazepin-6(7H)-one;
10-(3-isopropoxyphenyl)-1,2,3,4,4a,5-hexahydropyrazino
[1,2-a][1,5]benzodiazepin-6(7H)-one;
10-[3-(benzyloxy)phenyl]-1,2,3,4,4a,5-hexahydropyrazino
[1,2-a][1,5]benzodiazepin-6(7H)-one;
10-(3-isobutoxyphenyl)-1,2,3,4,4a,5-hexahydropyrazino[1,
2-a][1,5]benzodiazepin-6(7H)-one;
N-(6-oxo-1,2,3,4,4a,5,6,7-octahydropyrazino[1,2-a][1,5]
benzodiazepin-9-yl)biphenyl-2-sulfonamide;
2-methyl-N-(6-oxo-1,2,3,4,4a,5,6,7-octahydropyrazino[1,2-
a][1,5]benzodiazepin-9-yl)benzenesulfonamide;
4-methyl-N-(6-oxo-1,2,3,4,4a,5,6,7-octahydropyrazino[1,2-
a][1,5]benzodiazepin-9-yl)benzenesulfonamide;
3-methyl-N-(6-oxo-1,2,3,4,4a,5,6,7-octahydropyrazino[1,2-
a][1,5]benzodiazepin-9-yl)benzenesulfonamide;
3-chloro-N-(6-oxo-1,2,3,4,4a,5,6,7-octahydropyrazino[1,2-
a][1,5]benzodiazepin-9-yl)benzenesulfonamide;
4-chloro-N-(6-oxo-1,2,3,4,4a,5,6,7-octahydropyrazino[1,2-
a][1,5]benzodiazepin-9-yl)benzenesulfonamide;
2-fluoro-N-(6-oxo-1,2,3,4,4a,5,6,7-octahydropyrazino[1,2-
a][1,5]benzodiazepin-9-yl)benzenesulfonamide;
3-fluoro-N-(6-oxo-1,2,3,4,4a,5,6,7-octahydropyrazino[1,2-
a][1,5]benzodiazepin-9-yl)benzenesulfonamide;
4-fluoro-N-(6-oxo-1,2,3,4,4a,5,6,7-octahydropyrazino[1,2-
a][1,5]benzodiazepin-9-yl)benzenesulfonamide;
2-methoxy-N-(6-oxo-1,2,3,4,4a,5,6,7-octahydropyrazino[1,
2-a][1,5]benzodiazepin-9-yl)benzenesulfonamide;
3-methoxy-N-(6-oxo-1,2,3,4,4a,5,6,7-octahydropyrazino[1,
2-a][1,5]benzodiazepin-9-yl)benzenesulfonamide;
4-methoxy-N-(6-oxo-1,2,3,4,4a,5,6,7-octahydropyrazino[1,
2-a][1,5]benzodiazepin-9-yl)benzenesulfonamide;
N-(6-oxo-1,2,3,4,4a,5,6,7-octahydropyrazino[1,2-a][1,5]
benzodiazepin-9-yl)thiophene-2-sulfonamide;
8-chloro-1,2,3,4,4a,5-hexahydropyrazino[1,2-a][1,5]benzodiazepin-6(7H)-one;
10-(phenoxymethyl)-1,2,3,4,4a,5-hexahydropyrazino[1,2-a]
[1,5]benzodiazepin-6(7H)-one;
9-(phenylsulfonyl)-1,2,3,4,4a,5-hexahydropyrazino[1,2-a]
[1,5]benzodiazepin-6(7H)-one;
10-[(2-fluorophenoxy)methyl]-1,2,3,4,4a,5-hexahydropyrazino[1,2-a][1,5]benzodiazepin-6(7H)-one;
10-[(3-fluorophenoxy)methyl]-1,2,3,4,4a,5-hexahydropyrazino[1,2-a][1,5]benzodiazepin-6(7H)-one;
10-[(4-fluorophenoxy)methyl]-1,2,3,4,4a,5-hexahydropyrazino[1,2-a][1,5]benzodiazepin-6(7H)-one;
(4aS)-10-(2-fluorophenyl)-1,2,3,4,4a,5-hexahydropyrazino
[1,2-a][1,5]benzodiazepin-6(7H)-one;
(4aS)-10-(3-isopropoxyphenyl)-1,2,3,4,4a,5-hexahydropyrazino[1,2-a][1,5]benzodiazepin-6(7H)-one;
(4aS)-10-[2-(2-fluorophenyl)ethoxy]-1,2,3,4,4a,5-hexahydropyrazino[1,2-a][1,5]benzodiazepin-6(7H)-one;
2,6-dichloro-N-(6-oxo-1,2,3,4,4a,5,6,7-octahydropyrazino
[1,2-a][1,5]benzodiazepin-9-yl)benzenesulfonamide;
N-(6-oxo-1,2,3,4,4a,5,6,7-octahydropyrazino[1,2-a][1,5]
benzodiazepin-9-yl)-3-(trifluoromethoxy)benzenesulfonamid;
4-cyano-N-(6-oxo-1,2,3,4,4a,5,6,7-octahydropyrazino[1,2-
a][1,5]benzodiazepin-9-yl)benzenesulfonamide;
3-cyano-N-(6-oxo-1,2,3,4,4a,5,6,7-octahydropyrazino [1,2-
a][1,5]benzodiazepin-9-yl)benzenesulfonamide;
2,6-difluoro-N-(6-oxo-1,2,3,4,4a,5,6,7-octahydropyrazino
[1,2-a][1,5]benzodiazepin-9-yl)benzenesulfonamide;
N-(6-oxo-1,2,3,4,4a,5,6,7-octahydropyrazino [1,2-a][1,5]
benzodiazepin-9-yl)naphthalene-1-sulfonamide;
2,5-dimethyl-N-(6-oxo-1,2,3,4,4a,5,6,7-octahydropyrazino
[1,2-a][1,5]benzodiazepin-9-yl)benzenesulfonamide;
N-(6-oxo-1,2,3,4,4a,5,6,7-octahydropyrazino [1,2-a][1,5]
benzodiazepin-9-yl)-2-(trifluoromethyl)benzenesulfonamide;
5-chloro-N-(6-oxo-1,2,3,4,4a,5,6,7-octahydropyrazino [1,2-
a][1,5]benzodiazepin-9-yl)thiophene-2-sulfonamide;
N-(6-oxo-1,2,3,4,4a,5,6,7-octahydropyrazino [1,2-a][1,5]
benzodiazepin-9-yl)naphthalene-2-sulfonamide;
3,5-dimethyl-N-(6-oxo-1,2,3,4,4a,5,6,7-octahydropyrazino
[1,2-a][1,5]benzodiazepin-9-yl)benzenesulfonamide;
N-(6-oxo-1,2,3,4,4a,5,6,7-octahydropyrazino [1,2-a][1,5]
benzodiazepin-9-yl)-2-(trifluoromethoxy)benzenesulfonamide;
(4aS)-10-(difluoromethoxy)-1,2,3,4,4a,5-hexahydropyrazino[1,2-a][1,5]benzodiazepin-6(7H)-one;
(4aS)-3-methyl-2,3,4,4a,5,6-hexahydro-1H-pyrazino[2,1-
d][1,5]benzoxazepine;
(4aS)-10-methyl-2,3,4,4a,5,6-hexahydro-1H-pyrazino [2,1-
d][1,5]benzoxazepine;
(4aS)-10-methoxy-2,3,4,4a,5,6-hexahydro-1H-pyrazino
[2,1-d][1,5]benzoxazepine;
(4aS)-2,3,4,4a,5,6-hexahydro-1H-pyrazino[2,1-d][1,5]benzoxazepin-10-amine;
(4aS)-10-fluoro-2,3,4,4a,5,6-hexahydro-1H-pyrazino [2,1-
d][1,5]benzoxazepine;
(4aS)-9-methyl-2,3,4,4a,5,6-hexahydro-1H-pyrazino[2,1-d]
[1,5]benzoxazepine;
(4aS)-11-chloro-2,3,4,4a,5,6-hexahydro-1H-pyrazino [2,1-
d][1,5]benzoxazepine;

(4aS)-11-fluoro-2,3,4,4a,5,6-hexahydro-1H-pyrazino [2,1-d][1,5]benzoxazepine;
(4aS)-9-chloro-2,3,4,4a,5,6-hexahydro-1H-pyrazino [2,1-d][1,5]benzoxazepine;
10-[(E)-2-(2-fluorophenyl)vinyl]-1,2,3,4,4a,5-hexahydropyrazino[1,2-a][1,5]benzodiazepin-6(7H)-one;
10-{(E)-2-[2-(trifluoromethyl)phenyl]vinyl}-1,2,3,4,4a,5-hexahydropyrazino[1,2-a][1,5]benzodiazepin-6(7H)-one;
10-[(E)-2-(3,5-difluorophenyl)vinyl]-1,2,3,4,4a,5-hexahydropyrazino[1,2-a][1,5]benzodiazepin-6(7H)-one;
10-[2-(2-fluorophenyl)ethyl]-1,2,3,4,4a,5-hexahydropyrazino[1,2-a][1,5]benzodiazepin-6(7H)-one;
10-[2-(3-fluorophenyl)ethyl]-1,2,3,4,4a,5-hexahydropyrazino[1,2-a][1,5]benzodiazepin-6(7H)-one;
10-{2-[2-(trifluoromethyl)phenyl]ethyl}-1,2,3,4,4a,5-hexahydropyrazino[1,2-a][1,5]benzodiazepin-6(7H)-one;
10-[2-(3,5-difluorophenyl)ethyl]-1,2,3,4,4a,5-hexahydropyrazino[1,2-a][1,5]benzodiazepin-6(7H)-one;
(4aS)-8-chloro-1,2,3,4,4a,5-hexahydropyrazino[1,2-a][1,5]benzodiazepin-6(7H)-one;
10-(benzyloxy)-1,2,3,4,4a,5-hexahydropyrazino[1,2-a][1,5]benzodiazepin-6(7H)-one;
7,7a,8,9,10,11-hexahydropyrazino[1,2-d]pyrido[3,2-b][1,4]diazepin-6(5H)-one;
7-methyl-10-(2-phenylethyl)-1,2,3,4,4a,5-hexahydropyrazino[1,2-a][1,5]benzodiazepin-6(7H)-one;
10-[2-(3-fluorophenyl)ethoxy]-1,2,3,4,4a,5-hexahydropyrazino[1,2-a][1,5]benzodiazepin-6(7H)-one;
10-[(1R)-1-phenylethoxy]-1,2,3,4,4a,5-hexahydropyrazino[1,2-a][1,5]benzodiazepin-6(7H)-one;
10-[(1S)-1-phenylethoxy]-1,2,3,4,4a,5-hexahydropyrazino[1,2-a][1,5]benzodiazepin-6(7H)-one;
10-[(2-fluorobenzyl)oxy]-1,2,3,4,4a,5-hexahydropyrazino[1,2-a][1,5]benzodiazepin-6(7H)-one;
10-[(3-fluorobenzyl)oxy]-1,2,3,4,4a,5-hexahydropyrazino[1,2-a][1,5]benzodiazepin-6(7H)-one;
10-{[2-(trifluoromethyl)benzyl]oxy}-1,2,3,4,4a,5-hexahydropyrazino[1,2-a][1,5]benzodiazepin-6(7H)-one;
10-(2-phenylethoxy)-1,2,3,4,4a,5-hexahydropyrazino[1,2-a][1,5]benzodiazepin-6(7H)-one;
10-{[(2R)-1-phenylpropan-2-yl]oxy}-1,2,3,4,4a,5-hexahydropyrazino[1,2-a][1,5]benzodiazepin-6(7H)-one;
10-{[(2S-1-phenylpropan-2-yl)oxy}-1,2,3,4,4a,5-hexahydropyrazino[1,2-a][1,5]benzodiazepin-6(7H)-one;
10-[(1R)-1-(2-fluorophenyl)ethoxy]-1,2,3,4,4a,5-hexahydropyrazino[1,2-a][1,5]benzodiazepin-6(7H)-one;
10-[(1S)-1-(2-fluorophenyl)ethoxy]-1,2,3,4,4a,5-hexahydropyrazino[1,2-a][1,5]benzodiazepin-6(7H)-one;
(4aS)-10-{[(2S-1-phenylpropan-2-yl)oxy]-1,2,3,4,4a,5-hexahydropyrazino[1,2-a][1,5]benzodiazepin-6(7H)-one;
(4aS)-10-[2-(3-fluorophenyl)ethoxy]-1,2,3,4,4a,5-hexahydropyrazino[1,2-a][1,5]benzodiazepin-6(7H)-one;
(4aS)-10-{[(2R)-1-phenylpropan-2-yl]oxy}-1,2,3,4,4a,5-hexahydropyrazino[1,2-a][1,5]benzodiazepin-6(7H)-one;
(4aR)-10-{[(2R)-1-phenylpropan-2-yl]oxy}-1,2,3,4,4a,5-hexahydropyrazino[1,2-a][1,5]benzodiazepin-6(7H)-one;
(4aR)-10-{[(2S-1-phenylpropan-2-yl)oxy}-1,2,3,4,4a,5-hexahydropyrazino[1,2-a][1,5]benzodiazepin-6(7H)-one;
(4aS)-3-benzyl-2,3,4,4a,5,6-hexahydro-1H-pyrazino[2,1-d][1,5]benzoxazepine;
(4aS)-2,3,4,4a,5,6-hexahydro-1H-pyrazino[2,1-d][1,5]benzoxazepine;
(4aS)-10-(cyclopropylmethoxy)-1,2,3,4,4a,5-hexahydropyrazino[1,2-a][1,5]benzodiazepin-6(7H)-one;
(4aS)-10-[2-(pyridin-2-yl)ethoxy]-1,2,3,4,4a,5-hexahydropyrazino[1,2-a][1,5]benzodiazepin-6(7H)-one;
(4aS)-10-[2-(2-chlorophenyl)ethoxy]-1,2,3,4,4a,5-hexahydropyrazino[1,2-a][1,5]benzodiazepin-6(7H)-one;
(4aS)-10-{2-[3-(trifluoromethyl)phenyl]ethoxy}-1,2,3,4,4a,5-hexahydropyrazino[1,2-a][1,5]benzodiazepin-6(7H)-one;
(4aS)-10-sec-butoxy-1,2,3,4,4a,5-hexahydropyrazino[1,2-a][1,5]benzodiazepin-6(7H)-one;
(4aS)-10-[2-(3-chlorophenyl)ethoxy]-1,2,3,4,4a,5-hexahydropyrazino[1,2-a][1,5]benzodiazepin-6(7H)-one;
(4aS)-10-[2-(3-methylphenyl)ethoxy]-1,2,3,4,4a,5-hexahydropyrazino[1,2-a][1,5]benzodiazepin-6(7H)-one;
(4aS)-10-(1-phenylpropoxy)-1,2,3,4,4a,5-hexahydropyrazino[1,2-a][1,5]benzodiazepin-6(7H)-one;
(4aS)-10-[(1R)-1-(2,5-difluorophenyl)ethoxy]-1,2,3,4,4a,5-hexahydropyrazino[1,2-a][1,5]benzodiazepin-6(7H)-one;
(4aS)-10-chloro-2,3,4,4a,5,6-hexahydro-1H-pyrazino[2,1-d][1,5]benzoxazepine;
cis-1,2,3,4,4a,5,6,11b-octahydro-7H-pyrido[3,4-d][2]benzazepin-7-one;
(4aS)-10-ethoxy-1,2,3,4,4a,5-hexahydropyrazino[1,2-a][1,5]benzodiazepin-6(7H)-one;
1,2,3,4,4a,5,6,7-octahydropyrazino [1,2-a][1]benzazepine;
3-methyl-1,2,3,4,4a,5,6,7-octahydropyrazino [1,2-a][1]benzazepine;
N-(7-oxo-1,2,3,4,4a,5,6,7-octahydropyrazino [1,2-a][1,4]benzodiazepin-9-yl)-3-(trifluoromethyl)benzenesulfonamide;
10-benzyl-1,2,3,4,4a,5-hexahydropyrazino[1,2-a][1,5]benzodiazepin-6(7H)-one;
(4aS)-3-benzyl-9-chloro-2,3,4,4a,5,6-hexahydro-1H-pyrazino [2,1-d][1,5]benzoxazepine;
(4aS)-9-phenyl-2,3,4,4a,5,6-hexahydro-1H-pyrazino [2,1-d][1,5]benzoxazepine;
(4aS)-9-chloro-3-methyl-2,3,4,4a,5,6-hexahydro-1H-pyrazino [2,1-d][1,5]benzoxazepine;
(4aS)-9-(2-methylphenyl)-2,3,4,4a,5,6-hexahydro-1H-pyrazino [2,1-d][1,5]benzoxazepine;
(4aS)-9-(3-methylphenyl)-2,3,4,4a,5,6-hexahydro-1H-pyrazino [2,1-d][1,5]benzoxazepine;
(4aS)-9-(4-methylphenyl)-2,3,4,4a,5,6-hexahydro-1H-pyrazino [2,1-d][1,5]benzoxazepine;
(4aS)-9-(2-methoxyphenyl)-2,3,4,4a,5,6-hexahydro-1H-pyrazino [2,1-d][1,5]benzoxazepine;
(4aS)-9-(3-methoxyphenyl)-2,3,4,4a,5,6-hexahydro-1H-pyrazino [2,1-d][1,5]benzoxazepine;
(4aS)-9-(4-methoxyphenyl)-2,3,4,4a,5,6-hexahydro-1H-pyrazino [2,1-d][1,5]benzoxazepine;
(4aS)-9-[2-methylsulfonyl)phenyl]-2,3,4,4a,5,6-hexahydro-1H-pyrazino [2,1-d][1,5]benzoxazepine;
(4aS)-9-[3-methylsulfonyl)phenyl]-2,3,4,4a,5,6-hexahydro-1H-pyrazino [2,1-d][1,5]benzoxazepine;
1-{2-[(4aS)-2,3,4,4a,5,6-hexahydro-1H-pyrazino[2,1-d][1,5]benzoxazepin-9-yl]phenyl}ethanone;
1-{3-[(4aS)-2,3,4,4a,5,6-hexahydro-1H-pyrazino [2,1-d][1,5]benzoxazepin-9-yl]phenyl}ethanone;
1-{4-[(4aS)-2,3,4,4a,5,6-hexahydro-1H-pyrazino[2,1-d][1,5]benzoxazepin-9-yl]phenyl}ethanone;
2-[(4aS)-2,3,4,4a,5,6-hexahydro-1H-pyrazino[2,1-d][1,5]benzoxazepin-9-yl]phenol;
3-[(4aS)-2,3,4,4a,5,6-hexahydro-1H-pyrazino[2,1-d][1,5]benzoxazepin-9-yl]phenol;
4-[(4aS)-2,3,4,4a,5,6-hexahydro-1H-pyrazino[2,1-d][1,5]benzoxazepin-9-yl]phenol;
(4aS)-9-(2-fluorophenyl)-2,3,4,4a,5,6-hexahydro-1H-pyrazino[2,1-d][1,5]benzoxazepine;
(4aS)-9-(3-fluorophenyl)-2,3,4,4a,5,6-hexahydro-1H-pyrazino[2,1-d][1,5]benzoxazepine;

(4aS)-9-(4-fluorophenyl)-2,3,4,4a,5,6-hexahydro-1H-pyrazino[2,1-d][1,5]benzoxazepine;
(4aS)-9-(pyridin-3-yl)-2,3,4,4a,5,6-hexahydro-1H-pyrazino[2,1-d][1,5]benzoxazepine; or
(4aS)-9-(pyridin-4-yl)-2,3,4,4a,5,6-hexahydro-1H-pyrazino[2,1-d][1,5]benzoxazepine.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present application contemplates various stereoisomers and mixtures thereof and these are specifically included within the scope of this application. Stereoisomers include enantiomers and diastereomers, mixtures of enantiomers or diastereomers and mixtures of enantiomers and diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the compounds of the present invention. The present invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the present invention encompasses any tautomeric or stereoisomeric form, and mixtures thereof, and is not to be limited merely to any one tautomeric or stereoisomeric form utilized within the naming of the compounds or formulae drawings.

The present invention also includes isotopically-labeled compounds, which are identical to those recited in Formula I, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, fluorine, and chlorine, such as, but not limited to $^2$H, $^3$H, $^{13}$C, $^{14}$C, $^{15}$N, $^{18}$O, $^{17}$O, $^{31}$P, $^{32}$P, $^{35}$S, $^{18}$F, and $^3$Cl, respectively. Substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

c. BIOLOGICAL DATA

To determine the effectiveness of compounds having a formula (I), these compounds can be evaluated in a radioligand binding assay for the agonist site of the human serotonin 5-HT$_2$c receptor or in vitro models of cellular function.

Abbreviations which have been used in the descriptions of Biological Data that follow are: BSA for bovine serum albumin; CHO for Chinese hamster ovary; DMEM for Dulbecco's modified Eagle's medium; dFBS for dialyzed fetal bovine serum; dFCS for dialyzed fetal calf serum; DMSO for dimethyl sulfoxide; EDTA for ethylenediaminetetraacetic acid; FLIPR for fluorometric imaging plate reader; HEPES for 4-(2-hydroxyethyl)-1-piperazineethanesulfonic acid; ip for intraperitoneal; PBS for phosphate buffered saline; PEI for polyethylenimine; rpm for revolutions per minute; RPMI for Roswell Park Memorial Institute; Tris for tris(hydroxymethyl)aminomethane; and Tris-Cl for tris(hydroxymethyl) aminomethane hydrochloride.

(i) Human 5-HT$_{2c}$ Receptor Radioligand Binding Assay

Affinity of compounds for the agonist site of the 5-HT$_2$c receptor in transfected CHO cells was determined in a radioligand binding assay essentially as described by Bryant, H. U., et al., Life Sciences (1996) 59(15), 1259-1268. In brief, cell membrane homogenate with 40 μg of protein were incubated for 15 minutes at 37° C. with 0.2 nM [$^{125}$I](±)(1-(4-iodo-2,5-dimethoxyphenyl)isopropylamine (DOI) with or without test compounds in a buffer containing 50 mM Tris-HCl, 5 mM MgCl$_2$ and 0.3% BSA. Nonspecific binding was determined in the presence of 10 μM (±)DOI. The amount of binding was determined by radioactivity quantitation with scintillation counter. IC$_{50}$s were determined from a standard curve of the reference compound (±)DOI. Ki's as shown in Table 1 were derived from the IC$_{50}$s in the standard method.

TABLE 1

5-HT$_{2c}$ Agonist Site Radioligand Binding

| Example | Ki (μM) |
| --- | --- |
| 1 | 0.086 |
| 2 | 0.016 |
| 3 | 0.012 |
| 4 | 0.0069 |
| 5 | 0.074 |
| 6 | 0.0035 |
| 7 | 0.041 |
| 8 | 0.14 |
| 9 | 0.0032 |
| 10 | 0.0083 |
| 11 | 0.19 |
| 12 | 0.038 |
| 13 | 0.23 |
| 14 | 0.17 |
| 15 | 0.017 |
| 16 | 0.004 |
| 17 | 0.14 |
| 18 | 0.018 |
| 19 | 0.14 |
| 20 | 0.22 |
| 21 | 0.097 |
| 22 | 0.085 |

TABLE 1-continued

5-HT$_{2C}$ Agonist Site Radioligand Binding

| Example | Ki (µM) |
|---|---|
| 23 | 0.19 |
| 24 | 0.36 |
| 25 | 0.0014 |
| 26 | 0.032 |
| 27 | 0.013 |
| 28 | 0.036 |
| 29 | 0.011 |
| 30 | 0.016 |
| 31 | 0.087 |
| 32 | 0.042 |
| 33 | 0.042 |
| 34 | 0.19 |
| 35 | 0.11 |
| 36 | 0.0091 |
| 37 | 0.014 |
| 38 | 0.2 |
| 39 | 0.034 |
| 40 | 0.035 |
| 41 | 0.005 |
| 42 | 0.00071 |
| 43 | 0.066 |
| 44 | 0.15 |
| 46 | 0.033 |
| 47 | 33 |
| 48 | 27 |

(ii) Human 5-HT$_{2C}$ Functional Assay in 1321N1 Cells

Functional activity was determined by testing the effect of the compounds on intracellular calcium levels in 1321N1 cells stably transfected with the human 5-HT$_{2C}$ receptor. Cells were seeded into 96-well plates at 50,000 cells/well and grown overnight in tissue culture medium (DMEM with Glutamax I (Invitrogen), containing 10% dFCS, 50 µg/mL Gentamicin, 400 µg/mL Geneticin) at 37° C. and 7% CO$_2$. Growth medium was replaced by medium without dFCS for overnight incubation. Cells were loaded with a fluorescent calcium-sensitive dye in the presence of 1% probenicid according to the manufacturer's protocol (Fluo4 AM, Molecular Devices). Serial compound dilutions (final concentrations $10^{-10}$ to $10^{-5}$M) were added to the cells either alone or in the presence of serotonin ($10^{-9}$M) and the maximum calcium response was determined using a FLIPR instrument (Molecular Devices). Concentration-response curves were fitted using a four-parameter logistic equation (GraphPad Prism). The concentration at which the compound exerts half its maximal effect is named the 'effective concentration 50' or 'EC$_{50}$' and is listed in Table 2.

Emax is the maximum functional response or efficacy expressed as a percentage relative to the effect of serotonin.

TABLE 2

5-HT$_{2C}$ Agonist Activity

| Example | EC$_{50}$ (µM) | Emax (%) |
|---|---|---|
| 1 | 0.0135 | 100 |
| 2 | 0.0192 | 90 |
| 3 | 0.0017 | 93 |
| 4 | 0.0028 | 92 |
| 5 | 0.0849 | 86 |
| 6 | 0.0298 | 89.5 |
| 7 | 0.0279 | 86 |
| 10 | 0.0030 | 99 |
| 11 | 0.0938 | 104 |
| 12 | 0.0381 | 83.5 |
| 13 | 0.0683 | 79 |
| 15 | 0.0081 | 103.5 |
| 16 | 0.0018 | 91 |
| 17 | 0.0730 | 111 |
| 18 | 0.0037 | 107.5 |
| 19 | 0.0283 | 85.5 |
| 20 | 0.0759 | 103 |
| 21 | 0.0440 | 93 |
| 22 | 0.0697 | 80.5 |
| 23 | 0.1650 | 87 |
| 24 | 0.9420 | |
| 25 | 0.0145 | 101 |
| 26 | 0.0855 | 98.5 |
| 27 | 0.1830 | 96.5 |
| 28 | 0.1310 | 92 |
| 29 | 0.0043 | 104 |
| 30 | 0.0017 | 113 |
| 31 | 0.0204 | 118.5 |
| 32 | 0.0258 | 101.5 |
| 33 | 0.0142 | 98 |
| 34 | 0.0893 | 100.5 |
| 35 | 0.0520 | 100 |
| 36 | 0.0015 | 104 |
| 37 | 0.0032 | 99.5 |
| 38 | 0.0663 | 68 |
| 39 | >10 | |
| 40 | 0.0068 | 89.5 |
| 41 | 0.0020 | 99.5 |
| 42 | 0.0011 | 95 |
| 43 | 0.0138 | 86 |
| 44 | 0.0445 | 90 |
| 46 | 0.0059 | 93 |
| 47 | >10 | |
| 48 | >10 | |

(iii) Human 5-HT$_{2C}$ and 5-HT$_{2B}$ Functional Assay in CHO-K1 Cells

CHO-K1 cells over-expressing 5HT$_{2C}$ or 5HT$_{2B}$ receptors were grown in 1272 cm$^2$ flasks to 70-80% confluency in UltraCHO media supplemented with 1% dialyzed fetal bovine serum (FBS), 250 µg/mL zeocin, 100 U/mL penicillin/streptomycin, and 400 µg/mL geneticin. The cells were dissociated from the flasks using 0.05% trypsin, resuspended in freezing media and stored in liquid nitrogen until use. Calcium flux experiments were done using frozen cells. The cells were diluted in media containing 1% dialyzed FBS and 100 U/mL pencillin/streptomycin and plated into 384-well poly-D-Lysine coated plates (15,000 cells/well). Then the plates were incubated overnight in a cell incubator at 37° C., 5% CO$_2$. On the next day, the growth media was replaced with media without FBS and further incubated overnight. On day three, the changes in intracellular Ca$^{2+}$ were determined using calcium sensitive fluorescent dye, Ca4 (MDS Analytical Technologies, Sunnyvale, Calif.) by loading 15 µL of diluted dye with 2.5 mM probenecid into the cells containing media and incubated at room temperature for 60 minutes in dark.

Fluorescence measurements were read at 25° C. at an excitation wavelength of 480 nm and an emission wavelength of 530 nm in FLIPR (MDS). Baseline fluorescence was measured for the first 10 seconds and then 15 µL of 4× concentrations of serotonin/test compounds was added to the cell plate. The fluorescence intensity was captured every second for the first 1 minute followed by every 5 seconds for an additional 2 minutes. The increase in fluorescent response was determined and was normalized to the response of serotonin. The concentration response of compounds was done from a starting concentration of 10 µM, 1:10 dilution across 6 wells with a final dimethyl sulfoxide concentration of 0.2% and was fitted using a 4-parameter logistic equation. The concentration at which a compound exerts half its maximal effect was named as 'effective concentration 50' or '$EC_{50}$'.

Emax is the maximum functional response or efficacy expressed as a percentage relative to the effect of serotonin.

TABLE 3

5-$HT_{2C}$ Agonist Activity

| Example | $EC_{50}$ (µM) | Emax (%) |
|---|---|---|
| 19 | 0.02 | >120% |
| 32 | 0.008 | 100% |
| 33 | 0.01 | >120% |
| 35 | 0.02 | >120% |
| 36 | 0.002 | >120% |
| 37 | 0.0008 | 100% |
| 38 | 0.08 | 100% |
| 40 | 0.005 | 110% |
| 41 | 0.0008 | >120% |
| 42 | 0.0004 | >120% |
| 43 | 0.01 | >120% |
| 44 | 0.03 | >120% |
| 46 | 0.008 | >120% |
| 48 | >10 | |
| 49 | 0.06 | 100% |
| 50 | 0.2 | 80% |
| 51 | 0.07 | 90% |
| 52 | 0.05 | >80% |
| 53 | 0.006 | >120% |
| 54 | 0.07 | 110% |
| 55 | 0.02 | >120% |
| 56 | 1 | 110% |
| 57 | 0.9 | 100% |
| 58 | 0.2 | 110% |
| 59 | 0.04 | >120% |
| 60 | 0.4 | >120% |
| 61 | 0.1 | >120% |
| 62 | 0.06 | >120% |
| 63 | 0.09 | 110% |
| 64 | 0.03 | 110% |
| 65 | 0.05 | >120% |
| 66 | 0.09 | 100% |
| 67 | 0.2 | 110% |
| 68 | 0.09 | >120% |
| 69 | 0.02 | 110% |
| 70 | 0.06 | >120% |
| 71 | 0.002 | >120% |
| 72 | 0.07 | >120% |
| 73 | 0.03 | 110% |
| 74 | 0.07 | 100% |
| 75 | 1 | 80% |
| 76 | >100 | |
| 77 | 0.2 | 100% |
| 78 | 1 | 50% |
| 79 | 0.03 | 100% |
| 80 | 0.6 | 100% |
| 81 | 0.05 | >120% |
| 82 | 0.6 | 90% |
| 83 | 0.7627 | >120% |
| 84 | 0.067 | 90% |
| 85 | 0.0051 | >120% |
| 86 | 0.008 | >120% |
| 87 | 0.9 | >120% |
| 88 | 0.03 | >120% |
| 89 | 0.07 | >120% |
| 90 | 0.02 | >120% |
| 91 | 0.01 | >120% |
| 92 | 0.02 | >120% |
| 93 | 0.007 | >120% |
| 94 | 0.008 | >120% |
| 95 | 0.02 | >120% |
| 96 | 0.02 | >120% |
| 110 | 0.005 | >120% |
| 111 | 0.02 | >120% |
| 112 | >10 | |
| 113 | 0.05 | >120% |
| 114 | 0.05 | >120% |
| 115 | 0.2 | >120% |
| 116 | 0.008 | >120% |
| 117 | 0.001 | >120% |
| 118 | 0.009 | >120% |
| 131 | 0.04 | 110% |
| 132 | 0.007 | >120% |
| 133 | 0.01 | 100% |
| 134 | 0.05 | 100% |
| 135 | 1 | 80% |
| 136 | 0.002 | >120% |
| 137 | 0.002 | >120% |
| 138 | 0.0007 | >120% |
| 139 | 0.0004 | >120% |
| 140 | 0.0005 | >120% |
| 141 | 0.004 | 88% |
| 142 | 0.08 | >120% |
| 143 | 0.02 | >120% |
| 144 | 0.002 | >120% |
| 145 | 0.006 | >120% |
| 146 | 0.005 | >120% |
| 147 | 0.01 | >120% |
| 148 | 0.007 | >120% |
| 149 | 0.02 | >120% |
| 150 | 0.2 | >120% |
| 151 | 0.07 | 110% |
| 152 | 0.01 | 100% |
| 153 | 0.01 | 110% |
| 154 | 0.10251 | >120% |
| 155 | 0.03838 | >120% |
| 156 | 0.0059 | >120% |
| 157 | 0.02948 | >120% |
| 158 | 0.02502 | >120% |
| 159 | 0.00402 | >120% |
| 160 | 0.07968 | >120% |
| 161 | 0.01 | 120% |
| 162 | 0.07 | >120% |
| 163 | 0.07 | >120% |
| 164 | 0.007 | >120% |
| 165 | 0.008 | >120% |
| 166 | 0.04 | >120% |
| 167 | 1 | 110% |
| 168 | 0.9 | 50% |
| 169 | 0.001 | >120% |
| 170 | 0.02 | >120% |
| 171 | 0.9 | 100% |
| 172 | 0.002 | >120% |
| 173 | 0.004 | 110% |
| 174 | 0.007 | >120% |
| 175 | 0.001 | >120% |
| 176 | 0.002 | 100% |
| 177 | 0.06 | 110% |
| 178 | 0.001 | 100% |
| 179 | 0.008 | >120% |
| 180 | 0.2 | >120% |
| 181 | 0.02 | >120% |
| 182 | 0.007 | >120% |
| 183 | 0.003 | >120% |
| 184 | >10 | |
| 185 | 0.03 | >120% |
| 186 | 0.8 | >120% |
| 187 | 0.03 | >120% |
| 188 | 0.01 | 70% |
| 189 | 0.03 | >120% |
| 190 | 0.02 | >120% |
| 191 | 0.4 | >120% |
| 192 | 0.03 | >120% |
| 193 | 0.008 | >120% |
| 194 | 0.4 | >120% |
| 195 | 0.007 | >120% |
| 196 | 0.009 | >120% |
| 197 | 0.07 | >120% |
| 198 | 0.01 | >120% |
| 199 | 0.9 | >120% |
| 200 | 0.01 | >120% |
| 201 | 0.2 | >120% |
| 202 | 0.005 | >120% |
| 203 | 0.02 | >120% |
| 204 | 0.05 | >120% |
| 205 | 0.05 | >120% |

TABLE 3-continued

5-HT$_{2C}$ Agonist Activity

| Example | EC$_{50}$ (μM) | Emax (%) |
|---|---|---|
| 206 | 0.07 | >120% |
| 207 | 0.8 | >120% |

TABLE 4

5-HT$_{2B}$ Agonist Activity

| Example | EC$_{50}$ (μM) | Emax (%) |
|---|---|---|
| 19 | >10 | |
| 32 | >10 | |
| 33 | >10 | |
| 35 | 0.6 | 80% |
| 36 | 0.008 | 100% |
| 37 | 0.003 | 100% |
| 38 | >10 | |
| 40 | >10 | |
| 41 | 0.006 | 110% |
| 42 | 5 | 55% |
| 43 | 0.06 | 80% |
| 44 | >10 | |
| 46 | 0.3 | 80% |
| 48 | >10 | |
| 49 | >10 | |
| 50 | >10 | |
| 51 | >10 | |
| 52 | >10 | |
| 53 | 3 | 60% |
| 54 | >10 | |
| 55 | >10 | |
| 56 | >10 | |
| 57 | >10 | |
| 58 | >10 | |
| 59 | >10 | |
| 60 | 3 | 50% |
| 61 | >10 | |
| 62 | 0.9 | 60% |
| 63 | >10 | |
| 64 | 1 | 15% |
| 65 | >10 | |
| 66 | >10 | |
| 67 | >10 | |
| 68 | >10 | |
| 69 | 0.09 | 80% |
| 70 | >10 | |
| 71 | 0.02 | 100% |
| 72 | 2 | 20% |
| 73 | >10 | |
| 74 | >10 | |
| 75 | >10 | |
| 77 | >10 | |
| 78 | >10 | |
| 79 | >10 | |
| 80 | >10 | |
| 81 | 1 | 20% |
| 82 | >10 | |
| 83 | 1.05 | 27% |
| 84 | >10 | |
| 85 | >10 | |
| 86 | >10 | |
| 87 | >10 | |
| 88 | >10 | |
| 89 | >10 | |
| 90 | >10 | |
| 91 | >10 | |
| 92 | >10 | |
| 93 | >10 | |
| 94 | >10 | |
| 95 | >10 | |
| 96 | >10 | |
| 110 | >10 | |
| 111 | 0.7 | 20% |
| 112 | 0.9 | 90% |

TABLE 4-continued

5-HT$_{2B}$ Agonist Activity

| Example | EC$_{50}$ (μM) | Emax (%) |
|---|---|---|
| 113 | 0.2 | 50% |
| 114 | 0.4 | 30% |
| 115 | >10 | |
| 116 | 0.05 | 30% |
| 117 | >10 | |
| 118 | >10 | |
| 131 | 0.08 | 20% |
| 132 | >10 | |
| 133 | >10 | |
| 134 | >10 | |
| 135 | >10 | |
| 136 | 0.1 | 20% |
| 137 | 0.05 | 60% |
| 138 | >10 | |
| 139 | 0.06 | 20% |
| 140 | 0.03 | 60% |
| 142 | >10 | |
| 143 | 1 | 60% |
| 144 | >10 | 50% |
| 145 | >10 | |
| 146 | >10 | |
| 147 | >10 | |
| 148 | >10 | |
| 149 | 1 | 30% |
| 150 | >10 | |
| 151 | 5 | 30% |
| 152 | >10 | |
| 153 | 0.1 | 20% |
| 154 | 0.7 | 44% |
| 155 | >10 | |
| 156 | 0.35 | 77% |
| 157 | >10 | |
| 158 | >10 | |
| 159 | >10 | |
| 160 | >10 | |
| 161 | 1 | 20% |
| 162 | 1 | 20% |
| 163 | >10 | |
| 164 | >10 | |
| 165 | >10 | |
| 166 | >10 | |
| 167 | >10 | |
| 168 | >10 | |
| 169 | >10 | |
| 170 | >10 | |
| 171 | >10 | |
| 172 | >10 | |
| 173 | >10 | |
| 174 | >10 | |
| 175 | 0.5 | 20% |
| 176 | 1 | 10% |
| 177 | >10 | |
| 178 | 0.04 | 45% |
| 179 | >10 | |
| 180 | >10 | |
| 181 | >10 | |
| 182 | 0.1 | 40% |
| 183 | >10 | |
| 184 | >10 | |
| 185 | >10 | |
| 186 | >10 | |
| 187 | 6 | 10% |
| 188 | >10 | |
| 189 | 1 | 20% |
| 190 | >10 | |
| 191 | >10 | |
| 192 | 1 | 10% |
| 193 | 1 | 25% |
| 194 | >10 | |
| 195 | 0.3 | 55% |
| 196 | >10 | |
| 197 | 1 | 15% |
| 198 | 1 | 25% |
| 199 | 8 | 10% |
| 200 | >10 | |
| 201 | >10 | |

TABLE 4-continued

5-HT$_{2B}$ Agonist Activity

| Example | EC$_{50}$ (μM) | Emax (%) |
|---|---|---|
| 202 | 1 | 15% |
| 203 | 2 | 15% |
| 204 | >10 | |
| 205 | 5 | 10% |
| 206 | >10 | |
| 207 | >10 | |

(iv) Human 5-HT$_6$ Receptor Radioligand Binding Assay

Preparation of Membranes by Ultrasonic Treatment and Differential Centrifugation Cells from stable clonal cell lines expressing the corresponding receptor (5-HT$_6$) were washed with PBS (without Ca$^{++}$, Mg$^{++}$) and harvested in PBS with 0.02% EDTA. The cells were collected by centrifugation at 500 g for 10 minutes at 4° C., washed with PBS and centrifuged (500 g, 10 minutes at 4° C.). The pellets were stored at −80° C. until use. For membrane preparation, the thawed cell pellet was resuspended in ice-cold sucrose buffer (0.25 M sucrose, 10 mM HEPES (pH 7.4), 1 mM phenylmethylsulfonyl fluoride (PMSF) in DMSO, 5 μg/ml Pepstatin-A, 3 mM EDTA, 0.025% Bacitracin) and homogenized with a Branson Sonifier W-250 (Settings: Timer 4; Output Control 3; Duty Cycle constant; 2 to 3 cycles). Cell disruption was checked with the aid of a microscope. Remaining unbroken cells were pelleted at 1,000 g for 10 minutes at 4° C. The sucrose buffer supernatant was then centrifuged at 60,000 g for 1 hour at 4° C. (Beckman Ultrazentrifuge XL 80). The pellet was resuspended in 30 mL of ice-cold Tris buffer (20 mM TRIS (pH 7.4), 5 μg/mL Pepstatin A, 0.1 mM PMSF, 3 mM EDTA) by pipetting through a 10 mL serological pipet and centrifuged for 1 hour at 4° C. at 60,000 g. A final resuspension was performed in a small volume of ice-cold Tris buffer (see above) by pressing through a serological pipet followed by ultrasonic treatment with a Branson Sonifier W-250 (Settings: Timer 1; Output Control 3; Duty Cycle constant; 1 cycle). Protein concentration was determined (BCA-Kit; Pierce) and aliquots stored at −80° C. or in liquid nitrogen for long-term storage.

Receptor Binding Experiments

All receptor binding experiments were carried out in the corresponding assay buffer in a total volume of 200 μL in the presence of various concentrations of test compound (10$^{-5}$ M to 10$^{-9}$ M, tenfold serial dilution, duplicate determinations). The assays were terminated by filtration on polyethylenimine (PEI 0.1% or 0.3%) presoaked Packard Unifilter Plates (GF/C or GF/B) with a Tomtec MachIII U 96 well-plate harvester. After the plates had been dried for 2 hours at 55° C. in a drying chamber scintillation cocktail (BetaPlate Scint; PerkinElmer) was added. Radioactivity was measured in a Microbeta Trilux two hours after the addition of the scintillation mixture.

5-HT$_6$ Receptor Binding Assay

HEK293 cells stably expressing the h-5-HT$_6$ receptor (NCBI Reference Sequence XM 001435) were cultured in RPMI1640 medium supplemented with 25 mM HEPES, 10% fetal calf serum and 1-2 mM glutamine. The membrane preparation was performed as described above. For these membranes a K$_D$ of 1.95 nM for [$^3$H]-LSD (Lysergic Acid Diethylamide; Amersham, TRK1038) was determined by means of saturation binding experiments. On the day of the assay, the membranes were thawed, diluted in assay buffer (50 mM Tris-HCl, 5 mM CaCl$_2$, 0.1% ascorbic acid, 10 μM pargyline, pH 7.4) to a concentration of 8 μg protein/assay and homogenized by gentle vortexing. For inhibition studies, 1 nM [$^3$H]-lysergic acid diethylamide was incubated in the presence of various concentrations of test compound in assay buffer. Non-specific binding was defined with 1 μM methiothepin. The binding reaction was carried out for 3.5 hours at room temperature. During the incubation, the plates were shaken on a plate shaker at 100 rpm and terminated by filtration on Packard Unifilter GF/C (0.1% PEI) plates, followed by 2 wash cycles with ice-cold 50 mM Tris-HCl, 5 mM CaCl$_2$.

Data Analysis

Data derived from liquid scintillation counting were analyzed by iterative non-linear regression analysis with the use of the Statistical Analysis System (SAS): a program similar to "LIGAND" as described by Munson and Rodbard (Anal. Biochem. 1980, 107, 220-239). Fitting was performed according to formulae described by Feldman (Anal. Biochem. 1972, 48, 317-338). IC$_{50}$, nH and K$_i$ values were expressed as geometrical mean. For receptors with a low affinity for the test compound, where the highest tested compound concentration inhibited less than 30% of specific radioligand binding, K$_i$-values were determined according to the equation of Cheng and Prusoff (Biochem. Pharmacol. 1973, 22, 2099-2108) and expressed as greater than (>).

The results of the receptor binding studies are expressed as receptor binding constants K$_i$(5-HT$_6$) as described herein before, and given in Table 5.

TABLE 5

5-HT$_6$ Agonist Site Radioligand Binding

| Example | Ki (μM) |
|---|---|
| 47 | 0.821 |
| 48 | 0.045 |
| 76 | 0.025 |
| 97 | 0.0024 |
| 98 | 0.0224 |
| 99 | 0.0221 |
| 100 | 0.0475 |
| 101 | 0.0223 |
| 102 | 0.0092 |
| 103 | 0.0299 |
| 104 | 0.0596 |
| 105 | 0.0208 |
| 106 | 0.0260 |
| 107 | 0.0220 |
| 108 | 0.0669 |
| 109 | 0.0556 |
| 112 | 0.0170 |
| 119 | 0.0378 |
| 120 | 0.0183 |
| 121 | 0.6209 |
| 122 | 0.1896 |
| 123 | 0.0583 |
| 124 | 0.0068 |
| 125 | 0.0156 |
| 126 | 0.0234 |
| 127 | 0.0443 |
| 128 | 0.0043 |
| 129 | 0.0132 |
| 130 | 0.0181 |
| 184 | 0.008 |

In these tests, the compounds according to the invention exhibit good affinity for the 5-HT$_6$ receptor (K$_i$<1000 nM or >5 nM).

(v) Assessment of Effects on Psychostimulant-Induced Hyperlocomotion in Mice

In both humans and experimental animals amphetamine profoundly affects motor activity, sensorimotor function, sleep, attention, aggressive and sexual behaviors, learning and memory, operant behaviors, appetite and food intake. In addition, amphetamine induces psychotic reactions in normal individuals and exacerbates symptoms of schizophrenia in patients. In experimental animals several distinct behaviors are considered to be correlates of amphetamine psychosis. For example, amphetamine-induced hyperactivity in rodents is believed to model the psychotic symptoms of schizophrenia. Reversal of these behaviors is used to predict potential antipsychotic activity of drugs in pre-clinical studies.

In humans, phencyclidine (PCP) is known to produce a syndrome of behavioral effects which have many characteristics in common with schizophrenia. Therefore, antagonism of PCP effects might be evidence for antipsychotic efficacy of a compound.

Animals

Male NMRI mice (5-week old, Janvier, France) or C57BL/6J mice (6-week old, Janvier, France) were group housed and allowed ad-libitum access to food and water. A 12 hour light/dark cycle was imposed with lights-on period between 0530 and 1730 hours. All testing occurred between 700 and 1300 hours. All procedures were approved by Abbott Institutional Animal Care and Use Committee (USA) or Animal Welfare Officer (Germany) and were conducted in accordance with the National Institutes of Health Guide for Care and Use of Laboratory Animals guidelines and applicable national laws in the facilities accredited by the Association for the Assessment and Accreditation of Laboratory Animal Care.

Methods

On the day of experiment, animals were brought from the animal facility into the experimental room and were allowed to acclimatize for at least 30 minutes. Animals were then placed in the test cages for a habituation period of 60 minutes. The animals were then injected ip with the test compound and returned to the test cage. 30 Minutes later, the mice were injected with d-amphetamine (2.0 mg/kg, AMP, Sigma, #A5880, sc) or phencyclidine (2.0 mg/kg, PCP, Sigma, #P3029, sc), and returned to the test cages for 90 minutes. Each treatment group consisted of 8-10 animals. The data was acquired by Cage rack Photobeam system (SDI, San Diego Instruments, CA). The analyzed data were: fine movements, ambulations and total movements (fine+ambulations). Data was subjected to one- or two-way distribution-free ANOVA followed by Dunnett's and Tukey's post hoc tests.

Results

Example 42 attenuated AMP-induced hyperactivity significantly and in a dose dependent manner (main effect $F(3, 29)=6.2$, $P<0.001$) (FIG. 1).

Figure 2A:
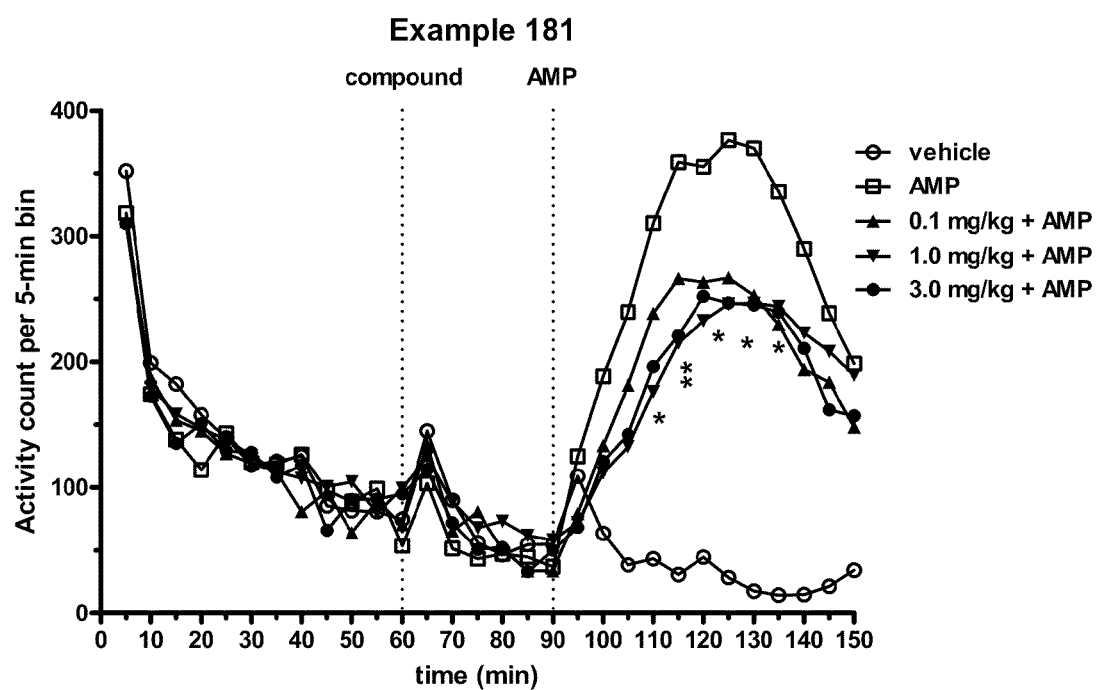
FIG. 2a shows a graphical representation of the concentration-dependent effects of Example 181 attenuating the affect of d-amphetamine. Animals were treated with vehicle, d-amphetamine or a dose of Example 181 followed by d-amphetamine. The X-axis represents time (minutes), and the Y-axis represents activity counts per 5 minute time period.
Figure 2B:
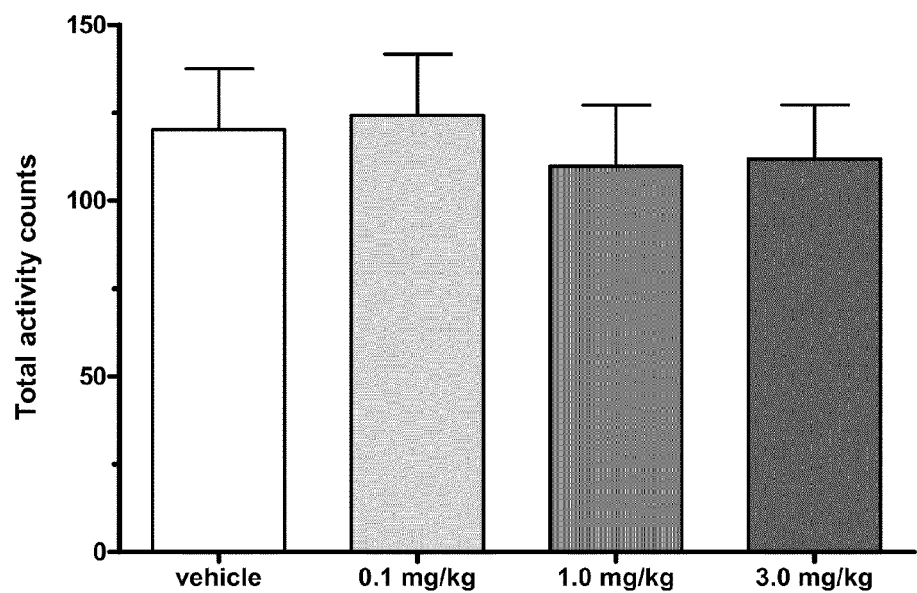
FIG. 2b shows a graphical representation of the lack of effects of Example 181 on spontaneous activity. Animals were treated with vehicle or a dose of Example 181. No change in spontaneous activity regardless of dose was noted over the course of the experiment. The X-axis represents the dose of Example 181, and the Y-axis represents the total activity counts per given dose over the course of the experiment.

Example 181 given to the animals at 1.0 and 3.0 mg/kg before AMP attenuated AMP-induced hyperactivity significantly and in a dose dependent manner (main effect $F(7,29)= 11.5, P<0.0001$) (FIG. 2a). In addition, no effects of Example 181 were seen in spontaneous activity (FIG. 2b).

Figure 3A:
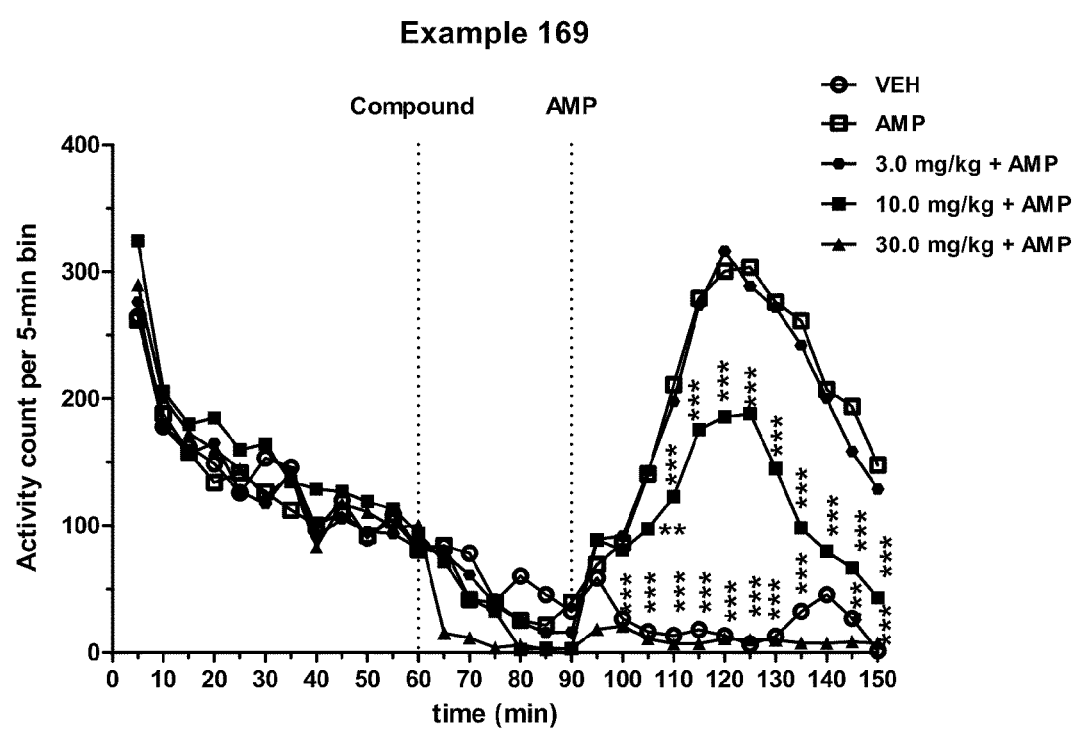
FIG. 3a shows a graphical representation of the concentration-dependent effects of Example 169 attenuating the affect of d-amphetamine. Animals were treated with vehicle, d-amphetamine or a dose of Example 169 followed by d-amphetamine. The X-axis represents time (minutes), and the Y-axis represents activity counts per 5 minute time period.
Figure 3B:
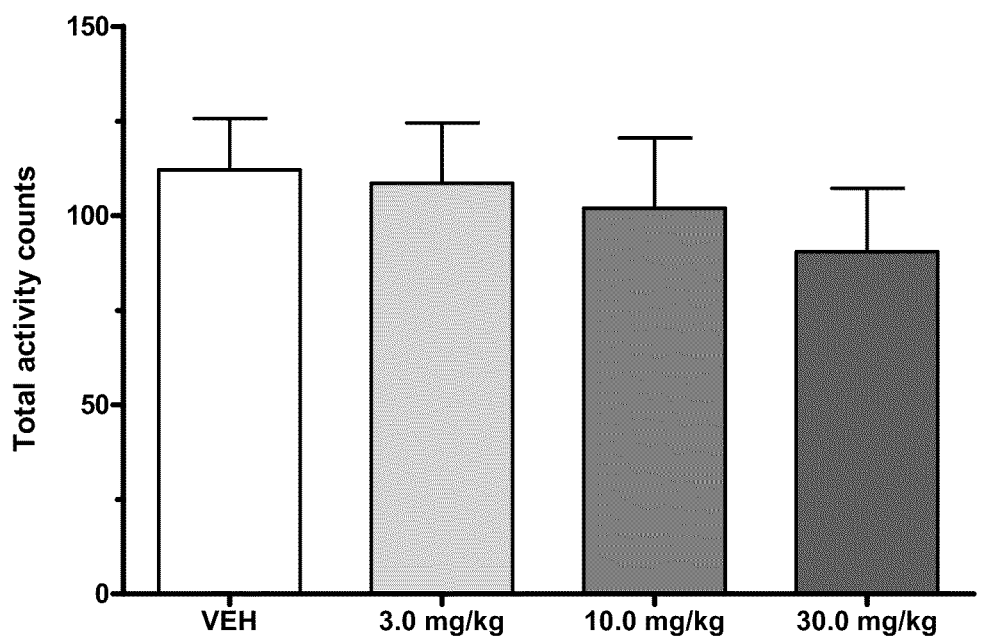
FIG. 3b shows a graphical representation of the lack of effects of Example 169 on spontaneous activity. Animals were treated with vehicle or a dose of Example 169. No change in spontaneous activity regardless of dose was noted over the course of the experiment. The X-axis represents the dose of Example 169, and the Y-axis represents the total activity counts per given dose over the course of the experiment.

Example 169 given to the animals at 10 and 30 mg/kg before AMP; attenuated AMP-induced hyperactivity significantly and in a dose dependent manner (main effect $F(7,29)= 12.6, P<0.0001$) (FIG. 3a). In addition, no effects of Example 169 were seen in spontaneous activity (FIG. 3b).

Figure 4:
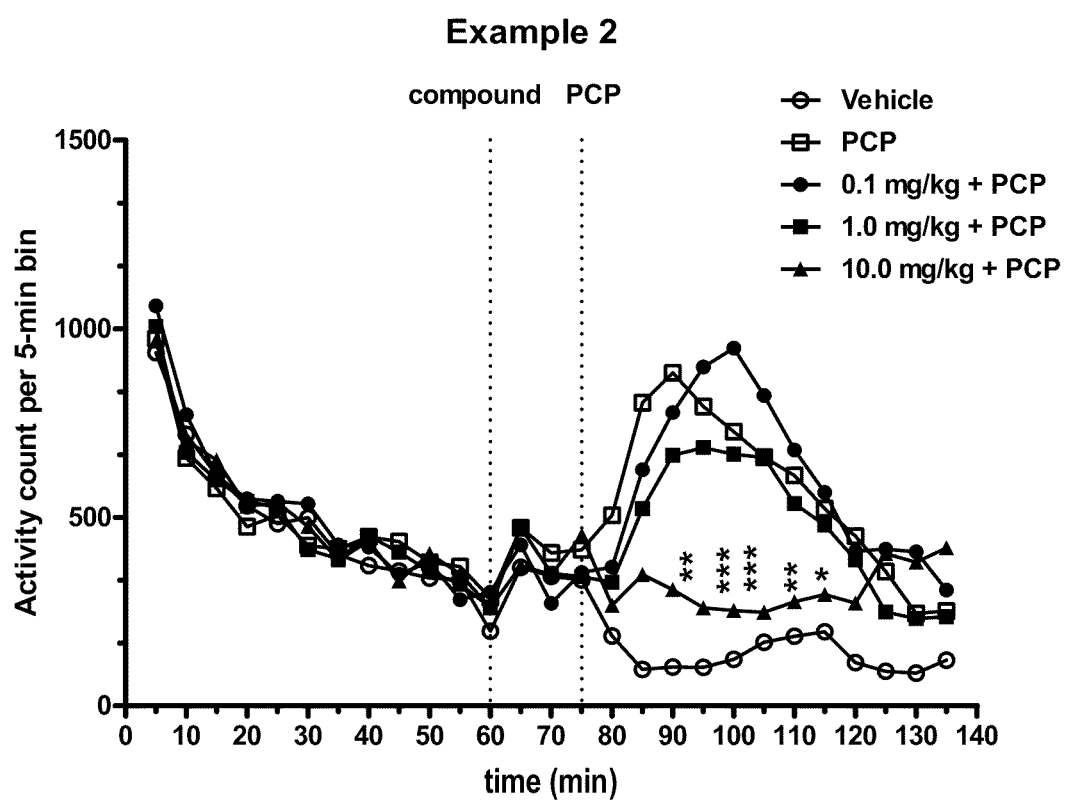
FIG. 4 shows a graphical representation of the concentration-dependent effects of Example 2 attenuating the affect of phencyclidine (PCP) Animals were treated with vehicle, PCP or a dose of Example 2 followed by PCP. The X-axis represents time (minutes), and the Y-axis represents activity counts per 5 minute time period.

Example 2 attenuated PCP-induced hyperactivity significantly and in a dose dependent manner (main effect $F(4,26)= 3.5, P<0.05$) (FIG. 4).

d. METHODS OF USING THE COMPOUNDS

The compounds of this invention are modulators of the $5\text{-HT}_{2C}$ receptor or the $5\text{-HT}_6$ receptor or modulators of both the $5\text{-HT}_{2C}$ and $5\text{-HT}_6$ receptors. In certain embodiments of the invention, the compounds of formula (I) are agonists and partial agonists of the $5\text{-HT}_{2C}$ receptor or antagonists of the $5\text{-HT}_6$ receptor. In certain other embodiments of the invention, the compounds of formula (I) are agonists and partial agonists of the $5\text{-HT}_{2C}$ receptor and also antagonists of the $5\text{-HT}_6$ receptor. Thus, such compounds are of interest in the prevention or treatment of disease conditions associated with one of or both the $5\text{-HT}_{2C}$ and $5\text{-HT}_6$ receptors. Accordingly, the present invention provides a method for preventing or treating such a disease condition in a subject in need of treatment thereof. The subject in need of treatment thereof can be a mammal, such as, but not limited to, a human.

In one aspect, the disease condition is a cognitive dysfunction, attention deficit/hyperactivity syndrome, personality disorders, affective disorders, motion or motor disorders, migraine, sleep disorders, feeding disorders, gastrointestinal disorders, diseases associated with neurodegeneration, addiction diseases, obesity, diabetes, psoriasis, or ocular hypertension. Examples of cognitive dysfunction are deficits in memory, cognition, and learning, Alzheimer's disease, age-related cognitive decline, and mild cognitive impairment, or any combinations thereof. Examples of personality disorders are schizophrenia and cognitive deficits related to schizophrenia. Examples of affective disorders are depression, anxiety, bipolar disorder and obsessive compulsive disorders, or any combination thereof. Examples of motion or motor disorders are Parkinson's disease and epilepsy. Examples of feeding disorders are anorexia and bulimia. Examples of gastrointestinal disorders are irritable bowel syndrome. Examples of diseases associated with neurodegeneration are stroke, spinal or head trauma, and head injuries.

In certain embodiments, the disease condition is a pain condition including nociceptive pain, neuropathic pain or a combination thereof. Such pain conditions or disorders can include, but are not limited to, post-operative pain, osteoarthritis pain, pain due to inflammation, rheumatoid arthritis pain, musculoskeletal pain, burn pain (including sunburn), ocular pain, the pain associated with dental conditions (such as dental caries and gingivitis), post-partum pain, bone fracture, herpes, HIV, traumatic nerve injury, stroke, post-ischemia, fibromyalgia, reflex sympathetic dystrophy, complex regional pain syndrome, spinal cord injury, sciatica, phantom limb pain, diabetic neuropathy, hyperalgesia and cancer. In certain other embodiments, the disease condition is bladder dysfunction, including urinary incontinence.

In still yet another embodiment, the present invention relates to a method for preventing (the development of) a disease condition, such as cognitive dysfunction, attention deficit/hyperactivity syndrome, personality disorders, affective disorders, motion or motor disorders, migraine, pain, urinary incontinence, sleep disorders, feeding disorders, gastrointestinal disorders, diseases associated with neurodegeneration, addiction diseases, obesity, diabetes, psoriasis, or ocular hypertension. As used herein, the term "prevent" a disease condition, such as a cognitive dysfunction, attention deficit/hyperactivity syndrome, personality disorders, affective disorders, motion or motor disorders, migraine, sleep disorders, feeding disorders, gastrointestinal disorders, diseases associated with neurodegeneration, addiction diseases, obesity, diabetes, psoriasis, or ocular hypertension by administration of any of the compounds described herein means that the detectable physical characteristics or symptoms of the disease or condition do not develop following the administration of the compound described herein. Specifically, the method of the present invention comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug.

In still yet another embodiment, the present invention relates to a method for preventing the progression (e.g., worsening) of a disease condition, such as a cognitive dysfunction, attention deficit/hyperactivity syndrome, personality disorders, affective disorders, motion or motor disorders, migraine, pain, urinary incontinence, sleep disorders, feeding disorders, gastrointestinal disorders, diseases associated with neurodegeneration, addiction diseases, obesity, diabetes, psoriasis, or ocular hypertension. The method comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof.

There are several lines of evidence suggesting that 5-$HT_{2C}$ agonists or partial agonists would have therapeutic use in a variety of diseases, disorders and conditions.

Knockout mice models lacking the 5-$HT_{2C}$ receptor exhibit hyperphagia, obesity and are more prone to seizures and sudden death [Tecott L H, Sun L M, Akana S F, Strack A M, Lowenstein D H, Dallman M F, Julius D (1995) Eating disorder and epilepsy in mice lacking 5-$HT_{2C}$ serotonin receptors. Nature 374:542-546]. They also exhibit compulsive-like behavior [Chou-Green J M, Holscher T D, Dallman M F, Akana S F (2003). Compulsive behavior in the 5-$HT_{2C}$ receptor knockout mouse. Phys. Behav. 78:641-649], hyperresponsiveness to repeated stress [Chou-Green J M, Holscher T D, Dallman M F, Akana S F (2003). Repeated stress in young and old 5-$HT_{2C}$ receptor knockout mouse. Phys. Behav. 79:217-226], wakefulness [Frank M G, Stryker M P, Tecott L H (2002). Sleep and sleep homeostasis in mice lacking the 5-$HT_{2C}$ receptor. Neuropsychopharmacology 27:869-873], hyperactivity and drug dependence [Rocha B A, Goulding E H, O'Dell L E, Mead A N, Coufal N G, Parsons L H, Tecott L H (2002), Enhanced locomotor, reinforcing and neurochemical effects of cocaine in serotonin 5-hydroxytryptamine 2C receptor mutant mice. J. Neurosci. 22:10039-10045].

5-$HT_{2C}$ is unique among other G-protein-coupled receptors (GPCRs) in that its pre-mRNA is a substrate for base modification via hydrolytic deamination of adenosines to yield inosines. Five adenosines, located within a sequence encoding the putative second intracellular domain can be converted to inosines. This editing can alter the coding potential of the triplet codons and allows for the generation of multiple different receptor isoforms. The edited receptor isoforms were shown to have reduced ability to interact with G-proteins in the absence of agonist stimulation [Werry, T D, Loiacono R, Sexton P A, Christopoulos A (2008). RNA editing of the serotonin 5-$HT_{2C}$ receptor and its effects on cell signaling, pharmacology and brain function. Pharmac. Therap. 119:7-23].

Edited 5-$HT_{2C}$ isoforms with reduced function are significantly expressed in the brains of depressed suicide victims [Schmauss C (2003) Serotonin 2C receptors: suicide, serotonin, and runaway RNA editing. Neuroscientist 9:237-242. Iwamoto K, Kato T (2003). RNA editing of serotonin 2C receptor in human postmortem brains of major mental disorders. Neurosci. Lett. 346:169-172] and in the learned helplessness rats (a well established animal model of depression) [Iwamotoa K, Nakatanib N, Bundoa M, Yoshikawab T, Katoa T (2005). Altered RNA editing of serotonin 2C receptor in a rat model of depression. Neurosci. Res. 53: 69-76] suggesting a link between 5-$HT_{2C}$ function and depression. There are also implications of edited 5-$HT_{2C}$ isoforms and spatial memory [Du Y, Stasko M, Costa A C, Davissone M T, Gardiner K J (2007). Editing of the serotonin 2C receptor pre-mRNA Effects of the Morris Water Maze. Gene 391:186-197]. In addition, fully edited isoforms of the human 5-$HT_{2C}$ receptor display a striking reduction in sensitivity to lysergic acid diethylamide (LSD) and to atypical antipsychotic drugs clozapine and loxapine, suggesting a possible role of the receptor in the etiology and pharmacology of schizophrenia [Niswender C M, Herrick-Davis K., Dilley G E, Meltzer H Y, Overholser J C, Stockmeier C A, Emeson R B, Sanders-Bush E (2001). RNA Editing of the Human Serotonin 5-$HT_{2C}$ Receptor: Alterations in Suicide and Implications for Serotonergic Pharmacotherapy. Neuropsychopharm. 24:478-491].

Recently, the availability of potent and selective 5-$HT_{2C}$ receptor agonists made it possible to directly investigate the effects of 5-$HT_{2C}$ agonists and their therapeutic potential. Thus recent studies demonstrated that selective 5-$HT_{2C}$ agonists resulted in decreased food intake and body weight gain in normal and obese rats [Smith B M, et al. (2008). Discovery and structure-activity relationship of (1R)-8-chloro-2,3,4,5-tetrahydro-1-methyl-1H-3-benzazepine (Lorcaserin), a selective serotonin 5-$HT_{2C}$ receptor agonist for the treatment of obesity. J Med Chem 51:305-313. Thomsen W J, Grottick A J, Menzaghi F, Reyes-Saldana H, Espitia S, Yuskin D, Whelan K, Martin M, Morgan M, Chen W, Al-Shama H, Smith B, Chalmers D, Behan D (2008) Lorcaserin, A Novel Selective Human 5-$HT_{2C}$ Agonist: In Vitro and In Vivo Pharmacological Characterization. J Pharmacol Exp Ther. 325: 577-587. Rosenzweig-Lipson S, Zhang J, Mazandarani H, Harrison B L, Sabb A, Sabalski J, Stack G, Welmaker G, Barrett J E, Dunlop J (2006) Antiobesity-like effects of the 5-$HT_{2C}$ receptor agonist WAY-161503. Brain Res. 1073-1074:240-251. Dunlop J, Sabb A L, Mazandarani H, Zhang J, Kalgaonker S, Shukhina E, Sukoff S, Vogel R L, Stack G, Schechter L, Harrison B L, Rosenzweig-Lipson S (2005). WAY-163909 [97bR, 10aR)-1,2,3,4,8,9,10,10a-octahydro-7bH-cyclopenta-[b][1,4]diazepino[6,7,1hi]indole], a novel 5-hydroxytryptamine 2C receptor—selective agonist with anorectic activity. J Pharmacol Exp Ther. 313:862-869.].

Furthermore, selective 5-$HT_{2C}$ receptor agonists produce antidepressant effects in animal models of depression comparable to those of SSRIs but with a much faster onset of action and a therapeutic window that avoids antidepressant-induced sexual dysfunction. These agonists were also effective in animal models of compulsive behavior such as scheduled induced polydipsia and they also exhibited decreased hyperactivity and aggression in rodents [Rosenzweig-Lipson S, Sabb A, Stack G, Mitchell P, Lucki I, Malberg J E, Grauer S, Brennan J, Cryan J F, Sukoff Rizzo S J, Dunlop J, Barrett J E, Marquis K L (2007) Antidepressant-like effects of the novel, selective, 5-$HT_{2C}$ receptor agonist WAY-163909 in rodents. Psychopharmacology (Berlin) 192:159-170. Rosenzweig-Lipson S, Dunlop J, Marquis K L (2007) 5-$HT_{2C}$ receptor agonists as an innovative approach for psychiatric disorders. Drug news Perspect, 20: 565-571. Cryan, J F, Lucki I (2000). Antidepressant-like behavioral effects mediated by 5-Hydroxytryptamine 2C receptors. J. Pharm. Exp. Ther. 295:1120-1126.].

Acute or chronic administration of 5-$HT_{2C}$ agonists decreases the firing rate of ventral tegmental area dopamine neurons but not that of substantia nigra. In addition 5-HT$_{2C}$ agonists reduce dopamine levels in the nucleus accumbens but not in the striatum (the region of the brain mostly associated with extrapyramidal side effects) [Di Matteo, V., Di Giovanni, G., Di Mascio, M., & Esposito, E. (1999). SB 242084, a selective serotonin 2C receptor antagonist, increases dopaminergic transmission in the mesolimbic system. *Neuropharmacology* 38, 1195-1205. Di Giovanni, G., Di Matteo, V., Di Mascio, M., & Esposito, E. (2000). Preferential modulation of mesolimbic vs. nigrostriatal dopaminergic function by serotonin2C/2B receptor agonists: a combined in vivo electrophysiological and microdialysis study. *Synapse* 35, 53-61. Marquis K L, Sabb A L, Logue S F, Brennan J A, Piesla M J, Comery T A, Grauer S M, Ashby C R, Jr., Nguyen H Q, Dawson L A, Barrett J E, Stack G, Meltzer H Y, Harrison B L, Rosenzweig-Lipson S (2007) WAY-163909 [(7bR,10aR)-1,2,3,4,8,9,10,10a-octahydro-7bH-cyclopenta-[b][1,4]diazepino[6,7,1hi]indole]: A novel 5-hydroxytryptamine 2C receptor-selective agonist with preclinical antipsychotic-like activity. *J Pharmacol Exp Ther* 320:486-496.]. Therefore it is expected that 5-HT$_{2C}$ receptor agonists will selectively decrease mesolimibic dopamine levels without affecting the nigrostriatal pathway thus avoiding the EPS side effects of typical antipsychotics. Several 5-HT$_{2C}$ receptor agonists have shown antipsychotic activity in animal models of schizophrenia without EPS based on the lack of effect in catalepsy [Marquis K L, Sabb A L, Logue S F, Brennan J A, Piesla M J, Comery T A, Grauer S M, Ashby C R, Jr., Nguyen H Q, Dawson L A, Barrett J E, Stack G, Meltzer H Y, Harrison B L, Rosenzweig-Lipson S (2007) WAY-163909 [(7bR,10aR)-1,2,3,4,8,9,10,10a-octahydro-7bH-cyclopenta-[b][1,4]diazepino[6,7,1hi]indole]: A novel 5-hydroxytryptamine 2C receptor-selective agonist with preclinical antipsychotic-like activity. *J Pharmacol Exp Ther* 320:486-496. Siuciak J A, Chapin D S, McCarthy S A, Guanowsky V, Brown J, Chiang P, Marala R, Patterson T, Seymour P A, Swick A, Iredale P A (2007) CP-809,101, a selective 5-HT$_{2C}$ agonist, shows activity in animal models of antipsychotic activity. *Neuropharmacology* 52:279-290]. The antipsychotic activity of 5-HT$_{2C}$ receptor agonists without EPS coupled with their beneficial effects in mood disorders and cognition and their antiobesity like effects render 5-HT$_{2C}$ receptor agonists as unique agents to treat schizophrenia [Rosenzweig-Lipson S, Dunlop J, Marquis K L (2007) 5-HT$_{2C}$ receptor agonists as an innovative approach for psychiatric disorders. *Drug news Perspect,* 20: 565-571. Dunlop J, Marquis K L, Lim H K, Leung L, Kao J, Cheesman C, Rosenzweig-Lipson S (2006). Pharmacological profile of the 5-HT$_{2C}$ receptor agonist WAY-163909; therapeutic potential in multiple indications. *CNS Dug Rev.* 12:167-177.].

In addition 5-HT$_{2C}$ modulation has been implicated in epilepsy [Isaac M (2005). Serotonergic 5-HT$_{2C}$ receptors as a potential therapeutic target for the antiepileptic drugs. *Curr. Topics Med. Chem.* 5:59:67], psoriasis [Thorslund K, Nordlind K (2007). Serotonergic drugs-a possible role in the treatment of psoriasis? *Drug News Perspect* 20:521-525], Parkinson's disease and related motor disorders [Esposito E, Di Matteo V, Pierucci M, Benigno A, Di Giavanni, G (2007). Role of central 5-HT$_{2C}$ receptor in the control of basal ganglia functions. *The Basal Ganglia Pathophysiology: Recent Advances* 97-127], behavioral deficits [Barr A M, Lahmann-Masten V, Paulus M, Gainetdinov R P, Caron M G, Geyer M A (2004). The selective serotonin-2A receptor antagonist M100907 reverses behavioral deficits in dopamine transporter knockout mice. *Neuropsychopharmacology* 29:221-228], anxiety [Dekeyne A, Mannoury la Cour C, Gobert A, Brocco M, Lejeune F, Serres F, Sharp T, Daszuta A, Soumier A, Papp M, Rivet J M, Flik G, Cremers T I, Muller O, Lavielle G, Millan M J (2208). S32006, a novel 5-HT$_{2C}$ receptor antagonists displaying broad-based antidepressant and anxiolytic properties in rodent models. *Psychopharmacology* 199:549-568. Nunes-de-Souza V, Nunes-de-Souza R L, Rodgers R J, Canto-de-Souza A (2008). 5-HT2 receptor activation in the midbrain periaqueductal grey (PAG) reduces anxiety-like behavior in mice. *Behav. Brain Res.* 187:72-79.], migraine [Leone M, Rigamonti A, D'Amico D, Grazzi L, Usai S, Bussone G (2001). The serotonergic system in migraine. *Journal of Headache and Pain* 2(Suppl. 1):S43-S46], Alzheimer's disease [Arjona A A, Pooler A M, Lee R K, Wurtman R J (2002). Effect of a 5-HT$_{2C}$ serotonin agonist, dexnorfenfluramine, on amyloid precursor protein metabolism in guinea pigs. *Brain Res.* 951:135-140], pain and spinal cord injury [Nakae A, Nakai K, Tanaka T, Hagihira. S, Shibata M, Ueda K, Masimo T (2008). The role of RNA editing of the serotonin 2C receptor in a rat model of oro-facial neuropathic pain. *The European Journal of Neuroscience* 27:2373-2379. Nakae A, Nakai K, Tanaka T, Takashina M, Hagihira S, Shibata M, Ueda K, Mashimo T (2008). Serotonin 2C receptor mRNA editing in neuropathic pain model. *Neurosci. Res.* 60:228-231. Kao T, Shumsky J S, Jacob-Vadakot S, Timothy H B, Murray M, Moxon, K A (2006). Role of the 5-HT$_{2C}$ receptor in improving weight-supported stepping in adult rats spinalized as neonates. *Brain Res.* 1112:159-168.], sexual dysfunction [Motofei I G (2008). A dual physiological character for sexual function: the role of serotonergic receptors. *BJU International* 101:531-534. Shimada I, Maeno K, Kondoh Y, Kaku H, Sugasawa K, Kimura Y, Hatanaka K; Naitou Y, Wanibuchi F, Sakamoto S; Tsukamoto S (2008). Synthesis and structure-activity relationships of a series of benzazepine derivatives as 5-HT$_{2C}$ receptor agonists. *Bioorg. Med. Chem.* 16:3309-3320.], smoking cessation [Fletcher P J, Le A D, Higgins G A (2008). Serotonin receptors as potential targets for modulation of nicotine use and dependence. *Progress Brain Res.* 172:361-83], substance dependence [Bubar M J, Cunningham K A (2008). Prospects for serotonin 5-HT2R pharmacotherapy in psychostimulant abuse. *Progress Brain Res.* 172:319-46], and ocular hypertension [Sharif N A, McLaughlin M A, Kelly C R (2006). AL-34662: a potent, selective, and efficacious ocular hypotensive serotonin-2 receptor agonist. *J Ocul Pharmacal Ther.* 23:1-13].

Further, 5HT modulation can be useful in the treatment of pain, both neuropathic and nociceptive pain, see for example U.S. Patent application publication US2007/0225277. Obata, Hideaki; Ito, Naomi; Sasaki, Masayuki; Saito, Shigeru; Goto, Fumio. Possible involvement of spinal noradrenergic mechanisms in the antiallodynic effect of intrathecally administered 5-HT2C receptor agonists in the rats with peripheral nerve injury. European Journal of Pharmacology (2007), 567(1-2), 89-94. Serotonin2C receptor mRNA editing in neuropathic pain model. Nakae, Aya; Nakai, Kunihiro; Tanaka, Tatsuya; Takashina, Masaki; Hagihira, Satoshi; Shibata, Masahiko; Ueda, Koichi; Mashimo, Takashi. Department of Anesthesiology & Intensive Care Medicine, Graduate School of Medicine, Osaka University, *Neuroscience Research* (Amsterdam, Netherlands) (2008), 60(2), 228-231. Antiallodynic effects of intrathecally administered 5-HT2C receptor agonists in rats with nerve injury. Obata, Hideaki; Saito, Shigeru; Sakurazawa, Shinobu; Sasaki, Masayuki; Usui, Tadashi; Goto, Fumio. Department of Anesthesiology, Gunma University Graduate School of Medicine, Maebashi, Gunma, Japan. *Pain* (2004), 108(1-2), 163-169. Influence of 5,7-dihydroxytryptamine (5,7-DHT) on the antinociceptive effect of serotonin (5-HT) 5-HT2C receptor agonist in male and female rats. Brus, Ryszard; Kasperska, Alicj a; Oswiecimska, Joanna; Szkilnik, Ryszard. Department of Pharmacology, Silesian Medical University, Zabrze, Pol. *Medical Science Monitor* (1997), 3(5), 654-656.

Modulation of 5HT2 receptors may be beneficial in the treatment of conditions related to bladder function, in particular, urinary incontinence. [Discovery of a novel azepine series of potent and selective 5-HT2C agonists as potential treatments for urinary incontinence. Brennan, Paul E.; Whitlock, Gavin A.; Ho, Danny K. H.; Conlon, Kelly; McMurray, Gordon. *Bioorganic & Medicinal Chemistry Letters* (2009), 19(17), 4999-5003. Investigation of the role of 5-HT2 receptor subtypes in the control of the bladder and the urethra in the anesthetized female rat. Mbaki, Y.; Ramage, A. G. Department of Pharmacology, University College London, London, UK. *British Journal of Pharmacology* (2008), 155(3), 343-356.]In particular, compounds with agonist activity at $5\text{-HT}_{2C}$ have been shown to be useful in treating urinary incontinence, see for example U.S. Patent application publications US2008/0146583 and US 2007/0225274.

Because of their binding profile, the compounds can be used for treating diseases which respond to $5\text{-HT}_6$ receptor ligands (or which are susceptible to treatment with a $5\text{-HT}_6$ receptor ligand), i.e. they are effective for treating those medical disorders or diseases in which exerting an influence on (modulating) the $\text{S-HT}_6$ receptors leads to an improvement in the clinical picture or to the disease being cured. Examples of these diseases are disorders or diseases of the central nervous system.

Disorders or diseases of the central nervous system are understood as meaning disorders which affect the spinal cord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are in particular disorders which respond to a modulation of the $5\text{-HT}_6$ receptor. They include cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, drug addiction and obesity.

The addiction diseases include psychiatric disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula (I) which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of $5\text{-HT}_6$ receptors.

According to another aspect of the present invention, the treatment is directed, in particular, toward those disorders which can be influenced, within the sense of an expedient medicinal treatment, by the binding of preferably exogenously administered binding partners (ligands) to $5\text{-HT}_6$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds of formula (I) can be used to treat a large number of signs, symptoms and/or malfunctions which are connected with the disorders of the central nervous system and, in particular, the above-mentioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-La-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

The compounds according to the invention are preferentially suitable for treating diseases of the central nervous system, more preferably for treating cognitive dysfunctions and in particular, for treating cognitive dysfunctions associated with schizophrenia or with Alzheimer's disease.

According to another aspect of the invention the compounds of formula (I) are particularly suitable for treating addiction diseases caused for instance by the abuse of psychotropic substances, such as pharmaceuticals, narcotics, nicotine or alcohol, including psychic disorders and behavioral disturbances related thereto.

According to another aspect of the invention the compounds of formula (I) are particularly suitable for treating nutritional disorders, such as obesity, as well as diseases related thereto, such as cardiovascular diseases, digestive diseases, respiratory diseases, cancer or type 2 diabetes.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

Actual dosage levels of active ingredients in the pharmaceutical compositions of the present invention can be varied so as to obtain an amount of the active compound(s) that is effective to achieve the desired therapeutic response for a particular subject (e.g., a mammal, preferably, a human (patient)), compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the present invention can also be administered to a subject as a pharmaceutical composition comprising the compounds of interest in combination with at least one pharmaceutically acceptable carriers. The phrase "therapeutically effective amount" of the compound of the present invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a subject (namely, a mammal, such as a human) ranges from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions may contain such amounts or submultiples thereof to make up the daily dose.

e. PHARMACEUTICAL COMPOSITIONS

In yet another embodiment, the present invention provides pharmaceutical compositions. The pharmaceutical compositions of the present invention comprise the compounds of the present invention or a pharmaceutically acceptable salt or solvate thereof. The pharmaceutical compositions of the present invention comprise compounds of the present invention that can be formulated together with at least one non-toxic pharmaceutically acceptable carrier.

In yet another embodiment, the present invention provides a pharmaceutical composition comprising compounds of the present invention, or a pharmaceutically acceptable salt thereof, and one or more pharmaceutically acceptable carriers, alone or in combination with one or more compounds that are not the compounds of the present invention. Examples of one or more compounds that can be combined with the compounds of the present invention in pharmaceutical compositions, include, but are not limited to, one or more cognitive enhancing drugs.

The pharmaceutical compositions of this present invention can be administered to a subject (e.g., a mammal, such as a human) orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of the present invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of the present invention include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq.). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention also contemplates compounds of the present invention formed by synthetic means or formed by in vivo biotransformation of a prodrug.

The compounds of the present invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. GENERAL SYNTHESIS

This invention is intended to encompass compounds of the present invention whether prepared by synthetic processes or by metabolic processes. Preparation of the compounds by metabolic processes includes those occurring in the human or animal body (in vivo) or processes occurring in vitro.

The compounds of the present invention may be prepared by a variety of processes that will be understood by one skilled in the art and described in the following Schemes and Examples. For example, the compounds of the present invention wherein the groups $G^1$, $G^2$, $R^1$, $R^2$, $R^3$, $R^4$, $R^5$, $R^6$, $R^{4a}$, $R^{5a}$, $R^{14}$, $X_1$, $X^2$, $X^3$, $X^4$, $Y^3$, and $Y^4$ have the meanings as set forth in the Summary of the Invention section unless otherwise noted, can be synthesized as shown in Schemes 1-20.

Abbreviations which have been used in the descriptions of the Schemes that follow are: Bn for benzyl; Boc for t-butoxycarbonyl; $Boc_2O$ for di-tert-butyl dicarbonate; Bu for butyl; BuLi for butyllithium; DIAD for diisopropyl azodicarboxylate; DMF for N,N-dimethylformamide; EDAC or EDCI for N-(3-dimethylaminopropyl)-N'-ethylcarbodiimide hydrochloride; Et for ethyl; $Et_3N$ for triethylamine; EtOH for ethanol; Fmoc for 9-fluorenylmethoxycarbonyl; HOAc for acetic acid; mCPBA for m-chloroperoxybenzoic acid; Me for methyl; MeOH for methanol; MP for macroporous resin; NBS for N-bromosuccinimide; i-Pr for isopropyl; Ph for phenyl; $PPh_3$ for triphenylphosphine; THF for tetrahydrofuran; and Tr for trityl or triphenylmethyl.

Scheme 1

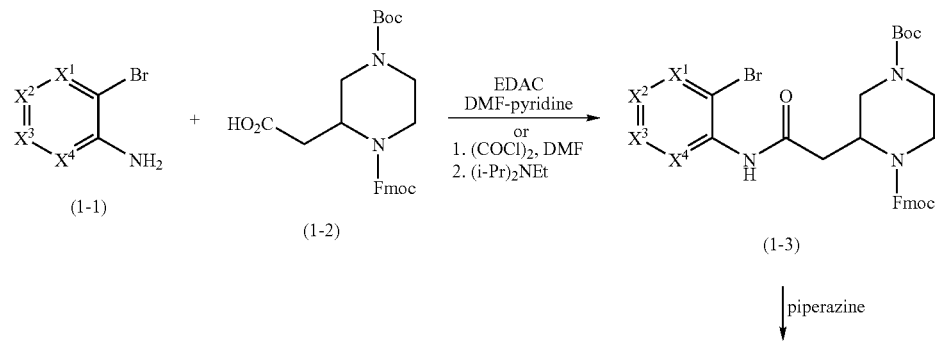

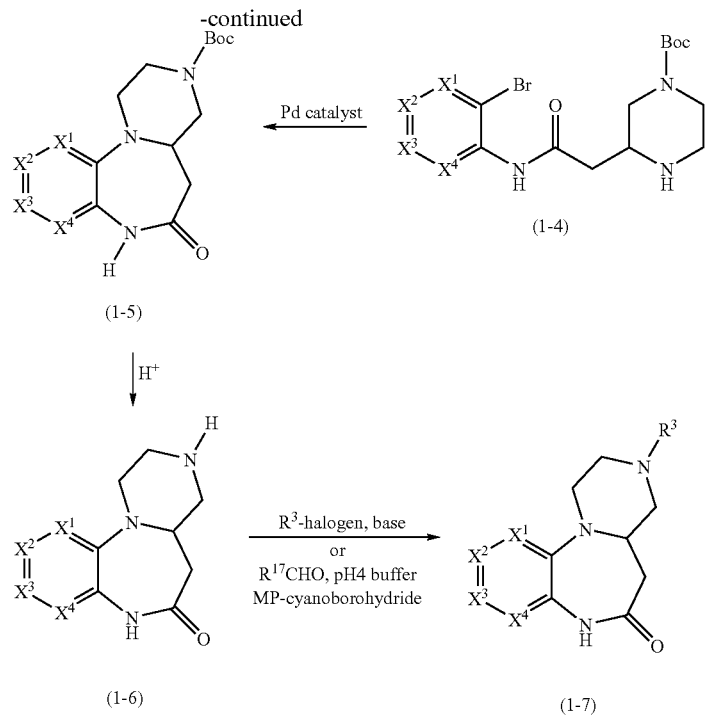

As outlined in Scheme 1, compounds of formula (1-6) and (1-7), wherein $X^1$, $X^2$, $X^3$, $X^4$ are as defined in the Summary of the Invention and $R^3$ is hydrogen, alkyl or —$(CR^{4a}R^{5a})_m$-$G^1$, which are representative of compounds of formula (I), can be prepared from a compound of formula (1-1). o-Bromoaniline (1-1) can be coupled with 2-(1-(((9H-fluoren-9-yl)methoxy)carbonyl)-4-(tert-butoxycarbonyl)piperazin-2-yl)acetic acid (1-2) utilizing conditions known to those skilled in the art which couple carboxylic acids to amines to generate amides will provide compounds of formula (1-3). Examples of conditions known to generate amides from a mixture of a carboxylic acid and an amine include but are not limited to adding a coupling reagent such as but not limited to N-(3-dimethylaminopropyl)-N'-ethylcarbodiimide hydrochloride (EDCI, EDAC), 1,3-dicyclohexylcarbodiimide (DCC), bis(2-oxo-3-oxazolidinyl)phosphinic chloride (BOPCl), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU). The coupling reagents may be added as a solid, a solution or as the reagent bound to a solid support resin. In addition to the coupling reagents, auxiliary-coupling reagents may facilitate the coupling reaction. Auxiliary coupling reagents that are often used in the coupling reactions include but are not limited to 4-dimethylaminopyridine (DMAP), 1-hydroxy-7-azabenzotriazole (HOAT) and 1-hydroxybenzotriazole (HOBT). The coupling reaction may be carried out in solvents such as but not limited to tetrahydrofuran, N,N,-dimethylformamide, pyridine and ethyl acetate or a combination thereof. The reaction may be conducted at ambient or elevated temperatures. The ((9H-fluoren-9-yl)methoxy)carbonyl (Fmoc) moiety can be selectively removed by treatment with piperazine between ambient temperature and 40° C. over 2-24 hours in dichloromethane with methanol added to make the reaction homogeneous to provide compounds of formula (1-4).

Alternatively compounds of formula (1-3) can be produced from compounds of formula (1-1) and (1-2) by initially converting (1-2) to the corresponding acid chloride. The acid chloride can be typically prepared by suspending the carboxylic acid (1-2) in a solvent such as dichloromethane and then adding oxalyl chloride and a catalytic amount of N,N,-dimethylformamide. The solvent may be removed by evaporation, and the acid chloride redissolved in a solvent such as tetrahydrofuran or pyridine. Addition of a compound of formula (1-1) in the presence of Hunig's base will furnish compounds of formula (1-3). The reaction may be conducted at ambient or elevated temperatures over a period ranging from several hours to several days.

Compounds of formula (1-4) can be converted to compounds of formula (1-5) with a palladium catalyzed coupling reaction. For example, compounds of formula (1-4) in a solvent such as dioxane can be treated with tris(dibenzylideneacetone)dipalladium (0) in the presence of a ligand like 1,3-bis(2,6-diisopropyl-phenyl)imidazolium chloride and a base such as sodium t-butoxide heated to 90-120° C. for 1 to 5 days to supply compounds of formula (1-5). Alternatively, the cross-coupling reaction may use a catalyst such as tris(dibenzylideneacetone)dipalladium (0) in the presence of a ligand, dicyclohexyl(2',6'-dimethoxybiphenyl-2-yl)phosphine, and base, sodium t-butoxide, in a solvent such as t-butanol heated with microwave irradiation at 120° C. for approximately 20 minutes.

The t-butoxycarbonyl (Boc) protecting group of compounds of formula (1-5) can be removed by treatment with an acid such as hydrochloric acid in dioxane or trifluoroacetic acid in a solvent such as dichloromethane to give compounds of formula (1-6) which are representative of compounds of formula (I). The orthogonal protecting group scheme used in this sequence is only representative of possible schemes. One skilled in the art can use other pairs of orthogonal protecting groups to achieve compounds of formula (1-6). Compounds of formula (1-6) can be converted to compounds of formula (1-7) which are also representative of compounds of formula (I) either through an alkylation or reductive amination procedure, wherein $R^3$ is alkyl or $—(CR^{4a}R^{5a})_m-G^1$ and $R^{4a}$, $R^{5a}$, m and $G^1$ are as defined in the Summary of the Invention. Treatment of compounds of formula (1-6) with an alkyl halide in the presence of a base such as potassium carbonate heated (40-70° C.) in a solvent such as N,N-dimethylformamide for 6 to 24 hours gives compounds of formula (1-7). Alternatively, compounds of formula (1-6) can be converted to compounds of formula (1-7) by treatment with an aldehyde of formula $R^{17}CHO$, wherein $R^{17}$ is hydrogen, alkyl or arylalkyl, in the presence of a reductant such as MP-cyanoborohydride in an acidic environment such as pH4 buffer solution either at ambient temperature or heated conventionally or with microwave irradiation.

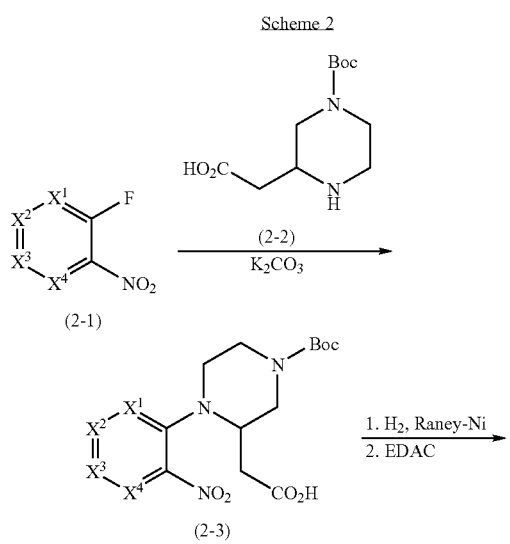

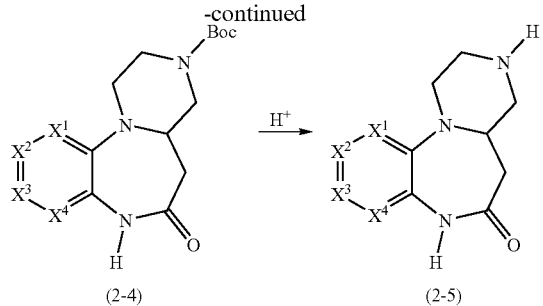

As outlined in Scheme 2, compounds of formula (2-5) which are representative of compounds of formula (I), wherein $X^1$, $X^2$, $X^3$, and $X^4$ are as defined in the Summary of the Invention can be prepared from compounds of formula (2-1). A compound of formula (2-1) can be reacted with a compound of formula (2-2) in the presence of a base such as potassium carbonate in a mixture of water and acetonitrile heated to 50-80° C. for 12 to 36 hours to give compounds of formula (2-3). Alternatively, compounds of formula (2-1) and (2-2) can be combined in a mixture of N,N-dimethylformamide and water and treated with a base such as triethylamine heated to approximately 50° C. from 12 to 30 hours to provide compounds of formula (2-3). The nitro group of compounds of formula (2-3) can then be reduced with hydrogen in the presence of a catalyst such as Raney®-nickel in a solvent such as methanol at room temperature. The resultant corresponding aniline can then be coupled intramolecularly with the carboxylic acid moiety using the amide bond forming conditions described in Scheme 1 to give the diazapinone of formula (2-4). The t-butoxycarbonyl group of compounds of formula (2-4) can be removed under acidic conditions described in Scheme 1 to yield compounds of formula (2-5).

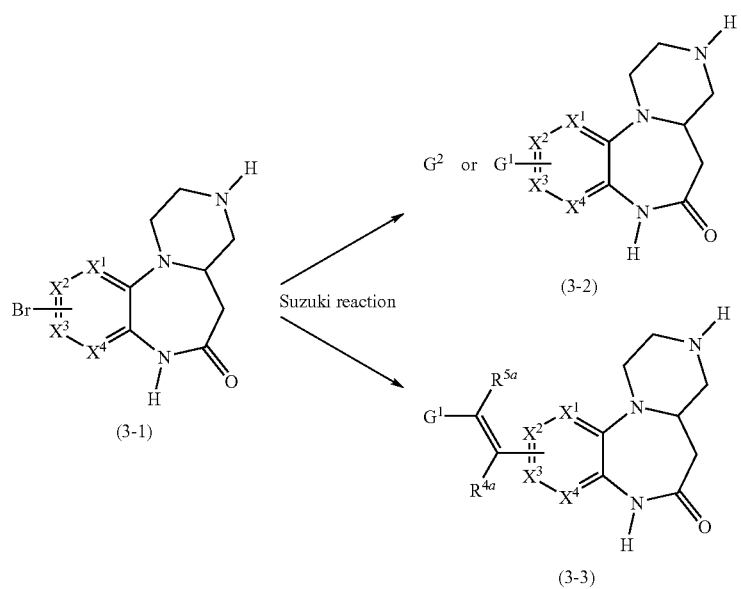

As outlined in Scheme 3, compounds of formula (3-2) and (3-3) which are representative of compounds of formula (I), wherein $G^1$, $G^2$, $R^{4a}$, $R^{5a}$, $X^1$, $X^2$, $X^3$, and $X^4$ are as defined in the Summary of the Invention can be prepared from compounds of formula (3-1), wherein one of $X^1$, $X^2$, $X^3$, or $X^4$ is CBr. Compounds of formula (3-1) are transformed to compounds of formula (3-2) and (3-3) under Suzuki reaction conditions wherein compounds of (3-1) are reacted with an aryl, heteroaryl, heterocyclic, cycloalkyl, or vinyl boronic acid or boronate. The reaction typically requires the use of a base and a catalyst. Examples of bases include but are not limited to $K_2CO_3$, potassium t-butoxide, $Na_2CO_3$, $Cs_2CO_3$, and CsF. Examples of catalysts include but are not limited to tetrakis(triphenylphosphine)palladium (0), dichloro[1,1'-bis(diphenylphosphino)ferrocene]palladium(II) dichloromethane adduct, tris(dibenzylideneacetone)dipalladium (0), palladium(II) acetate, dichlorobis(triphenylphosphine)palladium(II), FC1007™. The reaction may be conducted in a solvent such as but not limited to water, dioxane, 1,2-dimethoxyethane, N,N-dimethylformamide, toluene, ethanol, tetrahydrofuran and the like or mixtures thereof. The reaction may be conducted at ambient or elevated temperatures using conventional heating or microwave irradiation.

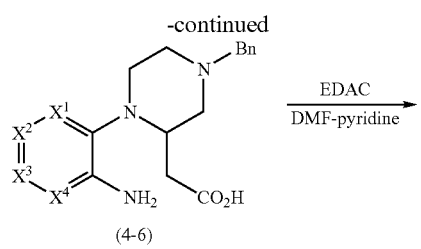

(4-6)

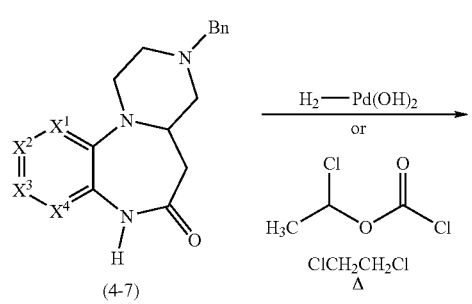

(4-7)

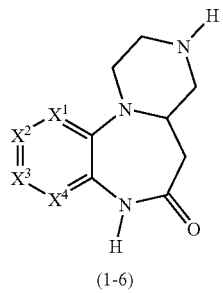

(1-6)

Scheme 4

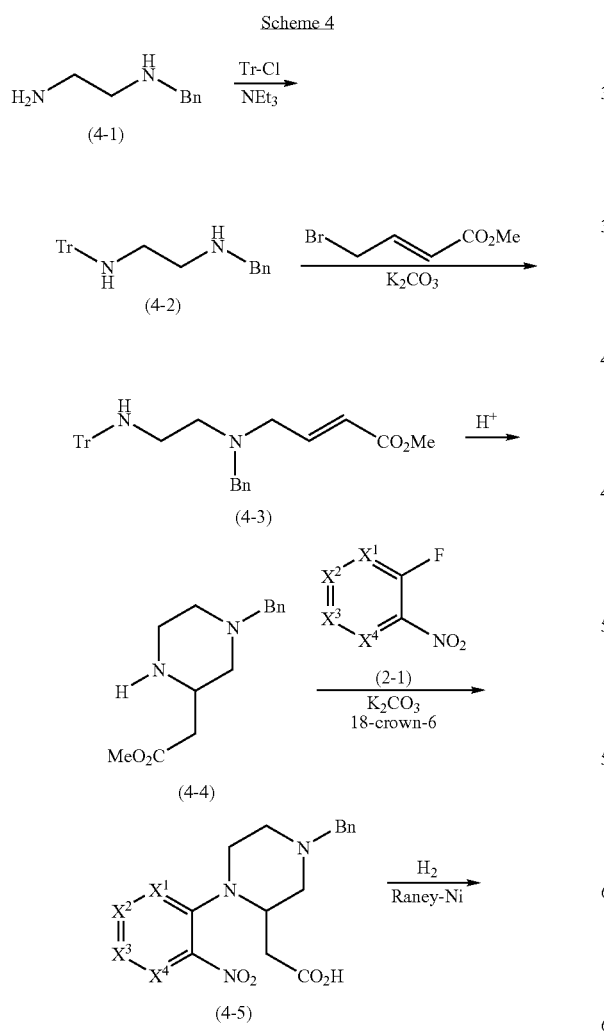

Scheme 4 outlines an alternative approach to compounds of formula (1-6), wherein $X^1$, $X^2$, $X^3$, and $X^4$ are as defined in the Summary of the Invention, starting with compound (4-1). Accordingly, compound (4-1) in dichloromethane chilled in an ice bath can be reacted with trityl chloride in the presence of triethylamine to give compound (4-2). Compound (4-2) can subsequently be reacted with (E)-methyl 4-bromobut-2-enoate in the presence of potassium carbonate in heated acetonitrile to give compound (4-3). Treatment with acid in a heated methanol solution removes the trityl group and induces cyclization to compound (4-4). Heating compound (4-4) at reflux in acetonitrile with compounds of formula (2-1) in the presence of potassium carbonate and 18-crown-6 delivers compounds of formula (4-5). Exposure of compounds of formula (4-5) to hydrogen in the presence of Raney®-nickel in methanol gives the corresponding anilines, compounds (4-6). Compounds of formula (4-6) are cyclized to compounds of formula (4-7) using the amide bond coupling conditions described in Schemes 1 and 2. The benzyl group of compounds of formula (4-7) can be removed with hydrogen in the presence of a catalyst such as palladium hydroxide on carbon in optionally warmed ethanol to give compounds of formula (1-6). Alternatively, compounds of formula (1-6) can be obtained from compounds of formula (4-7) upon treatment with 1-chloroethyl carbonochloridate in dichloroethane initially at 0° C. and then increasing to 85° C. Subsequently, the solvent is switched to methanol, and heating at 40-65° C. delivers compounds of formula (1-6). Both compounds of formula (4-7) and (1-6) are representative of compounds of formula (I).

Scheme 5

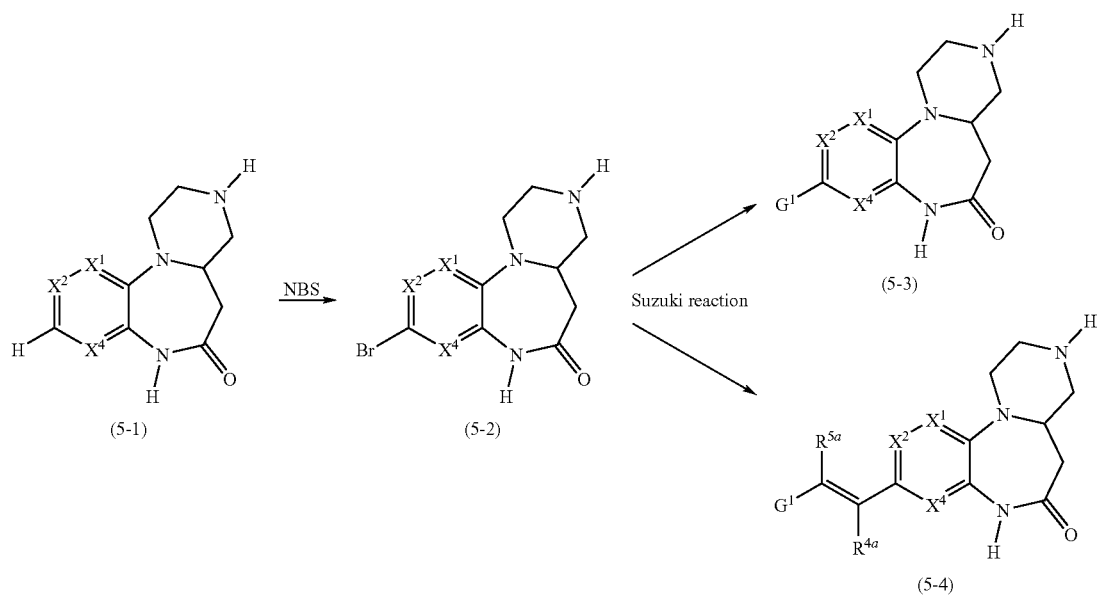

As outlined in Scheme 5, compounds of formulas (5-3) and (5-4) can be prepared from compounds of formula (5-1), wherein $G^1$, $R^{4a}$, $R^{5a}$, $X^1$, $X^2$, and $X^4$ are as defined in the Summary of the Invention. Accordingly, compounds of formula (5-1) can be treated with N-bromosuccinimide in a mixture of acetic acid and water at ambient temperature to deliver compounds of formula (5-2). Compounds of formula (5-2) can then be treated with aryl, heteroaryl or vinyl boronic acids or boronates under the Suzuki reaction conditions described in Scheme 3 to provide compounds of formulas (5-3) and (5-4) which are representative of compounds of formula (I).

Scheme 6

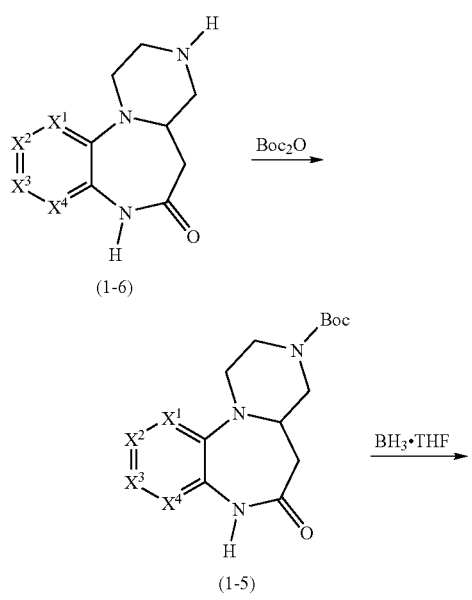

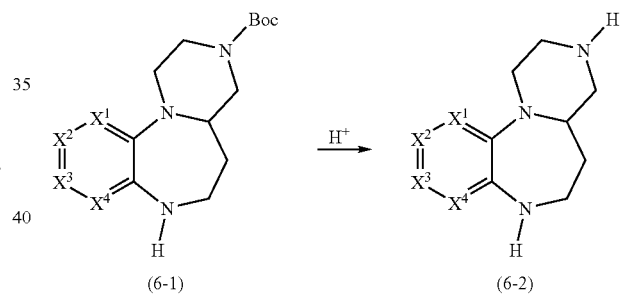

As outlined in Scheme 6, compounds of formula (1-6) can be converted to compounds of formula (6-2), wherein $X^1$, $X^2$, $X^3$, and $X^4$ are as defined in the Summary of the Invention. The secondary amine of compounds of formula (1-6) can be protected by one skilled in the art. One particular protecting group is the t-butoxycarbonyl moiety that can be installed upon treatment with di-tert-butyl dicarbonate in the presence of a base such as triethylamine in heated dichloromethane thus giving compounds of formula (1-5). Compounds of formula (1-5) can be reduced with borane in heated tetrahydrofuran to give diazepines of formula (6-1). The t-butoxycarbonyl group can be removed from compounds of formula (6-1) by treatment with an acid such as hydrochloric acid or trifluoroacetic acid in a solvent such as dioxane or dichloromethane at ambient or elevated temperature to give compounds of formula (6-2) which are representative of compounds of formula (I).

Scheme 6

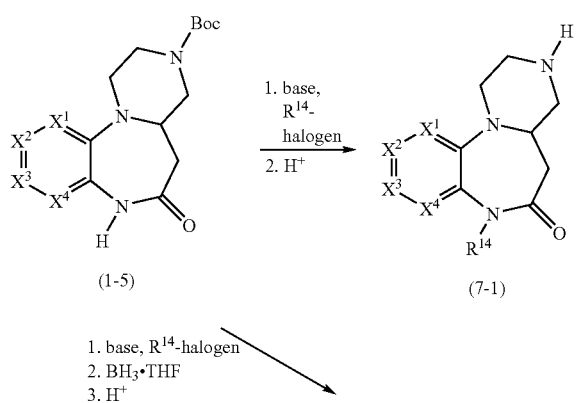

As outlined in Scheme 7, compounds of formula (7-1) and (7-2), wherein $R^{14}$, $X^1$, $X^2$, $X^3$ and $X^4$ are as defined in the Summary of the Invention provided that $R^{14}$ is other than hydrogen, can be prepared from compounds of formula (1-5). To that end, compounds of formula (1-5) can be treated with a base such as sodium hydride in a solvent such as N,N-dimethylformamide at ambient temperature. Subsequent addition with a compound of formula $R^{14}$-halogen, i.e., methyl iodide, ethyl iodide or a benzyl bromide, introduces the $R^{14}$ group. Removal of the t-butoxycarbonyl group as described in Scheme 6 provides compounds of formula (7-1) which are representative of compounds of formula (I). After introduction of the $R^{14}$ group, the diazepinone can be reduced to the corresponding diazepine with borane as described in Scheme 6. Removal of the t-butoxycarbonyl group provides compounds of formula (7-2) which are also representative of compounds of formula (I).

Scheme 8

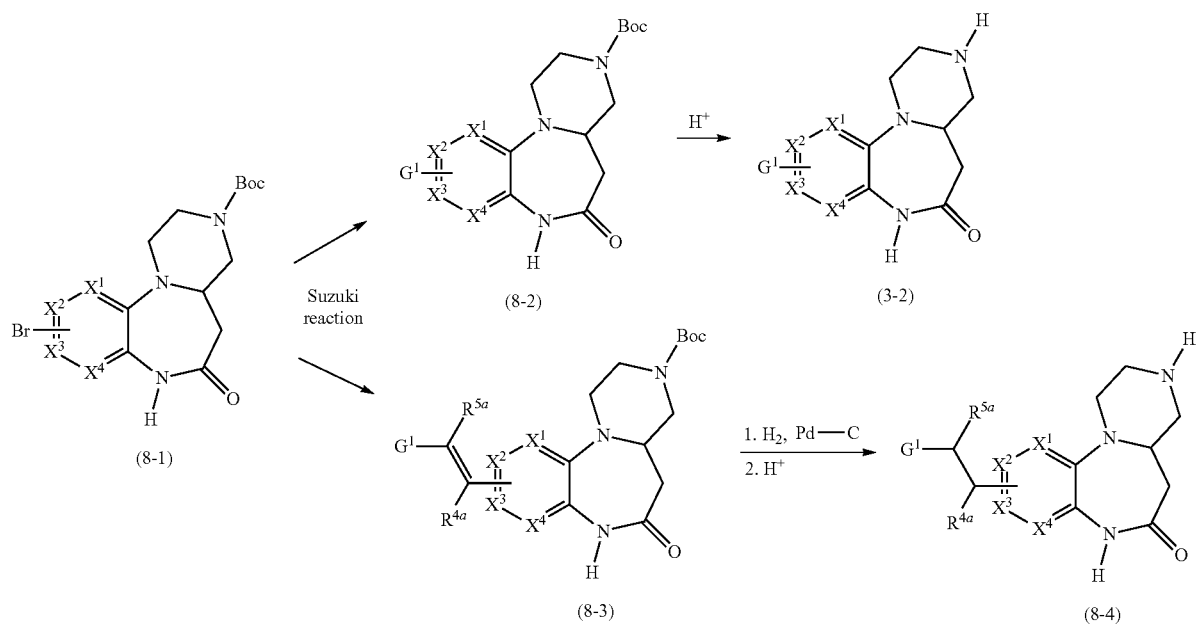

-continued

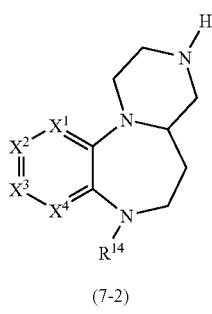

(7-2)

As outlined in Scheme 8, compounds of formula (8-1) can be transformed to compounds of formulas (3-2) or (8-4), wherein $G^1$, $R^{4a}$, $R^{5a}$, $X^1$, $X^2$, $X^3$ and $X^4$ are as defined in the Summary of the Invention. Compounds of formula (8-1), wherein one of $X^1$, $X^2$, $X^3$ or $X^4$ is CBr, can undergo a Suzuki reaction as described in Scheme 3 to give compounds of formulas (8-2) or (8-3). Compounds of formula (8-2) can be treated with an acid such as hydrochloric acid or trifluoroacetic acid in solvents such as dioxane or dichloromethane to give compounds of formula (3-2). Compounds of formula (8-3) can be reduced with hydrogen in the presence of a catalyst such as palladium on carbon in a solvent such as ethanol. Subsequent removal of the t-butoxycarbonyl moiety delivers compounds of formula (8-4). Compounds of formulas (3-2) and (8-4) are representative of compounds of formula (I).

Scheme 9

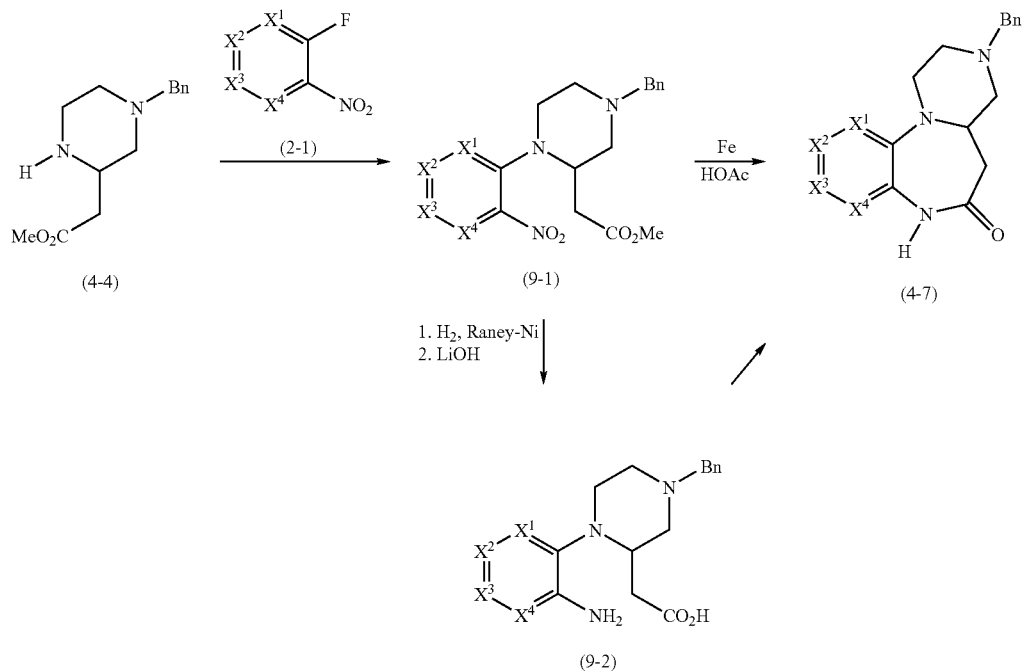

Scheme 9 outlines an alternative approach to the synthesis of compounds of formula (4-7), wherein $X^1$, $X^2$, $X^3$ and $X^4$ are as defined in the Summary of the Invention. Compound (4-4) can be reacted with compounds of formula (2-1) either heated neat or in the presence of a base such as potassium carbonate in heated N,N-dimethylformamide to supply compounds of formula (9-1). Compounds of formula (9-1) can then be reduced and cyclized in one step upon treatment with iron in heated acetic acid to provide compounds of formula (4-7). Alternatively, compounds of formula (9-1) can be reduced with hydrogen in the presence of Raney®-nickel to give the corresponding aniline. Subsequently the ester moiety can be hydrolyzed with a base such as lithium hydroxide provides compounds of formula (9-2). Compounds of formula (9-2) are cyclized to compounds of formula (4-7) using the amide bond coupling conditions described in Schemes 1 and 2. Compounds of formula (4-7) are representative of compounds of formula (I).

Scheme 10

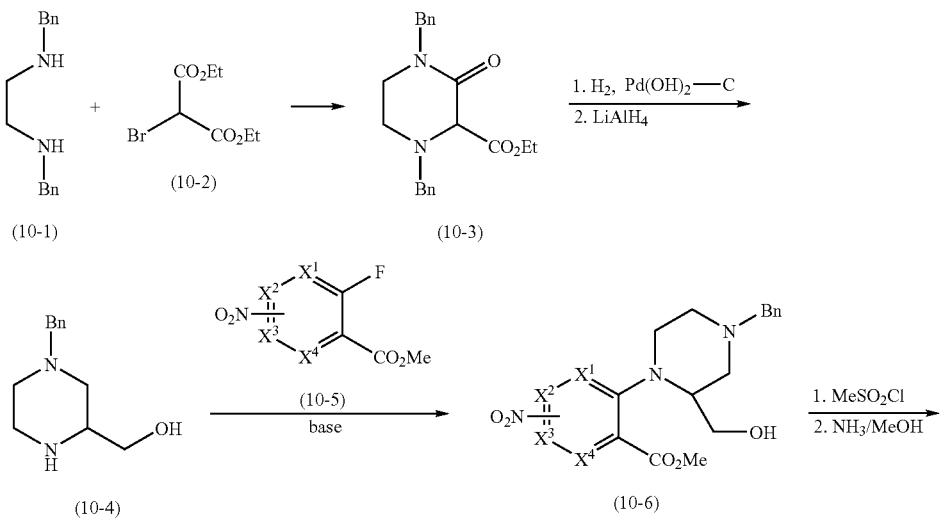

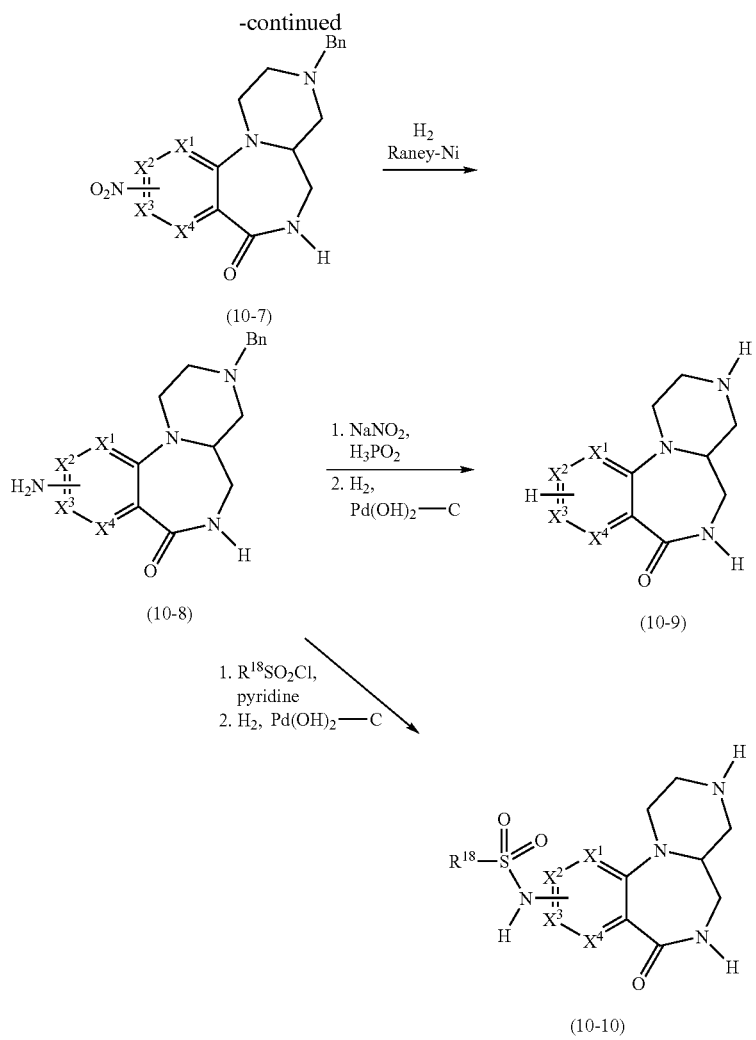

As outlined in Scheme 10, compounds of formula (10-1) and (10-2) are starting materials in the synthetic sequence for the preparation of compounds of formulas (10-9) and (10-10) wherein $X^1$, $X^2$, $X^3$ and $X^4$ are as defined in the Summary of the Invention and $R^{18}$ is alkyl, aryl or heteroaryl. Combining compounds of formulas (10-1) and (10-2) in heated acetonitrile gives compound (10-3). Hydrogenation in the presence of palladium hydroxide on carbon in heated ethanol selectively removes the benzyl group from the nitrogen in the position alpha to the carboethoxy group. Subsequent reduction with lithium aluminum hydride in tetrahydrofuran at ambient temperature removes all carbonyl functionalities and delivers compound (10-4). Reaction of compound (10-4) with compounds of formula (10-5) in the presence of a base such as diisopropylethylamine in heated N-methyl-2-pyrrolidinone gives compounds of formula (10-6). Activation of the hydroxy moiety of compounds of formula (10-6) is achieved with exposure methanesulfonyl chloride in dichloromethane in the presence of triethylamine. Subsequent exposure to ammonia in ethanol in a heated pressure reactor results in displacement of the sulfonate by ammonia and cyclization to diazepinones of formula (10-7). The nitro group of compounds of formula (10-7) can then be reduced to the corresponding amine by treatment with hydrogen and Raney®-nickel in a pressure reactor in heated methanol to supply compounds of formula (10-8). The amine of compounds of formula (10-8) can then be removed by treatment with sodium nitrite and hypophosphorous acid in water. The benzyl group can then be removed by hydrogenation in the presence of palladium hydroxide on carbon in heated ethanol in a pressure reactor to give compounds of formula (10-9) which are representative of compounds of formula (I) wherein one of $X^1$, $X^2$, $X^3$ or $X^4$ is CH. Alternatively, compounds of formula (10-8) can be sulfonylated with $R^{18}SO_2Cl$ in pyridine. Hydrogenation removes the benzyl group to give compounds of formula (10-10) which are representative of compounds of formula (I).

Scheme 11

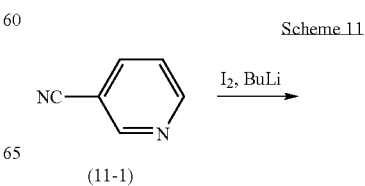

-continued

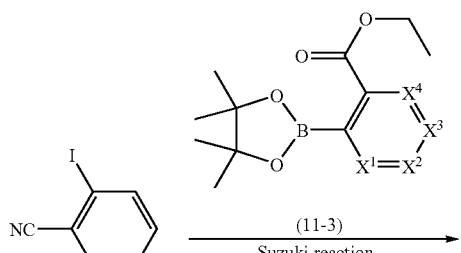

(11-2)

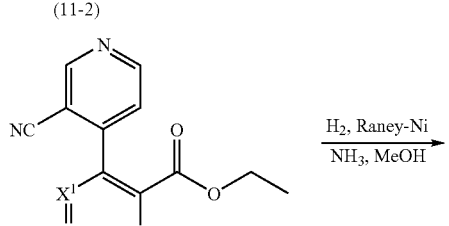

(11-4)

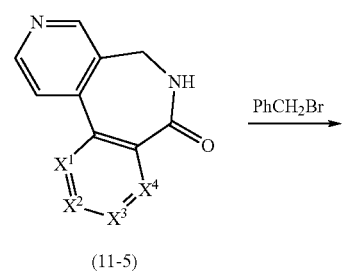

(11-5)

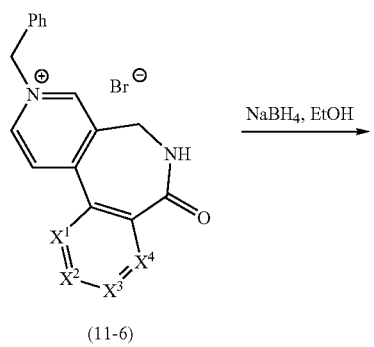

(11-6)

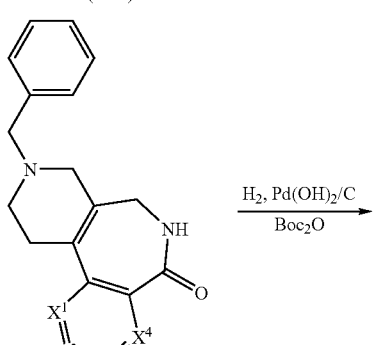

(11-7)

-continued

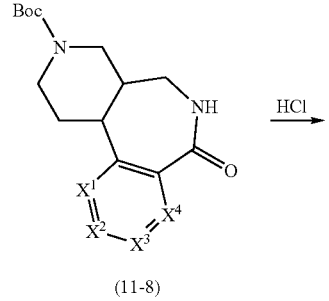

(11-8)

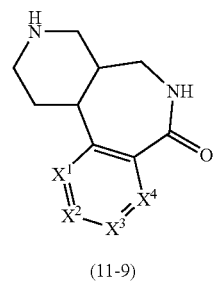

(11-9)

As outlined in Scheme 11, compounds of formula (11-9), wherein $X^1$, $X^2$, $X^3$ and $X^4$ are as defined in the Summary of the Invention, can be prepared from compound (11-1). Upon treatment with butyllithium and iodine, compound (11-1) is converted to compound (11-2). Compound (11-2) can then be treated with a compound of formula (11-3) or the corresponding boronic acid using the Suzuki reaction conditions described in Scheme 3 to supply compounds of formula (11-4). Compounds of formula (11-4) can then be treated with hydrogen in the presence of Raney® nickel and ammonia in a heated solvent such as methanol or ethanol to give compounds of formula (11-5). Compounds of formula (11-5) can then be treated with benzyl bromide in a solvent such as toluene or acetonitrile which may optionally be heated to supply compounds of formula (11-6). Compounds of formula (11-6) can then be reduced with a reagent such as sodium borohydride in a solvent such as ethanol to give compounds of formula (11-7). Compounds of formula (11-7) can then be reduced with hydrogen in the presence of a catalyst such as palladium(II) hydroxide on carbon to remove the benzyl group and completely saturate the piperidine ring. Inclusion of di-tert-butyl dicarbonate in the reaction mixture results in in situ introduction of a t-butoxycarbonyl group to deliver compounds of formula (11-8). The lactam nitrogen can optionally be functionalized at this point as described in Scheme 7. The t-butoxycarbonyl group of compounds of formula (11-8) can be removed under the acidic conditions describe in Scheme 1 to supply compounds of formula (11-9) which are representative of compounds of formula (I). Compounds of formula (11-9) can be further elaborated on the piperidine nitrogen as described in Scheme 1.

Scheme 12

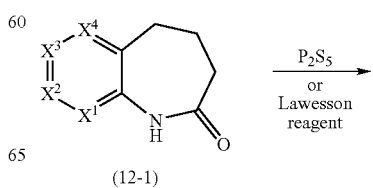

(12-1)

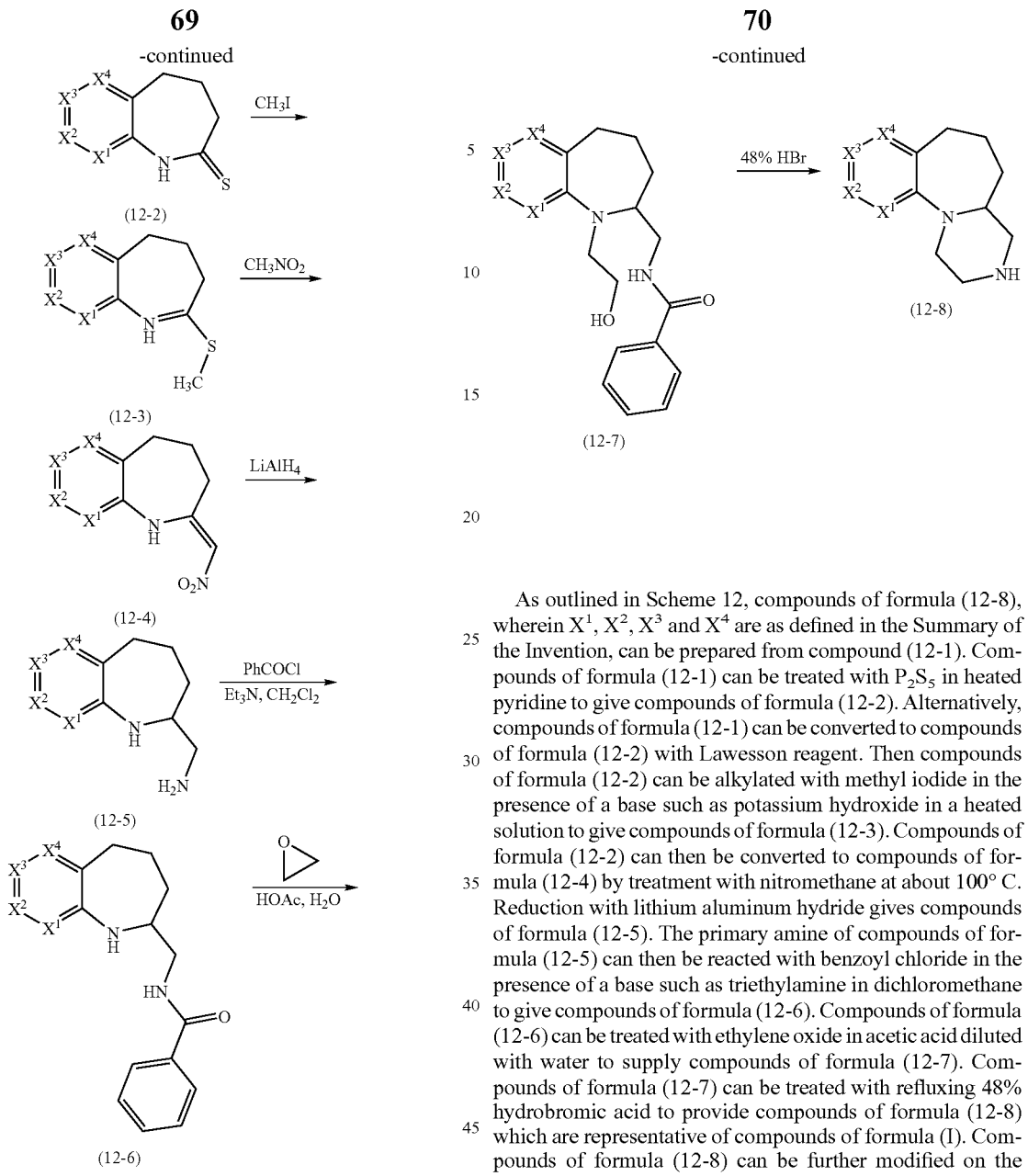

As outlined in Scheme 12, compounds of formula (12-8), wherein $X^1$, $X^2$, $X^3$ and $X^4$ are as defined in the Summary of the Invention, can be prepared from compound (12-1). Compounds of formula (12-1) can be treated with $P_2S_5$ in heated pyridine to give compounds of formula (12-2). Alternatively, compounds of formula (12-1) can be converted to compounds of formula (12-2) with Lawesson reagent. Then compounds of formula (12-2) can be alkylated with methyl iodide in the presence of a base such as potassium hydroxide in a heated solution to give compounds of formula (12-3). Compounds of formula (12-2) can then be converted to compounds of formula (12-4) by treatment with nitromethane at about 100° C. Reduction with lithium aluminum hydride gives compounds of formula (12-5). The primary amine of compounds of formula (12-5) can then be reacted with benzoyl chloride in the presence of a base such as triethylamine in dichloromethane to give compounds of formula (12-6). Compounds of formula (12-6) can be treated with ethylene oxide in acetic acid diluted with water to supply compounds of formula (12-7). Compounds of formula (12-7) can be treated with refluxing 48% hydrobromic acid to provide compounds of formula (12-8) which are representative of compounds of formula (I). Compounds of formula (12-8) can be further modified on the piperazine NH as described in Scheme 1.

Scheme 13

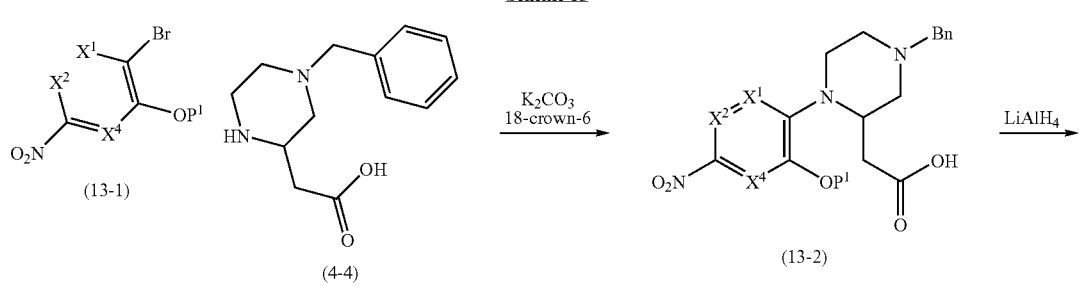

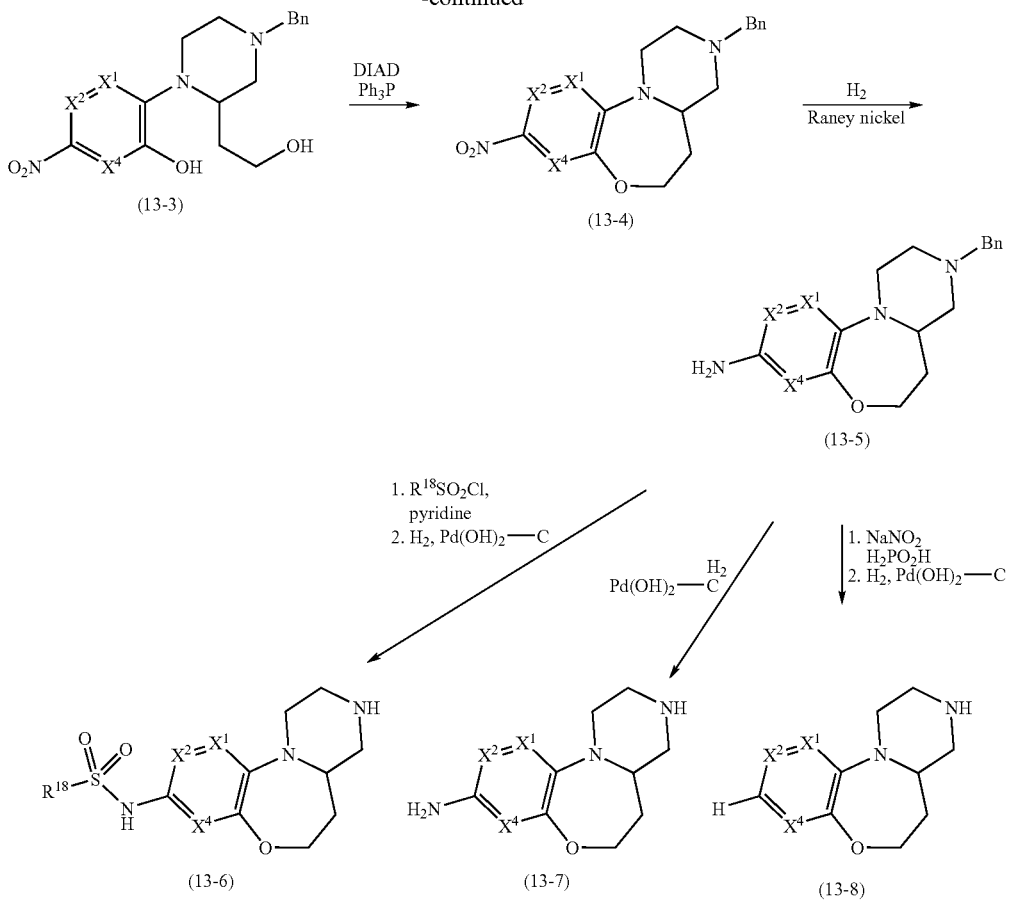

As outlined in Scheme 13, compounds of formula (13-5), (13-6), (13-7) and (13-8) wherein $X^1$, $X^2$ and $X^4$ are as described in the Summary of the Invention can be prepared from compounds of formula (13-1) wherein $P^1$ is hydrogen or a protecting group installed appropriately by one with skill in the art. Compounds of formula (13-1) can be reacted with compound (4-4) in the presence of a base such as potassium carbonate and 18-crown-6 in heated N,N-dimethylformamide to give compounds of formula (13-2). Compounds of formula (13-2) can subsequently be reduced with lithium aluminum hydride to give compounds of formula (13-3). For compounds of formula (13-2), wherein $P^1$ is a protecting group, one skilled in the art would remove the protecting group at this point. Then a Mitsunobu reaction with diisopropyl azodicarboxylate and triphenylphosphine gives cyclization to compounds of formula (13-4). Then nitro group of compounds of formula (13-4) can be reduced to the corresponding anilines of formula (13-5) with hydrogen and Raney® nickel catalyst. Compounds of formula (13-5) can be sulfonylated followed by subsequent benzyl group removal as described in the transformation of (10-8) to (10-10) to give compounds of formula (13-6) which are representative of compounds of formula (I) wherein $R^{18}$ is as described in Scheme 10. Compounds of formula (13-5) can also by hydrogenated to give compounds of formula (13-7) which are representative of compounds of formula (I). Also, the aniline of compounds of formula (13-5) can be removed with Sandmeyer reaction conditions and the benzyl group removed by hydrogenolysis to give compounds of formula (13-8) which are representative of compounds of formula (I).

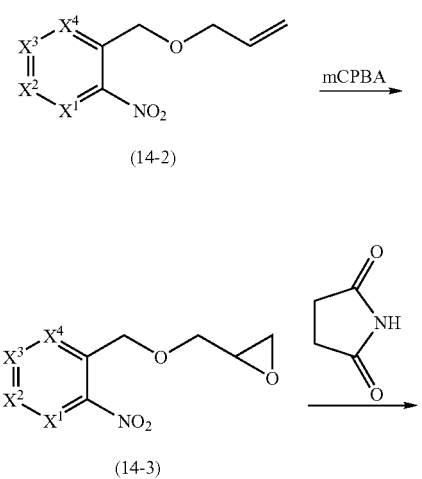

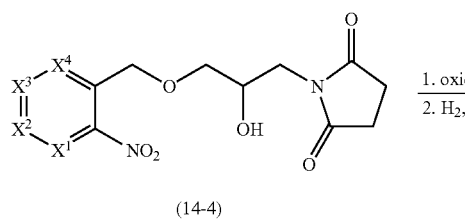

(14-4)

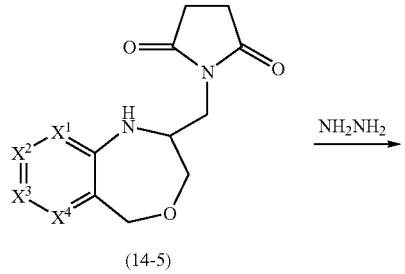

(14-5)

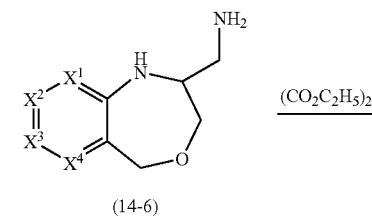

(14-6)

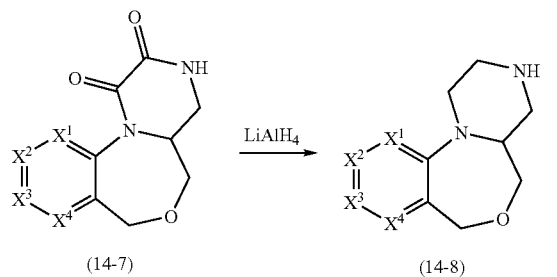

(14-7)   (14-8)

As outlined in Scheme 14, compounds of formula (14-8) wherein $X^1$, $X^2$, $X^3$ and $X^4$ are as defined in the Summary of the Invention, can be prepared from compound (14-1). Compounds of formulas (14-2), (14-3), (14-4), (14-5), and (14-6) can be prepared as described in Banzatti, C. et al., *J. Heterocyclic Chemistry* 1983, 139-144. In brief, compounds of formula (14-1) can be treated with sodium allyloxide to give compounds of formula (14-2). Compounds of formula (14-2) can be converted to the corresponding epoxides (14-3) upon treatment with m-chloroperoxybenzoic acid in dichloromethane. The epoxide can be opened with succinimide in the presence of a base such as pyridine in refluxing ethanol to give compounds of formula (14-4). The secondary alcohol group in compounds of formula (14-4) can be oxidized with Jones reagent, Dess-Martin periodinane, or pyridinium chlorochromate or other means by one with ordinary skill in the art. Subsequent reduction of the nitro group with hydrogen in the presence of palladium on carbon in warmed ethanol results in cyclization to oxazepines (14-5). Treatment of compounds of formula (14-5) with hydrazine reveals the primary amine in compounds of formula (14-6) which upon reaction with diethyl oxalate gives compounds of formula (14-7). Reduction with a reagent such as lithium aluminum hydride provides compounds of formula (14-8) which are representative of compounds of formula (I).

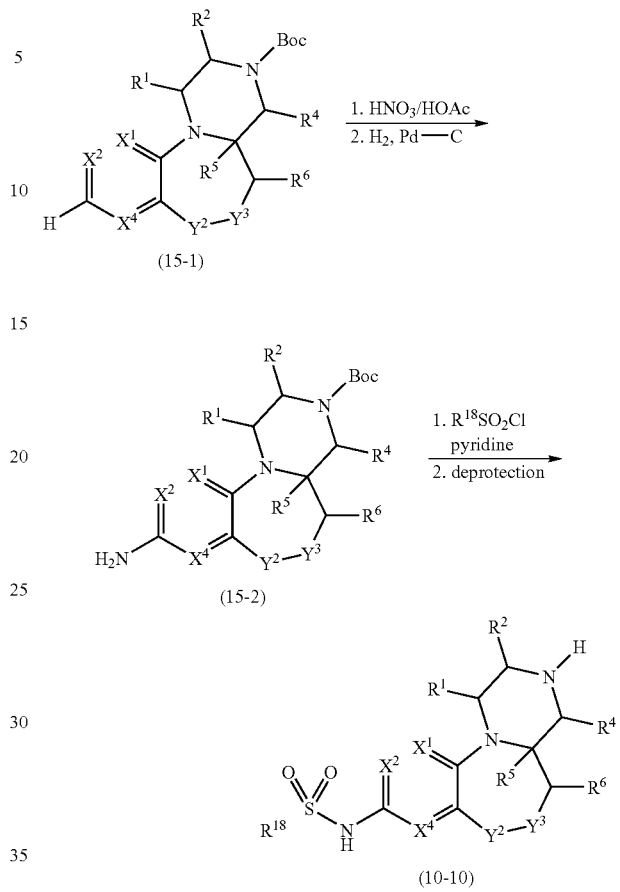

As outlined in Scheme 15, compounds of formula (10-10) which are representative of compounds of formula (I), wherein $R^1$, $R^2$, $R^4$, $R^5$, $R^6$, $X^1$, $X^2$, $X^4$, $Y^2$, and $Y^3$ are as defined in the Summary of the Invention and $R^{18}$ is alkyl, aryl or heteroaryl, can be prepared from compounds of formula (15-1). Compounds of formula (15-1) can be nitrated with nitric acid in acetic acid, and the introduced nitro moiety may be subsequently reduced with hydrogen in the presence of a catalyst to give compounds of formula (15-2). Compounds of (15-2) can then be reacted with a sulfonyl chloride of formula $R^{18}SO_2Cl$ in pyridine to form the corresponding sulfonamide. The piperazine protecting group can then be removed under acid conditions well known to one skilled in the art to give compounds of formula (10-10).

Scheme 16

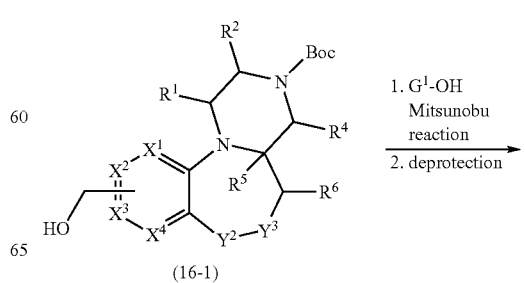

(16-1)

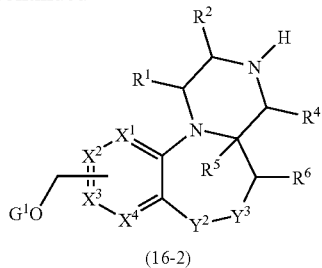

(16-2)

As outlined in Scheme 16, compounds of formula (16-2) which are representative of compounds of formula (I), wherein $G^1$, $R^1$, $R^2$, $R^4$, $R^5$, $R^6$, $X^1$, $X^2$, $X^3$, $X^4$, $Y^2$, and $Y^3$ are as defined in the Summary of the Invention, can be prepared from compounds of formula (16-1) Compounds of formula (16-1) can be reacted with compounds of formula $G^1$-OH under Mitsunobu reaction conditions known to one skilled in the art. For example, compound (16-1) may be dissolved in a solvent such as tetrahydrofuran in the presence of triphenylphosphine, optionally on a polymer support, and di-tert-butyl azodicarboxylate and reacted at room temperature over 8 to 24 hours with an optionally substituted phenol Subsequent removal of the tert-butoxy carbonyl group under acidic conditions can deliver compounds of formula (16-2).

Subsequent removal of the tert-butoxy carbonyl group under acidic conditions can deliver compounds of formula (17-2).

Similarly, compounds of formula (17-1) can be reacted with compounds of formulas $G^1$-$(CR^{4a}R^{5a})_m$—OH or $G^2$-$(CR^{4a}R^{5a})_m$—OH, wherein $G^1$, $G^2$, $R^{4a}$, $R^{5a}$, and $m$ are as defined in the Summary of the Invention, under Mitsunobu reaction conditions to give compounds of formula (17-3). Alternatively, compounds of formula (17-1) can be alkylated with compounds of formulas $G^1$-$(CR^{4a}R^{5a})_m$—Br or $G^2$-$(CR^{4a}R^{5a})_m$—Br in the presence of a base such as but not limited to potassium carbonate and sodium iodide in solvent such as acetone to provide compounds of formula (17-3).

Scheme 18

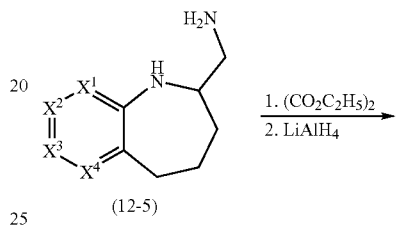

(12-5)

Scheme 17

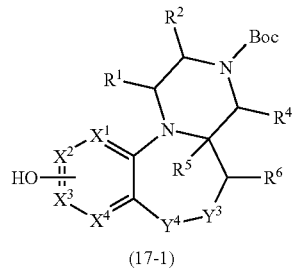

(17-1)

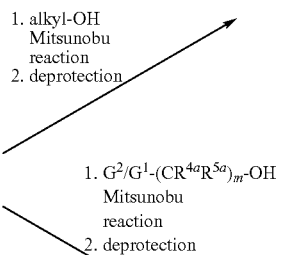

(17-2)

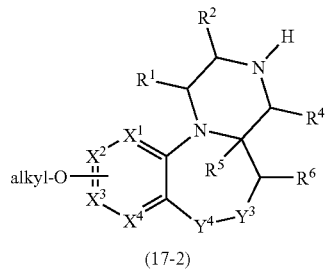

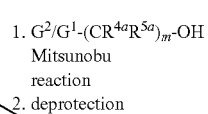

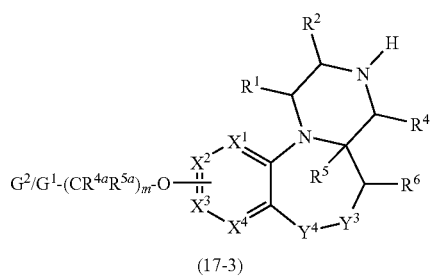

(17-3)

As outlined in Scheme 17, compounds of formula (17-2) and (17-3) which are representative of compounds of formula (I), wherein $G^1$, $G^2$, $R^1$, $R^2$, $R^4$, $R^5$, $R^6$, $X^1$, $X^2$, $X^3$, $X^4$, $Y^2$, and $Y^3$ are as defined in the Summary of the Invention, can be prepared from compounds of formula (17-1) Compounds of formula (17-1) can be reacted with compounds of formula alkyl-OH under Mitsunobu reaction conditions known to one skilled in the art. For example, compound (17-1) may be dissolved in a solvent such as tetrahydrofuran in the presence of triphenylphosphine, optionally on a polymer support, and di-tert-butyl azodicarboxylate and reacted at room temperature over 8 to 24 hours with an optionally substituted phenol -continued

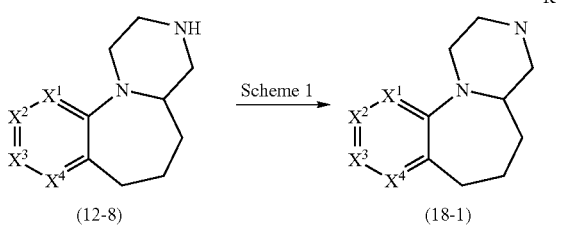

(12-8)      (18-1)

As depicted in Scheme 18, compounds of formula (12-5), wherein $X^1$, $X^2$, $X^3$ and $X^4$ are as defined in the Summary of the Invention, can be converted to compounds of formulas (12-8) and subsequently compounds of formula (18-1). Compounds of formula (12-5) can be reacted with diethyl oxalate and the resultant intermediate can then be reduced with lithium aluminum hydride as described in Scheme 14 to give compounds of formula (12-8). Compounds of formula (12-8) can then be converted to compounds of formula (18-1) using the methodologies described in Scheme 1 to introduce $R^3$. $R^3$ is as defined in the Summary of the Invention. Compounds of formulas (12-8) and (18-1) are representative of compounds of formula (I).

Scheme 19

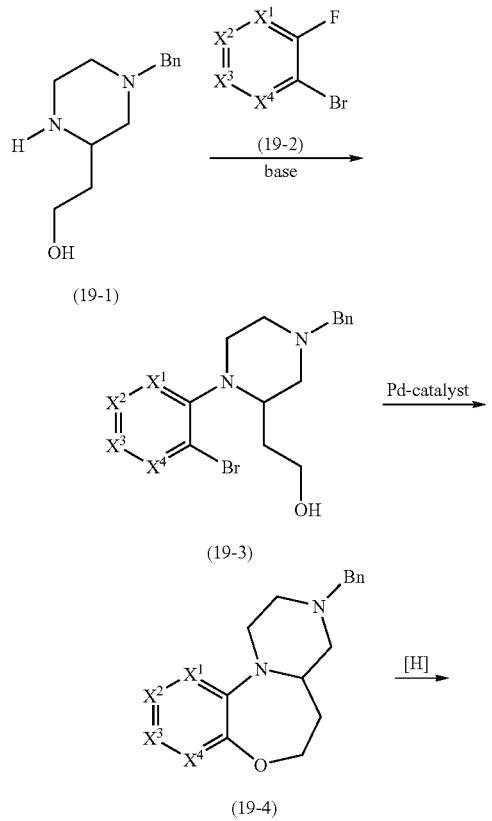

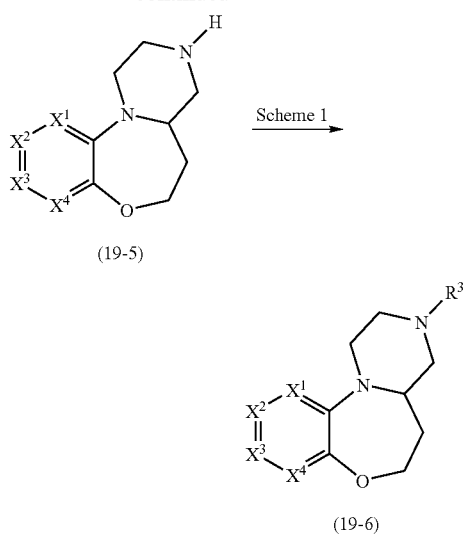

As shown in Scheme 19, compounds of formulas (19-5) and (19-6), wherein $R^3$, $X^1$, $X^2$, $X^3$ and $X^4$ are as defined in the Summary of the Invention, can be prepared from a compound of formula (19-1). A compound of formula (19-1) can be reacted with a compound of formula (19-2) in the presence of a base such as sodium tert-butoxide in dimethyl sulfoxide over 8 to 24 hours to supply compounds of formula (19-3). Compounds of formula (19-3) can then be cyclized in the presence of a palladium catalyst such as tris(dibenzylideneacetone)dipalladium (0), ligand such as 2'-(di-tert-butylphosphino)-N,N-dimethylbiphenyl-2-amine, and base such as sodium or potassium tert-butoxide in toluene either conventionally heated or heated in a microwave reactor to give compounds of formula (19-4). Then benzyl group of compounds of formula (19-4) can be reductively removed with hydrogen in the presence of a palladium catalyst to give compounds of formula (19-5). Compounds of formula (19-5) can be converted to compounds of formula (19-6) using the methodologies described in Scheme 1 to introduce $R^3$. Compounds of formulas (19-4), (19-5) and (19-6) are representative of compounds of formula (I).

Scheme 20

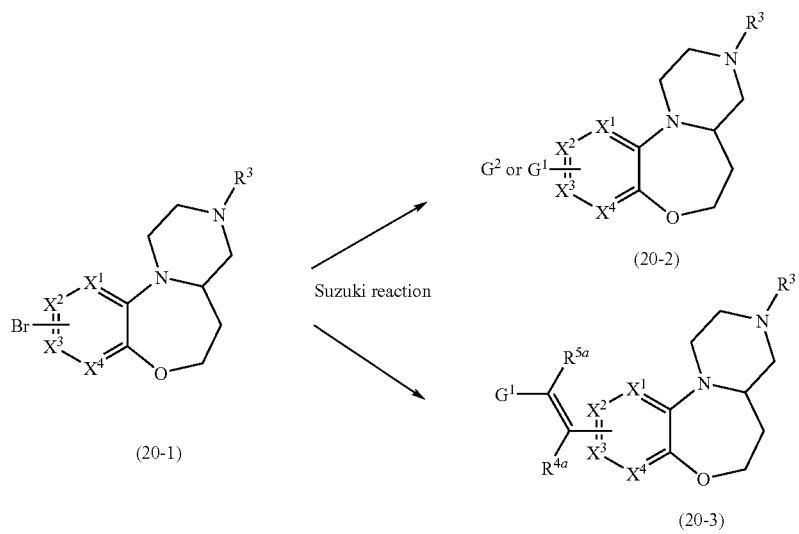

As outlined in Scheme 20, compounds of formula (20-2) and (20-3) which are representative of compounds of formula (I), wherein $G^1$, $G^2$, $R^{4a}$, $R^{5a}$, $X^1$, $X^2$, $X^3$, and $X^4$ are as defined in the Summary of the Invention can be prepared from compounds of formula (20-1), wherein one of $X^1$, $X^2$, $X^3$, or $X^4$ is CBr. Compounds of formula (20-1) are transformed to compounds of formula (20-2) and (20-3) under Suzuki reaction conditions wherein compounds of (20-1) are reacted with an aryl, heteroaryl, heterocyclic, cycloalkyl or vinyl boronic acid or boronate. The reaction typically requires the use of a base and a catalyst. Examples of bases include but are not limited to $K_2CO_3$, potassium t-butoxide, $Na_2CO_3$, $Cs_2CO_3$, and CsF. Examples of catalysts include but are not limited to tetrakis(triphenylphosphine)palladium (0), dichloro[1,1'-bis(diphenylphosphino)ferrocene]palladium(II) dichloromethane adduct, tris(dibenzylideneacetone)dipalladium (0), palladium(II) acetate, dichlorobis(triphenylphosphine)palladium(II), FC1007™. An optional ligand may be added such as dicyclohexyl(2',6'-dimethoxybiphenyl-2-yl-phosphine. The reaction may be conducted in a solvent such as but not limited to water, dioxane, 1,2-dimethoxyethane, N,N-dimethylformamide, toluene, ethanol, tetrahydrofuran and the like or mixtures thereof. The reaction may be conducted at ambient or elevated temperatures using conventional heating or microwave irradiation.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

g. EXAMPLES

The compounds and processes of the present invention will be better understood by reference to the following Examples, which are intended as an illustration of and not a limitation upon the scope of the application.

Abbreviations: APCI for atmospheric pressure chemical ionization; Boc for tert-butoxy carbonyl; Bu for butyl; DCI for desorption chemical ionization; DMSO for dimethyl sulfoxide; eq for equivalent(s); ESI for electrospray ionization; HPLC for high performance liquid chromatography; id for internal diameter; LC/MS for liquid chromatography/mass spectrometry; MP for macroporous resin; PS for polymer supported; psi for pounds per square inch; SFC for supercritical fluid chromatography; SPE for solid phase extraction, and tBu for tert-butyl.

Preparative HPLC procedure: Samples were purified by preparative HPLC on a Phenomenex Luna C8(2) 5 μm 100 Å AXIA column (30 mm×75 mm) A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). Samples were injected in 1.5 mL dimethyl sulfoxide:methanol (1:1). With specified samples, ammonium acetate was used instead of trifluoroacetic acid. A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan LCQ using 70:30 methanol:10 mM $NH_4OH$ (aqueous) at a flow rate of 0.8 mL/minute. Loop-injection mass spectra were acquired using a Finnigan LCQ running LCQ Navigator 1.2 software and a Gilson 215 liquid handler for fraction injection controlled by an Abbott developed Visual Basic application.

Example 1

1,2,3,4,4a,5-hexahydropyrazino[1,2-a][1,5]benzodiazepin-6(7H)-one

Example 1A 1-(9H-fluoren-9-yl)methyl 4-tert-butyl 2-(2-(2-bromophenylamino)-2-oxoethyl)piperazine-1,4-dicarboxylate To a solution of 2-bromoaniline (3.69 g, 21.44 mmol), and 2-(1-(((9H-fluoren-9-yl)methoxy)carbonyl)-4-(tert-butoxycarbonyl)piperazin-2-yl)acetic acid (10 g, 21.44 mmol) in a 1:1 solution of N,N-dimethylformamide:pyridine (100 mL) was added N-(3-dimethylaminopropyl)-N'-ethylcarbodiimide hydrochloride (10.27 g, 53.6 mmol). The reaction mixture was stirred at ambient temperature for 16 hours. The reaction mixture was partitioned between water and ethyl acetate. The organic layer was separated and was subsequently washed with brine (3×) and 1 M HCl (3×). The organic solution was then concentrated onto silica gel and purified via flash chromatography (10-70% ethyl acetate/hexanes) to afford the title compound. $^1$H NMR (400 MHz, DMSO-$d_6$) δ ppm 9.43 (s, 1 H), 7.81-7.95 (m, J=7.67 Hz, 2 H), 7.53-7.75 (m, 4 H), 7.22-7.48 (m, 5 H), 7.10 (dd, J=7.21 Hz, 1 H), 4.56 (s, 1 H), 4.17-4.42 (m, 3 H), 3.61-3.98 (m, 3 H), 2.89-3.18 (m, 2 H), 2.62-2.88 (m, 2 H), 2.49-2.58 (m, 1 H), 1.32-1.50 (m, 9 H); MS (APCI+) m/z 522.2 (M-Boc+H)$^+$.

Example 1B tert-butyl 3-(2-(2-bromophenylamino)-2-oxoethyl)piperazine-1-carboxylate To a solution of Example 1A (8.76 g, 14.12 mmol) in dichloromethane (100 mL) was added piperazine (3.65 g, 42.4 mmol). Methanol (50 mL) was added to the solution for solubility, and the resultant mixture was warmed to 40° C. for 14 hours. Once the reaction was complete, purification via flash chromatography (20-100% ethyl acetate/hexanes) afforded the title compound. $^1$H NMR (300 MHz, DMSO-$d_6$) δ ppm 10.34 (s, 1 H), 7.83 (d, J=7.12 Hz, 1 H), 7.64 (dd, J=7.97, 1.53 Hz, 1 H), 7.35 (dd, 1 H), 7.08 (dd, 1 H), 3.69-3.85 (m, 2 H), 2.70-2.99 (m, 3 H), 2.53-2.67 (m, 2 H), 2.42 (d, J=6.44 Hz, 2 H), 1.34-1.46 (m, 9 H); MS (APCI+) m/z 400.0 (M+H)$^+$.

Example 1C tert-butyl 6-oxo-1,2,4a,5,6,7-hexahydrobenzo[b]pyrazino[1,2-d][1,4]diazepine-3(4H)-carboxylate A pressure vial was loaded with Example 1B (4.81 g, 12.08 mmol), 1,3-bis(2,6-diisopropyl-phenyl)imidazolium chloride (2.053 g, 4.83 mmol), sodium t-butoxide (1.625 g, 16.91 mmol) and tris(dibenzylideneacetone)dipalladium (0) (1.106 g, 1.208 mmol) in dioxane (100 mL). The solution was heated at 120° C. for 3 days, or until starting material was gone according to LC/MS. The reaction mixture was concentrate onto silica gel and purified via flash chromatography (30-100% ethyl acetate/hexanes) to afford the title compound. $^1$H NMR (300 MHz, DMSO-$d_6$) δ ppm 9.57 (s, 1 H) 6.88-7.22 (m, 4 H), 3.80-4.00 (m, 2 H), 2.69-3.21 (m, 5 H), 2.52-2.61 (m, 1 H), 2.00 (d, J=13.48 Hz, 1 H), 1.43 (s, 9 H); MS (APCI+) m/z 318.1 (M+H)$^+$.

Example 1D 1,2,3,4,4a,5-hexahydropyrazino[1,2-a][1,5]benzodiazepin-6(7H)-one To a solution of Example 1C (1.78 g, 5.61 mmol) in dichloromethane (100 mL) was added 4 M HCl/dioxane (14.02 mL, 56.1 mmol). The solution was stirred for 2-4 hours at room temperature, and title compound was collected by filtration as the hydrochloric acid salt. $^1$H NMR (500 MHz, pyridine-$d_5$) δ ppm 7.34-7.42 (m, 1 H), 7.24-7.31 (m, 1 H), 7.16-7.23 (m, 1 H), 7.11 (d, J=7.02 Hz, 1 H), 3.92-4.00 (m, 1 H), 3.88 (d, J=11.90 Hz, 1 H), 3.80 (d, J=12.82 Hz, 1 H), 3.64-3.74 (m, 1 H), 3.57 (t, J=11.90 Hz, 1 H), 3.11-3.24 (m, 2 H), 2.64 (dd, J=13.43, 7.02 Hz, 1 H), 2.37 (d, J=12.82 Hz, 1 H); MS (ESI) m/z 217.9 (M+H)$^+$.

Example 2

(4aS)-1,2,3,4,4a,5-hexahydropyrazino[1,2-a][1,5]benzodiazepin-6(7H)-one

Example 2A (S)-tert-butyl 6-oxo-1,2,4a,5,6,7-hexahydrobenzo[b]pyrazino[1,2-d][1,4]diazepine-3(4H)-carboxylate Chiral separation was performed on Example 1C with a Berger Instruments PrepSFC™ system equipped with a Chiralpak® AD-H 21×250 mm SN column isocratically (30% methanol/CO$_2$). Retention time of the title compound was 14.8 minutes while that of the enantiomer was 5.5 minutes. $^1$H NMR (300 MHz, DMSO-$d_6$) δ ppm 9.57 (s, 1 H) 6.88-7.22 (m, 4 H) 3.80-4.00 (m, 2 H) 2.69-3.21 (m, 5 H) 2.52-2.61 (m, 1 H) 2.00 (d, J=13.48 Hz, 1 H) 1.43 (s, 9 H); MS (APCI+) m/z 318.1 (M+H)$^+$.

Example 2B (4aS)-1,2,3,4,4a,5-hexahydropyrazino[1,2-a][1,5]benzodiazepin-6(7H)-one The title compound was prepared according to the procedure outlined in Example 1D substituting Example 2A for Example 1C. $^1$H NMR (500 MHz, pyridine-$d_5$) δ ppm 7.34-7.42 (m, 1 H) 7.24-7.31 (m, 1 H) 7.16-7.23 (m, 1 H) 7.11 (d, J=7.02 Hz, 1 H) 3.92-4.00 (m, 1 H) 3.88 (d, J=11.90 Hz, 1 H) 3.80 (d, J=12.82 Hz, 1 H) 3.64-3.74 (m, 1 H) 3.57 (t, J=11.90 Hz, 1 H) 3.11-3.24 (m, 2 H) 2.64 (dd, J=13.43, 7.02 Hz, 1 H) 2.37 (d, J=12.82 Hz, 1 H); MS (ESI) m/z 217.9 (M+H)$^+$.

Example 3

10-chloro-1,2,3,4,4a,5-hexahydropyrazino[1,2-a][1,5]benzodiazepin-6(7H)-one

Example 3A 1-(9H-fluoren-9-yl)methyl 4-tert-butyl 2-(2-(2-bromo-4-chlorophenylamino)-2-oxoethyl)piperazine-1,4-dicarboxylate The title compound was prepared according to the procedure outlined in Example 1A substituting 2-bromo-4-chloroaniline for 2-bromoaniline (3.32 g, 16.08 mmol). $^1$H NMR (300 MHz, DMSO-$d_6$) δ ppm 9.52 (s, 1 H), 7.88 (d, J=7.54 Hz, 2 H), 7.77 (s, 1 H), 7.62 (t, J=8.33 Hz, 3 H), 7.40 (t, J=7.14

Hz, 3 H), 7.31 (t, J=7.34 Hz, 2 H), 4.46-4.62 (m, 1 H), 4.15-4.42 (m, 3 H), 3.63-3.96 (m, 3 H), 2.89-3.17 (m, 2 H), 2.60-2.87 (m, 2 H), 2.52-2.58 (m, 1 H), 1.39 (s, 9 H); MS (APCI+) m/z 656.1 (M+H)+.

Example 3B tert-butyl 3-(2-(2-bromo-4-chlorophenylamino)-2-oxoethyl)piperazine-1-carboxylate The title compound was prepared according to the procedure outlined in Example 1B substituting Example 3A for Example 1A. $^1$H NMR (300 MHz, DMSO-d$_6$) δ ppm 7.90 (d, J=9.12 Hz, 1 H), 7.77 (d, J=2.38 Hz, 1 H), 7.44 (dd, J=8.72, 2.38 Hz, 1 H), 3.63-3.88 (m, 2 H), 2.70-2.98 (m, 3 H), 2.54-2.65 (m, J=8.33 Hz, 2 H), 2.42 (d, J=6.35 Hz, 2 H); MS (APCI+) m/z 434.2 (M+H)+.

Example 3C tert-butyl 10-chloro-6-oxo-1,2,4a,5,6,7-hexahydrobenzo[b]pyrazino[1,2-d][1,4]diazepine-3(4H)-carboxylate A microwave vial was charged with Example 3B (1 eq, 102 mg, 0.236 mmol), dicyclohexyl(2',6'-dimethoxybiphenyl-2-yl)phosphine (0.2 eq, 19.5 mg, 0.047 mmol), sodium t-butoxide (1.4 eq, 31.9 mg, 0.331 mmol), tris(dibenzylideneacetone)dipalladium (0) (0.2 eq, 43.4 mg, 47 mmol) and t-butanol (2 mL). The reaction mixture was heated at 120° C. in a microwave (Biotage Initiator™, maximum 400 Watts) for 20 minutes. This was repeated 40 times. The solution from all tubes was combined, and concentrated onto silica gel. Purification via flash chromatography (0-50% ethyl acetate/hexanes) afforded the title compound. $^1$H NMR (300 MHz, DMSO-d$_6$) δ ppm 9.65 (s, 1 H), 7.03-7.13 (m, 2 H), 6.94 (d, J=8.33 Hz, 1 H), 3.85-4.00 (m, 2 H), 3.14-3.27 (m, 1 H), 2.95-3.13 (m, 2 H), 2.75-2.94 (m, 2 H), 2.58 (dd, J=13.48, 7.14 Hz, 1 H), 2.03 (d, J=13.48 Hz, 1H); MS (APCI+) m/z 352.1 (M+H)+.

Example 3D 10-chloro-1,2,3,4,4a,5-hexahydropyrazino[1,2-a][1,5]benzodiazepin-6(7H)-one To a solution of Example 3C (122 mg, 0.347 mmol) in dichloromethane (5 mL) was added HCl (4 M in dioxane, 0.867 mL, 3.47 mmol). After the reaction was complete by LC/MS analysis, the volatiles were removed in vacuo, and the residue was purified by preparative HPLC to afford the title compound. $^1$H NMR (500 MHz, DMSO-d$_6$/D$_2$O) δ ppm 7.12-7.20 (m, 2 H), 7.01 (d, J=8.24 Hz, 1 H), 3.61-3.69 (m, J=8.09 Hz, 1 H), 3.27-3.42 (m, 4 H), 2.94-3.08 (m, 2 H), 2.68 (dd, J=13.73, 7.02 Hz, 1 H), 2.08 (d, J=12.51 Hz, 1 H); MS (ESI) m/z 251.9 (M+H)+.

Example 4

10-bromo-1,2,3,4,4a,5-hexahydropyrazino[1,2-a][1,5]-benzodiazepin-6(7H)-one

Example 4A 2-(1-(5-bromo-2-nitrophenyl)-4-(tert-butoxycarbonyl)piperazin-2-yl)acetic acid 4-Bromo-2-fluoro-1-nitrobenzene (5.3 g, 24.1 mmol) was dissolved in acetonitrile (70 mL) and water (10 mL). To this mixture, potassium carbonate (10 g, 72.3 mmol) and 2-(4-(tert-butoxycarbonyl)piperazin-2-yl)acetic acid (7.1 g, 28.9 mmol) were added. The resulting mixture was heated at 70° C. for 2 days. The mixture thus obtained was concentrated and ethyl acetate was added. 1 N HCl was then added slowly to the reaction solution until pH=6. The water layer was separated and washed multiple times with ethyl acetate. The organic layers thus obtained were combined and concentrated. The crude material thus obtained was purified by silica gel chromatography eluting with a gradient of 0% to 10% of methanol in dichloromethane to afford the title compound. $^1$H NMR (300 MHz, DMSO-d$_6$) δ ppm 12.28 (br s), 7.71-7.83 (m, 1 H), 7.56-7.66 (m, 1 H), 7.30-7.40 (m, 1 H), 3.56-3.82 (m, 3 H), 3.33-3.44 (m, 1 H), 2.99-3.24 (m, 2 H), 2.87 (m, 1 H), 2.32-2.47 (m, 1 H), 2.17-2.29 (m, 1 H), 1.32-1.51 (s, 9 H); MS (DCI+) m/z 444.1 (M+H)+.

Example 4B tert-butyl 10-bromo-6-oxo-1,2,4a,5,6,7-hexahydrobenzo[b]pyrazino[1,2-d][1,4]diazepine-3(4H)-carboxylate Example 4A (4.6 g, 10.4 mmol) was dissolved in methanol (80 mL) and added to Raney®-nickel (water-wet, 8.26 g, 141 mmol) in a 250 mL stainless steel pressure bottle. The mixture was stirred under hydrogen (30 psi) at room temperature until HPLC indicated complete consumption of the starting material. The mixture was then filtered through a nylon membrane and concentrated. To this crude material were added N,N-dimethylformamide (20 mL), pyridine (20 mL) and N-(3-dimethylaminopropyl)-N'-ethylcarbodiimide hydrochloride (2.75 g, 14.3 mmol). The resulting mixture was shaken at room temperature for three hours at which point LC/MS indicated the completion of the reaction. The resulting solution was concentrated and partitioned between ethyl acetate and water. The water layer thus separated was washed two times with additional ethyl acetate. The organic layers were combined and concentrated. The crude material thus obtained was purified by silica gel chromatography eluting with a gradient of 0% to 60% of ethyl acetate in hexane to afford the title compound.
$^1$H NMR (300 MHz, DMSO-d$_6$) δ ppm 9.64 (br, 1 H), 7.17-7.25 (m, 2 H), 6.85-6.94 (m, 1 H), 3.92 (t, J=11, 10 Hz, 2 H), 3.15-3.26 (m, 1 H), 2.94-3.13 (m, 2 H), 2.85 (br, 2 H), 2.58 (dd, J=13.48, 6.74 Hz, 1 H), 2.03 (d, J=13.88 Hz, 1 H), 1.43 (s, 9 H); MS (DCI+) m/z 413.2 (m+NH$_4$)+.

Example 4C 10-bromo-1,2,3,4,4a,5-hexahydropyrazino[1,2-a][1,5]benzodiazepin-6(7H)-one Example 4B (24 mg, 0.061 mmol) in dioxane (0.1 mL) was added to 4 M HCl in dioxane (0.15 mL, 0.61 mmol). The mixture was shaken at room temperature overnight. The mixture was concentrated to afford the title compound as the bishydrochloric acid salt. $^1$H NMR (400 MHz, DMSO-d$_6$) δ ppm 9.74 (s, 1 H), 9.28 (br, 2 H), 7.19-7.35 (m, 2 H), 6.91 (d, J=7.98 Hz, 1 H), 3.61-3.75 (m, 1 H), 3.32-3.46 (m, 4 H), 2.89-3.10 (m, 2 H), 2.66 (dd, J=13.50, 6.75 Hz, 1 H), 2.07 (d, J=13.50 Hz, 1 H); MS (APCI+) m/z 295.8 (M+H)+.

Example 5

10-phenyl-1,2,3,4,4a,5-hexahydropyrazino[1,2-a][1,5]benzodiazepin-6(7H)-one

Example 4 (15 mg, 0.041 mmol) was added to a microwave tube (Biotage) followed by phenylboronic acid (6.0 mg, 0.049 mmol), ethanol (1 mL) and potassium carbonate (0.065 mL, 2 M aqueous solution). FC1007™ (10.4 mg, 0.36 mmol/g, Johnson Matthey) was then added, and the microwave tube was heated in a microwave (Biotage Initiator™) at 150° C. for 15 minutes. The reaction mixture thus obtained was passed through a 2 g Si-carbonate cartridge (SiliCylcle®) eluting with additional methanol. The solution thus collected was concentrated and purified by preparative HPLC to afford the title compound as the trifluoroacetic acid salt. $^1$H NMR (400 MHz, DMSO-$d_6$) δ ppm 9.75 (s, 1 H), 9.13 (br, 2 H), 7.68 (d, J=7.06 Hz, 2 H), 7.46 (t, J=7.67 Hz, 2 H), 7.29-7.40 (m, 3 H), 7.06 (d, J=7.98 Hz, 1 H), 3.56-3.70 (m, 1 H), 3.38-3.48 (m, 4 H), 2.96-3.16 (m, 2 H), 2.71 (dd, J=13.50, 7.06 Hz, 1 H), 2.09 (d, J=13.50 Hz, 1 H); MS (DCI+) m/z 294.2 (M+H)$^+$.

Example 6

10-[(E)-2-phenylvinyl]-1,2,3,4,4a,5-hexahydropyrazino[1,2-a][1,5]benzodiazepin-6(7H)-one The title compound was prepared as the bistrifluoroacetic acid salt according to the procedure outlined in Example 5 substituting cinnamylboronic acid for phenylboronic acid. $^1$H NMR (400 MHz, DMSO-$d_6$) δ ppm 9.73 (s, 1 H), 7.59 (d, J=7.36 Hz, 2 H), 7.21-7.45 (m, 7 H), 6.98 (d, J=7.98 Hz, 1 H), 3.55-3.64 (m, 1 H), 3.30-3.49 (m, 4H), 2.93-3.14 (m, 2 H), 2.62-2.73 (m, 1 H), 2.03-2.16 (m, 1 H); MS (DCI+) m/z 320.2 (M+H)$^+$.

Example 7

10-(3-chlorophenyl)-1,2,3,4,4a,5-hexahydropyrazino[1,2-a][1,5]benzodiazepin-6(7H)-one The title compound was prepared as the bistrifluoroacetic acid salt according to the procedure outlined in Example 5 substituting 3-chlorophenylboronic acid for phenylboronic acid. $^1$H NMR (400 MHz, DMSO-$d_6$) δ ppm 9.78 (br, 1 H), 9.05 (br, 2 H), 7.76 (t, J=1.84 Hz, 1 H), 7.66 (d, J=7.67 Hz, 1 H), 7.48 (t, J=7.98 Hz, 1 H), 7.34-7.43 (m, 3 H), 7.06 (d, J=7.98 Hz, 1 H), 3.59-3.67 (m, 1 H), 3.32-3.49 (m, 4H), 2.95-3.15 (m, 2 H), 2.70 (dd, J=13.35, 6.90 Hz, 1 H), 2.10 (d, J=13.50 Hz, 1 H); MS (DCI+) m/z 328.1 (M+H)$^+$.

Example 8

10-(2-chlorophenyl)-1,2,3,4,4a,5-hexahydropyrazino[1,2-a][1,5]benzodiazepin-6(7H)-one The title compound was prepared as the bistrifluoroacetic acid salt according to the procedure outlined in Example 5 substituting 2-chlorophenylboronic acid for phenylboronic acid. $^1$H NMR (400 MHz, DMSO-$d_6$) δ ppm 9.79 (br, 1 H), 8.83 br, 1 H), 7.53-7.59 (m, 1 H), 7.35-7.49 (m, 3 H), 7.11-7.19 (m, 2 H), 7.06 (d, J=7.98 Hz, 1 H), 3.55-3.67 (m, 1 H), 3.32-3.49 (m, 4H), 2.95-3.13 (m, J=11.97, 11.97 Hz, 2 H), 2.72 (dd, J=13.50, 7.06 Hz, 1 H), 2.10 (d, J=13.50 Hz, 1 H); MS (DCI+) m/z 328.1 (M+H)$^+$.

Example 9

10-[(E)-2-(3-fluorophenyl)vinyl]-1,2,3,4,4a,5-hexahydropyrazino[1,2-a][1,5]benzodiazepin-6(7H)-one The title compound was prepared as the trifluoroacetic acid salt according to the procedure outlined in Example 5 substituting (E)-3-fluorostyrylboronic acid for phenylboronic acid. $^1$H NMR (400 MHz, DMSO-$d_6$) δ ppm 9.71-9.79 (br, 1 H), 9.12 (br, 2 H), 7.56-7.74 (m, 2 H), 7.12-7.42 (m, 6 H), 6.95-7.03 (m, 1 H), 3.54-3.64 (m, 1 H), 3.32-3.46 (m, 4 H), 2.95-3.15 (m, 2 H), 2.64-2.72 (m, 1 H), 2.04-2.13 (m, 1 H); MS (DCI+) m/z 338.2 (M+H)$^+$.

Example 10

10-methyl-1,2,3,4,4a,5-hexahydropyrazino[1,2-a][1,5]benzodiazepin-6(7H)-one

Example 10A 2-(4-(tert-butoxycarbonyl)-1-(5-methyl-2-nitrophenyl)piperazin-2-yl)acetic acid The title compound was prepared according to the procedure outlined in Example 4A substituting 2-fluoro-4-methyl-1-nitrobenzene for 4-bromo-2-fluoro-1-nitrobenzene. $^1$H NMR (300 MHz, DMSO-$d_6$) δ ppm 12.30 (br, 1 H), 7.66-7.75 (s, 1 H), 7.14-7.34 (m, 1 H), 7.01 (d, J=8.33 Hz, 1 H), 3.40-3.73 (m, 4 H), 3.03-3.22 (m, 2 H), 2.82 (dd, J=8.53, 4.56 Hz, 1 H), 2.33-2.41 (m, 4 H), 2.07-2.20 (m, 1 H), 1.41 (s, 9 H); MS (DCI+) m/z 380.1 (M+H)$^+$.

Example 10B tert-butyl 10-methyl-6-oxo-1,2,4a,5,6,7-hexahydrobenzo[b]pyrazino[1,2-d][1,4]diazepine-3(4H)-carboxylate The title compound was prepared according to the procedure outlined in Example 4B substituting Example 10A for Example 4A. $^1$H NMR (300 MHz, DMSO-$d_6$) δ ppm 9.45 (br, 1 H), 6.89 (s, 1 H), 6.82 (br, 2 H), 3.82-3.98 (m, 2 H), 2.74-3.19 (m, 5 H), 2.47-2.53 (m, 1 H), 2.27 (s, 3 H), 1.91-2.04 (m, 1 H), 1.43 (s, 9 H); MS (DCI+) m/z 332.2 (M+H)$^+$.

Example 10C 10-methyl-1,2,3,4,4a,5-hexahydropyrazino[1,2-a][1,5]benzodiazepin-6(7H)-one The title compound was prepared as the hydrochloric acid salt according to the procedure outlined in Example 4C substituting Example 10B for Example 4B. $^1$H NMR (500 MHz, DMSO-$d_6$) δ ppm 9.58 (br, 1 H), 9.36 (br, 2 H), 6.94 (s, 1 H), 6.81-6.90 (m, 2 H), 3.58-3.65 (m, 2 H), 3.29-3.36 (m, 2 H), 3.24 (d, J=11.90 Hz, 1 H), 2.85-3.07 (m, 2 H), 2.59 (dd, J=13.43, 7.02 Hz, 1 H), 2.29 (s, 3 H), 2.02 (d, J=13.43 Hz, 1 H); MS (DCI+) m/z 230.0 (M+H)$^+$.

Example 11

6-oxo-1,2,3,4,4a,5,6,7-octahydropyrazino[1,2-a][1,5]benzodiazepine-10-carbonitrile Example 11A 2-(4-(tert-butoxycarbonyl)-1-(5-cyano-2-nitrophenyl)piperazin-2-yl)acetic acid The title compound was prepared according to the procedure outlined in Example 4A substituting 3-fluoro-4-nitrobenzonitrile for 4-bromo-2-fluoro-1-nitrobenzene. MS (DCI+) m/z 291.1 (M+H)$^+$.

Example 11B tert-butyl 10-cyano-6-oxo-1,2,4a,5,6,7-hexahydrobenzo[b]pyrazino[1,2-d][1,4]diazepine-3(4H)-carboxylate The title compound was prepared according to the procedure outlined in Example 4B substituting Example 11A for Example 4A. $^1$H NMR (300 MHz, DMSO-$d_6$) δ ppm 7.45-7.54 (m, 1 H), 7.07 (d, J=7.93 Hz, 1 H), 6.80-6.92 (m, 1 H), 3.82-3.99 (m, J=16.26 Hz, 2 H), 3.19-3.29 (m, 1 H), 2.74-3.18 (m, 4 H), 2.53-2.67 (m, J=6.74 Hz, 1 H), 1.91-2.17 (m, 1 H), 1.43 (s, 9 H); MS (DCI+) m/z 343.2 (M+H)$^+$.

Example 11C 6-oxo-1,2,3,4,4a,5,6,7-octahydropyrazino[1,2-a][1,5]benzodiazepine-10-carbonitrile The title compound was prepared as the hydrochloric acid salt according to the procedure outlined in Example 4C substituting Example 11B for Example 4B. $^1$H NMR (500 MHz, DMSO-$d_6$) δ ppm 10.11 (s, 1 H), 9.33 (s, 2 H), 7.61 (d, J=1.83 Hz, 1 H), 7.52 (dd, J=8.09, 1.68 Hz, 1 H), 7.10 (d, J=8.24 Hz, 1 H), 3.62-3.76 (m, 1 H), 3.36-3.52 (m, 4 H), 2.85-3.12 (m, 2 H), 2.69 (dd, J=13.58, 6.87 Hz, 1 H), 2.14 (d, J=13.73 Hz, 1 H); MS (DCI+) m/z 243.0 (M+H)$^+$.

Example 12

10-methoxy-1,2,3,4,4a,5-hexahydropyrazino[1,2-a][1,5]benzodiazepin-6(7H)-one

Example 12A

N$^1$-benzyl-N$^2$-tritylethane-1,2-diamine

Triethylamine (50.0 mL, 359 mmol) and a solution of trityl chloride (93 g, 326 mmol) in dichloromethane (251 mL) were added dropwise over 1 hour to an ice bath cooled solution of N$^1$-benzylethane-1,2-diamine (50 g, 326 mmol) in dichloromethane (251 mL) under argon. The mixture was then allowed to warm to room temperature and stirred for 48 hours. Water was added and the product was extracted with dichloromethane. The organic layer was washed with brine and water, dried over sodium sulfate and concentrated to afford the title compound. $^1$H NMR (500 MHz, DMSO-$d_6$) δ ppm 7.44-7.36 (m, 5H), 7.32-7.24 (m, 10H), 7.21-7.15 (m, 5H), 3.56 (s, 2H), 2.62 (t, J=6.1 Hz, 20H), 2.10 (d, J=6.6 Hz, 2H).

Example 12B (E)-methyl 4-(benzyl(2-(tritylamino)ethyl)amino)but-2-enoate

To a solution of Example 12A (128 g, 326 mmol) in acetonitrile (652 mL) was added (E)-methyl 4-bromobut-2-enoate (38.4 mL, 326 mmol) and potassium carbonate (90 g, 652 mmol), and the mixture was heated at 50° C. for 17 hours. A small amount of water was added, and the mixture was decanted into a separatory funnel. The solid left behind was washed three times with ethyl acetate, and the ethyl acetate washings were added to the separatory funnel followed by more water. The layers were separated and the organic layer was concentrated, then dissolved in dichloromethane and loaded onto a silica gel column packed in hexanes. The product was eluted with 15% ethyl acetate/hexanes to afford the title compound. $^1$H NMR (500 MHz, DMSO-$d_6$) δ ppm 7.38 (d, J=7.3 Hz, 5H), 7.31-7.12 (m, 15H), 6.83 (dt, J=5.6 Hz, 15.7 Hz, 1H), 6.07 (d, J=15.7 Hz, 1H), 3.67 (s, 3H), 3.42 (s, 2H), 3.05 (d, J=4.4 Hz, 2H), 2.58-2.49 (m, 2H), 2.11 (dd, J=6.2 Hz, 12.9 Hz, 2H).

Example 12C methyl 2-(4-benzylpiperazin-2-yl)acetate

To a solution of Example 12B (160 g, 326 mmol) in methanol (652 mL) was added 4 M HCl in dioxane (408 mL, 1630 mmol) and the mixture was heated at 50° C. for 3 hours. The solvent was then evaporated and water was added. A solid precipitates. The water layer was decanted and washed once with ethyl acetate. The solid was dissolved in ethyl acetate and extracted with water once. The water layers were combined and treated with 1 N NaOH (1 L) until pH=10. The free amine was extracted twice with dichloromethane, dried over sodium sulfate and concentrated to afford the title compound. $^1$H NMR (500 MHz, DMSO-$d_6$) δ ppm 7.34-7.20 (m, 5H), 3.57 (s, 3H), 3.42 (q, J=13.4 Hz, 2H), 2.96 (qd, J=2.7 Hz, 6.9 Hz, 1H), 2.78 (dt, J=2.9 Hz, 11.9 Hz, 1H), 2.69-2.60 (m, 2H), 2.55 (d, J=10.8 Hz, 1H), 2.30 (dd, J=3.2 Hz, 6.7 Hz, 2H), 1.92 (td, J=2.8 Hz, 10.6 Hz, 1H), 1.68 (t, J=10.0 Hz, 1H); MS (ESI) m/z 249.0 (M+H)$^+$.

Example 12D 2-(4-benzyl-1-(5-methoxy-2-nitrophenyl)piperazin-2-yl)acetic acid To a solution of Example 12C (0.907 g, 3.65 mmol) in acetonitrile (11.69 mL) was added 2-fluoro-4-methoxy-1-nitrobenzene (0.50 g, 2.92 mmol) and potassium carbonate (2.019 g, 14.61 mmol) in water (2.92 mL) followed by 18-crown-6 (0.039 g, 0.146 mmol), and the mixture was heated with an oil bath at 90° C. (reflux) for 24 hours. The solvent was evaporated and water was added followed by dichloromethane. The water phase was washed three times with dichloromethane to remove starting material and then acidified with 1 N HCl until pH=1. The acid product was extracted three times with dichloromethane, dried quickly with sodium sulfate and concentrated to give the title compound. MS (ESI) m/z 386.1 (M+H)$^+$.

Example 12E 2-(1-(2-amino-5-methoxyphenyl)-4-benzylpiperazin-2-yl)acetic acid Example 12D (0.50 g, 1.297 mmol) was added to a 250 mL stainless steel pressure bottle containing water-wet Raney®-nickel (2.350 g, 40.0 mmol) that had been washed three times with methanol. Methanol (47 mL) was added and the mixture was shaken at 50° C. under hydrogen (30 psi) for 30 minutes. Hydrogen uptake ceased at 20 minutes. HPLC analysis (Zorbax 4.6×75 mm SB—C8 3.5 μm, 20% to 90% acetonitrile/0.1% aqueous H$_3$PO$_4$ over 3 minutes, then hold for 3 minutes, 1.5 mL/minute. Retention times: starting material 1.95 minutes; product 0.52 minutes) confirmed clean and complete conversion. The mixture was filtered through a nylon membrane, the solution was evaporated and the title compound was used without additional purification. MS (ESI) m/z 356.1 (M+H)$^+$.

Example 12F 3-benzyl-10-methoxy-1,2,3,4,4a,5-hexahydrobenzo[b]pyrazino[1,2-d][1,4]diazepin-6(7H)-one To a solution of Example 12E (0.390 g, 1.097 mmol) in N,N-dimethylformamide (3.66 mL) were added pyridine (4.44 mL, 54.9 mmol) and N-(3-dimethylaminopropyl)-N'-ethylcarbodiimide hydrochloride (0.421 g, 2.195 mmol) and the mixture was stirred at room temperature for 1 hour. The solution was concentrated, water was added to the residue, and the product was extracted twice with ethyl acetate. The combined organic washes were dried over sodium sulfate, concentrated and dried under vacuum at room temperature overnight. It was then passed through a 5 gram silica gel cartridge eluting first with dichloromethane, then with 2% methanol/dichloromethane and finally with 5% methanol/dichloromethane to obtain the title compound. An aliquot of material was further purified for analytical purposes by preparative HPLC to afford the title compound as the trifluoroacetic acid salt. $^1$H NMR (500 MHz, DMSO-$d_6$) δ ppm 10.21 (s, 1H), 9.52 (s, 1H), 7.54-7.48 (m, 5H), 6.90 (d, J=8.6, 1H), 6.70-6.60 (m, 2H), 4.45 (s, 2H), 3.74 (s, 3H), 3.67-3.07 (m, 7H), 3.22-3.04 (m, 2H), 2.61 (dd, J=7.0, 13.5, 1H), 2.00 (d, J=13.5, 1H); MS (ESI) m/z 338.1 (M+H)$^+$.

Example 12G 10-methoxy-1,2,3,4,4a,5-hexahydropyrazino[1,2-a][1,5]benzodiazepin-6(7H)-one Example 12F (0.13 g, 0.385 mmol) in ethanol (20 mL) was added to 20% palladium hydroxide on carbon (wet, 0.026 g, 0.185 mmol) in a 50 mL pressure bottle and shaken under hydrogen (30 psi) at 50° C. for 2 hours. HPLC indicated consumption of starting material. The mixture was filtered through a nylon membrane, the solvent was evaporated, and the crude mixture was purified by preparative HPLC to afford the title compound as the trifluoroacetic acid salt. $^1$H NMR (500 MHz, DMSO-$d_6$) δ ppm 9.49 (s, 1H), 9.05 (br s, 1H), 8.97 (br s, 1H), 6.90-6.89 (m, 1H), 6.69-6.62 (m, 2H), 3.75 (s, 3H), 3.57-3.49 (m, 1H), 3.41-3.14 (m, 4H), 3.08-2.83 (m, 2H), 2.62 (dd, J=7 Hz, 13 Hz, 1H), 2.01 (d, J=13 Hz, 1H); MS (ESI) m/z 247.9 (M+H)$^+$.

Example 13

9-bromo-1,2,3,4,4a,5-hexahydropyrazino[1,2-a][1,5]benzodiazepin-6(7H)-one

To a solution of Example 1D (1.54 g, 6.07 mmol) in acetic acid/water (1:1, 20 mL) was added N-bromosuccinimide (1.08 g, 6.07 mmol). The reaction mixture was stirred at room temperature for 2 hours. Product precipitated. The precipitate was collected to afford the title compound. $^1$H NMR (500 MHz, DMSO-$d_6$/$D_2O$) δ ppm 7.36 (d, J=8.54 Hz, 1H), 7.16 (s, 1H), 7.11 (d, J=8.85 Hz, 1H), 3.54-3.63 (m, 1H), 3.22-3.40 (m, 4H), 2.93-3.07 (m, 2H), 2.65-2.72 (m, 1H), 2.08 (d, J=13.73 Hz, 1H); MS (ESI) m/z 297.8 (M+H)$^+$.

Example 14

9-(4-chlorophenyl)-1,2,3,4,4a,5-hexahydropyrazino[1,2-a][1,5]-benzodiazepin-6(7H)-one Example 13 (30 mg, 0.08 mmol) was added to a Biotage microwave tube. 4-Chlorophenylboronic acid (15.3 mg, 0.1 mmol) was added followed by ethanol (1 mL) and potassium carbonate (0.11 mL, 2 M aqueous solution). FC1007™ (11.3 mg, 0.36 mmol/g, Johnson Matthey) was added to the mixture, and the reaction mixture was heated in a microwave (Biotage Initiator™) at 150° C. for 15 minutes. The reaction mixture was passed through a 2 g Si-carbonate cartridge (SiliCylcle™) eluting with methanol. The collected eluate was concentrated and the residue was purified by preparative HPLC with a gradient of acetonitrile and 0.1% trifluoroacetic acid in water to afford the title compound as the trifluoroacetic acid salt. $^1$H NMR (300 MHz, DMSO-$d_6$) δ ppm 9.77 (br, 1H), 8.91 (br, 2H), 7.57-7.71 (m, 2H), 7.41-7.56 (m, 3H), 7.17-7.31 (m, 2H), 3.52-3.72 (m, 1H), 3.24-3.39 (m, J=8.82 Hz, 4H), 2.91-3.18 (m, J=40.01 Hz, 2H), 2.63-2.83 (m, 1H), 2.10 (d, J=13.22 Hz, 1H); MS (DCI+) m/z 328.1 (M+H)$^+$.

Example 15

9,10-dichloro-1,2,3,4,4a,5-hexahydropyrazino[1,2-a][1,5]benzodiazepin-6(7H)-one

Example 15A 2-(4-(tert-butoxycarbonyl)-1-(4,5-dichloro-2-nitrophenyl)piperazin-2-yl)acetic acid 1,2-Dichloro-4-fluoro-5-nitrobenzene (0.125 mL, 0.952 mmol) and 2-(4-(tert-butoxycarbonyl)piperazin-2-yl)acetic acid (256 mg, 1.048 mmol) were dissolved in N,N-dimethylformamide (2 mL) and water (1 mL). Triethylamine (0.398 mL, 2.86 mmol) was slowly added. The resulting mixture was heated at 50° C. overnight. The mixture was concentrated and ethyl acetate was added. 1 N HCl was then added slowly until the pH=6. The water layer was separated and washed multiple times with ethyl acetate. The organic layers were then combined and concentrated. The crude material was purified by silica gel chromatography eluting with a gradient of 10% to 50% of ethyl acetate in hexane to afford the title compound. $^1$H NMR (300 MHz, DMSO-$d_6$) δ ppm 12.32 (br, 1H), 8.17 (s, 1H), 7.69 (s, 1H), 3.36-3.90 (m, 4H), 2.97-3.29 (m, 2H), 2.88 (dd, J=8.92, 3.37 Hz, 1H), 2.18-2.47 (m, 2H), 1.41 (s, 9H); MS (DCI+) m/z 434.1 (M+H)$^+$.

Example 15B tert-butyl 9,10-dichloro-6-oxo-1,2,4a,5,6,7-hexahydrobenzo[b]pyrazino[1,2-d][1,4]diazepine-3(4H)-carboxylate The title compound was prepared according to the procedure outlined in Example 4B substituting Example 15A for Example 4A. $^1$H NMR (400 MHz, DMSO-$d_6$) δ ppm 9.71 (s, 1H), 7.26 (s, 1H), 7.13 (s, 1H), 3.93 (t, J=11.05 Hz, 2H), 3.17-3.26 (m, 1H), 2.97-3.13 (m, 2H), 2.84 (br, 2H), 2.64 (dd, J=13.50, 6.75 Hz, 1H), 2.07 (d, J=13.50 Hz, 1H), 1.43 (s, 9H); MS (DCI+) m/z 403.1 (M+NH$_4$)$^+$.

Example 15C 9,10-dichloro-1,2,3,4,4a,5-hexahydropyrazino[1,2-a][1,5]benzodiazepin-6(7H)-one The title compound was prepared as the hydrochloric acid salt according to the procedure outlined in Example 4C substituting Example 15B for Example 4B. $^1$H NMR (300 MHz, DMSO-$d_6$) δ ppm 9.86 (s, 1H), 9.42 (br, 2H), 7.35 (s, 1H), 7.16 (s, 1H), 3.62-3.77 (m, 1H), 3.22-3.47 (m, 4H), 2.83-

3.13 (m, 2 H), 2.72 (dd, J=13.56, 6.78 Hz, 1 H), 2.11 (d, J=13.56 Hz, 1 H); MS (DCI+) m/z 286.0 (M+H)$^+$.

Example 16

9,10-dichloro-1,2,3,4,4a,5,6,7-octahydropyrazino[1,2-a][1,5]benzodiazepine

Example 16A tert-butyl 9,10-dichloro-1,2,4a,5,6,7-hexahydrobenzo[b]pyrazino[1,2-d][1,4]diazepine-3(4H)-carboxylate To a solution of Example 15B (168 mg, 0.435 mmol) in tetrahydrofuran (1.5 mL) was added borane in tetrahydrofuran (1.74 mL, 1 M solution). The resulting mixture was heated to 80° C. overnight. Methanol was then added, and the mixture was heated at 80° C. for 1 hour to destroy excess borane. The reaction was then cooled to room temperature and 1 M HCl was added. The mixture was allowed to stir for another 30 minutes. Aqueous sodium bicarbonate was slowly added to the mixture until the solution was basic (pH=8). Ethyl acetate was then added, and the water layer was separated and washed two times with additional ethyl acetate. The organic layers thus obtained were combined and concentrated. The crude material was purified by silica gel chromatography eluting with a gradient of 0% to 30% ethyl acetate in hexane to afford the title compound. $^1$H NMR (300 MHz, DMSO-d$_6$) δ ppm 6.88 (s, 1 H), 6.70 (s, 1 H), 5.75 (d, J=5.55 Hz, 1 H), 3.61-3.79 (m, 1 H), 3.36-3.58 (m, 2 H), 2.95-3.23 (m, 5 H), 2.82-2.94 (m, 1 H), 1.80-1.97 (m, 1 H), 1.56-1.74 (m, 1 H), 1.41 (s, 9 H); MS (DCI+) m/z 372.2 (M+H)$^+$.

Example 16B 9,10-dichloro-1,2,3,4,4a,5,6,7-octahydropyrazino[1,2-a][1,5]benzodiazepine The title compound was prepared as the hydrochloric acid salt according to the procedure outlined in Example 4C substituting Example 16A for Example 4B. $^1$H NMR (500 MHz, DMSO-d$_6$) δ ppm 9.45 (br, 2 H), 7.17 (b, 2 H), 3.43-3.53 (m, 1 H), 3.23-3.41 (m, 3 H), 3.06-3.23 (m, 5 H), 1.87-2.01 (m, 1 H), 1.78 (d, J=14.95 Hz, 1 H); MS (DCI+) m/z 272.0 (M+H)$^+$.

Example 17

1,2,3,4,4a,5,6,7-octahydropyrazino[1,2-a][1,5]benzodiazepine

Example 17A tert-butyl 1,2,4a,5,6,7-hexahydrobenzo[b]pyrazino[1,2-d][1,4]diazepine-3(4H)-carboxylate To a solution of Example 1C (1 g, 3.15 mmol) in tetrahydrofuran (10 mL) was added borane (1 M/tetrahydrofuran, 12.6 mL, 12.6 mmol). The solution was heated to 80° C. for 4 hours. Methanol (20 mL) was added, and the reaction heated at 80° C. for 1 hour. The reaction was cooled to room temperature and 1 M HCl (30 mL) was added. This solution was stirred for 30 minutes, before the solution was neutralized with sodium bicarbonate (aqueous). Dichloromethane was used to extract the product. The product was purified via flash chromatography (20-70% ethyl acetate/hexanes) to afford the title compound. $^1$H NMR (300 MHz, DMSO-d$_6$) δ ppm 6.77 (d, J=7.54 Hz, 1 H), 6.64-6.73 (m, 1 H), 6.48-6.59 (m, 2 H), 5.27 (s, 1 H), 3.54-3.67 (m, 1 H), 3.35-3.50 (m, 2 H), 3.20-3.29 (m, 1 H), 2.96-3.19 (m, 4 H), 2.85-2.96 (m, 1 H), 1.76-1.92 (m, 1 H), 1.59-1.75 (m, 1 H), 1.41 (s, 9 H); MS (APCI+) m/z 304.3 (M+H)$^+$.

Example 17B 1,2,3,4,4a,5,6,7-octahydropyrazino[1,2-a][1,5]benzodiazepine

To a solution of Example 17A (50 mg, 0.165 mmol) in dichloromethane (5 mL) was added HCl (4 M in dioxane, 824 μL, 3.30 mmol). After reaction completion as indicated by LC/MS analysis, the solution was concentrated and purified by preparative HPLC to afford the title compound. $^1$H NMR (500 MHz, DMSO-d$_6$/D$_2$O) δ ppm 7.48 (t, J=7.48 Hz, 1 H), 7.36 (d, J=7.02 Hz, 1 H), 7.19-7.29 (m, 2 H), 3.47-3.57 (m, 1 H), 3.35-3.44 (m, 2 H), 3.10-3.35 (m, 6 H), 1.76 (s, 2 H); MS (ESI) m/z 204.0 (M+H)$^+$.

Example 18

10-chloro-1,2,3,4,4a,5,6,7-octahydropyrazino[1,2-a][1,5]benzodiazepine tert-Butyl 10-chloro-1,2,4a,5,6,7-hexahydrobenzo[b]pyrazino[1,2-d][1,4]diazepine-3(4H)-carboxylate was prepared according to the procedure outlined in Example 17A substituting Example 3C for Example 1C. After reaction completion as indicated by LC/MS analysis, the solution was concentrated and purified by preparative HPLC to afford tert-butyl 10-chloro-1,2,4a,5,6,7-hexahydrobenzo[b]pyrazino[1,2-d][1,4]diazepine-3(4H)-carboxylate. This intermediate was dissolved in dichloromethane (5 mL) and HCl (4 M in dioxane, 0.918 mL, 3.67 mmol) was added. After reaction completion as indicated by LC/MS analysis, the solution was concentrated to afford the title compound as the hydrochloride salt. $^1$H NMR (500 MHz, DMSO-d$_6$/D$_2$O) δ ppm 7.53 (d, J=8.54 Hz, 1 H), 7.25-7.31 (m, 2 H), 3.43-3.54 (m, 2 H), 3.31-3.39 (m, 4 H), 3.18-3.31 (m, 3 H), 1.77-1.87 (m, 2 H); MS (ESI) m/z 237.9 (M+H)$^+$.

Example 19

9-bromo-1,2,3,4,4a,5,6,7-octahydropyrazino[1,2-a][1,5]benzodiazepine

To a solution of Example 13 (1.25 g, 4.22 mmol) and triethylamine (2.94 mL, 21.1 mmol) in dichloromethane (50 mL) was added di-tert-butyl dicarbonate (1.013 g, 4.64 mmol) in dichloromethane (10 mL). The reaction was stirred in a 50° C. oil bath for 14 hours. The solution was then concentrated onto silica gel, and purified via flash chromatography (20-70% ethyl acetate/hexanes) to afford tert-butyl 9-bromo-6-oxo-1,2,4a,5,6,7-hexahydrobenzo[b]pyrazino[1,2-d][1,4]diazepine-3(4H)-carboxylate.

tert-Butyl 9-bromo-1,2,4a,5,6,7-hexahydrobenzo[b]pyrazino[1,2-d][1,4]diazepine-3(4H)-carboxylate was prepared according to the procedure outlined in Example 17A substituting the tert-butyl 9-bromo-6-oxo-1,2,4a,5,6,7-hexahydrobenzo[b]pyrazino[1,2-d][1,4]diazepine-3(4H)-carboxylate for Example 1C. After reaction completion as indicated by LC/MS analysis, the solution was concentrated and purified by preparative HPLC. The t-butoxy carbonyl group was then removed with treatment of a solution of tert-butyl 9-bromo-1,2,4a,5,6,7-hexahydrobenzo[b]pyrazino[1,2-d][1,4]diazepine-3(4H)-carboxylate (24.8 mg) in dichloromethane (3 mL) with HCl (4 M in dioxane, 1 mL).

After reaction completion as indicated by LC/MS analysis, concentration afforded the title compound. $^1$H NMR (500 MHz, DMSO-d$_6$, D$_2$O) δ ppm 7.19 (d, J=8.54 Hz, 1 H), 7.16 (s, 1 H), 6.98 (d, J=8.54 Hz, 1 H), 3.45-3.54 (m, 1 H), 3.28-3.37 (m, 2 H), 3.07-3.23 (m, 6 H), 1.84-1.94 (m, 1 H), 1.71-1.79 (m, 1 H); MS (ESI) m/z 281.9 (M+H)$^+$.

Example 20

7-methyl-1,2,3,4,4a,5-hexahydropyrazino[1,2-a][1,5]benzodiazepin-6(7H)-one

To a solution of Example 1C (50 mg, 0.16 mmol) in N,N-dimethylformamide (1 mL) was added sodium hydride (65%, 6.98 mg, 0.19 mmol). The solution was allowed to stir at room temperature for 1 hour before addition of methyl iodide (11.77 μL, 0.19 mmol). The reaction mixture was stirred overnight. The solution was concentrated, and dichloromethane (1 mL) was added followed by HCl (4 M in dioxane, 394 μL, 1.6 mmol). After reaction completion as indicated by LC/MS analysis, the solution was concentrated and purified by preparative HPLC to afford the title compound. $^1$H NMR (300 MHz, DMSO-d$_6$) δ ppm 7.35 (d, J=7.80 Hz, 1 H), 7.13-7.30 (m, 3 H), 3.32-3.47 (m, 3 H), 3.17-3.32 (m, 5 H), 2.89-3.15 (m, 2 H), 2.62 (dd, J=13.22, 7.12 Hz, 1 H), 2.12 (d, J=13.56 Hz, 1 H); MS (ESI) m/z 231.9 (M+H)$^+$.

Example 21

7-(2-chlorobenzyl)-1,2,3,4,4a,5,6,7-octahydropyrazino[1,2-a][1,5]benzodiazepine

To a solution of Example 1C (50 mg, 0.16 mmol) in N,N-dimethylformamide (1 mL) was added sodium hydride (65%, 6.98 mg, 0.19 mmol). The solution was allowed to stir at room temperature for 1 hour before addition of 1-(bromomethyl)-2-chlorobenzene (37.2 mg, 0.181 mmol). The reaction mixture was stirred overnight. The solution was concentrated. To the concentrate was added tetrahydrofuran (10 mL) followed by borane (1 M in tetrahydrofuran, 1 mL, 1 mmol). The solution was heated in an 80° C. oil bath for 4 hours. Methanol (20 mL) was added and heating of the resultant solution was continued in the 80° C. bath for 1 hour before concentration. To the concentrate was added dichloromethane (10 mL), methanol (1 mL) and HCl (4 M in dioxane, 1 mL) Once LC/MS analysis indicated the reaction was complete the solution was concentrated and purified by preparative HPLC to afford the title compound. $^1$H NMR (500 MHz, DMSO-d$_6$/D$_2$O) δ ppm 7.46 (d, J=8.85 Hz, 1 H) 7.28-7.38 (m, 3 H) 6.95 (dd, J=7.93, 1.53 Hz, 1 H) 6.87-6.92 (m, 1 H) 6.82-6.87 (m, 1 H) 6.70 (dd, J=7.78, 1.37 Hz, 1 H) 4.56 (d, J=16.17 Hz, 1 H) 4.36 (d, J=16.48 Hz, 1 H) 3.46-3.56 (m, 1 H) 3.35-3.43 (m, 2 H) 3.06-3.28 (m, 4 H) 2.93-3.02 (m, 2 H) 1.89-1.99 (m, 1 H) 1.70-1.79 (m, 1 H) MS (ESI) m/z 328.0 (M+H)$^+$.

Example 22

7-(3-chlorobenzyl)-1,2,3,4,4a,5,6,7-octahydropyrazino[1,2-a][1,5]benzodiazepine

The title compound was prepared according to the procedure outlined in Example 21 substituting 1-(bromomethyl)-3-chlorobenzene for 1-(bromomethyl)-2-chlorobenzene. $^1$H NMR (500 MHz, DMSO-d$_6$/D$_2$O) δ ppm 7.37-7.40 (m, 1 H) 7.36 (d, J=7.93 Hz, 1 H) 7.24-7.32 (m, 2 H) 6.85-6.99 (m, 3 H) 6.78-6.83 (m, 1 H) 4.54 (d, J=16.17 Hz, 1 H) 4.32 (d, J=15.87 Hz, 1 H) 3.35-3.49 (m, 3 H) 3.17-3.29 (m, 2 H) 3.07-3.17 (m, 2 H) 2.89-3.01 (m, 2 H) 1.82-1.93 (m, 1 H) 1.69-1.76 (m, 1 H) MS (ESI) m/z 328.0 (M+H)$^+$.

Example 23

3-ethyl-1,2,3,4,4a,5-hexahydropyrazino[1,2-a][1,5]benzodiazepin-6(7H)-one

To a solution of Example 1D (30 mg, 0.14 mmol) in N,N-dimethylformamide (1 mL) was added potassium carbonate (57 mg, 0.41 mmol) and bromoethane (10.3 μl, 0.14 mmol). The reaction was warmed to 60° C. for 14 hours. Excess potassium carbonate was filtered off. The solution was passed through a PS-isocyanate cartridge (Silicycle, 2 g) to trap leftover starting material. The solution was concentrated and purified by preparative HPLC with a gradient of acetonitrile and 0.1% trifluoroacetic acid in water to afford the title compound. $^1$H NMR (500 MHz, DMSO-d$_6$/D$_2$O) δ ppm 7.19-7.24 (m, 1 H), 7.14-7.18 (m, 1 H), 7.09-7.13 (m, 1 H), 7.01 (dd, J=7.78, 1.37 Hz, 1 H), 3.52-3.64 (m, 3 H), 3.32-3.39 (m, 2 H), 3.19-3.27 (m, 2 H), 2.97-3.10 (m, 2 H), 2.66 (dd, J=13.73, 7.02 Hz, 1 H), 2.09 (d, J=13.12 Hz, 1 H), 1.27 (t, J=7.32 Hz, 3 H); MS (ESI) m/z 246.0 (M+H)$^+$.

Example 24

3-benzyl-10-chloro-1,2,3,4,4a,5-hexahydropyrazino[1,2-a][1,5]benzodiazepin-6(7H)-one Example 24A methyl 2-(4-benzyl-1-(5-chloro-2-nitrophenyl)piperazin-2-yl)acetate To a solution of 4-chloro-2-fluoro-1-nitrobenzene (14.3 g, 81 mmol) and Example 12C (20.2 g, 81 mmol) in N,N-dimethylformamide (100 mL) was added potassium carbonate (33.7 g, 244 mmol). The reaction was warmed to 85° C. for 16 hours. Water was added, and the product was extracted with ethyl acetate. The ethyl acetate was then washed with brine, and concentrated onto silica gel. Purification via flash chromatography (0-30% ethyl acetate/hexanes) provided the title compound. $^1$H NMR (300 MHz, DMSO-d$_6$) δ ppm 7.82 (d, J=8.82 Hz, 1 H), 7.38 (d, J=2.03 Hz, 1 H), 7.22-7.35 (m, 5 H), 7.13 (dd, J=8.82, 2.03 Hz, 1 H), 3.75-3.85 (m, 1 H), 3.41-3.59 (m, 2 H), 3.36 (s, 3 H), 3.23-3.34, (m, 1 H), 2.84-2.93 (m, 1 H), 2.63-2.73 (m, 2 H), 2.53-2.62 (m, 2 H), 2.37-2.45 (m, 1 H), 2.19-2.30 (m, 1 H); MS (APCI+) m/z 403.9 (M+H)$^+$.

Example 24B 3-benzyl-10-chloro-1,2,3,4,4a,5-hexahydropyrazino[1,2-a][1,5]benzodiazepin-6(7H)-one A round bottom flask was charged with methyl 2-(4-benzyl-1-(5-chloro-2-nitrophenyl)piperazin-2-yl)acetate (Example 24A, 19.4 g, 48.0 mmol) and iron (8.05 g, 144 mmol) followed by acetic acid (70 mL). The solution was heated at 85° C. for 2 hours. The solution was concentrated onto silica gel, and eluted through a silica column (0-10% methanol/dichloromethane). The product was then concentrated and redissolved in dichloromethane. Addition of sodium hydroxide (1 M) caused the title compound to precipitate. $^1$H NMR (300 MHz, DMSO-d$_6$) δ ppm 9.56 (s, 1 H), 7.22-7.40 (m, 5 H), 7.00-7.09 (m, 2 H), 6.88-6.96 (m, 1 H), 3.54 (s, 2 H), 3.07-3.21 (m, 1 H), 2.94-3.05 (m, 1 H), 2.71-2.87 (m, 2 H), 2.52-2.61 (m, 1 H), 2.04-2.27 (m, J=10.71 Hz, 2 H), 1.84-1.95 (m, 2 H); MS (ESI) m/z 341.9 (M+H)+.

Example 25

10-[(E)-2-(3-chlorophenyl)vinyl]-1,2,3,4,4a,5-hexahydropyrazino[1,2-a][1,5]benzodiazepin-6(7H)-one Example 4B (100 mg, 0.25 mmol) was added to a Biotage microwave tube. (E)-2-(3-chlorostyryl)-4,4,5,5-tetramethyl-1,3,2-dioxaborolane (80 mg, 0.30 mmol) was added followed by ethanol (2 mL) and potassium carbonate (0.15 mL, 2 M aqueous solution). FC1007™ (35 mg, 0.36 mmol/g, Johnson Matthey) was added to the mixture, and the reaction mixture was heated in a microwave (Biotage Initiator™) at 150° C. for 15 minutes. The reaction mixture was passed through a 2 g Si-carbonate cartridge (SiliCylcle™) eluting with methanol. The collected eluate was concentrated. To this, 1 mL of dioxane and HCl in dioxane (0.63 mL, 4 M solution) was added, and the mixture was shaken at room temperature overnight. The resulting mixture was concentrated and purified by preparative HPLC. $^1$H NMR (500 MHz, DMSO-$d_6$) ppm 9.79 (s, 1 H), 9.20 (br, 2H), 7.20-7.46 (m, 6 H), 6.99 (d, J=7.93 Hz, 1 H), 3.56-3.64 (m, 2 H), 3.30-3.46 (m, 4 H), 2.94-3.15 (m, 2 H), 2.68 (dd, J=13.58, 7.17 Hz, 1 H); MS (DCI+) m/z 354.2 (M+H)+.

Example 26

10-[(E)-2-(4-fluorophenyl)vinyl]-1,2,3,4,4a,5-hexahydropyrazino[1,2-a][1,5]benzodiazepin-6(7H)-one The title compound was prepared according to the procedure outlined in Example 25 substituting (E)-4-fluorostyrylboronic acid for (E)-2-(3-chlorostyryl)-4,4,5,5-tetramethyl-1,3,2-dioxaborolane. $^1$H NMR (500 MHz, DMSO-$d_6$) δ ppm 9.76 (s, 1 H), 9.02 (br, 2 H), 7.64 (dd, J=8.85, 5.49 Hz, 2 H), 7.15-7.40 (m, 6 H), 6.97 (d, J=7.93 Hz, 1 H), 3.54-3.64 (m, 1 H), 3.38-3.46 (m, 4 H), 2.93-3.15 (m, 2 H), 2.68 (dd, J=13.73, 7.02 Hz, 1 H), 2.07 (d, J=13.73 Hz, 1 H); MS (DCI+) m/z 338.2 (M+H)+.

Example 27

10-[(E)-2-(4-chlorophenyl)vinyl]-1,2,3,4,4a,5-hexahydropyrazino[1,2-a][1,5]benzodiazepin-6(7H)-one The title compound was prepared according to the procedure outlined in Example 25 substituting (E)-4-chlorostyrylboronic acid for (E)-2-(3-chlorostyryl)-4,4,5,5-tetramethyl-1,3,2-dioxaborolane. $^1$H NMR (500 MHz, DMSO-$d_6$) δ ppm 9.77 (s, 1 H), 8.94 (br, 2 H), 7.61 (d, J=8.85 Hz, 2 H), 7.44 (d, J=8.54 Hz, 2 H), 7.30 (m, 4 H), 6.97 (d, J=7.93 Hz, 1 H), 3.53-3.62 (m, 1 H), 3.36-3.47 (m, 4 H), 2.95-3.15 (m, J=11.60 Hz, 2 H), 2.68 (dd, J=13.43, 7.02 Hz, 1 H) 2.08 (d, J=13.73 Hz, 1 H); MS (DCI+) m/z 354.1 (M+H)+.

Example 28

10-[(E)-2-(2,4-difluorophenyl)vinyl]-1,2,3,4,4a,5-hexahydropyrazino[1,2-a][1,5]benzodiazepin-6(7H)-one The title compound was prepared according to the procedure outlined in Example 25 substituting (E)-2-(2,4-difluorostyryl)-4,4,5,5-tetramethyl-1,3,2-dioxaborolane for (E)-2-(3-chlorostyryl)-4,4,5,5-tetramethyl-1,3,2-dioxaborolane. $^1$H NMR (500 MHz, DMSO-$d_6$) δ ppm 9.79 (s, 1 H), 9.27 (br, 2 H), 7.73-7.95 (m, 1 H), 7.19-7.41 (m, 5 H), 7.11-7.19 (m, 1 H), 6.99 (d, J=7.93 Hz, 1 H), 3.54-3.67 (m, 1 H), 3.27-3.51 (m, 4 H), 2.92-3.13 (m, 2 H), 2.68 (dd, J=13.58, 7.17 Hz, 1 H), 2.09 (d, J=13.43 Hz, 1 H); MS (DCI+) m/z 356.2 (M+H)+.

Example 29

10-(2-phenylethyl)-1,2,3,4,4a,5-hexahydropyrazino[1,2-a][1,5]benzodiazepin-6(7H)-one Example 29A (E)-tert-butyl 6-oxo-10-styryl-1,2,4a,5,6,7-hexahydrobenzo[b]pyrazino[1,2-d][1,4]diazepine-3(4H)-carboxylate The title compound was prepared according to the procedure outlined in Example 5 substituting Example 4B for Example 4 and substituting cinnamylboronic acid for phenylboronic acid. MS (DCI+) m/z 420.2 (M+H)+.

Example 29B 10-(2-phenylethyl)-1,2,3,4,4a,5-hexahydropyrazino[1,2-a][1,5]benzodiazepin-6(7H)-one Example 29A (110 mg, 0.29 mmol) in methanol (11 mL) was added to 5% Pd—C, wet (22 mg) in a 100 mL pressure tube and stirred for 16 hour under hydrogen (30 psi) at room temperature. The mixture was filtered through a nylon membrane and concentrated. To the crude material, dioxane (1 mL) was added followed by HCl in dioxane (0.71 mL, 4M), and the mixture was stirred at room temperature overnight. The solution was concentrated and purified by preparative HPLC. $^1$H NMR (500 MHz, DMSO-$d_6$) δ ppm 9.60 (s, 1 H), 9.08 (s, 2 H), 7.13-7.34 (m, 5 H), 6.81-6.98 (m, 3 H), 3.45-3.60 (m, 1 H), 3.35-3.45 (m, 2 H), 3.15-3.30 (m, 2 H), 2.92-3.10 (m, 2 H), 2.78-2.92 (m, 4 H), 2.57-2.67 (m, 1 H), 1.97-2.08 (m, 1 H); MS (DCI+) m/z 322.2 (M+H)+.

Example 30

11-bromo-1,2,3,4,4a,5-hexahydropyrazino[1,2-a][1,5]benzodiazepin-6(7H)-one

Example 30A 2-(4-benzyl-1-(2-bromo-6-nitrophenyl)piperazin-2-yl)acetic acid

The title compound was prepared according to the procedure outlined in Example 12D substituting 1-bromo-2-fluoro-3-nitrobenzene for 2-fluoro-4-methoxy-1-nitrobenzene. MS (APCI+) m/z 435.90 (M+H)+.

Example 30B 2-(1-(2-amino-6-bromophenyl)-4-benzylpiperazin-2-yl)acetic acid

The title compound was prepared according to the procedure outlined in Example 12E substituting 30A for 12D. MS (APCI+) m/z 404.20 (M+H)+.

Example 30C 2-(1-(2-amino-6-bromophenyl)-4-benzylpiperazin-2-yl)acetic acid

The title compound was prepared according to the procedure outlined in Example 12F substituting 30B for 12E. MS (DCI+) m/z 388.1 (M+H)+.

Example 30D 11-bromo-1,2,3,4,4a,5-hexahydropyrazino[1,2-a][1,5]benzodiazepin-6(7H)-one Example 30C (40 mg, 0.1 mmol) was dissolved in dichloroethane (0.3 mL). 1-Chloroethyl carbonochloridate (16.3 mg, 0.11 mmol) in dichloroethane (0.3 mL) was added slowly at 0° C. and stirred at 0° C. for additional 15 minutes. Then the mixture was heated for 2 hours at 85° C. The resulting mixture was cooled to room temperature and concentrated. Methanol is added, and the mixture was heated at 40° C. for 2 hours. The resulting mixture was concentrated and purified by preparative HPLC to afford the title compound as the bis-trifluoroacetic acid salt. $^1$H NMR (500 MHz, DMSO-$d_6$) δ ppm 10.00 (s, 1 H), 9.03 (br, 2 H), 7.38 (dd, J=6.41, 3.05 Hz, 1 H), 7.01-7.10 (m, 2 H), 3.96-4.07 (m, 1 H), 3.84-3.91 (m, 1 H), 3.36 (dd, J=33.72, 12.36 Hz, 2 H), 3.04-3.14 (m, 1 H), 2.84-2.98 (m, 2 H), 2.66 (dd, J=14.04, 5.49 Hz, 1 H), 2.18 (d, J=14.04 Hz, 1 H); MS (DCI+) m/z 296.0 (M+H)+.

Example 31

10-(trifluoromethyl)-1,2,3,4,4a,5-hexahydropyrazino[1,2-a][1,5]benzodiazepin-6(7H)-one

Example 31A 2-(4-benzyl-1-(2-nitro-5-(trifluoromethyl)phenyl)piperazin-2-yl)acetic acid The title compound was prepared according to the procedure outlined in Example 12D substituting 2-fluoro-1-nitro-4-(trifluoromethyl)benzene for 2-fluoro-4-methoxy-1-nitrobenzene. MS (DCI+) m/z 424.2 (M+H)+.

Example 31B 2-(1-(2-amino-6-bromophenyl)-4-benzylpiperazin-2-yl)acetic acid

The title compound was prepared according to the procedure outlined in Example 12E substituting 31A for 12D. MS (m/z) 394.3 (M+H)+.

Example 31C 3-benzyl-10-(trifluoromethyl)-1,2,3,4,4a,5-hexahydrobenzo[b]pyrazino[1,2-d][1,4]diazepin-6(7H)-one The title compound was prepared according to the procedure outlined in Example 12F substituting 31B for 12E. MS (DCI+) m/z 376.2 (M+H)+.

Example 31D 10-(trifluoromethyl)-1,2,3,4,4a,5-hexahydropyrazino[1,2-a][1,5]benzodiazepin-6(7H)-one The title compound was prepared according to the procedure outlined in Example 12G substituting 31C for 12F. $^1$H NMR (500 MHz, DMSO-$d_6$) δ ppm 9.83 (s, 1 H), 7.25-7.40 (m, 2 H), 7.10 (d, J=8.24 Hz, 1 H), 3.18-3.27 (m, 1 H), 3.05-3.12 (m, 1 H), 2.84-3.01 (m, 3 H), 2.56-2.77 (m, 3 H), 1.97 (d, J=13.12 Hz, 1 H); MS (DCI+) m/z 286.1 (M+H)+.

Example 32

8-fluoro-1,2,3,4,4a,5-hexahydropyrazino[1,2-a][1,5]benzodiazepin-6(7H)-one

Example 32A tert-butyl 4((9H-fluoren-9-yl)methyl)-3-(2-(2-bromo-6-fluorophenylamino)-2-oxoethyl)piperazine-1-carboxylate To a solution of 2-(((9H-fluoren-9-yl)methoxy)carbonyl)-4-(tert-butoxycarbonyl)piperazin-2-yl)acetic acid (5 g, 10.72 mmol) in dichloromethane (100 mL) with N,N-dimethylformamide (2 drops) was added oxalyl dichloride (3.4 g, 26.8 mmol). The reaction mixture was stirred at room temperature for 1 hour, then concentrated. Tetrahydrofuran (100 mL) was added to the concentrate followed by the slow addition of a solution containing 2-bromo-6-fluoroanaline (3 g, 16 mmol) and diisopropylethylamine (9 mL) in tetrahydrofuran (20 mL). The solution was stirred at room temperature for 2 hours before the addition of piperazine (2.77 g, 32.2 mmol) after which the solution was stirred for 15 hours. The reaction mixture was concentrated onto silica gel and purified via flash chromatography (0-100% ethyl acetate/hexane, then 0-10% methanol/dichloromethane) to afford the title compound. $^1$H NMR (300 MHz, DMSO-$d_6$) δ ppm 7.47-7.65 (m, 1 H) 7.21-7.46 (m, 2 H) 3.55-4.05 (m, 2 H) 2.67-3.14 (m, 3 H) 2.49-2.67 (m, 2 H) 2.26-2.46 (m, 2 H) 1.39 (s, 9 H); MS (APCI+) m/z 418.2 (M+H)+.

Example 32B tert-butyl 8-fluoro-6-oxo-1,2,4a,5,6,7-hexahydrobenzo[b]pyrazino[1,2-d][1,4]diazepine-3(4H)-carboxylate Example 32A (617 mg, 1.48 mmol), dicyclohexyl(2',6'-dimethoxybiphenyl-2-yl)phosphine (122 mg, 0.296 mmol), sodium tert-butoxide (199 mg, 2.075 mmol), and tris(dibenzylideneacetone)dipalladium(0) (271 mg, 0.296 mmol) were divided into three microwave vials. Each vial was charged with tert-butanol (4 mL) and heated at 120° C. for 20 minutes in a microwave reactor (Biotage Initiator™, maximum 400 Watts). The solutions from the microwave vials were combined, concentrated onto silica gel, and then purified via flash chromatography (20-100% ethyl acetate/hexanes) to afford the title compound. $^1$H NMR (300 MHz, DMSO-$d_6$) δ ppm 9.49 (s, 1 H) 7.11-7.23 (m, 1 H) 6.87-6.98 (m, 2 H) 3.85-4.01 (m, 2 H) 2.75-3.23 (m, 5 H) 2.62 (dd, J=13.39, 6.95 Hz, 1 H) 2.03 (d, J=13.22 Hz, 1 H) 1.43 (s, 9 H); MS (APCI+) m/z 280 (M−tBu+H)+.

Example 32C 8-fluoro-1,2,3,4,4a,5-hexahydropyrazino[1,2-a][1,5]benzodiazepin-6(7H)-one The title compound was prepared according to the procedure outlined in Example 1D substituting 32B (192 mg, 0.572 mmol) for Example 1C and purified by preparative HPLC with a gradient of acetonitrile and 0.1% ammonium acetate in water to afford the title compound. $^1$H NMR (500 MHz, DMSO-d$_6$/D$_2$O) δ ppm 7.14-7.24 (m, 1 H) 6.91-7.00 (m, 1 H) 3.24-3.35 (m, 1 H) 2.91-3.14 (m, 2 H) 2.68-2.82 (m, 2 H) 2.56-2.65 (m, 2 H) 1.98 (d, J=13.43 Hz, 1 H); MS (APCI+) m/z 236.0 (M+H)$^+$.

Example 33

11-fluoro-1,2,3,4,4a,5-hexahydropyrazino[1,2-a][1,5]benzodiazepin-6(7H)-one

Example 33A tert-butyl 3-(2-(2-bromo-3-fluorophenylamino)-2-oxoethyl)piperazine-1-carboxylate The title compound was prepared according to the procedure outlined in Example 32A substituting 2-bromo-3-fluoroaniline (1.63 g, 12.9 mmol) for 2-bromo-6-fluoroanaline. $^1$H NMR (300 MHz, DMSO-d$_6$) δ ppm 7.74 (d, J=7.46 Hz, 1 H) 7.33-7.45 (m, 1 H) 7.08-7.21 (m, J=8.48, 8.48 Hz, 1 H) 3.65-3.89 (m, 2 H) 2.70-3.01 (m, 3 H) 2.53-2.70 (m, 2 H) 2.44 (d, J=6.10 Hz, 2 H) 1.39 (s, 9 H); MS (APCI+) m/z 417.8 (M+H)$^+$.

Example 33B 11-fluoro-1,2,3,4,4a,5-hexahydropyrazino[1,2-a][1,5]benzodiazepin-6(7H)-one The title compound was prepared according to the procedure outlined in Example 32B substituting Example 33A (600 mg, 1.44 mmol) for Example 32A followed by the procedure outlined in Example 1D. Purification via preparative HPLC afforded the title compound. $^1$H NMR (500 MHz, DMSO-d$_6$/D$_2$O) δ ppm 7.08-7.17 (m, 1 H) 7.00-7.08 (m, 1 H) 6.87 (d, J=7.93 Hz, 1 H) 3.59-3.71 (m, 1 H) 3.25-3.47 (m, 4 H) 2.87-3.04 (m, 2 H) 2.63-2.76 (m, 1 H) 2.00-2.17 (m, 1 H); MS (APCI+) m/z 235 (M+H)$^+$.

Example 34

9-fluoro-1,2,3,4,4a,5-hexahydropyrazino[1,2-a][1,5]-benzodiazepin-6(7H)-one

Example 34A tert-butyl 3-(2-(2-bromo-5-fluorophenylamino)-2-oxoethyl)piperazine-1-carboxylate The title compound was prepared according to the procedure outlined in Example 32A substituting 2-bromo-5-fluoroaniline (3.05 g, 16.1 mmol) for 2-bromo-6-fluoroanaline. $^1$H NMR (300 MHz, DMSO-d$_6$) δ ppm 7.91 (dd, J=11.36, 3.22 Hz, 1 H) 7.67 (dd, J=8.99, 5.93 Hz, 1 H) 6.89-7.02 (m, 1 H) 3.64-3.88 (m, 2 H) 2.73-3.01 (m, 3 H) 2.52-2.68 (m, 2 H) 2.45 (d, J=6.44 Hz, 2 H) 1.39 (s, 9 H); MS (APCI+) m/z 417.9 (M+H)$^+$.

Example 34B 9-fluoro-1,2,3,4,4a,5-hexahydropyrazino[1,2-a][1,5]-benzodiazepin-6(7H)-one The title compound was prepared according to the procedure outlined in Example 32B substituting Example 34A (1 g, 2.4 mmol) for Example 32A followed by the procedure outlined in Example 1D. Purification via preparative HPLC afforded the title compound. $^1$H NMR (500 MHz, DMSO-d$_6$/D$_2$O) δ ppm 7.17 (dd, J=9.00, 5.65 Hz, 1 H) 6.99-7.07 (m, 1 H) 6.84 (dd, J=9.61, 2.90 Hz, 1 H) 3.52-3.61 (m, 1 H) 3.19-3.42 (m, 4 H) 2.94-3.10 (m, 2 H) 2.67 (dd, J=13.58, 7.17 Hz, 1 H) 2.07 (d, J=12.51 Hz, 1 H); MS (APCI+) m/z 235.9 (M+H)$^+$.

Example 35

10-fluoro-1,2,3,4,4a,5-hexahydropyrazino[1,2-a][1,5]benzodiazepin-6(7H)-one

Example 35A tert-butyl 3-(2-(2-bromo-4-fluorophenylamino)-2-oxoethyl)piperazine-1-carboxylate The procedure outlined in Example 1A was followed substituting 2-bromo-4-fluoroaniline (2.2 g, 12 mmol) for 2-bromoaniline except piperazine (2.8 g, 3.2 mmol) was added after the amide coupling was complete. This solution was warmed to 40° C. for 15 hours. The solution was partitioned between ethyl acetate and water. The ethyl acetate was collected and washed with brine (3×). The ethyl acetate solution was concentrated onto silica gel and purified via flash chromatography (0-10% methanol/dichloromethane) to afford the title compound. $^1$H NMR (300 MHz, DMSO-d$_6$) δ ppm 10.27 (s, 1 H) 7.71-7.84 (m, 1 H) 7.53-7.67 (m, 1 H) 7.18-7.31 (m, 1 H) 3.64-3.91 (m, 2 H) 2.69-2.98 (m, 3 H) 2.53-2.68 (m, 2 H) 2.40 (d, J=6.44 Hz, 2 H) 1.39 (s, 9 H); MS (APCI+) m/z 418.3 (M+H)$^+$.

Example 35B tert-butyl 10-fluoro-6-oxo-1,2,4a,5,6,7-hexahydrobenzo[b]pyrazino[1,2-d][1,4]diazepine-3(4H)-carboxylate The title compound was prepared according to the procedure outlined in Example 32B substituting Example 35A (500 mg, 1.2 mmol) for Example 32A. The crude reaction was purified via preparative HPLC using a gradient of acetonitrile and 0.1% ammonium acetate in water to afford the title compound. $^1$H NMR (300 MHz, DMSO-d$_6$) δ ppm 9.56 (s, 1 H) 6.77-7.03 (m, 3 H) 3.85-4.02 (m, 2 H) 2.72-3.24 (m, 5 H) 2.57 (dd, J=13.29, 6.94 Hz, 1 H) 2.01 (d, J=13.48 Hz, 1 H) 1.42 (s, 9 H); MS (APCI+) m/z 335.9 (M+H)$^+$.

Example 35C 10-fluoro-1,2,3,4,4a,5-hexahydropyrazino[1,2-a][1,5]benzodiazepin-6(7H)-one The title compound was prepared according to the procedure outlined in Example 32C substituting Example 35B for Example 32B. $^1$H NMR (500 MHz, DMSO-d$_6$/D$_2$O) δ ppm 6.98-7.05 (m, 2 H) 6.90-6.95 (m, 1 H) 3.61-3.67 (m, 1 H) 3.28-3.41 (m, 4 H) 2.95-3.09 (m, 2 H) 2.67 (dd, J=13.73, 7.02 Hz, 1 H) 2.07 (d, J=11.90 Hz, 1 H); MS (APCI+) m/z 235.9 (M+H)$^+$.

Example 36

(4aS)-10-methyl-1,2,3,4,4a,5-hexahydropyrazino[1,2-a][1,5]benzodiazepin-6(7H)-one

Example 36A (S)-tert-butyl 10-methyl-6-oxo-1,2,4a,5,6,7-hexahydrobenzo[b]pyrazino[1,2-d][1,4]diazepine-3(4H)-carboxylate The title compound was prepared as racemic mixture according to the procedure outlined in Example 10B. The enantiomers were separated by supercritical fluid ($CO_2$) chromatography; Chiralpak® AD-H column, 21 mm id, 250 mm in length, oven temperature 35° C., pressure 100 bar, flow rate 40 mL/minute. Mobile phase modifier: methanol. Gradient: 10% modifier hold for 1 minute, ramp at 2.4%/minute to 50% and hold for 2 minute. Retention time of the title compound was 12. 4 minutes, and the retention time of the other enantiomer was 8.9 minutes. MS (DCI+) m/z 332.2 (M+H)+.

Example 36B (4aS)-10-methyl-1,2,3,4,4a,5-hexahydropyrazino[1,2-a][1,5]benzodiazepin-6(7H)-one Example 36A in dioxane was added to 4 MHO/dioxane. The mixture was shaken at room temperature overnight. The mixture was concentrated and purified by preparative HPLC to afford the title compound as the trifluoroacetate salt. $^1$H NMR (500 MHz, DMSO-$d_6$/$D_2O$) δ ppm 9.58 (s, 1 H), 9.00 (br, 2 H), 6.94 (s, 1 H), 6.83-6.89 (m, 2 H), 3.49-3.57 (m, 1 H), 3.19-3.43 (m, 4 H), 2.92-3.12 (m, 2 H), 2.60 (dd, J=13.43, 7.32 Hz, 1 H), 2.29 (s, 3 H), 2.02 (d, J=13.43 Hz, 1 H); MS (DCI+) m/z 232.1 (M+H)+.

Example 37

(4aS)-9,10-dichloro-1,2,3,4,4a,5-hexahydropyrazino[1,2-a][1,5]benzodiazepin-6(7H)-one

Example 37A (S)-tert-butyl 9,10-dichloro-6-oxo-1,2,4a,5,6,7-hexahydrobenzo[b]pyrazino[1,2-d][1,4]diazepine-3(4H)-carboxylate The title compound was prepared as racemic mixture according to the procedure outlined in Example 15B. The enantiomers were separated by supercritical fluid ($CO_2$) chromatography; Chiralpak® AD-H column, 21 mm id, 250 mm in length, oven temperature 35° C., pressure 100 bar, flow rate 40 mL/minute. Mobile phase modifier: methanol. Gradient: 20% modifier hold for 1 minute, ramp at 3.0%/minute to 60% and hold for 4.5 minute. Retention time of the title compound was 17.8 minutes, and the retention time of the enantiomer was 11.6 minutes.

Example 37B (4aS)-9,10-dichloro-1,2,3,4,4a,5-hexahydropyrazino[1,2-a][1,5]benzodiazepin-6(7H)-one To Example 37A (43 mg, 0.11 mmol) in dioxane (0.4 mL) was added 4 M HCl/dioxane (0.28 mL, 1.11 mmol). The mixture was shaken at room temperature overnight. The mixture was concentrated to afford the title compound as the HCl salt. $^1$H NMR (500 MHz, DMSO-$d_6$) δ ppm 9.77-9.95 (s, 1 H), 9.07-9.36 (br, 2 H), 7.36 (s, 1H), 7.16 (s, 1H), 3.60-3.71 (m, 1 H), 3.23-3.43 (m, 4 H), 2.86-3.10 (m, 2 H), 2.72 (dd, J=13.58, 6.87 Hz, 1 H), 2.11 (d, J=13.73 Hz, 1 H); MS (DCI+) m/z 286.1 (M+H)+.

Example 38

3-methyl-1,2,3,4,4a,5-hexahydropyrazino[1,2-a][1,5]benzodiazepin-6(7H)-one

To a solution of Example 1D (100 mg, 0.394 mmol) in a pH 4 buffer solution (2 mL, made from 48 g of acetic acid and 30.5 g of sodium acetate in 1 L of methanol) was added formaldehyde (65.7 mL, 0.788 mmol, 36% aqueous solution) and MP-cyanoborohydride (946 mg, 1.18 mmol, 1.25 mmol/g loading). The reaction was allowed to stir at ambient temperature for 2 hours before the MP-cyanoborohydride was filtered out. The crude reaction was purified by preparative HPLC using a gradient of acetonitrile and 0.1% trifluoroacetic acid in water to afford the title compound as the trifluoroacetic acid salt. $^1$H NMR (500 MHz, DMSO-$d_6$/$D_2O$) δ ppm 7.18-7.24 (m, 1 H) 7.13-7.18 (m, 1 H) 7.08-7.13 (m, 1 H) 7.00-7.04 (m, 1 H) 3.57-3.65 (m, 1 H) 3.53 (t, J=10.98 Hz, 2 H) 3.32-3.39 (m, 2 H) 3.08-3.19 (m, 2 H) 2.90 (s, 3 H) 2.66 (dd, J=13.58, 7.17 Hz, 1 H) 2.05 (d, J=12.82 Hz, 1 H); MS (DCI+) m/z 231.9 (M+H)+.

Example 39

3,3a,4,5,6,7-hexahydronaphtho[1,2-b]pyrazino[1,2-d][1,4]diazepin-2(1H)-one

Example 39A 2-bromonaphthalen-1-amine

To a solution of naphthalen-1-amine (10 g, 69.8 mmol) in N,N-dimethylformamide (50 mL) at 0° C. was added N-bromosuccinimide (12.4 g, 69.8 mmol) in N,N-dimethylformamide (50 mL). The reaction mixture stirred for 1 hour before the addition of water (400 mL). The product was extracted with ethyl acetate (3×200 mL), and the combined ethyl acetate washes were extracted with brine (3×50 mL). The ethyl acetate was concentrated, and the crude material was purified by flash chromatography (0-20% ethyl acetate/hexanes) to afford the title compound. $^1$H NMR (300 MHz, DMSO-$d_6$) δ ppm 8.15-8.24 (m, 1 H) 7.73-7.82 (m, 1 H) 7.40-7.52 (m, 3 H) 7.07 (d, J=8.82 Hz, 1 H) 5.87 (s, 2 H); MS (APCI+) m/z 222.0 (M+H)+.

Example 39B tert-butyl 3-(2-(2-bromonaphthalen-1-ylamino)-2-oxoethyl)piperazine-1-carboxylate The title compound was prepared according to the procedure outlined in Example 32A substituting 39A (1.57 g, 7.07 mmol) for 2-bromo-6-fluoroanaline. $^1$H NMR (300 MHz, DMSO-$d_6$) δ ppm 10.11 (s, 1 H) 7.90-8.02 (m, 2 H) 7.71-7.89 (m, 2 H) 7.54-7.63 (m, 2 H) 3.92-4.02 (m, 1 H) 3.68-3.80 (m, 1 H) 2.91-3.05 (m, 3 H) 2.69-2.85 (m, 2 H) 2.56-2.65 (m, 2 H) 1.40 (s, 3 H); MS (APCI+) m/z 447.9 (M+H)+.

Example 39C tert-butyl 2-oxo-2,3,3a,4,6,7-hexahydronaphtho[1,2-b]pyrazino[1,2-d][1,4]diazepine-5(1H)-carboxylate The title compound was prepared according to the procedure outlined in Example 32B substituting Example 39B (500 mg, 1.11 mmol) for Example 32A. $^1$H NMR (300 MHz, DMSO-$d_6$) δ ppm 9.84 (s, 1 H) 7.98 (d, J=8.33 Hz, 1 H) 7.88 (d, J=7.54 Hz, 1 H) 7.79 (d, J=8.73 Hz, 1 H) 7.40-7.56 (m, 3 H) 3.99 (t, J=13.09 Hz, 2 H) 3.24-3.31 (m, 1 H) 2.78-3.21 (m, 4 H) 2.57 (dd, J=13.09, 7.14 Hz, 1 H) 2.02 (d, J=13.09 Hz, 1 H) 1.44 (s, 9 H); MS (APCI+) m/z 369.8 (M+H-Boc)+.

Example 39D 3,3a,4,5,6,7-hexahydronaphtho[1,2-b]pyrazino[1,2-d][1,4]diazepin-2(1H)-one The title compound was prepared according to the procedure outlined in Example 1D substituting 39C (28 mg 0.076 mmol) for Example 1C. The crude reaction was purified by HPLC with a gradient of acetonitrile and 0.1% trifluoroacetic acid in water to afford title compound as the trifluoroacetic acid salt. $^1$H NMR (500 MHz, DMSO-$d_6$/D$_2$O) δ ppm 7.99 (d, J=8.54 Hz, 1 H) 7.92 (d, J=8.24 Hz, 1 H) 7.86 (d, J=8.85 Hz, 1 H) 7.46-7.59 (m, 3 H) 3.31-3.56 (m, 6 H) 3.04-3.14 (m, 2 H) 2.62-2.70 (m, 1 H); MS (ESI+) m/z 367.9 (M+H)+.

Example 40

8-methyl-1,2,3,4,4a,5-hexahydropyrazino[1,2-a][1,5]benzodiazepin-6(7H)-one

Example 40A tert-butyl 3-(2-(2-bromo-6-methylphenylamino)-2-oxoethyl)piperazine-1-carboxylate The title compound was prepared according to the procedure outlined in Example 32A substituting 2-bromo-6-methylaniline (1.32 g, 7.07 mmol) for 2-bromo-6-fluoroanaline. $^1$H NMR (300 MHz, DMSO-$d_6$) δ ppm 7.49 (d, J=7.80 Hz, 1 H) 7.26 (d, J=6.78 Hz, 1 H) 7.12 (t, J=7.80 Hz, 1 H) 3.91 (d, J=12.88 Hz, 1 H) 3.73 (d, J=12.21 Hz, 1 H) 2.81-2.97 (m, 2 H) 2.64-2.81 (m, 1 H) 2.53-2.62 (m, 1 H) 2.32-2.42 (m, 2 H) 2.12-2.26 (m, 4 H) 1.39 (s, 9 H); MS (APCI+) m/z 411.9 (M+H)+.

Example 40B tert-butyl 8-methyl-6-oxo-1,2,4a,5,6,7-hexahydrobenzo[b]pyrazino[1,2-d][1,4]diazepine-3(4H)-carboxylate The title compound was prepared according to the procedure outlined in Example 32B substituting Example 40A (800 mg 1.94 mmol) for Example 32A. $^1$H NMR (300 MHz, DMSO-$d_6$) δ ppm 9.10 (s, 1 H) 7.02-7.12 (m, 1 H) 6.95 (t, J=6.61 Hz, 2 H) 3.84-4.03 (m, 2 H) 2.74-3.14 (m, 5 H) 2.43-2.48 (m, 1 H) 2.21 (s, 3 H) 1.94 (d, J=13.22 Hz, 1 H) 1.43 (s, 9 H); MS (APCI+) m/z 332.0 (M+H)+.

Example 40C 8-methyl-1,2,3,4,4a,5-hexahydropyrazino[1,2-a][1,5]benzodiazepin-6(7H)-one The title compound was prepared according to the procedure outlined in Example 1D substituting 40B (114 mg 0.344 mmol) for Example 1C. $^1$H NMR (500 MHz, DMSO-$d_6$/D$_2$O) δ ppm 7.10-7.17 (m, 1 H) 7.02 (d, J=7.93 Hz, 2 H) 3.47-3.56 (m, 1 H) 3.28-3.42 (m, 4 H) 2.95-3.07 (m, 2 H) 2.55-2.61 (m, 1 H) 2.23 (s, 3 H) 2.00 (d, J=13.43 Hz, 1 H); MS (ESI+) m/z 332.0 (M+H)+.

Example 41

(4aS)-10-chloro-1,2,3,4,4a,5-hexahydropyrazino[1,2-a][1,5]benzodiazepin-6(7H)-one The title compound was obtained by chiral HPLC from the racemate prepared as described in Example 3 (2.2 g, 8.73 mmol) on a Chiralpak® column (AS 4.6 mm ID×250 mm) with a mobile phase containing hexanes/ethanol/methanol/diethylamine (50/25/25/0.1) at a flow rate of 1 mL/minute and a column temperature of 40° C. The retention time of the title compound was 6.9 minutes while the retention time of the enantiomer was 10.0 minutes. After the chiral separation the material was purified on an HPLC with a gradient of acetonitrile and 0.1% trifluoroacetic acid in water to afford the title compound as the trifluoroacetic acid salt. $^1$H NMR (400 MHz, DMSO-$d_6$/D$_2$O) δ ppm 7.12-7.19 (m, 2 H) 7.02 (d, J=8.24 Hz, 1 H) 3.62-3.69 (m, 1 H) 3.28-3.44 (m, 4 H) 2.96-3.11 (m, 2 H) 2.68 (dd, J=13.73, 7.02 Hz, 1 H) 2.09 (d, J=12.51 Hz, 1 H); MS (APCI+) m/z 251.9 (M+H)+.

Example 42

(4aS)-10-(2-phenylethyl)-1,2,3,4,4a,5-hexahydropyrazino[1,2-a][1,5]benzodiazepin-6(7H)-one

Example 42A (S)-tert-butyl 6-oxo-10-phenethyl-1,2,4a,5,6,7-hexahydrobenzo[b]pyrazino[1,2-d][1,4]diazepine-3(4H)-carboxylate Example 29A (110 mg, 0.29 mmol) in methanol (11 mL) was added to 5% palladium on carbon (22 mg, wet) in a 100 mL pressure tube and stirred for 16 hours under hydrogen (30 psi) at room temperature. The mixture was filtered through a nylon membrane and concentrated to afford the racemic title compound. The enantiomers were separated by supercritical fluid (CO$_2$) chromatography; Chiralpak® OD-H column, 21 mm id, 250 mm in length, oven temperature 35° C., pressure 100 bar, flow rate 40 mL/minute. Mobile phase modifier: methanol. Gradient: 10% modifier hold for 1 minute, ramp at 1.3%/minute to 30% and hold for 2 minute. The retention time of the title compound was 13.60 minutes, and the retention time of the enantiomer was 11.75 minutes. MS (DCI+) m/z 422.4 (M+H)+.

Example 42B (4aS)-10-(2-phenylethyl)-1,2,3,4,4a,5-hexahydropyrazino[1,2-a][1,5]benzodiazepin-6(7H)-one The title compound was prepared according to the procedure outlined in Example 37B substituting 42A for 37A. $^1$H NMR (500 MHz, DMSO-d$_6$) δ ppm 9.60 (s, 1 H), 9.08 (s, 2 H), 7.13-7.34 (m, 5 H), 6.81-6.98 (m, 3 H), 3.45-3.60 (m, 1 H), 3.35-3.45 (m, 2 H), 3.15-3.30 (m, 2 H), 2.92-3.10 (m, 2 H), 2.78-2.92 (m, 4 H), 2.57-2.67 (m, 1 H), 1.97-2.08 (m, 1 H); MS (DCI+) m/z 322.2 (M+H)$^+$.

Example 43

(4aS)-10-methoxy-1,2,3,4,4a,5-hexahydropyrazino[1,2-a][1,5]benzodiazepin-6(7H)-one

Example 43A (S)-3-benzyl-10-methoxy-1,2,3,4,4a,5-hexahydrobenzo[b]pyrazino[1,2-d][1,4]diazepin-6(7H)-one The title compound was prepared as racemic mixture according to the procedure outlined in Example 12F. The enantiomers were separated by supercritical fluid chromatography using Chiralpak® AD-H, 21 mm id, 250 mm in length from Chiral Technologies, Inc. Oven temperature 35° C., pressure 100 bar, flow rate 40 mL/minute, mobile phase modifier: methanol with 0.1% diethylamine, 10% modifier isocratic for 30 minutes.

The separated enantiomers were analyzed by supercritical fluid analytical HPLC (AD column, isocratic 5-50% methanol with 0.1% diethylamine/CO$_2$, 100 bar, 10 minutes). The retention time of the titled compound is 7.95 minutes while the enantiomer has a retention time of 5.41 minutes.

Example 43B (4aS)-10-methoxy-1,2,3,4,4a,5-hexahydropyrazino[1,2-a][1,5]benzodiazepin-6(7H)-one The title compound was prepared according to the procedure outlined in Example 12G substituting Example 43A for Example 12F. The crude material was concentrated and purified by passing through silica gel chromatography eluting with 10% methanol/dichloromethane to obtain a liquid which was dissolved in dioxane and treated with 4 M HCl/dioxane for 10 minutes at room temperature. The solid formed was collected by removing most of the liquid with a pipette and dried. Methanol was added and the solid was triturated twice with methanol to provide the title compound. $^1$H NMR (500 MHz, DMSO-d$_6$) δ ppm 9.48 (s, 1H), 9.14 (s, 2H), 6.89 (d, J=8.3, 1H), 6.72-6.51 (m, 2H), 3.75 (s, 3H), 3.61-3.50 (m, 1H), 3.40-3.21 (m, 4H), 3.02 (td, J=4.9, 11.6, 1H), 2.95 (t, J=11.9, 1H), 2.62 (dd, J=7.1, 13.4, 1H), 2.01 (d, J=13.5, 1H); MS (ESI) m/z 247.9 (M+H)$^+$.

Example 44

10-ethoxy-1,2,3,4,4a,5-hexahydropyrazino[1,2-a][1,5]benzodiazepin-6(7H)-one

The title compound was prepared according to the procedure outlined in Example 12 substituting 2-fluoro-4-ethoxy-1-nitrobenzene for 2-fluoro-4-methoxy-1-nitrobenzene. $^1$H NMR (500 MHz, DMSO-d$_6$) δ ppm 9.48 (s, 1H), 8.94 (br s, 1H), 8.88 (br s, 1H), 6.88 (d, J=8.3, 1H), 6.71-6.56 (m, 2H), 4.11-3.94 (m, 2H), 3.55-3.48 (m, 1H), 3.36 (t, J=12.5, 2H), 3.28-3.21 (m, 2H), 3.11-2.92 (m, 2H), 2.62 (dd, J=7.1, 13.4, 1H), 2.01 (d, J=13.5, 1H), 1.32 (t, J=7.0, 3H); MS (ESI) m/z 261.9 (M+H)$^+$.

Example 45

3-benzyl-2,3,4,4a,5,6-hexahydropyrazino[1,2-a][1,4]benzodiazepin-7(1H)-one

Example 45A ethyl 1,4-dibenzyl-3-oxopiperazine-2-carboxylate

To a solution of N,N'-dibenzylethylenediamine (14.12 mL, 60.2 mmol) in acetonitrile (100 mL) was added diethyl bromomalonate (5.14 mL, 30.1 mmol), and the mixture was heated with an oil bath at 90° C. (reflux) for 7 hours. The solvent was evaporated to provide a residue that was dissolved in 1 M NaOH (aqueous), and the mixture was extracted with ethyl acetate twice, dried over Na$_2$SO$_4$, and the solvent was evaporated. The crude mixture was purified by silica gel chromatography (Analogix IntelliFlash 280, SF40-150) eluting with 15%-30% ethyl acetate/hexanes to afford the title compound. $^1$H NMR (500 MHz, DMSO-d$_6$) δ ppm 7.38-7.20 (m, 10H), 4.54 (dd, J=15.0, 154.2, 2H), 4.20-4.10 (m, 2H), 4.03 (q, J=7.1, 1H), 3.96 (s, 1H), 3.61 (dd, J=13.5, 41.7, 2H), 3.27-3.14 (m, 2H), 3.05-2.95 (m, 1H), 2.60-2.52 (m, 1H), 1.23 (t, J=7.1, 3H); MS (ESI+) m/z 353.0 (M+H)$^+$.

Example 45B ethyl 4-benzyl-3-oxopiperazine-2-carboxylate

Example 45A (8.4 g, 23.83 mmol) in ethanol (84 mL) was added to 20% Pd(OH)$_2$ on carbon, wet (0.840 g, 5.98 mmol) in a 250 mL stainless steel pressure bottle. The mixture was shaken under 30 psi of hydrogen at 50° C. for 30 minutes. The mixture was filtered through a nylon membrane and was concentrated to afford the title compound. $^1$H NMR (500 MHz, DMSO-d$_6$) δ ppm 7.39-7.30 (m, 2H), 7.30-7.20 (m, 3H), 4.53 (dd, J=14.9, 105.7, 2H), 4.17-4.08 (m, 3H), 3.26-3.13 (m, 3H), 3.13-2.98 (m, 1H), 2.85 (dt, J=4.9, 13.2, 1H), 1.22 (t, J=7.1, 3H); MS (ESI+) m/z 262.9 (M+H)$^+$.

Example 45C (4-benzylpiperazin-2-yl)methanol

A solution of Example 45B (6 g, 22.87 mmol) in tetrahydrofuran (45.7 mL) was added to lithium aluminum hydride in tetrahydrofuran (30.9 mL, 61.8 mmol) dropwise with an addition funnel under nitrogen over 30 minutes. The reaction mixture was stirred at room temperature for 1 hour and then carefully quenched with water and 1 N NaOH (aqueous). The product was extracted once with dichloromethane, dried over Na$_2$SO$_4$ and concentrated to afford the title compound. $^1$H NMR (500 MHz, DMSO-d$_6$) δ ppm 7.37-7.17 (m, 5H), 4.48 (t, J=5.4, 1H), 3.60 (t, J=6.5, 1H), 3.42 (q, J=13.1, 2H), 3.27-3.15 (m, 2H), 2.80 (dt, J=2.7, 11.4, 1H), 2.73-2.55 (m, 4H), 1.92 (td, J=3.0, 10.8, 1H), 1.81-1.72 (m, 1H), 1.60 (t, J=10.1, 1H); MS (ESI+) m/z 206.9 (M+H)$^+$.

Example 45D methyl 2-fluoro-5-nitrobenzoate

To a solution of 2-fluoro-5-nitrobenzoic acid (5 g, 27.0 mmol) in methanol (135 mL) was added HCl (2.66 mL, 32.4 mmol, 12.2 M), and the mixture was heated with an oil bath at 70° C. for 24 hours. The solvent was evaporated, and the residue was dissolved in ethyl acetate and washed with saturated sodium bicarbonate and brine, dried over sodium sulfate, and concentrated to afford the title compound. $^1$H NMR (500 MHz, DMSO-$d_6$) δ ppm 8.63 (dd, J=3.0, 6.2, 1H), 8.58-8.50 (m, 1H), 7.74-7.61 (m, 1H), 3.92 (s, 3H).

Example 45E methyl 2-(4-benzyl-2-(hydroxymethyl)piperazin-1-yl)-5-nitrobenzoate

To a solution of Example 45C (1.942 g, 9.42 mmol) in N-methyl-2-pyrrolidinone (30.1 mL) was added Example 45D (1.5 g, 7.53 mmol) and diisopropylethylamine (1.973 mL, 11.30 mmol), and the mixture was heated with an oil bath at 50° C. for 36 hours. The reaction was then quenched with water, extracted once with ethyl acetate, dried over sodium sulfate, and the solvent was evaporated. The crude mixture was purified by silica gel chromatography (Analogix IntelliFlash 280, SF40-150) eluting with 30%-50% ethyl acetate/hexanes to afford the title compound. $^1$H NMR (500 MHz, DMSO-$d_6$) δ ppm 8.32 (d, J=2.9, 1H), 8.16 (dd, J=2.9, 9.4, 1H), 7.39-7.30 (m, 5H), 7.28-7.23 (m, 1H), 7.19 (d, J=9.4, 1H), 4.58 (s, 1H), 3.84 (s, 3H), 3.73-3.62 (m, 4H), 3.14 (d, J=12.6, 1H), 2.90 (d, J=11.0, 1H), 2.79 (d, J=10.8, 1H), 2.27 (d, J=11.0, 1H), 2.12 (td, J=3.2, 11.5, 1H); MS (ESI+) m/z 386.1 (M+H)$^+$.

Example 45F methyl 2-(4-benzyl-2-((methylsulfonyloxy)methyl) piperazin-1-yl)-5-nitrobenzoate To a vigorously stirred solution of Example 45E (1 g, 2.59 mmol) in dichloromethane (5.19 mL) was added triethylamine (0.542 mL, 3.89 mmol) and methanesulfonyl chloride (0.253 mL, 3.24 mmol). The reaction was stirred for 10 minutes and then quenched with brine, extracted twice with dichloromethane, dried over sodium sulfate, and the solvent was evaporated to afford the title compound. MS (ESI+) m/z 464.1 (M+H)$^+$.

Example 45G 3-benzyl-9-nitro-2,3,4,4a,5,6-hexahydrobenzo[f] pyrazino[1,2-a][1,4]diazepin-7(1H)-one Example 45F (1.2 g, 2.59 mmol) was transferred to a 180 mL stainless steel reactor with 10% ammonia/ethanol (100 mL). The solution was stirred at 100° C. for 18 hours. The homogeneous mixture was concentrated and purified by reverse phase HPLC to afford the title compound as the trifluoroacetic acid salt. $^1$H NMR (500 MHz, DMSO-$d_6$) δ ppm 10.16 (s, 1H), 8.55 (t, J=5.8, 1H), 8.31-8.08 (m, 2H), 7.51 (s, 5H), 7.22 (d, J=9.0, 1H), 4.61-4.30 (m, 2H), 3.79-3.60 (m, 4H), 3.37-2.95 (m, 7H); MS (ESI+) m/z 353.0 (M+H)$^+$.

Example 45H 9-amino-3-benzyl-2,3,4,4a,5,6-hexahydrobenzo[f] pyrazino[1,2-a][1,4]diazepin-7(1H)-one Example 45G (0.367 g, 0.787 mmol) in methanol (3.93 mL) was added to Raney® nickel, water-wet (0.734 g, 12.51 mmol) (washed once with methanol) in a 4 mL pressure bottle. The mixture was stirred under 50 psi of hydrogen in a 50° C. water bath that cooled to room temperature over 1 hour. The mixture was filtered through a polypropylene membrane and concentrated to afford the title compound. $^1$H NMR (500 MHz, DMSO-$d_6$) δ ppm 8.08 (s, 1H), 7.61-7.38 (m, 5H), 7.01-6.73 (m, 3H), 4.44 (s, 2H), 3.30-3.20 (m, 3H), 3.20-2.97 (m, 5H), 2.93 (dd, J=23.1, 29.6, 1H); MS (ESI+) m/z 323.0 (M+H)$^+$.

Example 45I 3-benzyl-2,3,4,4a,5,6-hexahydropyrazino[1,2-a][1,4] benzodiazepin-7(1H)-one A solution of sodium nitrite (0.033 g, 0.478 mmol) in water (2.171 mL) was added to an ice bath chilled solution of Example 45H (0.14 g, 0.434 mmol) in hypophosphorous acid, solution in water (9.03 mL, 87 mmol, 9.63 M) and HCl (2.140 mL, 26.1 mmol, 12.2 M). A sample was taken out after 10 minutes, quenched with 1 M NaOH (aqueous), and the reaction was determined to be complete by LC/MS. The reaction mixture was allowed to reach room temperature and was poured into 100 mL 1 M NaOH (aqueous). Additional 1 M NaOH (aqueous) was added until the pH=14. The product was extracted with dichloromethane three times, dried over sodium sulfate, and the solvent was evaporated. The residue was then purified by reverse phase HPLC to afford the title compound. $^1$H NMR (400 MHz, DMSO-$d_6$) δ ppm 10.03 (s, 1H), 8.19 (t, J=5.8, 1H), 7.61-7.50 (m, 5H), 7.50-7.39 (m, 2H), 7.11 (t, J=7.3, 1H), 7.04 (d, J=7.9, 1H), 4.47 (s, 2H), 3.37-3.10 (m, 6H), 3.02 (dd, J=6.5, 14.9, 1H); MS (ESI+) m/z 308.0 (M+H)$^+$.

Example 46

2,3,4,4a,5,6-hexahydropyrazino[1,2-a][1,4]benzodiazepin-7(1H)-one

Example 45 in ethanol (2 mL) was added to 20% Pd (OH)$_2$—C, wet (12.00 mg, 0.085 mmol) in a 4 mL pressure bottle and stirred under 60 psi of hydrogen at 50° C. for 2.5 hours. The mixture was filtered through a polypropylene membrane and concentrated to a residue that was suspended in dichloromethane/dioxane and treated for 5 minutes at room temperature with 4 M HCl in dioxane to yield a solid. The mixture was centrifuged, the solvent was removed, and the solid was dried to afford the title compound. $^1$H NMR (400 MHz, DMSO-$d_6$) δ pm 9.23 (s, 2H), 8.24 (t, J=5.7, 1H), 7.53-7.38 (m, 2H), 7.10 (t, J=7.4, 1H), 7.05 (d, J=8.0, 1H), 3.35 (d, J=5.2, 4H), 3.24 (dd, J=9.1, 14.2, 3H), 3.09-2.94 (m, 3H); MS (ESI+) m/z 217.9 (M+H)$^+$.

Example 47

N-(3-benzyl-7-oxo-1,2,3,4,4a,5,6,7-octahydropyrazino[1,2-a][1,4]benzodiazepin-9-yl)benzenesulfonamide To a solution of Example 45H (0.1 g, 0.310 mmol) in pyridine (1.034 mL) was added benzenesulfonyl chloride (0.050 mL, 0.388 mmol), and the mixture was vortexed for 1 minute. The reaction was stirred for an additional 10 minutes, and then the solvent was evaporated to provide a residue that was purified by reverse phase HPLC to afford the title compound as the trifluoroacetic acid salt. $^1$H NMR (400 MHz, DMSO-$d_6$) δ 10.28-10.17 (s, 1H), 9.99 (s, 1H), 8.18 (t, J=5.8, 1H), 7.76-7.71 (m, 2H), 7.65-7.52 (m, 3H), 7.51 (d, J=10.1, 5H), 7.24-7.12 (m, 2H), 6.93 (d, J=8.6, 1H), 4.43 (s, 2H), 3.24 (s, 4H), 3.13 (d, J=19.4, 4H), 2.97 (s, 1H); MS (ESI+) m/z 463.1 (M+H)$^+$.

Example 48

N-(7-oxo-1,2,3,4,4a,5,6,7-octahydropyrazino[1,2-a][1,4]benzodiazepin-9-yl)benzenesulfonamide Example 47 (0.044 g, 0.076 mmol) and ethanol (10 ml) were added to 20% Pd(OH)$_2$—C, wet (8.80 mg, 0.063 mmol) in a 50 mL pressure bottle and stirred for 2 hours at 30 psi and 50° C. The mixture was filtered through a nylon membrane. The filtrate was concentrated and the residue was suspended in dichloromethane/dioxane and treated with 4 M HCl in dioxane for 10 minutes at room temperature to yield a solid. The mixture was centrifuged, the solvent was removed, and the solid was dried. The title compound was obtained following several triturations with methanol. $^1$H NMR (500 MHz, DMSO-d$_6$) δ ppm 10.22 (s, 1H), 8.97 (s, 2H), 8.22 (t, J=8.2, 1H), 7.72 (d, J=7.3, 2H), 7.61 (t, J=7.4, 1H), 7.54 (t, J=7.6, 2H), 7.25-7.06 (m, 2H), 6.93 (d, J=8.7, 1H), 3.25-3.18 (m, 3H), 3.17-3.09 (m, 3H), 3.05-2.82 (m, 3H); MS (ESI+) m/z 372.9 (M+H)$^+$.

Example 49

9-methyl-1,2,3,4,4a,5-hexahydropyrazino[1,2-a][1,5]benzodiazepin-6(7H)-one

Example 49A methyl 2-(4-benzyl-1-(4-methyl-2-nitrophenyl)piperazin-2-yl)acetate To a solution of Example 12C (625 mg, 4.03 mmol) in acetonitrile (5 mL) was added 1-fluoro-4-methyl-2-nitrobenzene (1.00 g, 4.03 mmol) and potassium carbonate (1.11 g, 805 mmol). The reaction was heated in an oil bath at 60° C. overnight. The solution was concentrated onto silica gel and purified via flash chromatography (0-100% ethyl acetate/hexanes) to afford the title compound. $^1$H NMR (300 MHz, DMSO-d$_6$) δ ppm 7.55-7.60 (m, 1 H), 7.22-7.43 (m, 7 H), 3.55-3.65 (m, 1 H), 3.41-3.59 (m, 2 H), 3.36 (s, 3 H), 3.09-3.21 (m, 1 H), 2.77-2.88 (m, 1 H), 2.22-2.62 (m, 7 H); MS (APCI+) m/z 384 (M+H)$^+$.

Example 49B 3-benzyl-9-methyl-1,2,3,4,4a,5-hexahydropyrazino[1,2-a][1,5]benzodiazepin-6(7H)-one To a solution of Example 49A (150 mg, 0.392 mmol) in acetic acid (5 mL) was added iron powder (65.5 mg, 1.17 mmol), and the reaction was heated to 80° C. for 14 hours. The solution was then concentrated onto silica gel and purified via flash chromatography (0-30% methanol/dichloromethane). The pure fractions were partitioned between dichloromethane and 1 M NaOH. The organic layer was collected and dried with MgSO$_4$ to afford title compound. $^1$H NMR (300 MHz, DMSO-d$_6$) δ ppm 9.41 (s, 1 H), 7.20-7.41 (m, 5 H), 6.86-7.01 (m, 2 H), 6.73 (s, 1 H), 3.53 (s, 2 H), 3.02-3.27 (m, 2 H), 2.67-3.00 (m, 3 H), 2.42-2.48 (m, 1 H) 2.04-2.30 (m, 5 H), 1.84 (d, J=13.22 Hz, 1 H); MS (APCI+) m/z 322 (M+H)$^+$.

Example 49C 9-methyl-1,2,3,4,4a,5-hexahydropyrazino[1,2-a][1,5]benzodiazepin-6(7H)-one The title compound was prepared according to the procedure outlined in Example 30D substituting Example 49B for Example 30C. Purification via HPLC to provided the title compound as the trifluoroacetic acid salt. $^1$H NMR (300 MHz, DMSO-d$_6$) δ ppm 9.63 (s, 1 H), 7.00-7.06 (m, 1 H), 6.93-6.99 (m, 1 H), 6.78 (d, J=1.36 Hz, 1 H), 2.89-3.55 (m, 7 H), 2.60 (dd, J=13.39, 7.29 Hz, 1 H), 2.24 (s, 3 H), 2.02 (d, J=13.56 Hz, 1 H); MS (DCI+) m/z 232 (M+H)$^+$.

Example 50 ethyl 6-oxo-1,2,3,4,4a,5,6,7-octahydropyrazino[1,2-a][1,5]-benzodiazepine-10-carboxylate

Example 50A ethyl 3-(4-benzyl-2-(2-methoxy-2-oxoethyl)piperazin-1-yl)-4-nitrobenzoate The title compound was prepared according to the procedure outlined in Example 24A substituting ethyl 3-fluoro-4-nitrobenzoate for 4-chloro-2-fluoro-1-nitrobenzene. $^1$H NMR (500 MHz, DMSO-d$_6$) δ ppm 7.88 (d, J=8.24 Hz, 1 H), 7.79 (s, 1 H), 7.67 (d, J=8.24 Hz, 1 H), 7.24-7.38 (m, 5 H), 4.35 (q, J=7.02 Hz, 2 H), 3.72-3.79 (m, 4 H), 3.52 (dd, J=52.64, 13.27 Hz, 2 H), 3.23-3.31 (m, 1 H), 2.84-2.96 (m, 1 H), 2.56-2.69 (m, 2 H), 2.27-2.52 (m, 4 H), 1.34 (t, J=7.17 Hz, 3 H); MS (APCI+) m/z 442 (M+H)$^+$.

Example 50B ethyl 3-benzyl-6-oxo-1,2,3,4,4a,5,6,7-octahydropyrazino[1,2-a][1,5]-benzodiazepine-10-carboxylate The title compound was prepared according to the procedure outlined in Example 49B substituting Example 50A for Example 49A. $^1$H NMR (300 MHz, DMSO-d$_6$) δ ppm 9.83 (s, 1 H) 7.55-7.66 (m, 2 H) 7.20-7.41 (m, 5 H) 7.02 (d, J=8.73 Hz, 1 H) 4.29 (q, J=7.14 Hz, 2 H) 3.56 (s, 2 H) 3.33-3.43 (m, 1 H) 3.10-3.28 (m, 1 H) 2.96-3.09 (m, 1 H) 2.82 (dd, J=21.42, 10.71 Hz, 2 H) 2.52-2.61 (m, 1 H) 2.04-2.31 (m, 2 H) 1.94 (d, J=13.48 Hz, 1 H) 1.31 (t, J=7.14 Hz, 3 H); MS (APCI+) m/z 380 (M+H)$^+$.

Example 50C ethyl 6-oxo-1,2,3,4,4a,5,6,7-octahydropyrazino[1,2-a][1,5]benzodiazepine-10-carboxylate The title compound was prepared according to the procedure outline in Example 30D substituting Example 50B for Example 30C. A precipitate formed in the reaction mixture. The precipitate was collected by filtration, it was washed with dichloromethane and then dried to provide the title compound as the hydrochloride salt. $^1$H NMR (500 MHz, DMSO-d$_6$) δ ppm 7.69 (dd, J=8.24, 1.83 Hz, 1 H), 7.64 (d, J=1.83 Hz, 1 H), 7.10 (d, J=8.24 Hz, 1 H), 4.32 (q, J=6.81 Hz, 2 H), 3.64-3.71 (m, 1 H), 3.27-3.46 (m, 4 H), 2.95-3.08 (m, 2 H), 2.69 (dd, J=13.73, 7.32 Hz, 1 H), 2.12 (d, J=12.82 Hz, 1 H), 1.32 (t, J=7.02 Hz, 3 H); MS (DCI+) m/z 290 (M+H)$^+$.

Example 51

9-chloro-1,2,3,4,4a,5-hexahydropyrazino[1,2-a][1,5]benzodiazepin-6(7H)-one

Example 51A methyl 2-(4-benzyl-1-(4-chloro-2-nitrophenyl)piperazin-2-yl)acetate The title compound was prepared according to the procedure outlined in Example 24A substituting 4-chloro-1- fluoro-2-nitrobenzene for 4-chloro-2-fluoro-1-nitrobenzene. $^1$H NMR (300 MHz, DMSO-d$_6$) δ ppm 7.92 (d, J=2.71 Hz, 1 H), 7.62 (dd, J=8.82, 2.71 Hz, 1 H), 7.40 (d, J=8.82 Hz, 1 H), 7.19-7.37 (m, 5 H), 3.66-3.76 (m, 1 H), 3.40-3.60 (m, 2 H) 3.36 (s, 3 H), 3.15-3.27 (m, 1 H), 2.79-2.91 (m, 1 H), 2.53-2.67 (m, 2 H), 2.23-2.48 (m, 4 H); MS (APCI+) m/z 404 (M+H)$^+$.

Example 51B 3-benzyl-9-chloro-1,2,3,4,4a,5-hexahydropyrazino[1,2-a][1,5]benzodiazepin-6(7H)-one The title compound was prepared according to the procedure outlined in Example 49B substituting Example 51A for Example 49A. $^1$H NMR (300 MHz, DMSO-d$_6$) δ ppm 9.60 (s, 1 H), 7.21-7.40 (m, 5 H), 7.01-7.19 (m, 2 H), 6.95 (d, J=2.38 Hz, 1 H), 3.54 (s, 3 H), 3.02-3.20 (m, 1 H), 2.88-3.02 (m, 1 H), 2.70-2.87 (m, 2 H), 2.51-2.64 (m, 1 H), 2.20 (t, J=10.51 Hz, 1 H), 2.02-2.16 (m, 1 H), 1.90 (d, J=13.48 Hz, 1 H); MS (APCI+) m/z 342 (M+H)$^+$.

Example 51C 9-chloro-1,2,3,4,4a,5-hexahydropyrazino[1,2-a][1,5]benzodiazepin-6(7H)-one The title compound was prepared according to the procedure outline in Example 30D. A precipitate formed in the reaction mixture. The precipitate was collected by filtration, it was washed with dichloromethane and then dried to provide the title compound as the hydrochloride salt. $^1$H NMR (500 MHz, DMSO-d$_6$) δ ppm 7.19-7.25 (m, 1 H), 7.13-7.19 (m, 1 H), 7.02 (d, J=2.44 Hz, 1 H), 3.60-3.68 (m, 1 H), 3.31-3.41 (m, 3 H), 3.21-3.30 (m, 1 H), 2.99-3.07 (m, 1 H), 2.95 (t, J=11.90 Hz, 1 H), 2.67 (dd, J=13.73, 7.02 Hz, 1 H), 2.09 (d, J=12.51 Hz, 1 H); MS (DCI+) m/z 252 (M+H)$^+$.

Example 52

10-cyclopropyl-1,2,3,4,4a,5-hexahydropyrazino[1,2-a][1,5]benzodiazepin-6(7H)-one Between two microwave vials were divided Example 4B (200 mg, 0.505 mmol), cyclopropylboronic acid (65 mg, 0.757 mmol), tricyclohexylphosphine (14.2 mg, 0.050 mmol), K$_3$PO$_4$ (321 mg, 1.51 mmol), and palladium(II) acetate (5.67 mg, 0.025 mmol). Each microwave vial was then charged with toluene (4 mL) and water (100 μL) and heated in a microwave (Biotage Initiator™, maximum 400 Watts) to 160° C. for 40 minutes. Solids were removed by filtration and the product purified via HPLC. To a solution of the t-butoxycarbonyl protected title compound in dichloromethane (4 mL) was added HCl (4 M dioxane, 0.6 mL). When the reaction was complete according to the LC/MS, the solution was concentrated to afford the title compound as the HCl salt. $^1$H NMR (500 MHz, DMSO-d$_6$) δ ppm 6.88 (d, J=7.93 Hz, 1 H), 6.84 (d, J=1.53 Hz, 1 H), 6.75 (dd, J=8.24, 1.83 Hz, 1 H), 3.54-3.61 (m, 3 H), 3.25-3.39 (m, 4 H), 2.93-3.07 (m, 2 H), 2.62 (dd, J=13.58, 7.17 Hz, 1 H), 2.02 (d, J=12.51 Hz, 1 H), 1.87-1.96 (m, 1 H), 0.91-0.98 (m, 2 H), 0.62-0.71 (m, 2 H); MS (DCI+) m/z 258 (M+H)$^+$.

Example 53

11-methyl-1,2,3,4,4a,5-hexahydropyrazino[1,2-a][1,5]benzodiazepin-6(7H)-one

Example 53A tert-butyl 3-(2-(2-bromo-3-methylphenylamino)-2-oxoethyl)piperazine-1-carboxylate To a solution of 2-(((9H-fluoren-9-yl)methoxy)carbonyl)-4-(tert-butoxycarbonyl)piperazin-2-yl)acetic acid (3.00 g, 6.43 mmol) in dichloromethane (50 mL) with N,N-dimethylformamide (2 drops) was added oxalyl chloride (1.13 mL, 12.9 mmol) drop wise. The reaction mixture was stirred at room temperature for 1 hour, and then it was concentrated. The concentrate is taken up in tetrahydrofuran (50 mL) and 2-bromo-3-methyl aniline (1.33 g, 7.07 mmol) was added in tetrahydrofuran (5 mL) and diisopropylethylamine (5.62 mL, 36.2 mmol). The solution is heated to 70° C. for 2 hours. The mixture was then cooled to 50° C. and piperazine (1.66 g, 19.3 mmol) was added. The reaction mixture stirred for 16 hours before concentration onto silica gel. Purification via flash chromatography (0-20% methanol/dichloromethane) afforded the title compound. $^1$H NMR (300 MHz, DMSO-d$_6$) δ ppm 7.54-7.71 (m, 1 H), 7.06-7.31 (m, 2 H), 3.62-3.98 (m, 2 H), 2.26-3.45 (m, 10 H), 0.87-1.05 (m, 9 H); MS (APCI+) m/z 412, 414 (M+H)$^+$.

Example 53B 11-methyl-1,2,3,4,4a,5-hexahydropyrazino[1,2-a][1,5]benzodiazepin-6(7H)-one Between 10 microwave vials were divided Example 53B (1.00 g, 2.43 mmol), dicyclohexyl(2',6'-dimethoxybiphenyl-2-yl)phosphine (199 mg, 0.485 mmol), sodium ten-butoxide (326 mg, 3.20 mmol), and tris(dibenzylidene-acetone)dipalladium(0) (444 mg, 0.485 mmol). tert-Butanol (4 mL) was added to each microwave vial, and each vial was heated in a microwave (Biotage Initiator™, maximum 400 Watts) at 120° C. for 20 minutes. The solutions from all the microwave vials were combined. The crude material was purified via flash chromatography (0-100% ethyl acetate/hexanes) before HPLC purification. HCl (4 M dioxane, 1 mL) was added to this purified product in dichloromethane (5 mL). Concentration afforded the title compound as the HCl salt. $^1$H NMR (500 MHz, DMSO-d$_6$) δ ppm 6.96-7.04 (m, 2 H), 6.83-6.90 (m, 1 H), 3.93-4.01 (m, 1 H), 3.58-3.70 (m, 2 H), 3.37 (d, J=10.37 Hz, 1 H), 3.30 (d, J=12.21 Hz, 1 H), 3.12 (d, J=13.12 Hz, 1 H), 2.88 (d, 2 H), 2.60 (dd, J=13.58, 5.95 Hz, 1 H), 2.33 (s, 3 H), 2.08 (d, J=13.73 Hz, 1 H); MS (DCI+) m/z 232 (M+H)$^+$.

Example 54

(4aS)-9-bromo-1,2,3,4,4a,5,6,7-octahydropyrazino[1,2-a][1,5]benzodiazepine

To a solution of Example 2 (100 mg, 0.460 mmol) in acetic acid/water (1:1, 20 mL) was added N-bromosuccinimide (82.0 mg, 0.460 mmol). The reaction stirred at room temperature for 16 hours. before it was concentrated. Borane (1 M, tetrahydrofuran, 4.60 mL) was added, and the mixture was heated to 60° C. for 16 hours. Methanol (5 mL) was added to the solution at 60° C. The solution was cooled to room temperature and stirred for 60 hours. Then the solution was concentrated and purified via HPLC to afford the title compound as the trifluoroacetic acid salt. $^1$H NMR (500 MHz, DMSO-$d_6$) δ ppm 7.21 (dd, J=8.54, 2.14 Hz, 1 H), 7.16 (d, J=2.14 Hz, 1 H), 6.99 (d, J=8.54 Hz, 1 H), 3.47-3.58 (m, 1 H), 3.27-3.39 (m, 2 H), 3.15-3.25 (m, 3 H), 3.14-3.24 (m, J=12.66, 3.81 Hz, 4 H), 3.05-3.15 (m, 2 H), 1.84-1.95 (m, 1 H), 1.70-1.81 (m, 1 H); MS (DCI+) m/z 282, 284 (M+H)$^+$.

Example 55

(4aS)-9-chloro-1,2,3,4,4a,5-hexahydropyrazino[1,2-a][1,5]benzodiazepin-6(7H)-one Example 55A methyl 2-(4-benzyl-1-(4-chloro-2-nitrophenyl)piperazin-2-yl)acetate The title compound was prepared according to the procedure outlined in Example 24A substituting 4-chloro-1-fluoro-2-nitrobenzene for 4-chloro-2-fluoro-1-nitrobenzene. The title compound was used directly in Example 55B.

Example 55B (4aS)-3-benzyl-9-chloro-1,2,3,4,4a,5-hexahydropyrazino[1,2-a][1,5]-benzodiazepin-6(7H)-one The title compound was prepared according to the procedure outlined in Example 49B substituting Example 55A for Example 49A. Chiral separation via SFC (Chiralpak® AS, 21×250 mm, 5 nm, 10-30% methanol with 0.1% diethyl amine-CO$_2$ gradient over 15 minutes, at 40 mL/minute, retention time=18.5 minutes) afforded the title compound. $^1$H NMR (300 MHz, DMSO-$d_6$) δ ppm 9.59 (s, 1 H), 7.22-7.37 (m, 5 H), 7.04-7.18 (m, 2 H), 6.94 (d, J=2.71 Hz, 1 H), 3.54 (s, 2 H), 3.25-3.35 (m, 1 H), 3.06-3.18 (m, 1 H), 2.92-3.01 (m, 1 H), 2.72-2.85 (m, 2 H), 2.51-2.59 (m, 1 H), 2.20 (t, J=10.68 Hz, 1 H), 2.03-2.15 (m, 1 H), 1.90 (d, J=13.22 Hz, 1 H); MS (APCI+) m/z 342 (M+H, M+H)$^+$.

Example 55C (4aS)-9-chloro-1,2,3,4,4a,5-hexahydropyrazino[1,2-a][1,5]benzodiazepin-6(7H)-one The title compound was prepared according to the procedure outlined in Example 30D substituting Example 55B for Example 30C. A precipitate formed in the reaction mixture. The precipitate was collected by filtration, it was washed with dichloromethane and then dried to provide the title compound as the hydrochloride salt. $^1$H NMR (300 MHz, DMSO-$d_6$) δ ppm 9.12 (s, 1 H), 7.00 (d, J=1.98 Hz, 1 H), 3.52-3.66 (m, 1 H), 3.20-3.44 (m, 4 H), 2.87-3.11 (m, 2 H), 2.67 (dd, J=13.48, 7.14 Hz, 1 H), 2.08 (d, J=13.48 Hz, 1 H); MS (DCI+) m/z 252 (M+H, M+H)$^+$.

Example 56

10-(1-benzyl-1H-pyrazol-4-yl)-1,2,3,4,4a,5-hexahydropyrazino[1,2-a][1,5]benzodiazepin-6(7H)-one A microwave vial was charged with Example 4 (35 mg, 0.12 mmol), 1-benzyl-4-(4,4,5,5-tetramethyl-1,3,2-dioxaborolan-2-yl)-1H-pyrazole (40 mg, 0.14 mmol), FibreCat 1032 (26.0 mg, 0.012 mmol) and potassium carbonate (1 M, 0.24 mL, 0.24 mmol) and ethanol (1.5 mL). The reaction mixture was heated in a microwave (Biotage Initiator™ maximum 400 Watts) at 120° C. for 15 minutes. The catalyst was removed via filtration and the filtrate was concentrated. Purification of the residue via HPLC afforded the title compound as the trifluoroacetic acid salt. $^1$H NMR (500 MHz, pyridine-$d_5$) δ ppm 2.36 (d, J=13.43 Hz, 1 H), 2.98 (q, J=13.43, 7.02 Hz, 1 H), 3.25-3.32 (m, J=10.83, 10.83 Hz, 2 H), 3.69-3.79 (m, 3 H), 3.90 (d, J=11.60 Hz, 1 H), 4.07-4.13 (m, 1 H), 5.51 (s, 2 H), 7.27-7.37 (m, 4 H), 7.41-7.47 (m, 4 H), 8.27 (d, J=2.75 Hz, 2 H), 11.14 (s, 1 H); MS (ESI+) m/z 374 (M+H)$^+$.

Example 57

10-(2-naphthyl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting naphthalen-2-ylboronic acid for 1-benzyl-4-(4,4,5,5-tetramethyl-1,3,2-dioxaborolan-2-yl)-1H-pyrazole. $^1$H NMR (500 MHz, pyridine-$d_5$) δ ppm 2.40 (d, J=13.73 Hz, 1 H), 3.03 (dd, J=13.43, 7.02 Hz, 1 H), 3.21-3.40 (m, 2 H), 3.59-3.87 (m, 4 H), 4.03-4.12 (m, J=8.54 Hz, 1 H), 7.41 (d, J=7.63 Hz, 1 H), 7.53-7.57 (m, 2 H), 7.59-7.62 (m, 2 H), 7.94 (dd, J=8.54, 1.53 Hz, 1 H), 8.00 (d, J=7.63 Hz, 1 H), 8.04-8.11 (m, 2 H), 8.34 (s, 1 H), 11.26 (s, 1 H); MS (ESI+) m/z 344 (M+H)$^+$.

Example 58

10-(4-methoxyphenyl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting 4-methoxyphenylboronic acid for 1-benzyl-4-(4,4,5,5-tetramethyl-1,3,2-dioxaborolan-2-yl)-1H-pyrazole. $^1$H NMR (500 MHz, pyridine-$d_5$) δ ppm 2.38 (d, J=13.43 Hz, 1 H), 2.99 (dd, J=13.43, 7.02 Hz, 1 H), 3.27-3.37 (m, 2 H), 3.72-3.77 (m, 2 H), 3.78 (s, 3 H), 3.79-3.94 (m, 2 H), 4.07-4.15 (m, 1 H), 7.16-7.19 (m, 2 H), 7.34 (d, J=7.93 Hz, 1 H), 7.42-7.49 (m, 2 H), 7.73 (d, J=8.85 Hz, 2 H), 11.20 (s, 1 H); MS (ESI+) m/z 324 (M+H)$^+$.

A-1200204.2

Example 59

10-(biphenyl-3-yl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting 3-biphenylboronic acid for 1-benzyl-4-(4,4,5,5-tetramethyl-1,3,2-dioxaborolan-2-yl)-1H-pyrazole. $^1$H NMR (500 MHz, pyridine-$d_5$) δ ppm 2.40 (d, J=13.73 Hz, 1 H), 2.97-3.05 (m, J=13.43, 7.02 Hz, 1 H), 3.22-3.43 (m, 2 H), 3.67-3.88 (m, 4 H), 4.05-4.16 (m, 1 H), 7.35-7.45 (m, 2 H), 7.51 (t, J=7.63 Hz, 2 H), 7.54-7.57 (m, 2 H), 7.62 (t, J=7.78 Hz, 1 H), 7.71-7.76 (m, 2 H), 7.82 (d, J=7.63 Hz, 2 H), 8.09 (s, 1 H), 11.26 (s, 1 H); MS (ESI+) m/z 370 (M+H)$^+$.

Example 60

10-(1-methyl-1H-pyrazol-4-yl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting 1-methyl-1H-pyrazol-4-ylboronic acid for 1-benzyl-4-(4,4,5,5-tetramethyl-1,3,2-dioxaborolan-2-yl)-1H-pyrazole. $^1$H NMR (500 MHz, pyridine-d$_5$) δ ppm 2.94-3.00 (m, J=13.43, 7.02 Hz, 1 H), 3.27-3.36 (m, 2 H), 3.71-3.84 (m, 4 H), 3.89 (s, 3 H), 3.89-3.92 (m, 1 H), 4.05-4.14 (m, J=7.93 Hz, 1 H), 7.29 (d, J=8.24 Hz, 1 H), 7.42-7.49 (m, 2 H), 8.02 (s, 1 H), 8.19 (s, 1 H), 11.15 (s, 1 H); MS (ESI+) m/z 298 (M+H)$^+$.

Example 61

10-(3-fluorophenyl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting 3-fluorophenylboronic acid for 1-benzyl-4-(4,4,5,5-tetramethyl-1,3,2-dioxaborolan-2-yl)-1H-pyrazole. $^1$H NMR (500 MHz, pyridine-d$_5$) δ ppm 2.39 (d, J=13.73 Hz, 1 H), 2.98 (dd, J=13.43, 7.02 Hz, 1 H), 3.23-3.37 (m, 2 H), 3.65-3.86 (m, 4 H), 4.02-4.10 (m, 1 H), 7.16-7.19 (m, J=2.44 Hz, 1 H), 7.36 (d, J=8.24 Hz, 1 H), 7.42-7.50 (m, 3 H) 7.51-7.56 (m, 2 H) 11.26 (s, 1 H); MS (ESI+) m/z 312 (M+H)$^+$.

Example 62

10-(quinolin-3-yl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting quinolin-3-ylboronic acid for 1-benzyl-4-(4,4,5,5-tetramethyl-1,3,2-dioxaborolan-2-yl)-1H-pyrazole. $^1$H NMR (500 MHz, pyridine-d$_5$\D$_2$O) δ ppm 2.44 (d, J=13.43 Hz, 1 H), 3.06 (dd, J=13.73, 7.02 Hz, 1 H), 3.31-3.44 (m, 2 H), 3.71-3.94 (m, 4 H), 4.14-4.21 (m, 1 H), 7.41-7.46 (m, 1 H), 7.59-7.65 (m, 3 H), 7.72-7.79 (m, 1 H), 8.02 (d, J=7.63 Hz, 1 H), 8.42 (d, J=8.24 Hz, 1 H), 8.58 (d, J=2.14 Hz, 1 H), 9.53 (d, J=2.14 Hz, 1 H), 11.34 (s, 1 H); MS (ESI+) m/z 345 (M+H)$^+$.

Example 63

10-(2-methoxyphenyl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting 2-methoxyphenylboronic acid for 1-benzyl-4-(4,4,5,5-tetramethyl-1,3,2-dioxaborolan-2-yl)-1H-pyrazole. $^1$H NMR (500 MHz, pyridine-d$_5$\D$_2$O) δ ppm 2.33 (d, J=13.43 Hz, 1 H), 2.87-2.94 (m, J=13.43, 7.02 Hz, 1 H), 3.26-3.39 (m, 2 H), 3.69-3.77 (m, 5 H), 3.77-3.89 (m, 2 H), 4.04-4.14 (m, J=8.85 Hz, 1 H), 7.09 (d, J=8.24 Hz, 1 H), 7.16 (t, J=7.32 Hz, 1 H), 7.34 (d, J=8.24 Hz, 1 H), 7.40-7.52 (m, 4 H), 11.22 (s, 1 H); MS (ESI+) m/z 324 (M+H)$^+$.

Example 64

10-(biphenyl-2-yl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting 2-biphenylboronic acid for 1-benzyl-4-(4,4,5,5-tetramethyl-1,3,2-dioxaborolan-2-yl)-1H-pyrazole. $^1$H NMR (500 MHz, pyridine-d$_5$\D$_2$O) δ ppm 2.32 (d, J=13.43 Hz, 1 H), 2.74 (d, J=12.21 Hz, 1 H), 2.82-2.92 (m, J=13.43, 7.02 Hz, 1 H), 3.10-3.21 (m, 1 H), 3.35-3.46 (m, 1 H), 3.57-3.68 (m, 2 H) 3.75-3.83 (m, 1 H), 3.87-3.97 (m, 1 H), 6.86 (d, J=1.53 Hz, 1 H), 7.17-7.19 (m, 1 H), 7.23-7.27 (m, 6 H), 7.49-7.56 (m, 3 H), 7.64 (d, J=7.02 Hz, 1 H), 11.13 (s, 1 H); MS (ESI+) m/z 370 (M+H)$^+$.

Example 65

10-(3-methoxyphenyl)-1,2,3,4,4a,5-hexahydropyrazino[1,2-a][1,5]benzodiazepin-6(7H)-one A microwave vial was charged with Example 4 (100 mg, 0.338 mmol), 3-methoxyphenylboronic acid (56 mg, 0.369 mmol), FibreCat 1007 (0.36 mmol/g, 46.9 g, 0.17 mmol), potassium carbonate (2 M, 0.506 mL) and ethanol (2 mL). The reaction mixture was heated in a microwave (Biotage Initiator™, maximum 400 Watts) at 120° C. for 15 minutes. The catalyst was removed by filtration. After concentration, the material was purified via HPLC to afford the title compound as the trifluoroacetic acid salt. $^1$H NMR (500 MHz, DMSO-d$_6$) δ ppm 7.37-7.43 (m, 2 H), 7.34 (d, J=1.53 Hz, 1 H), 7.26 (d, J=7.93 Hz, 1 H), 7.18-7.22 (m, 1 H), 7.11 (d, J=8.24 Hz, 1 H), 6.96 (dd, J=8.24, 2.14 Hz, 1 H), 3.84 (s, 3 H), 3.64-3.71 (m, 1 H), 3.38-3.50 (m, 4 H), 3.01-3.14 (m, 2 H), 2.73 (dd, J=13.43, 7.02 Hz, 1 H), 2.12 (d, J=12.82 Hz, 1 H); MS (DCI+) m/z 324 (M+H)$^+$.

Example 66

10-(1-benzothiophen-3-yl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting benzo[b]thiophen-3-ylboronic acid for 1-benzyl-4-(4,4,5,5-tetramethyl-1,3,2-dioxaborolan-2-yl)-1H-pyrazole. $^1$H NMR (500 MHz, pyridine-d$_5$\D$_2$O) δ ppm 2.40 (d, J=13.73 Hz, 1 H), 3.02 (dd, J=13.43, 7.02 Hz, 1 H), 3.22-3.39 (m, 2 H), 3.56-3.84 (m, 4 H), 4.04 (s, 1 H), 7.41-7.49 (m, 5 H), 7.69-7.77 (m, 1 H), 8.01-8.13 (m, 2 H), 11.29 (s, 1 H); MS (ESI+) m/z 350 (M+H)$^+$.

Example 67

10-(1-naphthyl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting naphthalen-1-ylboronic acid for 1-benzyl-4-(4,4,5,5-tetramethyl-1,3,2-dioxaborolan-2-yl)-1H-pyrazole. $^1$H NMR (500 MHz, pyridine-d$_5$\D$_2$O) δ ppm 2.42 (d, J=13.43 Hz, 1 H), 3.06 (dd, J=13.43, 7.32 Hz, 1 H), 3.29-3.42 (m, 2 H), 3.67-3.83 (m, 3 H), 3.85-3.94 (m, 1 H), 4.08-4.18 (m, J=8.85 Hz, 1 H), 7.30-7.38 (m, 2 H), 7.42-7.46 (m, 1 H), 7.48-7.52 (m, J=7.17, 7.17 Hz, 1 H), 7.55-7.56 (m, 2 H), 7.60-7.65 (m, 1 H), 8.02 (dd, J=21.36, 8.24 Hz, 2 H), 8.12 (d, J=8.54 Hz, 1 H), 11.35 (s, 1 H); MS (ESI+) m/z 344 (M+H)+.

Example 68

10-(1H-indol-4-yl)-1,2,3,4,4a,5-hexahydropyrazino[1,2-a][1,5]benzodiazepin-6(7H)-one The title compound was prepared as the trifluoroacetic acid salt according to the procedure outline in Example 65 substituting 1H-indol-4-ylboronic acid for 3-methoxyphenylboronic acid. $^1$H NMR (500 MHz, DMSO-d$_6$) δ ppm 7.34-7.49 (m, 4 H), 7.21 (t, J=7.63 Hz, 1 H), 7.14 (d, J=8.24 Hz, 2 H), 6.61 (d, J=2.44 Hz, 1 H), 3.60-3.71 (m, 1 H), 3.33-3.51 (m, 4 H), 2.98-3.15 (m, 2 H), 2.77 (dd, J=13.58, 7.17 Hz, 1 H), 2.11 (d, J=13.12 Hz, 1 H); MS (DCI+) m/z 333 (M+H)+.

Example 69

10-(3-furyl)-1,2,3,4,4a,5-hexahydropyrazino[1,2-a][1,5]benzodiazepin-6(7H)-one

The title compound was prepared as the trifluoroacetic acid salt according to the procedure outlined in Example 56 substituting furan-3-ylboronic acid for 1-benzyl-4-(4,4,5,5-tetramethyl-1,3,2-dioxaborolan-2-yl)-1H-pyrazole. $^1$H NMR (500 MHz, pyridine-d$_5$\D$_2$O) δ ppm 2.36 (d, J=13.43 Hz, 1 H), 2.96 (dd, J=13.58, 7.17 Hz, 1 H), 3.23-3.30 (m, 2 H), 3.60-3.86 (m, 4 H), 3.99-4.07 (m, 1 H), 7.02 (s, 1 H) 7.28 (d, J=7.93 Hz, 1 H), 7.40-7.46 (m, 2 H), 7.78 (s, 1 H), 8.23 (s, 1 H), 11.17 (s, 1 H); MS (ESI+) m/z 284 (M+H)+.

Example 70

10-(2-fluorophenyl)-1,2,3,4,4a,5-hexahydropyrazino[1,2-a][1,5]benzodiazepin-6(7H)-one The title compound was prepared as the trifluoroacetic acid salt according to the procedure outline in Example 65 substituting 2-fluorophenylboronic acid for 3-methoxyphenylboronic acid. $^1$H NMR (500 MHz, DMSO-d$_6$) δ ppm 7.55-7.61 (m, 1 H), 7.39-7.48 (m, 1 H), 7.24-7.36 (m, 4 H), 7.11 (d, J=7.93 Hz, 1 H), 3.59-3.69 (m, 1 H), 3.34-3.44 (m, 4 H), 2.98-3.12 (m, 2 H), 2.74 (dd, J=13.73, 7.02 Hz, 1 H), 2.11 (d, J=12.82 Hz, 1 H); MS (DCI+) m/z 312 (M+H)+.

Example 71

10-(pyridin-2-yl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting pyridin-2-ylboronic acid for 1-benzyl-4-(4,4,5,5-tetramethyl-1,3,2-dioxaborolan-2-yl)-1H-pyrazole. $^1$H NMR (500 MHz, pyridine-d$_5$\D$_2$O) δ ppm 11.19 (s, 1 H), 8.68-8.80 (m, 1 H), 7.53-7.64 (m, 2 H), 7.30-7.36 (m, 2 H), 7.17-7.26 (m, 1 H), 7.12 (d, J=7.93 Hz, 1 H), 3.92-4.05 (m, 1 H), 3.70-3.85 (m, 1 H), 3.52-3.70 (m, 3 H), 3.07-3.26 (m, 2 H), 2.88 (dd, J=13.43, 7.02 Hz, 1 H), 2.34 (d, J=13.43 Hz, 1 H).

Example 72

10-(3-thienyl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting thiophen-3-ylboronic acid for 1-benzyl-4-(4,4,5,5-tetramethyl-1,3,2-dioxaborolan-2-yl)-1H-pyrazole. $^1$H NMR (500 MHz, pyridine-d$_5$\D$_2$O) δ ppm 2.35 (d, J=13.43 Hz, 1 H), 2.95 (dd, J=13.43, 7.02 Hz, 1 H), 3.17-3.32 (m, 2 H), 3.55-3.76 (m, 4 H), 3.91-3.98 (m, 1 H), 7.30 (d, J=8.54 Hz, 1 H), 7.50-7.53 (m, 2 H), 7.60-7.64 (m, 2 H), 7.82 (d, J=1.83 Hz, 1 H), 11.16 (s, 1 H); MS (ESI+) m/z 300 (M+H)+.

Example 73

10-[3-(1H-pyrazol-1-yl)phenyl]-1,2,3,4,4a,5-hexahydropyrazino[1,2-a][1,5]benzodiazepin-6(7H)-one The title compound was prepared as the trifluoroacetic acid salt according to the procedure outlined in Example 56 substituting 3-(1H-pyrrol-1-yl)phenylboronic acid for 1-benzyl-4-(4,4,5,5-tetramethyl-1,3,2-dioxaborolan-2-yl)-1H-pyrazole. $^1$H NMR (500 MHz, pyridine-d$_5$\D$_2$O) δ ppm 2.40 (d, J=13.43 Hz, 1 H), 3.00 (dd, J=13.58, 7.17 Hz, 1 H), 3.28-3.37 (m, 2 H), 3.70-3.84 (m, 3 H), 3.90 (d, J=11.29 Hz, 1 H), 4.10-4.17 (m, 1 H), 6.59 (t, J=1.98 Hz, 1 H), 7.33-7.36 (m, 1 H), 7.48-7.51 (m, J=3.97, 2.44 Hz, 2 H), 7.60-7.65 (m, 2 H), 7.98 (d, J=1.53 Hz, 1 H), 8.02 (d, J=7.93 Hz, 1 H), 8.39 (s, 1 H), 8.52 (d, J=2.44 Hz, 1 H), 11.28 (s, 1 H); MS (ESI+) m/z 360 (M+H)+.

Example 74

10-(4-fluorophenyl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting 4-fluorophenylboronic acid for 1-benzyl-4-(4,4,5,5-tetramethyl-1,3,2-dioxaborolan-2-yl)-1H-pyrazole. $^1$H NMR (500 MHz, pyridine-d$_5$\D$_2$O) δ ppm 2.38 (d, J=13.43 Hz, 1 H), 2.98 (dd, J=13.27, 7.17 Hz, 1 H), 3.20-3.37 (m, 2 H), 3.60-3.78 (m, 4 H), 3.94-4.07 (m, 1 H), 7.27-7.36 (m, 3 H) 7.37-7.46 (m, 2 H), 7.66-7.76 (m, 2 H), 11.21 (s, 1 H); MS (ESI+) 312 (M+H)+.

Example 75

10-(1-benzothiophen-2-yl)-1,2,3,4,4a,5-hexahydropyrazino[1,2-a][1,5]benzodiazepin-6(7H)-one The title compound was prepared as the trifluoroacetic acid salt according to the procedure outlined in Example 56 substituting benzo[b]thiophen-2-ylboronic acid for 1-benzyl-4-(4,4,5,5-tetramethyl-1,3,2-dioxaborolan-2-yl)-1H-pyrazole. $^1$H NMR (500 MHz, pyridine-d$_5$) d ppm 2.39 (d, J=13.43 Hz, 1 H) 2.91-3.01 (m, J=13.58, 7.17 Hz, 1 H) 3.19-3.35 (m, 2 H) 3.56-3.77 (m, 4 H) 3.94-4.01 (m, 1 H) 7.31 (d, J=8.54 Hz, 1 H) 7.35-7.48 (m, 2 H) 7.60 (s, 2 H) 7.82 (s, 1 H) 7.92 (d, J=7.93 Hz, 1 H) 8.01 (d, J=7.93 Hz, 1 H) 11.27 (s, 1 H) MS (ESI+) m/z 350 (M+H)+.

Example 76

N-(6-oxo-1,2,3,4,4a,5,6,7-octahydropyrazino[1,2-a][1,5]benzodiazepin-9-yl)benzenesulfonamide

Example 76A tert-butyl 9-nitro-6-oxo-1,2,4a,5,6,7-hexahydropyrazino[1,2-a][1,5]benzodiazepine-3(4H)-carboxylate Nitric acid (65% solution, 0.20 mL, 3.2 mmol) was added to a solution of Example 1C (1.0 g, 3.2 mmol) in acetic acid (5 mL) at room temperature. The solution was stirred for 3 hours, and then the reaction mixture was poured into water (200 mL). The precipitate was collected by filtration from the aqueous solution to afford the title compound. $^1$H NMR (300 MHz, DMSO-$d_6$) d ppm 8.00 (dd, J=8.92, 2.58 Hz, 1 H), 7.79 (d, J=2.78 Hz, 1 H), 7.24 (d, J=9.12 Hz, 1 H), 3.86-4.10 (m, 2 H), 3.36-3.50 (m, 1 H), 3.20-3.29 (m, 1 H), 2.81-2.99 (m, 1 H), 2.62-2.77 (m, 1 H), 2.18 (d, J=13.48 Hz, 1 H); MS (APCI+) m/z 307 (M+H-tBu)$^+$.

Example 76B tert-butyl 9-amino-6-oxo-1,2,4a,5,6,7-hexahydropyrazino[1,2-a][1,5]-benzodiazepine-3(4H)-carboxylate A 250 mL pressure bottle was charged with Example 76A (2.24 g, 6.18 mmol), tetrahydrofuran (40 mL) and 5% Pd—C, (wet, 0.448 g, 4.21 mmol). The reaction mixture was stirred for 16 hours under $H_2$ (30 psi) at room temperature. The mixture was filtered through a nylon membrane and the filtrate was concentrated. Purification of the residue via flash chromatography (30-100% ethyl acetate/hexanes) afforded title compound. $^1$H NMR (300 MHz, DMSO-$d_6$) δ ppm 9.26-9.41 (m, 1 H), 6.77 (d, J=8.73 Hz, 1 H), 6.34 (dd, J=8.53, 2.58 Hz, 1 H), 6.21 (d, J=2.38 Hz, 1 H), 4.89 (s, 2 H), 3.77-3.98 (m, 2 H), 2.67-3.03 (m, 5 H), 2.42-2.48 (m, 1 H), 1.90 (d, J=13.09 Hz, 1 H); MS (APCI+) m/z 333 (M+H)$^+$.

Example 76C

N-(6-oxo-1,2,3,4,4a,5,6,7-octahydropyrazino[1,2-a][1,5]benzodiazepin-9-yl)benzenesulfonamide To a solution of Example 76B (100 mg 0.301 mmol) in pyridine (5 mL) was added benzenesulfonyl chloride (53.0 mg, 0.301 mmol). The reaction was stirred at 60° C. for 16 hours before concentration onto silica gel. Purification via flash chromatography (0-100% ethyl acetate/hexanes) afforded tert-butyl 9-amino-6-oxo-1,2,4a,5,6,7-hexahydropyrazino[1,2-a][1,5]benzodiazepine-3(4H)-carboxylate which was directly dissolved in dichloromethane (4 mL). HCl (4 M, dioxane, 1 mL) was added. When the reaction appeared complete according to LC/MS, the reaction mixture was concentrated and purified via HPLC to afford title compound as the trifluoroacetic acid salt. $^1$H NMR (500 MHz, DMSO-$d_6$) δ ppm 7.78 (d, J=7.63 Hz, 2 H), 7.52-7.67 (m, 3 H), 7.00 (d, J=8.54 Hz, 1 H), 6.80-6.91 (m, 2 H), 2.80-3.57 (m, 8 H), 1.98-2.05 (m, 1 H); MS (DCI+) m/z 373 (M+H)$^+$.

Example 77

9-chloro-7-ethyl-1,2,3,4,4a,5-hexahydropyrazino[1,2-a][1,5]-benzodiazepin-6(7H)-one Example 77A tert-butyl 9-chloro-6-oxo-1,2,4a,5,6,7-hexahydropyrazino[1,2-a][1,5]benzodiazepine-3(4H)-carboxylate To a solution of Example 51 (980 mg, 3.40 mmol) in dichloromethane (30) was added triethylamine (0.948, 6.80 mmol) and di-tert-butyl dicarbonate (816 mg, 3.74 mmol). The solution was stirred for 16 hours before concentration onto silica gel. Purification via flash chromatography (30-100% ethyl acetate/hexanes) afforded title compound. $^1$H NMR (300 MHz, DMSO-$d_6$) δ ppm 9.64-9.73 (m, 1 H), 7.13-7.21 (m, 1 H), 7.04-7.12 (m, 1 H), 6.93-7.00 (m, 1 H), 3.84-4.01 (m, 2 H), 2.70-3.23 (m, 5 H), 2.59 (dd, J=13.39, 6.95 Hz, 1 H), 2.04 (d, J=13.56 Hz, 1 H); MS (APCI+) m/z 252 (M+H)$^+$.

Example 77B 9-chloro-7-ethyl-1,2,3,4,4a,5-hexahydropyrazino[1,2-a][1,5]-benzodiazepin-6(7H)-one To a solution of Example 77A (500 mg, 1.42 mmol) in N,N-dimethylformamide (3 mL) was added NaH (65%, 63 mg, 1.70 mmol). The solution was allowed to stir at room temperature for 1 hour before addition of ethyl iodide (266 mg, 1.70 mmol). The reaction mixture stirred for 3 hours. LC/MS showed 50% starting material left. More NaH (100 mg) was added, and the reaction mixture was stirred for 16 hours. Addition of water caused precipitation. The precipitate was collected by filtration, taken up in dichloromethane, filtered through MgSO$_4$, and concentrated to give a white solid. A portion of the precipitate (40 mg) was dissolved in dichloromethane (2 mL) and HCl (4 M, dioxane, 1 mL) was added. When the reaction was complete, according to LC/MS, HPLC purification afforded the title compound as the trifluoroacetic acid salt. $^1$H NMR (300 MHz, DMSO-$d_6$) δ ppm 7.42 (d, J=2.71 Hz, 1 H), 7.25-7.34 (m, 1 H), 7.14 (d, J=8.82 Hz, 1 H), 3.81-4.11 (m, 3 H), 3.43-3.63 (m, 1 H), 2.62-3.11 (m, 5 H), 2.52-2.61 (m, 1 H), 2.05 (d, J=13.22 Hz, 1 H), 1.42 (s, 9 H) 0.98 (t, 3 H); MS (DCI+) m/z 280 (M+H)$^+$.

Example 78

9-chloro-7-ethyl-3-methyl-1,2,3,4,4a,5-hexahydropyrazino[1,2-a][1,5]benzodiazepin-6(7H)-one To a solution of Example 77 (265 mg, 0.947 mmol) in a pH 4 buffer solution (10 mL, made from 48 g acetic acid and 30.5 g sodium acetate in 1 L methanol) was added formaldehyde (36% solution, 158 mg, 1.89 mmol) and MP-cyanoborohydride (1.25 mmol/g, 2.27 g, 2.84 mmol). The reaction was allowed to stir for 2 hours. before MP-cyanoborohydride was removed by filtration. The filtrate was concentrated and purified via HPLC to afford the title compound as the trifluoroacetic acid salt. $^1$H NMR (400 MHz, DMSO-$d_6$) δ ppm 7.47 (d, J=2.44 Hz, 1 H), 7.34 (dd, J=8.70, 2.29 Hz, 1 H), 7.21 (d, J=8.54 Hz, 1 H), 3.95-4.09 (m, 1 H), 3.49-3.62 (m, 3 H), 3.38-3.49 (m, 1 H), 3.24-3.37 (m, 2 H), 3.00-3.14 (m, 2 H), 2.88-2.94 (m, 3 H), 2.65 (dd, J=13.73, 7.32 Hz, 1 H), 2.07 (d, J=13.73 Hz, 1 H), 1.01 (t, J=7.02 Hz, 3 H); MS (DCI+) m/z 294 (M+H)$^+$.

Example 79

8-fluoro-3-methyl-1,2,3,4,4a,5-hexahydropyrazino[1,2-a][1,5]benzodiazepin-6(7H)-one The title compound was prepared as the trifluoroacetic acid salt according to the procedure outlined in Example 78 substituting Example 32 for Example 77. $^1$H NMR (400 MHz, DMSO-$d_6$) δ ppm 7.18-7.28 (m, 1H), 6.90-7.09 (m, 2H) 3.04-3.69 (m, 7H), 2.90 (s, 3H), 2.73 (dd, J=13.58, 7.17 Hz, 1H), 2.06 (d, J=13.43 Hz, 1H); MS (DCI+) m/z 250 (M+H)$^+$.

Example 80

9-chloro-7-methyl-1,2,3,4,4a,5-hexahydropyrazino[1,2-a][1,5]benzodiazepin-6(7H)-one The title compound was prepared as the trifluoroacetic acid salt according to the procedure outlined in Example 77B substituting methyl iodide for ethyl iodide. $^1$H NMR (500 MHz, DMSO-d$_6$) δ ppm 7.46 (s, 1 H), 7.32 (d, J=8.54 Hz, 1 H), 7.19 (d, J=8.54 Hz, 1 H), 3.33-3.48 (m, 3 H), 3.15-3.32 (m, 5 H), 2.90-3.10 (m, 2 H), 2.67 (dd, J=13.58, 7.17 Hz, 1 H), 2.14 (d, J=13.73 Hz, 1 H); MS (DCI+) m/z 266 (M+H)$^+$.

Example 81

9-chloro-7-methyl-1,2,3,4,4a,5,6,7-octahydropyrazino [1,2-a][1,5]benzodiazepine

To a solution of Example 80 (390 mg, 1.06 mmol) in tetrahydrofuran (10 mL) was added borane (1 M in tetrahydrofuran, 4.26 mL, 4.26 mmol). The solution was heated to 80° C. for 3 hours. According to LC/MS, the reaction was not complete. More borane (2 mL, 2 mmol) was added, and the reaction mixture was stirred at 80° for 16 hours. Methanol (20 mL) was added, and the reaction heated at 80° C. for 1 hour. The reaction was cooled to room temperature and 1 M HCl was added (60 mL). This solution was stirred for 30 minutes before the reaction was neutralized with saturate aqueous NaHCO$_3$. The mixture was extracted with dichloromethane. The organic phase was concentrated. The concentrate was dissolved in dichloromethane (2 mL) and HCl (4 M in dioxane, 1 mL) was added. When the LC/MS showed the reaction was complete, the solution was concentrated. Purification via HPLC afforded the title compound as the trifluoroacetic acid salt. $^1$H NMR (500 MHz, DMSO-d$_6$) δ ppm 6.94-6.98 (m, 2 H), 6.84-6.87 (m, 1 H), 3.85-3.90 (m, 3 H), 3.51-3.59 (m, 1 H), 3.29-3.38 (m, 2 H), 2.99-3.22 (m, 5 H), 2.85-2.91 (m, 1 H), 1.66-1.83 (m, 2 H); MS (DCI+) m/z 252 (M+H)$^+$.

Example 82

9-chloro-7-ethyl-3-methyl-1,2,3,4,4a,5,6,7-octahydropyrazino [1,2-a][1,5]benzodiazepine The title compound was prepared as the trifluoroacetic acid salt according to the procedure outlined in Example 81 substituting Example 78 for Example 80. $^1$H NMR (500 MHz, DMSO-d$_6$) δ ppm 6.93-6.99 (m, 2 H), 6.90 (s, 1 H), 3.88-3.97 (m, 3 H), 3.44-3.58 (m, 2 H), 3.15-3.35 (m, 5 H), 3.05-3.16 (m, 2 H), 2.95-3.04 (m, 2 H), 1.70-1.81 (m, 1 H), 1.60-1.69 (m, 1 H); MS (DCI+) m/z 280 (M+H)$^+$.

Example 83

(4aR)-8-fluoro-1,2,3,4,4a,5-hexahydropyrazino[1,2-a][1,5]benzodiazepin-6(7H)-one Example 83A 3-benzyl-8-fluoro-1,2,3,4,4a,5-hexahydropyrazino[1,2-a][1,5]benzodiazepin-6(7H)-one 1,3-Difluoro-2-nitrobenzene (9.15 g, 57.5 mmol) and Example 12C (7.14 g, 28.8 mmol) were heated neat to 100° C. for 16 hours. Acetic acid (50 mL) and iron powder (7.14 g, 28.8 mmol) were added. The reaction mixture was stirred an additional 16 hours before concentration onto silica gel. The product fractions were collected after flash chromatography (0-30% methanol/dichloromethane) and mixed with NaOH (1 M, pH>10). The dichloromethane was separated and dried with MgSO$_4$ to afford the title compound. $^1$H NMR (300 MHz, DMSO-d$_6$) δ ppm 7.22-7.37 (m, 5 H), 7.08-7.20 (m, 1 H), 6.87-6.98 (m, 2 H), 3.54 (d, J=2.71 Hz, 2 H), 2.96-3.14 (m, 2 H), 2.70-2.87 (m, 2 H), 2.57 (dd, J=13.39, 7.29 Hz, 1 H), 2.24 (t, J=10.68 Hz, 1 H), 2.05-2.18 (m, 1 H), 1.90 (d, J=13.56 Hz, 1 H); MS (APCI+) m/z 326 (M+H)$^+$.

Example 83B (4aR)-3-benzyl-8-fluoro-1,2,3,4,4a,5-hexahydropyrazino[1,2-a][1,5]-benzodiazepin-6(7H)-one Chiral separation of Example 83A via SFC (Chiralpak® IA, 21×250 mm, 5 µm, 10-30% methanol with 0.1% diethylamine-CO$_2$ gradient over 15 minutes, at 40 mL/minute, retention time=7.0 minutes) afforded the title compound. $^1$H NMR (300 MHz, DMSO-d$_6$) δ ppm 7.22-7.37 (m, 5 H), 7.08-7.20 (m, 1 H), 6.87-6.98 (m, 2 H), 3.54 (d, J=2.71 Hz, 2 H), 2.96-3.14 (m, 2 H), 2.70-2.87 (m, 2 H), 2.57 (dd, J=13.39, 7.29 Hz, 1 H), 2.24 (t, J=10.68 Hz, 1 H), 2.05-2.18 (m, 1 H), 1.90 (d, J=13.56 Hz, 1 H); MS (APCI+) m/z 326 (M+H)$^+$.

Example 83C (4aR)-8-fluoro-1,2,3,4,4a,5-hexahydropyrazino[1,2-a][1,5]benzodiazepin-6(7H)-one The title compound was prepared as the trifluoroacetic acid salt according to the procedure outlined in Example 30D substituting Example 83B for Example 30C. $^1$H NMR (500 MHz, DMSO-d$_6$/D$_2$O) δ ppm 7.14-7.24 (m, 1 H) 6.91-7.00 (m, 1 H) 3.24-3.35 (m, 1 H) 2.91-3.14 (m, 2 H) 2.68-2.82 (m, 2 H) 2.56-2.65 (m, 2 H) 1.98 (d, J=13.43 Hz, 1 H); MS (APCI+) m/z 236 (M+H)$^+$.

Example 84

(4aS)-10-chloro-3-methyl-1,2,3,4,4a,5-hexahydropyrazino[1,2-a][1,5]benzodiazepin-6(7H)-one The title compound was prepared as the trifluoroacetic acid salt according to the procedure outlined in Example 83 substituting Example 41 for Example 77. $^1$H NMR (500 MHz, DMSO-d$_6$/D$_2$O) δ ppm 7.13-7.20 (m, 2 H), 7.01 (d, J=8.24 Hz, 1 H), 3.61-3.67 (m, 1 H), 3.47-3.56 (m, 2 H), 3.30-3.42 (m, 2 H), 3.07-3.18 (m, 2 H), 2.87-2.93 (m, 3 H), 2.69 (dd, J=13.73, 7.02 Hz, 1 H), 2.06 (d, J=13.43 Hz, 1 H); MS (DCI+) m/z 266 (M+H)$^+$ Example 85

(4aS)-8-fluoro-1,2,3,4,4a,5-hexahydropyrazino[1,2-a][1,5]benzodiazepin-6(7H)-one The title compound was prepared as the trifluoroacetic acid salt according to the procedure in Example 83, using fraction 2 from the chiral separation in 83B (retention time=8.2 minutes). in the procedure outlined in Example 30D substituting Example 83B for Example 30C. $^1$H NMR (500 MHz, DMSO-d$_6$/D$_2$O) δ ppm 7.14-7.24 (m, 1 H) 6.91-7.00 (m, 1 H) 3.24-3.35 (m, 1 H) 2.91-3.14 (m, 2 H) 2.68-2.82 (m, 2 H) 2.56-2.65 (m, 2 H) 1.98 (d, J=13.43 Hz, 1 H); MS (APCI+) m/z 236 (M+H)$^+$.

Example 86

(4aS)-11-fluoro-1,2,3,4,4a,5-hexahydropyrazino[1,2-a][1,5]benzodiazepin-6(7H)-one Example 86A 3-benzyl-11-fluoro-1,2,3,4,4a,5-hexahydropyrazino [1,2-a][1,5]benzodiazepin-6(7H)-one The title compound was prepared according to the procedure outlined in Example 83A substitution 1,2-difluoro-3- nitrobenzene for 1,3-difluoro-2-nitrobenzene. $^1$H NMR (300 MHz, DMSO-$d_6$) δ ppm 7.20-7.36 (m, 5 H), 6.88-7.05 (m, 2 H), 6.73-6.82 (m, 1 H), 3.37-3.61 (m, 4 H), 2.91-3.10 (m, 1 H), 2.68-2.84 (m, 2 H), 2.52-2.60 (m, 1 H), 1.83-2.24 (m, 3 H); MS (APCI+) m/z 326 (M+H)$^+$.

Example 86B (4aS)-3-benzyl-11-fluoro-1,2,3,4,4a,5-hexahydropyrazino[1,2-a][1,5]benzodiazepin-6(7H)-one Chiral separation of Example 86A via SFC (Chiralpak® AS, 21×250 mm, 5 µm, 10-30% methanol-$CO_2$ gradient over 20 minutes, at 40 mL/minute, retention time=16.5 minutes) afforded the title compound. $^1$H NMR (300 MHz, DMSO-$d_6$) δ ppm 7.20-7.36 (m, 5 H), 6.88-7.05 (m, 2 H), 6.73-6.82 (m, 1 H), 3.37-3.61 (m, 4 H), 2.91-3.10 (m, 1 H), 2.68-2.84 (m, 2 H), 2.52-2.60 (m, 1 H), 1.83-2.24 (m, 3 H); MS (APCI+) m/z 326 (M+H)$^+$.

Example 86C (4aS)-11-fluoro-1,2,3,4,4a,5-hexahydropyrazino[1,2-a][1,5]benzodiazepin-6(7H)-one To a 50 mL pressure bottle was added Example 86B (189 mg, 0.581 mmol), 2,2,2-trifluoroethanol (10 mL), and Pd(OH)$_2$—C, (20% wet, 18.90 mg, 0.135 mmol). The reaction mixture stirred for 2 hours under $H_2$ (30 psi) at 50° C. After concentration, HPLC afforded the title compound as the trifluoroacetic acid salt. $^1$H NMR (500 MHz, DMSO-$d_6$/$D_2O$) δ ppm 7.08-7.17 (m, 1 H) 7.00-7.08 (m, 1 H) 6.87 (d, J=7.93 Hz, 1 H) 3.59-3.71 (m, 1 H) 3.25-3.47 (m, 4 H) 2.87-3.04 (m, 2 H) 2.63-2.76 (m, 1 H) 2.00-2.17 (m, 1 H); MS (DCI+) m/z 235 (M+H)$^+$.

Example 87

(4aR)-11-fluoro-1,2,3,4,4a,5-hexahydropyrazino[1,2-a][1,5]benzodiazepin-6(7H)-one The title compound was prepared as the trifluoroacetic acid salt according to the procedure outlined in Example 86 using fraction 1 from the chiral separation in Example 86B (retention time=12.5 minutes). $^1$H NMR (500 MHz, DMSO-$d_6$/$D_2O$) δ ppm 7.08-7.17 (m, 1 H) 7.00-7.08 (m, 1 H) 6.87 (d, J=7.93 Hz, 1 H) 3.59-3.71 (m, 1 H) 3.25-3.47 (m, 4 H) 2.87-3.04 (m, 2 H) 2.63-2.76 (m, 1 H) 2.00-2.17 (m, 1 H); MS (DCI+) m/z 235 (M+H)$^+$.

Example 88

(4aS)-8-fluoro-3-methyl-1,2,3,4,4a,5-hexahydropyrazino[1,2-a][1,5]benzodiazepin-6(7H)-one The title compound was prepared as the trifluoroacetic acid salt according to the procedure outlined in Example 78 substituting Example 85 for Example 77. $^1$H NMR (500 MHz, DMSO-$d_6$) δ ppm 7.09-7.17 (m, 1 H), 6.86-6.93 (m, 2 H), 3.71 (s, 3 H), 3.25-3.33 (m, 1 H), 3.04-3.14 (m, 1 H), 2.98 (d, J=11.60 Hz, 1 H), 2.80 (d, J=11.29 Hz, 1 H), 2.75 (d, J=10.68 Hz, 1 H), 2.51-2.59 (m, 1 H), 2.15 (t, J=10.83 Hz, 1 H), 2.02-2.11 (m, 1 H), 1.93 (d, J=12.82 Hz, 1 H); MS (DCI+) m/z 250 (M+H)$^+$.

Example 89

10-(3-methylphenyl)-1,2,3,4,4a,5-hexahydropyrazino[1,2-a][1,5]benzodiazepin-6(7H)-one A microwave vial was charged with Example 4 (54.0 mg, 0.182 mmol), 3-methylphenylboronic acid (27.3 mg, 0.301 mmol), FibreCat 1007 (0.36 mmol/g, 25.3 mg, 9.12 µmol), potassium carbonate (2 M, 0.506 mL) and ethanol (273 µL). The reaction mixture was heated in a microwave (Biotage Initiator™, maximum 400 Watts) at 120° C. for 15 minutes. The catalyst was removed by filtration. After filtration, the compound was purified via HPLC to afford the title compound as the trifluoroacetic acid salt. $^1$H NMR (500 MHz, DMSO-$d_6$) δ ppm 7.65 (s, 1 H), 7.62 (d, J=7.63 Hz, 1 H), 7.47-7.54 (m, 3 H), 7.35 (d, J=7.63 Hz, 1 H), 7.24 (d, J=8.24 Hz, 1 H), 3.76-3.83 (m, 1 H), 3.51-3.62 (m, 4 H), 3.15-3.27 (m, 2 H), 2.87 (dd, J=13.58, 7.17 Hz, 1 H), 2.54 (s, 3 H), 2.25 (d, J=13.43 Hz, 1 H); MS (DCI+) m/z 308 (M+H)$^+$.

Example 90

10-[3-(trifluoromethyl)phenyl]-1,2,3,4,4a,5-hexahydropyrazino[1,2-a][1,5]benzodiazepin-6(7H)-one The title compound was prepared as the trifluoroacetic acid salt according to the procedure outlined in Example 89 substituting 3-(trifluoromethyl)phenylboronic acid for 3-methylphenylboronic acid. $^1$H NMR (500 MHz, DMSO-$d_6$) δ ppm 7.97-8.03 (m, 2 H), 7.70-7.77 (m, 2 H), 7.47 (dd, J=8.09, 1.98 Hz, 1 H), 7.42 (d, J=2.14 Hz, 1 H), 7.13 (d, J=8.24 Hz, 1 H), 3.62-3.71 (m, 1 H), 3.37-3.50 (m, 4 H), 3.00-3.13 (m, 2 H), 2.73 (dd, J=13.73, 7.02 Hz, 1 H), 2.12 (d, J=12.51 Hz, 1 H); MS (DCI+) m/z 362 (M+H)$^+$.

Example 91

10-(3-ethylphenyl)-1,2,3,4,4a,5-hexahydropyrazino[1,2-a][1,5]-benzodiazepin-6(7H)-one The title compound was prepared as the trifluoroacetic acid salt according to the procedure outlined in Example 89 substituting 3-ethylphenylboronic acid for 3-methylphenylboronic acid. $^1$H NMR (500 MHz, DMSO-$d_6$) δ ppm 7.39-7.49 (m, 2 H), 7.30-7.38 (m, 2 H), 7.23-7.30 (m, 1 H), 7.17 (d, J=7.63 Hz, 1 H), 7.05 (d, J=8.24 Hz, 1 H), 3.56-3.65 (m, 1 H), 3.32-3.44 (m, 4 H), 2.93-3.09 (m, 2 H), 2.59-2.72 (m, 3 H), 2.06 (d, J=12.51 Hz, 1 H), 1.18 (t, J=7.63 Hz, 3 H); MS (DCI+) m/z 322 (M+H)$^+$.

Example 92

10-(3-isopropylphenyl)-1,2,3,4,4a,5-hexahydropyrazino[1,2-a][1,5]benzodiazepin-6(7H)-one The title compound was prepared as the trifluoroacetic acid salt according to the procedure outlined in Example 89 substituting 3-isopropylphenylboronic acid for 3-methylphenylboronic acid. $^1$H NMR (500 MHz, DMSO-$d_6$) δ ppm 7.45-7.53 (m, 2 H), 7.35-7.43 (m, 2 H), 7.31-7.34 (m, 1 H), 7.26 (d, J=7.63 Hz, 1 H), 7.10 (d, J=8.24 Hz, 1 H), 3.62-3.71 (m, 1 H), 3.37-3.49 (m, 4 H), 2.93-3.13 (m, 3 H), 2.72 (dd, J=13.43, 7.02 Hz, 1 H), 2.11 (d, J=12.51 Hz, 1 H), 1.26 (d, J=7.02 Hz, 6 H); MS (DCI+) m/z 336 (M+H)+.

Example 93

10-[3-(trifluoromethoxy)phenyl]-1,2,3,4,4a,5-hexahydropyrazino[1,2-a][1,5]benzodiazepin-6(7H)-one The title compound was prepared as the trifluoroacetic acid salt according to the procedure outlined in Example 89 substituting 3-trifluoromethoxyphenylboronic acid for 3-methylphenylboronic acid. $^1$H NMR (500 MHz, DMSO-$d_6$) δ ppm 7.70 (d, J=7.93 Hz, 1 H), 7.61 (s, 1 H), 7.56 (t, J=7.93 Hz, 1 H), 7.35-7.41 (m, 1 H), 7.28-7.35 (m, 2 H), 7.07 (d, J=8.24 Hz, 1 H), 3.58-3.67 (m, 1 H), 3.32-3.45 (m, 4 H), 2.94-3.09 (m, 2 H), 2.67 (dd, J=13.43, 7.02 Hz, 1 H), 2.07 (d, J=12.21 Hz, 1 H); MS (DCI+) m/z 378 (M+H)+.

Example 94

10-(3-isopropoxyphenyl)-1,2,3,4,4a,5-hexahydropyrazino[1,2-a][1,5]benzodiazepin-6(7H)-one The title compound was prepared as the trifluoroacetic acid salt according to the procedure outlined in Example 89 substituting 3-isopropoxyphenylboronic acid for 3-methylphenylboronic acid. $^1$H NMR (500 MHz, DMSO-$d_6$) δ ppm 7.34-7.40 (m, 2 H), 7.29-7.33 (m, 1 H), 7.22 (d, J=8.24 Hz, 1 H), 7.13-7.17 (m, 1 H), 7.09 (d, J=8.24 Hz, 1 H), 6.93 (dd, J=8.09, 2.29 Hz, 1 H), 4.64-4.75 (m, 1 H), 3.62-3.71 (m, 1 H), 3.37-3.48 (m, 4 H), 3.00-3.14 (m, 2 H), 2.72 (dd, J=13.58, 7.17 Hz, 1 H), 2.11 (d, J=12.51 Hz, 1 H), 1.30 (d, J=5.80 Hz, 6 H); MS (APCI+) m/z 352 (M+H)+.

Example 95

10-[3-(benzyloxy)phenyl]-1,2,3,4,4a,5-hexahydropyrazino[1,2-a][1,5]benzodiazepin-6(7H)-one The title compound was prepared as the trifluoroacetic acid salt according to the procedure outlined in Example 89 substituting 3-benzyloxyphenylboronic acid for 3-methylphenylboronic acid. $^1$H NMR (500 MHz, DMSO-$d_6$) δ ppm 7.29-7.35 (m, 2 H), 7.16-7.28 (m, 5 H), 7.07-7.15 (m, 3 H), 6.93 (d, J=8.24 Hz, 1 H), 6.85 (dd, J=8.09, 1.98 Hz, 1 H), 5.02 (s, 2 H), 3.44-3.54 (m, 1 H), 3.21-3.32 (m, 4 H), 2.82-2.97 (m, 2 H), 2.55 (dd, J=13.73, 7.02 Hz, 1 H), 1.94 (d, J=12.82 Hz, 1 H); MS (APCI+) m/z 400 (M+H)+.

Example 96

10-(3-isobutoxyphenyl)-1,2,3,4,4a,5-hexahydropyrazino[1,2-a][1,5]benzodiazepin-6(7H)-one The title compound was prepared as the trifluoroacetic acid salt according to the procedure outlined in Example 89 substituting 3-isobutoxyphenylboronic acid for 3-methylphenylboronic acid. $^1$H NMR (500 MHz, DMSO-$d_6$) δ ppm 7.35-7.42 (m, 2 H), 7.30-7.35 (m, 1 H), 7.24 (d, J=7.63 Hz, 2 H), 7.16-7.20 (m, 1 H), 7.09 (d, J=7.93 Hz, 1 H), 6.94 (dd, J=8.24, 1.83 Hz, 1 H), 3.82 (d, J=6.41 Hz, 2 H), 3.61-3.70 (m, 1 H), 3.36-3.50 (m, 4 H), 2.99-3.13 (m, 2 H), 2.72 (dd, J=13.43, 7.02 Hz, 1 H), 2.11 (d, J=12.82 Hz, 1 H), 1.97-2.08 (m, 1 H), 1.01 (d, J=6.71 Hz, 6 H); MS (DCI+) m/z 366 (M+H)+.

Example 97

N-(6-oxo-1,2,3,4,4a,5,6,7-octahydropyrazino[1,2-a][1,5]benzodiazepin-9-yl)biphenyl-2-sulfonamide The title compound was prepared according to the procedure outlined in Example 76C substituting biphenyl-2-sulfonyl chloride for benzenesulfonyl chloride followed by filtration through a 2 g Si-carbonate cartridge (SiliCylcle®) eluting with additional methanol to afford the title compound. $^1$H NMR (500 MHz, DMSO-$d_6$) δ ppm 7.99 (d, J=7.93 Hz, 1 H), 7.60-7.70 (m, 1 H), 7.51-7.60 (m, 1 H), 7.35-7.44 (m, 3 H), 7.21-7.33 (m, 3 H), 6.91 (d, J=8.85 Hz, 1 H), 6.73 (dd, J=8.54, 2.44 Hz, 1 H), 6.65 (d, J=2.44 Hz, 1 H), 3.09-3.16 (m, 1 H), 2.73-3.01 (m, 3 H), 2.55-2.72 (m, 3 H), 2.45 (dd, J=13.12, 7.32 Hz, 1 H), 1.90 (d, J=12.82 Hz, 1 H); MS (DCI+) m/z 449 (M+H)+.

Example 98

2-methyl-N-(6-oxo-1,2,3,4,4a,5,6,7-octahydropyrazino[1,2-a][1,5]benzodiazepin-9-yl)benzenesulfonamide The title compound was prepared according to the procedure outlined in Example 76C substituting 2-methylbenzene-1-sulfonyl chloride for benzenesulfonyl chloride followed by filtration through a 2 g Si-carbonate cartridge (SiliCylcle®) eluting with additional methanol to afford the title compound. $^1$H NMR (500 MHz, DMSO-$d_6$) δ ppm 7.86 (d, J=7.02 Hz, 1 H), 7.50 (t, J=7.48 Hz, 1 H), 7.31-7.41 (m, 2 H), 6.91 (d, J=8.85 Hz, 1 H), 6.81 (dd, J=8.70, 2.59 Hz, 1 H), 6.77 (d, J=2.44 Hz, 1 H), 3.06-3.15 (m, 1 H), 2.84-2.99 (m, 2 H), 2.77-2.85 (m, 2 H), 2.61-2.70 (m, 2 H), 2.41 (dd, J=13.12, 7.32 Hz, 1 H), 1.87 (d, J=12.51 Hz, 1 H); MS (DCI+) m/z 387 (M+H)+.

Example 99

4-methyl-N-(6-oxo-1,2,3,4,4a,5,6,7-octahydropyrazino[1,2-a][1,5]benzodiazepin-9-yl)benzenesulfonamide The title compound was prepared according to the procedure outlined in Example 76C substituting 4-methylbenzene-1-sulfonyl chloride for benzenesulfonyl chloride followed by filtration through a 2 g Si-carbonate cartridge (SiliCylcle®) eluting with methanol to afford the title compound. $^1$H NMR (500 MHz, DMSO-$d_6$) δ ppm 7.65 (d, J=8.24 Hz, 2 H), 7.34 (d, J=8.24 Hz, 2 H), 6.92 (d, J=8.85 Hz, 1 H), 6.80 (d, 2 H), 3.07-3.14 (m, 1 H), 2.76-2.98 (m, 4 H), 2.62-2.69 (m, 1 H), 2.55-2.62 (m, 1 H), 2.43 (dd, J=13.12, 7.32 Hz, 1 H), 1.88 (d, J=12.82 Hz, 1 H); MS (DCI+) m/z 387 (M+H)+.

Example 100

3-methyl-N-(6-oxo-1,2,3,4,4a,5,6,7-octahydropyrazino[1,2-a][1,5]benzodiazepin-9-yl)benzenesulfonamide The title compound was prepared as the trifluoroacetic acid salt according to the procedure outlined in Example 76C substituting 3-methylbenzene-1-sulfonyl chloride for benzenesulfonyl chloride. $^1$H NMR (500 MHz, DMSO-$d_6$) δ ppm 7.54-7.63 (m, 2 H), 7.41-7.48 (m, 2 H), 7.01 (d, J=8.54 Hz, 1 H), 6.82-6.91 (m, 2 H), 3.46-3.55 (m, 1 H), 3.30-3.39 (m, 2

H), 3.14-3.29 (m, 2 H), 2.90-3.05 (m, 2 H), 2.56-2.60 (m, 1 H), 2.33-2.39 (m, 3 H), 2.02 (d, J=12.82 Hz, 1 H); MS (DCI+) m/z 387 (M+H)+.

Example 101

3-chloro-N-(6-oxo-1,2,3,4,4a,5,6,7-octahydropyrazino[1,2-a][1,5]benzodiazepin-9-yl)benzenesulfonamide The title compound was prepared as the trifluoroacetic acid salt according to the procedure outlined in Example 76C substituting 3-chlorobenzene-1-sulfonyl chloride for benzenesulfonyl chloride. $^1$H NMR (500 MHz, DMSO-d$_6$) δ ppm 7.68-7.78 (m, 2 H), 7.56-7.64 (m, 1 H), 7.04 (d, J=8.54 Hz, 1 H), 6.88 (dd, J=8.70, 2.59 Hz, 1 H), 6.84 (d, J=2.44 Hz, 1 H), 3.48-3.56 (m, 1 H), 3.30-3.39 (m, 2 H), 3.22-3.30 (m, 1 H), 3.14-3.21 (m, 1 H), 2.91-3.05 (m, 2 H), 2.55-2.60 (m, 1 H), 2.04 (d, J=12.82 Hz, 1 H); MS (DCI+) m/z 407 (M+H)+.

Example 102

4-chloro-N-(6-oxo-1,2,3,4,4a,5,6,7-octahydropyrazino[1,2-a][1,5]benzodiazepin-9-yl)benzenesulfonamide The title compound was prepared as the trifluoroacetic acid salt according to the procedure outlined in Example 76C substituting 4-chlorobenzene-1-sulfonyl chloride for benzenesulfonyl chloride. $^1$H NMR (500 MHz, DMSO-d$_6$) δ ppm 7.78 (d, J=8.54 Hz, 2 H), 7.64 (d, J=8.85 Hz, 2 H), 7.03 (d, J=8.54 Hz, 1 H), 6.88 (dd, J=8.54, 2.75 Hz, 1 H), 6.84 (d, J=2.44 Hz, 1 H), 3.49-3.56 (m, 1 H), 3.31-3.39 (m, 2 H), 3.22-3.30 (m, 1 H), 3.15-3.22 (m, 1 H), 2.91-3.04 (m, 2 H), 2.51-2.62 (m, 2 H), 2.03 (d, J=12.82 Hz, 1 H); MS (DCI+) m/z 407 (M+H)+.

Example 103

2-fluoro-N-(6-oxo-1,2,3,4,4a,5,6,7-octahydropyrazino [1,2-a][1,5]benzodiazepin-9-yl)benzenesulfonamide The title compound was prepared as the trifluoroacetic acid salt according to the procedure outlined in Example 76C substituting 2-fluorobenzene-1-sulfonyl chloride for benzenesulfonyl chloride. $^1$H NMR (500 MHz, DMSO-d$_6$) δ ppm 7.80-7.86 (m, 1 H), 7.66-7.74 (m, 1 H), 7.34-7.45 (m, 2 H), 7.02 (d, J=8.85 Hz, 1 H), 6.92 (dd, J=8.70, 2.59 Hz, 1 H), 6.85 (d, J=2.44 Hz, 1 H), 3.47-3.55 (m, 1 H), 3.29-3.38 (m, 2 H), 3.21-3.30 (m, 1 H), 3.14-3.20 (m, 1 H), 2.89-3.03 (m, 2 H), 2.50-2.56 (m, 2 H), 2.02 (d, J=12.82 Hz, 1 H); MS (DCI+) m/z 391 (M+H)+.

Example 104

3-fluoro-N-(6-oxo-1,2,3,4,4a,5,6,7-octahydropyrazino [1,2-a][1,5]benzodiazepin-9-yl)benzenesulfonamide The title compound was prepared as the trifluoroacetic acid salt according to the procedure outlined in Example 76C substituting 3-fluorobenzene-1-sulfonyl chloride for benzenesulfonyl chloride. $^1$H NMR (500 MHz, DMSO-d$_6$) δ ppm 7.59-7.66 (m, 2 H), 7.56 (d, J=8.54 Hz, 1 H), 7.46-7.53 (m, 1 H), 7.03 (d, J=8.85 Hz, 1 H), 6.89 (dd, J=8.54, 2.75 Hz, 1 H), 6.86 (d, J=2.44 Hz, 1 H), 3.47-3.56 (m, 1 H), 3.30-3.40 (m, 2 H), 3.22-3.30 (m, 1 H), 3.15-3.22 (m, 1 H), 2.91-3.04 (m, 2 H), 2.55-2.61 (m, 1 H), 2.03 (d, J=12.82 Hz, 1 H); MS (DCI+) m/z 391 (M+H)+.

Example 105

4-fluoro-N-(6-oxo-1,2,3,4,4a,5,6,7-octahydropyrazino [1,2-a][1,5]benzodiazepin-9-yl)benzenesulfonamide The title compound was prepared as the trifluoroacetic acid salt according to the procedure outlined in Example 76C substituting 4-fluorobenzene-1-sulfonyl chloride for benzenesulfonyl chloride. $^1$H NMR (500 MHz, DMSO-d$_6$) δ ppm 7.84 (dd, J=8.85, 5.19 Hz, 2 H), 7.39 (t, J=8.70 Hz, 2 H), 7.02 (d, J=8.54 Hz, 1 H), 6.88 (dd, J=8.54, 2.44 Hz, 1 H), 6.85 (d, J=2.75 Hz, 1 H), 3.48-3.57 (m, 1 H), 3.31-3.40 (m, 2 H), 3.22-3.31 (m, 1 H), 3.15-3.22 (m, 1 H), 2.92-3.05 (m, 2 H), 2.56-2.62 (m, 1 H), 2.04 (d, J=13.12 Hz, 1 H); MS (DCI+) m/z 391 (M+H)+.

Example 106

2-methoxy-N-(6-oxo-1,2,3,4,4a,5,6,7-octahydropyrazino [1,2-a][1,5]benzodiazepin-9-yl)benzenesulfonamide The title compound was prepared as the trifluoroacetic acid salt according to the procedure outlined in Example 76C substituting 2-methoxybenzene-1-sulfonyl chloride for benzenesulfonyl chloride. $^1$H NMR (500 MHz, DMSO-d$_6$) δ ppm 7.69 (dd, J=7.63, 1.53 Hz, 1 H), 7.45-7.57 (m, 1 H), 7.13 (d, J=8.24 Hz, 1 H), 6.99 (t, J=7.63 Hz, 1 H), 6.90-6.95 (m, 1 H), 6.83-6.89 (m, 1 H), 6.77 (d, J=2.44 Hz, 1 H), 3.86 (s, 3 H), 3.40-3.48 (m, 1 H), 3.28 (t, J=10.53 Hz, 2 H), 3.15-3.23 (m, 1 H), 3.06-3.12 (m, 1 H), 2.84-2.96 (m, 2 H), 2.45 (dd, J=13.58, 7.17 Hz, 1 H), 1.95 (d, J=13.12 Hz, 1 H); MS (DCI+) m/z 403 (M+H)+.

Example 107

3-methoxy-N-(6-oxo-1,2,3,4,4a,5,6,7-octahydropyrazino [1,2-a][1,5]benzodiazepin-9-yl)benzenesulfonamide The title compound was prepared as the trifluoroacetic acid salt according to the procedure outlined in Example 76C substituting 3-methoxybenzene-1-sulfonyl chloride for benzenesulfonyl chloride. $^1$H NMR (500 MHz, DMSO-d$_6$) δ ppm 7.48 (t, J=8.09 Hz, 1 H), 7.35 (d, J=7.93 Hz, 1 H), 7.27 (s, 1 H), 7.19 (dd, J=8.24, 2.44 Hz, 1 H), 7.02 (d, J=8.85 Hz, 1 H), 6.90 (dd, J=8.85, 2.44 Hz, 1 H), 6.86 (d, J=2.14 Hz, 1 H), 3.77-3.80 (m, 3 H), 3.48-3.56 (m, 1 H), 3.35 (t, J=10.37 Hz, 2 H), 3.22-3.30 (m, 1 H), 3.14-3.21 (m, 1 H), 2.91-3.04 (m, 2 H), 2.55-2.59 (m, 1 H), 2.03 (d, J=13.12 Hz, 1 H); MS (DCI+) m/z 403 (M+H)+.

Example 108

4-methoxy-N-(6-oxo-1,2,3,4,4a,5,6,7-octahydropyrazino [1,2-a][1,5]benzodiazepin-9-yl)benzenesulfonamide The title compound was prepared as the trifluoroacetic acid salt according to the procedure outlined in Example 76C substituting 4-methoxybenzene-1-sulfonyl chloride for benzenesulfonyl chloride. $^1$H NMR (500 MHz, DMSO-d$_6$) δ ppm 7.72 (d, J=8.85 Hz, 2 H), 7.07 (d, J=8.85 Hz, 2 H), 7.00 (d, J=8.85 Hz, 1 H), 6.83-6.92 (m, 2 H), 3.80 (s, 3 H), 3.46-3.55 (m, 1 H), 3.34 (t, J=10.37 Hz, 2 H), 3.22-3.30 (m, 1 H), 3.13-3.21 (m, 1 H), 2.91-3.04 (m, 2 H), 2.55-2.60 (m, 1 H), 2.02 (d, J=13.12 Hz, 1 H); MS (DCI+) m/z 403 (M+H)+.

Example 109

N-(6-oxo-1,2,3,4,4a,5,6,7-octahydropyrazino[1,2-a][1,5]benzodiazepin-9-yl)thiophene-2-sulfonamide The title compound was prepared as the trifluoroacetic acid salt according to the procedure outlined in Example 76C substituting thiophen-2-sulfonyl chloride for benzenesulfonyl chloride. $^1$H NMR (500 MHz, DMSO-$d_6$) δ ppm 7.58 (d, J=3.66 Hz, 1 H), 7.10-7.19 (m, 1 H), 7.06 (d, J=8.85 Hz, 1 H), 6.94 (dd, J=8.70, 2.59 Hz, 1 H), 6.88 (d, J=2.44 Hz, 1 H), 3.49-3.57 (m, 1 H), 3.32-3.39 (m, 1 H), 3.24-3.31 (m, 1 H), 3.17-3.23 (m, 1 H), 2.90-3.06 (m, 2 H), 2.55-2.62 (m, 1 H), 2.04 (d, J=12.82 Hz, 1 H); MS (DCI+) m/z 379 (M+H)+.

Example 110

8-chloro-1,2,3,4,4a,5-hexahydropyrazino[1,2-a][1,5]benzodiazepin-6(7H)-one

Example 110A 2-(4-benzyl-1-(3-chloro-2-nitrophenyl)piperazin-2-yl)acetic acid

The title compound was prepared according to the procedure outlined in Example 12D substituting 1-chloro-3-fluoro-2-nitrobenzene for 2-fluoro-4-methoxy-1-nitrobenzene. MS (DCI) m/z 390.0 (M+H)+.

Example 110B 2-(1-(2-amino-3-chlorophenyl)-4-benzylpiperazin-2-yl)acetic acid

The title compound was prepared according to the procedure outlined in Example 12E substituting 110A for 12D. The product was carried to the following step without further purification.

Example 110C 3-benzyl-8-chloro-1,2,3,4,4a,5-hexahydropyrazino[1,2-a][1,5]benzodiazepin-6(7H)-one The title compound was prepared according to the procedure outlined in Example 12F substituting 110B for 12E. The product was carried to the following step without further characterization. MS (DCI+) m/z 342.1 (M+H)+.

Example 110D 8-chloro-1,2,3,4,4a,5-hexahydropyrazino[1,2-a][1,5]benzodiazepin-6(7H)-one The title compound was prepared according to the procedure outlined in Example 30D substituting 110C for 30C. Instead of purification by HPLC, the crude material was purified by flash chromatography eluting with a gradient of 10-50% of methanol (2 M NH$_3$ solution) in CH$_2$Cl$_2$ to afford the title compound. $^1$H NMR (500 MHz, DMSO-$d_6$) δ ppm 9.21 (bs, 2H), 7.16 (s, 1H), 7.07 (dd, J=6.3, 3.2 Hz, 2H), 3.33 (m, 1H), 3.14-3.05 (m, 1H), 3.03-2.95 (m, 1H), 2.92-2.85 (m, 2H), 2.81 (d, J=10.0 Hz, 1H), 2.76-2.69 (m, 1H), 2.67-2.59 (m, 1H), 1.90 (d, J=13.1 Hz, 1H); MS (DCI+) m/z 252.0 (M+H)+.

Example 111

10-(phenoxymethyl)-1,2,3,4,4a,5-hexahydropyrazino[1,2-a][1,5]benzodiazepin-6(7H)-one Example 111A tert-butyl 10-(hydroxymethyl)-6-oxo-1,2,4a,5,6,7-hexahydropyrazino[1,2-a][1,5]benzodiazepine-3(4H)-carboxylate To a solution of LiBH$_4$ (654 mg, 30.0 mmol) in tetrahydrofuran (10 mL) at 0° C. was added Example 50 (1.17 g, 3.00 mmol). The reaction mixture was stirred at 60° C. for 6 hours. Additional LiBH$_4$ (500 mg) was added and the reaction was stirred for 2 hours at 60°C., and then for 16 hours. at room temperature. The reaction mixture was neutralized with HCl (1 M) and extracted with ethyl acetate. The organic solution was concentrate onto silica gel. Purification via flash chromatography (30-100% ethyl acetate/hexanes) afforded the title compound. $^1$H NMR (300 MHz, DMSO-$d_6$) δ ppm 9.51 (s, 1 H), 7.00-7.06 (m, 1 H), 6.92-6.99 (m, 1 H), 6.86-6.92 (m, 1 H), 5.12 (t, 1 H), 4.45 (d, J=5.43 Hz, 2 H), 3.82-3.99 (m, 2 H), 2.75-3.19 (m, 5 H), 2.51-2.58 (m, 1 H), 1.91-2.03 (m, 1 H), 1.38-1.47 (m, 9 H); MS (APCI+) m/z 248 (M+H-Boc)+.

Example 111B 10-(phenoxymethyl)-1,2,3,4,4a,5-hexahydropyrazino[1,2-a][1,5]benzodiazepin-6(7H)-one To a solution of Example 111A (200 mg, 0.576 mmol) in tetrahydrofuran (20 mL) was added phenol (54.2 mg, 0.576 mmol), PS-triphenylphosphine (576 mg, 1.727 mmol) and (Z)-di-tert-butyl diazene-1,2-dicarboxylate (199 mg, 0.864 mmol). The reaction mixture stirred for 16 hours before solids were filtered off. Purification via HPLC afforded the title compound as the trifluoroacetic acid salt. $^1$H NMR (500 MHz, DMSO-$d_6$) δ ppm 7.29-7.35 (m, 2 H), 7.23 (s, 1 H), 7.18 (d, J=8.24 Hz, 1 H), 7.00-7.04 (m, 3 H), 6.97 (t, J=7.32 Hz, 1 H), 5.06 (s, 2 H), 3.58-3.64 (m, 1 H), 3.26-3.42 (m, 4 H), 2.97-3.09 (m, 2 H), 2.67 (dd, J=13.58, 7.17 Hz, 1 H), 2.07 (d, J=12.82 Hz, 1 H); MS (APCI+) m/z 324 (M+H)+.

Example 112

9-(phenylsulfonyl)-1,2,3,4,4a,5-hexahydropyrazino[1,2-a][1,5]benzodiazepin-6(7H)-one Example 112A 3-benzyl-1,2,3,4,4a,5-hexahydropyrazino[1,2-a][1,5]benzodiazepin-6(7H)-one The title compound was prepared according to the procedure outlined in Example 83A substituting 1-fluoro-2-nitrobenzene for 1,3-difluoro-2-nitrobenzene. The title compound was carried directly into Example 112B.

Example 112B 3-benzyl-9-bromo-1,2,3,4,4a,5-hexahydropyrazino[1,2-a][1,5]benzodiazepin-6(7H)-one To a solution of Example 112A (1.30 g, 4.23 mmol) in acetic acid (20 mL) was added N-bromosuccinimide (0.828, 4.65 mmol). The reaction stirred for 16 hours. The reaction solution was concentrated, then partitioned between NaOH (1 M) and dichloromethane. The dichloromethane layer was separated and concentrated onto silica gel. Purification via flash chromatography (30-100% ethyl acetate/hexanes) afforded the title compound. $^1$H NMR (300 MHz, DMSO-$d_6$) δ ppm 7.22-7.38 (m, 6 H), 7.07 (d, J=2.37 Hz, 1 H), 7.01 (d, J=8.81 Hz, 1 H), 3.50-3.58 (m, 2 H), 3.24-3.30 (m, 1 H), 3.05-3.17 (m, 1 H), 2.91-3.01 (m, 1 H), 2.71-2.86 (m, 2 H), 2.52-2.61 (m, 1 H), 2.05-2.25 (m, 2 H), 1.90 (d, J=13.22 Hz, 1 H); MS (APCI+) m/z 386, 388 (M+H)$^+$.

Example 112C 9-(phenylsulfonyl)-1,2,3,4,4a,5-hexahydropyrazino[1,2-a][1,5]benzodiazepin-6(7H)-one Two microwave vials were each charged with Example 112B (200 mg, 0.518 mmol), benzenesulfinic acid (81 mg, 0.57 mmol), CuI (434, 2.28 mmol) and dimethyl sulfoxide (3 mL) under a $N_2$ atmosphere. The vials were heated in a microwave (Biotage Initator™ maximum 400 Watts) to 150° C. for 20 minutes. The two reaction mixtures were combined. To the reaction mixture was added ammonia (7 N, methanol, 2 mL). The solution was then partitioned between water and ethyl acetate. The organic layer was separated and concentrated onto silica gel. The intermediate was purified via flash chromatography (40-100% ethyl acetate/hexanes). To the intermediate was added trifluoroethanol (20 mL) and Pd(OH)$_2$—C (20%, wet 23.20 mg, 0.165 mmol). The reaction was stirred for 16 hours under H$_2$ (30 psi) at 50° C. Purification via HPLC afforded the title compound as the trifluoroacetic acid salt. $^1$H NMR (500 MHz, DMSO-$d_6$) δ ppm 7.84-7.93 (m, 2 H), 7.63-7.72 (m, 2 H), 7.59 (t, J=7.48 Hz, 2 H), 7.50 (d, J=2.44 Hz, 1 H), 7.28 (d, J=8.54 Hz, 1 H), 3.64-3.74 (m, 1 H), 3.28-3.40 (m, 4 H), 2.90-3.04 (m, 2 H), 2.68 (dd, J=13.88, 6.56 Hz, 1 H), 2.08 (d, J=13.73 Hz, 1 H); MS (DCI+) m/z 358 (M+H)$^+$.

Example 113

10-[(2-fluorophenoxy)methyl]-1,2,3,4,4a,5-hexahydropyrazino[1,2-a][1,5]-benzodiazepin-6(7H)-one The title compound was prepared as the trifluoroacetic acid salt according to the procedure outlined in Example 111 substituting 2-fluorophenol for phenol. $^1$H NMR (500 MHz, DSMO-$d_6$) δ ppm 7.19-7.30 (m, 3 H), 7.11-7.17 (m, 2 H), 7.01 (d, J=7.93 Hz, 1 H), 6.93-7.00 (m, 1 H), 5.13 (s, 2 H), 3.43-3.51 (m, 1 H), 3.11-3.27 (m, 4 H), 2.85-2.95 (m, 2 H), 2.63 (dd, J=13.43, 7.32 Hz, 1 H), 2.03 (d, J=12.82 Hz, 1 H); MS (DCI+) m/z 342 (M+H)$^+$.

Example 114

10-[(3-fluorophenoxy)methyl]-1,2,3,4,4a,5-hexahydropyrazino[1,2-a][1,5]benzodiazepin-6(7H)-one The title compound was prepared as the trifluoroacetic acid salt according to the procedure outlined in Example 111 substituting 3-fluorophenol for phenol. $^1$H NMR (500 MHz, DMSO-$d_6$) δ ppm 7.34 (q, J=8.04 Hz, 1 H), 7.19 (s, 1 H), 7.13 (dd, J=7.93, 1.53 Hz, 1 H), 7.01 (d, J=7.93 Hz, 1 H), 6.84-6.93 (m, 2 H), 6.75-6.82 (m, 1 H), 5.07 (s, 2 H), 3.35-3.43 (m, 1 H), 3.06-3.23 (m, 4 H), 2.79-2.90 (m, 2 H), 2.60 (dd, J=13.27, 7.17 Hz, 1 H), 2.01 (d, J=12.82 Hz, 1 H); MS (DCI+) m/z 342 (M+H)$^+$.

Example 115

10-[(4-fluorophenoxy)methyl]-1,2,3,4,4a,5-hexahydropyrazino[1,2-a][1,5]benzodiazepin-6(7H)-one The title compound was prepared as the trifluoroacetic acid salt according to the procedure outlined in Example 111 substituting 4-fluorophenol for phenol. $^1$H NMR (500 MHz, DMSO-$d_6$) δ ppm 7.17-7.21 (m, 1 H), 7.09-7.15 (m, 3 H), 6.97-7.06 (m, 3 H), 5.03 (s, 2 H), 3.41-3.48 (m, 1 H), 3.10-3.26 (m, 4 H), 2.89 (t, J=11.75 Hz, 2 H), 2.61 (dd, J=13.43, 7.02 Hz, 1 H), 2.02 (d, J=12.51 Hz, 1 H); MS (DCI+) m/z 342 (M+H)$^+$.

Example 116

(4aS)-10-(2-fluorophenyl)-1,2,3,4,4a,5-hexahydropyrazino[1,2-a][1,5]benzodiazepin-6(7H)-one

Example 116A 3-benzyl-10-bromo-1,2,3,4,4a,5-hexahydropyrazino[1,2-a][1,5]benzodiazepin-6(7H)-one The title compound was prepared according to the procedure outlined in Example 83A substituting 4-bromo-2-fluoro-1-nitrobenzene for 1,3-difluoro-2-nitrobenzene. $^1$H NMR (300 MHz, DMSO-$d_6$) δ ppm 9.55 (s, 1 H), 7.23-7.37 (m, 5 H), 7.12-7.19 (m, 2 H), 6.86 (d, J=8.82 Hz, 1 H), 3.54 (s, 2 H), 3.27-3.38 (m, 1 H), 3.07-3.20 (m, 1 H), 2.93-3.05 (m, 1 H), 2.70-2.86 (m, 2 H), 2.52-2.60 (m, 1 H), 2.03-2.27 (m, 2 H), 1.90 (d, J=13.56 Hz, 1 H); MS (APCI+) m/z 286, 288 (M+H)$^+$.

Example 116B (4aS)-3-benzyl-10-bromo-1,2,3,4,4a,5-hexahydropyrazino[1,2-a][1,5]benzodiazepin-6(7H)-one Chiral separation of 116A via SFC (Chiralpak® I A, 21×250 mm, 5 nm, 20-50% methanol-CO$_2$ gradient over 20 minutes at 40 mL/minute, retention time=16.0 minutes) afforded the title compound. $^1$H NMR (300 MHz, DMSO-$d_6$) δ ppm 9.55 (s, 1 H), 7.23-7.37 (m, 5 H), 7.12-7.19 (m, 2 H), 6.86 (d, J=8.82 Hz, 1 H), 3.54 (s, 2 H), 3.27-3.38 (m, 1 H), 3.07-3.20 (m, 1 H), 2.93-3.05 (m, 1 H), 2.70-2.86 (m, 2 H), 2.52-2.60 (m, 1 H), 2.03-2.27 (m, 2 H), 1.90 (d, J=13.56 Hz, 1 H); MS (APCI+) m/z 286, 288 (M+H)$^+$.

Example 116C (4aS)-10-(2-fluorophenyl)-1,2,3,4,4a,5-hexahydropyrazino[1,2-a][1,5]benzodiazepin-6(7H)-one (4aS)-3-Benzyl-10-(2-fluorophenyl)-1,2,3,4,4a,5-hexahydropyrazino[1,2-a][1,5]benzodiazepin-6(7H)-one was prepared according to the procedure outlined in Example 89 substituting 2-fluorophenylboronic acid for 3-methylphenylboronic acid and Example 116B for Example 4. The intermediate (4aS)-3-benzyl-10-(2-fluorophenyl)-1,2,3,4,4a,5-hexahydropyrazino[1,2-a][1,5]benzodiazepin-6(7H)-one was purified via HPLC, and underwent benzyl removal in ethanol (20 mL) with Pd(OH)$_2$—C (20%, 1 wet, 76 mg, 1.250 mmol) which was stirred for 2 hours under H$_2$ (30 psi) at room temperature. The catalyst was removed by filtration. HPLC purification afforded the title compound. as the trifluoroacetic acid salt. $^1$H NMR (500 MHz, DMSO-d$_6$) δ ppm 7.50-7.56 (m, 1 H), 7.36-7.43 (m, 1 H), 7.20-7.30 (m, 4 H), 7.07 (d, J=8.24 Hz, 1 H), 3.57-3.63 (m, 1 H), 3.31-3.40 (m, 4 H), 2.95-3.07 (m, 2 H), 2.70 (dd, J=13.58, 7.17 Hz, 1 H), 2.07 (d, J=12.51 Hz, 1 H); MS (DCI+) m/z 312 (M+H)$^+$.

Example 117

(4aS)-10-(3-isopropoxyphenyl)-1,2,3,4,4a,5-hexahydropyrazino[1,2-a][1,5]benzodiazepin-6(7H)-one The title compound was prepared as the trifluoroacetic acid salt according to the procedure outlined in Example 116c substituting 3-isopropoxyphenylboronic acid for 2-fluorophenylboronic acid. $^1$H NMR (500 MHz, DMSO-d$_6$) δ ppm 7.38 (t, J=7.78 Hz, 2 H), 7.31 (d, J=1.53 Hz, 1 H), 7.22 (d, J=7.93 Hz, 1 H), 7.15 (d, J=2.14 Hz, 1 H), 7.08 (d, J=7.93 Hz, 1 H), 6.93 (dd, J=8.24, 2.44 Hz, 1 H), 4.65-4.75 (m, 1 H), 3.61-3.68 (m, 1 H), 3.36-3.47 (m, 4 H), 2.98-3.13 (m, 2 H), 2.72 (dd, J=13.43, 7.02 Hz, 1 H), 2.10 (d, J=12.82 Hz, 1 H), 1.30 (d, J=6.10 Hz, 6 H); MS (APCI+) m/z 352 (M+H)$^+$.

Example 118

(4aS)-10-[2-(2-fluorophenyl)ethoxy]-1,2,3,4,4a,5-hexahydropyrazino[1,2-a][1,5]benzodiazepin-6(7H)-one The title compound was prepared according to the procedure outlined in Example 152 substituting 2-(2-fluorophenyl)ethanol for 2-(3-fluorophenyl)ethanol and substituting Example 163A for Example 149E. The product thus obtained was purified further by preparative HPLC to give the title compound as the trifluoroacetic acid salt. 1H NMR (400 MHz, DMSO-d$_6$) δ ppm 9.49 (s, 1H), 8.98 (br, 2H), 7.42 (td, J=7.6, 1.6 Hz, 1H), 7.33-7.24 (m, 1H), 7.22-7.12 (m, 2H), 6.87 (d, J=8.6 Hz, 1H), 6.70-6.58 (m, 2H), 4.29-4.08 (m, 2H), 3.55-3.45 (m, 1H), 3.41-3.18 (m, 4H), 3.11-2.89 (m, 4H), 2.61 (dd, J=13.4, 7.0 Hz, 1H), 2.00 (d, J=13.5 Hz, 1H).

Example 119

2,6-dichloro-N-(6-oxo-1,2,3,4,4a,5,6,7-octahydropyrazino [1,2-a][1,5]benzodiazepin-9-yl)benzenesulfonamide The title compound was prepared as the trifluoroacetic acid salt according to the procedure outlined in Example 76C substituting 2,6-dichlorobenzene-1-sulfonyl chloride for benzenesulfonyl chloride. $^1$H NMR (500 MHz, pyridine-d$_5$\D$_2$O) δ ppm 2.43 (d, J=13.43 Hz, 1 H), 1.92 (dd, J=13.28, 7.17 Hz, 1 H), 1.65-1.56 (m, 1 H), 1.53-1.41 (m, 1 H), 1.07-0.93 (m, 3 H), 0.86 (d, J=10.68 Hz, 1 H), 0.77-0.68 (m, 1 H), 2.35 (d, J=8.54 Hz, 1 H), 2.56 (d, J=7.93 Hz, 1 H), 2.74-2.79 (m, 3 H), 2.88 (d, J=2.44 Hz, 1 H), 6.72 (s, 1 H); MS (ESI+) m/z 441 (M+H)$^+$.

Example 120

N-(6-oxo-1,2,3,4,4a,5,6,7-octahydropyrazino[1,2-a][1,5]benzodiazepin-9-yl)-3-(trifluoromethoxy)benzenesulfonamide The title compound was prepared as the trifluoroacetic acid salt according to the procedure outlined in Example 76C substituting 3-trifluoromethoxybenzene-1-sulfonyl chloride for benzenesulfonyl chloride. $^1$H NMR (500 MHz, pyridine-d$_5$\D$_2$O) δ ppm 2.31 (d, J=13.43 Hz, 1 H), 2.84 (dd, J=13.43, 7.02 Hz, 1 H), 3.12-3.32 (m, 2 H), 3.64-3.78 (m, 3 H), 3.86 (d, J=10.99 Hz, 1 H), 3.97-4.07 (m, 1 H), 7.03 (d, J=8.54 Hz, 1 H), 7.32 (dd, J=8.70, 2.59 Hz, 1 H), 7.41-7.46 (m, 1 H), 7.48-7.55 (m, 2 H), 8.01-8.10 (m, 2 H), 11.36 (s, 1 H); MS (ESI+) m/z 457 (M+H)$^+$.

Example 121

4-cyano-N-(6-oxo-1,2,3,4,4a,5,6,7-octahydropyrazino [1,2-a][1,5]benzodiazepin-9-yl)benzenesulfonamide The title compound was prepared as the trifluoroacetic acid salt according to the procedure outlined in Example 76C substituting 4-cyanobenzene-1-sulfonyl chloride for benzenesulfonyl chloride. MS (ESI+) m/z 398 (M+H)$^+$.

Example 122

3-cyano-N-(6-oxo-1,2,3,4,4a,5,6,7-octahydropyrazino [1,2-a][1,5]benzodiazepin-9-yl)benzenesulfonamide The title compound was prepared according to the procedure outlined in Example 76C substituting 3-cyanobenzene-1-sulfonyl chloride for benzenesulfonyl chloride. MS (ESI+) m/z 398 (M+H)$^+$.

Example 123

2,6-difluoro-N-(6-oxo-1,2,3,4,4a,5,6,7-octahydropyrazino [1,2-a][1,5]benzodiazepin-9-yl)benzenesulfonamide The title compound was prepared as the trifluoroacetic acid salt according to the procedure outlined in Example 76C substituting 2,6-difluorobenzene-1-sulfonyl chloride for benzenesulfonyl chloride. $^1$H NMR (500 MHz, pyridine-d$_5$\D$_2$O) δ ppm 2.26 (d, J=13.43 Hz, 1 H), 2.79 (dd, J=13.43, 7.32 Hz, 1 H), 3.06-3.11 (m, 1 H), 3.16-3.30 (m, 1 H), 3.60-3.73 (m, 3 H), 3.83 (d, J=10.68 Hz, 1 H), 3.94-4.04 (m, 1 H), 6.95-7.09 (m, 3 H), 7.36-7.47 (m, 2 H), 7.64 (d, J=2.44 Hz, 1 H), 11.43 (s, 1 H); MS (ESI+) m/z 409 (M+H)$^+$.

Example 124

N-(6-oxo-1,2,3,4,4a,5,6,7-octahydropyrazino[1,2-a][1,5]benzodiazepin-9-yl)napthalene-1-sulfonamide The title compound was prepared as the trifluoroacetic acid salt according to the procedure outlined in Example 76C substituting naphthalene-1-sulfonyl chloride for benzenesulfonyl chloride. $^1$H NMR (500 MHz, pyridine-d$_5$\D$_2$O) δ ppm 2.21 (d, J=13.43 Hz, 1 H), 2.69 (dd, J=13.28, 7.17 Hz, 1 H), 2.97-3.05 (m, 1 H), 3.13-3.26 (m, 1 H), 3.57-3.60 (m, 1 H), 3.63-3.71 (m, 2 H), 3.76-3.82 (m, 1 H), 3.87-3.98 (m, 1

H), 6.86 (d, J=8.85 Hz, 1 H), 7.25 (dd, J=8.70, 2.59 Hz, 1 H), 7.39-7.46 (m, 2 H), 7.54-7.57 (m, 1 H), 7.59-7.63 (m, 1 H), 7.91-7.97 (m, 1 H), 8.01 (d, J=8.24 Hz, 1 H), 8.59 (dd, J=7.32, 1.22 Hz, 1 H), 9.29 (d, J=8.24 Hz, 1 H), 11.25 (s, 1 H); MS (ESI+) m/z 423 (M+H)$^+$.

Example 125

2,5-dimethyl-N-(6-oxo-1,2,3,4,4a,5,6,7-octahydro-pyrazino [1,2-a][1,5]benzodiazepin-9-yl)benzene-sulfonamide The title compound was prepared as the trifluoroacetic acid salt according to the procedure outlined in Example 76C substituting 2,5 dimethylphenyl-1-sulfonyl chloride for benzenesulfonyl chloride. $^1$H NMR (500 MHz, pyridine-d$_5$\D$_2$O) δ ppm 2.06 (s, 3 H), 2.24 (d, J=13.43 Hz, 1 H), 2.75 (dd, J=13.28, 7.17 Hz, 1 H), 2.84 (s, 3 H), 3.00-3.09 (m, 1 H), 3.15-3.26 (m, 1 H), 3.62-3.68 (m, 3 H), 3.74-3.83 (m, 1 H), 3.87-3.95 (m, 1 H), 6.96 (d, J=8.54 Hz, 1 H), 7.11-7.20 (m, 2 H), 7.34 (dd, J=8.54, 2.75 Hz, 1 H), 7.52 (d, J=2.44 Hz, 1 H), 8.17 (s, 1 H), 11.32 (s, 1 H); MS (ESI+) m/z 401(M+H)$^+$.

Example 126

N-(6-oxo-1,2,3,4,4a,5,6,7-octahydropyrazino[1,2-a][1,5]benzodiazepin-9-yl)-2-(trifluoromethyl)benzenesulfonamide The title compound was prepared as the trifluoroacetic acid salt according to the procedure outlined in Example 76C substituting 2-trifluoromethylphenyl-1-sulfonyl chloride for benzenesulfonyl chloride. $^1$H NMR (500 MHz, pyridine-d$_5$\D$_2$O) δ ppm 2.27 (d, J=13.43 Hz, 1 H), 2.79 (dd, J=13.43, 7.02 Hz, 1 H), 3.08-3.17 (m, 1 H), 3.20-3.30 (m, 1 H), 3.63-3.78 (m, 3 H), 3.85 (d, J=10.68 Hz, 1 H), 3.96-4.07 (m, 1 H), 7.01 (d, J=8.85 Hz, 1 H), 7.35 (dd, J=8.54, 2.44 Hz, 1 H), 7.53 (d, J=2.44 Hz, 1 H), 7.55-7.58 (m, 2 H), 7.84-7.92 (m, 1 H), 8.45-8.54 (m, 1 H), 11.35 (s, 1 H); MS (ESI+) m/z 441 (M+H)$^+$.

Example 127

5-chloro-N-(6-oxo-1,2,3,4,4a,5,6,7-octahydropyrazino[1,2-a][1,5]benzodiazepin-9-yl)thiophene-2-sulfonamide The title compound was prepared as the trifluoroacetic acid salt according to the procedure outlined in Example 76C substituting 5-chlorothiophene-2-sulfonyl chloride for benzenesulfonyl chloride. $^1$H NMR (500 MHz, pyridine-d$_5$\D$_2$O) δ ppm 2.32 (d, J=13.43 Hz, 1 H), 2.88 (dd, J=13.43, 7.02 Hz, 1 H), 3.14-3.33 (m, 2 H), 3.65-3.80 (m, 3 H), 3.87 (d, J=10.38 Hz, 1 H), 3.95-4.10 (m, 1 H), 6.89-6.94 (m, 1 H), 7.08 (d, J=8.54 Hz, 1 H), 7.39 (dd, J=8.70, 2.59 Hz, 1 H), 7.59-7.67 (m, 2 H), 11.41 (s, 1 H); MS (ESI+) m/z 413 (M+H)$^+$.

Example 128

N-(6-oxo-1,2,3,4,4a,5,6,7-octahydropyrazino [1,2-a][1,5]benzodiazepin-9-yl)naphthalene-2-sulfonamide The title compound was as the trifluoroacetic acid salt prepared according to the procedure outlined in Example 76C substituting naphthalene-2-sulfonyl chloride for benzene-sulfonyl chloride. $^1$H NMR (500 MHz, pyridine-d$_5$\D$_2$O) δ ppm 2.24 (d, J=13.43 Hz, 1 H), 2.77 (dd, J=13.28, 7.17 Hz, 1 H), 3.02-3.12 (m, 1 H), 3.15-3.29 (m, 1 H), 3.61-3.70 (m, 3 H), 3.75-3.84 (m, 1 H), 3.88-4.00 (m, 1 H), 6.96 (d, J=8.54 Hz, 1 H), 7.39 (dd, J=8.54, 2.44 Hz, 1 H), 7.45-7.56 (m, 2 H), 7.85 (t, J=7.78 Hz, 2 H), 7.94 (d, J=8.85 Hz, 1 H), 8.16 (dd, J=8.55, 1.83 Hz, 1 H), 8.79 (d, J=1.53 Hz, 1 H), 11.32 (s, 1 H); MS (ESI+) m/z 423(M+H)$^+$.

Example 129

3,5-dimethyl-N-(6-oxo-1,2,3,4,4a,5,6,7-octahydro-pyrazino [1,2-a][1,5]benzodiazepin-9-yl)benzene-sulfonamide The title compound was prepared as the trifluoroacetic acid salt according to the procedure outlined in Example 76C substituting 3,5-dimethylphenyl-2-sulfonyl chloride for benzenesulfonyl chloride. $^1$H NMR (500 MHz, pyridine-d$_5$\D$_2$O) δ ppm 2.06-2.10 (m, 6 H), 2.27 (d, J=13.43 Hz, 1 H), 2.79 (dd, J=13.43, 7.32 Hz, 1 H), 3.04-3.12 (m, 1 H), 3.16-3.29 (m, 1 H), 3.62-3.72 (m, 3 H), 3.82 (d, J=10.38 Hz, 1 H), 3.91-4.05 (m, 1 H), 6.94-7.01 (m, 2 H), 7.39 (dd, J=8.54, 2.44 Hz, 1 H), 7.55-7.58 (m, 1 H), 7.78 (s, 2 H), 11.34 (s, 1 H); MS (ESI+) m/z 401 (M+H)$^+$.

Example 130

N-(6-oxo-1,2,3,4,4a,5,6,7-octahydropyrazino[1,2-a][1,5]benzodiazepin-9-yl)-2-(trifluoromethoxy)benzenesulfonamide The title compound was prepared as the trifluoroacetic acid salt according to the procedure outlined in Example 76C substituting 2-(trifluoromethoxy)benzenesulfonyl chloride for benzenesulfonyl chloride. $^1$H NMR (500 MHz, pyridine-d$_5$\D$_2$O) δ ppm 2.27 (d, J=13.43 Hz, 1 H), 2.78 (dd, J=13.43, 7.02 Hz, 1 H), 3.06-3.14 (m, 1 H), 3.17-3.29 (m, 1 H), 3.63-3.77 (m, 3 H), 3.84 (d, J=10.68 Hz, 1 H), 3.95-4.03 (m, 1 H), 7.00 (d, J=8.54 Hz, 1 H), 7.25-7.37 (m, 2 H), 7.46-7.55 (m, 3 H), 8.29 (dd, J=7.93, 1.83 Hz, 1 H), 11.36 (s, 1 H); MS (ESI+) m/z 457 (M+H)$^+$.

Example 131

(4aS)-10-(difluoromethoxy)-1,2,3,4,4a,5-hexahydro-pyrazino[1,2-a][1,5]benzodiazepin-6(7H)-one Example 131A 4-(difluoromethoxy)-2-fluoro-1-nitrobenzene N,N-Dimethylformamide (15 mL) was added to 3-fluoro-4-nitrophenol (1.01 g, 6.43 mmol) and potassium carbonate (5.33 g, 38.6 mmol) in a 50 mL stainless steel reactor. The vessel was sparged briefly with CF$_2$HCl, chilled with dry ice, and then chlorodifluoromethane (3.34 g, 38.6 mmol) was transferred into the reactor through a polypropylene tube. The mixture was stirred at 85° C. for 2 hours. The supernatant mixture was concentrated onto silica gel. Purification via flash chromatography (0-40% ethyl acetate/hexanes) afforded the title compound. $^1$H NMR (300 MHz, DMSO-d$_6$) δ ppm 8.28 (t, J=9.16 Hz, 1 H), 7.51-7.57 (m, 1 H), 7.50 (t, J=72.39 Hz, 1 H), 7.21-7.29 (m, 1 H)

Example 131B methyl [(2S)-4-benzylpiperazin-2-yl]acetate

To a solution of Example 12C (63 g, 254 mmol) in ethanol (200 mL) was slowly added a solution of (2R,3R)-2,3-bis (benzoyloxy)succinic acid (45.5 g, 127 mmol in 400 mL of ethanol). The resulting orange solution was stirred at ambient temperature for 2 hours. The precipitate was collected by filtration to afford a 2:1 amine:succinic acid-salt (74.4 g). The salt was recrystallized from 4-5 volumes of 5% water/ethanol and collected by filtration. This recrystallization process was repeated until the appropriate chiral purity was obtained (29.9 g of salt, >95% e.e.). The salt was taken up in 300 mL of dichloromethane and washed with 3×200 mL of 1 M NaOH aqueous solution. The organic layer was then washed with 400 mL brine, filtered through $MgSO_4$, and concentrated to afford the title compound. $^1H$ NMR (500 MHz, DMSO-$d_6$) δ ppm 7.34-7.20 (m, 5H), 3.57 (s, 3H), 3.42 (q, J=13.4 Hz, 2H), 2.96 (qd, J=2.7 Hz, 6.9 Hz, 1H), 2.78 (dt, J=2.9 Hz, 11.9 Hz, 1H), 2.69-2.60 (m, 2H), 2.55 (d, J=10.8 Hz, 1H), 2.30 (dd, J=3.2 Hz, 6.7 Hz, 2H), 1.92 (td, J=2.8 Hz, 10.6 Hz, 1H), 1.68 (t, J=10.0 Hz, 1H); MS (ESI+) m/z 249.0 (M+H)$^+$.

Example 131C (4aS)-3-benzyl-10-(difluoromethoxy)-1,2,3,4,4a,5-hexahydropyrazino[1,2-a][1,5]benzodiazepin-6(7H)-one The title compound was prepared according to the procedure outlined in Example 83A substituting Example 131A for 1,3-difluoro-2-nitrobenzene and Example 131B for Example 12C. The title compound was carried directly into step 131D.

Example 131D (4aS)-10-(difluoromethoxy)-1,2,3,4,4a,5-hexahydropyrazino[1,2-a][1,5]benzodiazepin-6(7H)-one The title compound was prepared as the trifluoroacetic acid salt according to the procedure outline in Example 12G substituting Example 131C for Example 12F. $^1H$ NMR (500 MHz, DMSO-$d_6$) δ ppm 7.05 (d, J=8.54 Hz, 1 H), 7.18 (t, J=74.15 Hz, 1 H), 6.89-6.95 (m, 2 H), 3.60-3.68 (m, 1 H), 3.29-3.43 (m, 4 H), 2.97-3.10 (m, 2 H), 2.68 (dd, J=13.73, 7.02 Hz, 1 H), 2.09 (d, J=14.95 Hz, 1 H); MS (DCI+) m/z 284 (M+H)$^+$.

Example 132

(4aS)-3-methyl-2,3,4,4a,5,6-hexahydro-1H-pyrazino[2,1-d][1,5]benzoxazepine

The title compound was prepared as the trifluoroacetic acid salt according to the procedure outlined in Example 78 substituting Example 169 for Example 77. $^1H$ NMR (300 MHz, DMSO-$d_6$) δ ppm 6.87-7.07 (m, 3 H), 6.76-6.85 (m, 1 H), 4.45 (t, J=10.17 Hz, 1 H), 4.02-4.15 (m, 1 H), 3.52 (d, J=11.53 Hz, 1 H), 3.22 (d, 6 H), 2.87 (s, 3 H), 1.97-2.16 (m, 1 H), 1.65-1.83 (m, 1 H); MS (DCI+) m/z 219 (M+H)$^+$.

Example 133

(4aS)-10-methyl-2,3,4,4a,5,6-hexahydro-1H-pyrazino [2,1-d][1,5]benzoxazepine

Example 133A (S)-2-(4-benzyl-1-(2-bromo-5-methylphenyl)piperazin-2-yl)ethanol

To a solution of (S)-2-(4-benzylpiperazin-2-yl)ethanol (150 mg, 0.681 mmol) and 1-bromo-2-fluoro-4-methylbenzene (167 mg, 885 mmol) in dimethyl sulfoxide (5 mL) was added sodium tert-butoxide (164 mg, 1.70 mmol). The reaction mixture was allowed to stir for 16 hours at room temperature before addition of water and ethyl acetate. The organic layer was separated and concentrated onto silica gel. Purification via flash chromatography (0-30% methanol/dichloromethane) afforded the title compound. $^1H$ NMR (300 MHz, DMSO-$d_6$) δ ppm 7.40 (d, J=7.80 Hz, 1 H), 7.18-7.35 (m, 5 H), 6.92 (d, J=1.36 Hz, 1 H), 6.65-6.73 (m, 1 H), 4.08 (t, J=6.44 Hz, 2 H), 3.36-3.51 (m, 2 H), 2.55-2.89 (m, 6 H), 1.87-1.99 (m, 1 H), 1.68-1.77 (m, 2 H); MS (APCI+) m/z 389, 391 (M+H)$^+$.

Example 133B (4aS)-3-benzyl-10-methyl-2,3,4,4a,5,6-hexahydro-1H-pyrazino[2,1-d][1,5]benzoxazepine A microwave vial was charged with Example 133A (214 mg, 0.550 mmol), 2'-(di-tert-butylphosphino)-N,N-dimethylbiphenyl-2-amine (18.7 mg, 0.055 mmol), tris(dibenzylidene-acetone)dipalladium(0) (25.2 mg, 0.025 mmol), sodium tert-butoxide (68.4 mg, 0.715 mmol) and toluene (4 mL). The reaction mixture was heated in a microwave (Biotage Initiator™, maximum 400 Watts) at 120° C. for 30 minutes. Purification via HPLC afforded the title compound as the trifluoroacetic acid salt. $^1H$ NMR (300 MHz, DMSO-$d_6$) δ ppm 7.22-7.36 (m, 5 H), 6.82 (d, J=8.14 Hz, 1 H), 6.66-6.71 (m, 1 H), 6.56 (d, J=2.03 Hz, 1 H), 4.29-4.41 (m, 1 H), 3.98-4.11 (m, 1 H), 3.51 (s, 2 H), 2.96-3.14 (m, 3 H), 2.62-2.73 (m, 1 H), 2.52-2.56 (m, 1 H), 2.18-2.37 (m, 2 H), 2.15 (s, 3 H), 1.84-1.98 (m, 2 H); MS (APCI+) m/z 309 (M+H)$^+$.

Example 133C (4aS)-10-methyl-2,3,4,4a,5,6-hexahydro-1H-pyrazino [2,1-d][1,5]benzoxazepine To a solution of Example 133B (53 mg, 0.172 mmol) in 2,2,2-trifluoroethanol (10 mL) was added Pd(OH)$_2$—C (20%, wet, 10.60 mg, 0.075 mmol) and the mixture was stirred for 2 hours under H$_2$ (30 psi) at 50° C. The mixture was filtered and the filtrate concentrated. Purification via HPLC afforded the title compound as a trifluoroacetic acid salt. $^1H$ NMR (300 MHz, DMSO-$d_6$) δ ppm 6.82-6.91 (m, 1 H), 6.71-6.80 (m, 1 H), 6.63 (s, 1 H), 4.33-4.47 (m, 1 H), 4.00-4.13 (m, 1 H), 2.94-3.38 (m, 7 H), 2.18 (s, 3 H), 1.95-2.10 (m, 1 H), 1.79-1.92 (m, 1 H); MS (DCI+) m/z 219 (M+H)$^+$.

Example 134

(4aS)-10-methoxy-2,3,4,4a,5,6-hexahydro-1H-pyrazino [2,1-d][1,5]benzoxazepine

The title compound was prepared as the trifluoroacetic acid salt according to the procedure outlined in Example 133 substituting 1-bromo-2-fluoro-4-methoxybenzene for bromo-2-fluoro-4-methylbenzene. $^1H$ NMR (300 MHz, DMSO-$d_6$) δ ppm 6.90 (d, J=8.73 Hz, 1 H), 6.54 (dd, J=8.72, 3.17 Hz, 1 H), 6.40 (d, J=2.78 Hz, 1 H), 4.39-4.59 (m, 1 H), 4.01-4.12 (m, 1 H), 3.63-3.70 (m, 3 H), 3.26-3.39 (m, 1 H), 2.94-3.24 (m, 6 H), 1.96-2.13 (m, 1 H), 1.79-1.93 (m, 1 H); MS (DCI+) m/z 135 (M+H)$^+$.

Example 135

(4aS)-2,3,4,4a,5,6-hexahydro-1H-pyrazino[2,1-d][1,5]benzoxazepin-10-amine

The title compound was prepared as the trifluoroacetic acid salt according to the procedure outlined in Example 133 substituting 1-bromo-2-fluoro-4-nitrobenzene for bromo-2-fluoro-4-methylbenzene. $^1$H NMR (500 MHz, DMSO-d$_6$) δ ppm 7.02 (d, J=8.54 Hz, 1 H), 6.83 (dd, J=8.39, 2.59 Hz, 1 H), 6.69 (d, J=2.75 Hz, 1 H), 4.38-4.55 (m, 1 H), 4.03-4.20 (m, 1 H), 2.97-3.40 (m, 7 H), 1.98-2.15 (m, 1 H), 1.83-1.95 (m, 1 H); MS (DCI+) m/z 220 (M+H)$^+$.

Example 136

(4aS)-10-fluoro-2,3,4,4a,5,6-hexahydro-1H-pyrazino[2,1-d][1,5]benzoxazepine

The title compound was prepared as the trifluoroacetic acid salt according to the procedure outlined in Example 133 substituting 2,4-difluoro-bromobenzene for bromo-2-fluoro-4-methylbenzene. $^1$H NMR (500 MHz, DMSO-d$_6$) δ ppm 7.01 (dd, J=8.85, 6.10 Hz, 1 H), 6.74-6.85 (m, 1 H), 6.67 (dd, J=9.76, 3.05 Hz, 1 H), 4.43-4.57 (m, 1 H), 4.04-4.16 (m, 1 H), 3.00-3.30 (m, 7 H), 2.01-2.14 (m, 1 H), 1.82-1.93 (m, 1 H); MS (DCI+) m/z 223 (M+H)$^+$.

Example 137

(4aS)-9-methyl-2,3,4,4a,5,6-hexahydro-1H-pyrazino[2,1-d][1,5]benzoxazepine

The title compound was prepared as the trifluoroacetic acid salt according to the procedure outlined in Example 133 substituting 5-methyl-2-fluoro-bromobenzene for bromo-2-fluoro-4-methylbenzene. $^1$H NMR (300 MHz, DMSO-d$_6$) δ ppm 6.77-6.81 (m, 1 H), 6.67-6.73 (m, 2 H), 4.23-4.38 (m, 1 H), 3.98-4.10 (m, 1 H), 2.92-3.36 (m, 7 H), 2.17-2.24 (m, 3 H), 1.93-2.09 (m, 1 H), 1.78-1.92 (m, 1 H); MS (DCI+) m/z 219 (M+H)$^+$.

Example 138

(4aS)-11-chloro-2,3,4,4a,5,6-hexahydro-1H-pyrazino[2,1-d][1,5]benzoxazepine

Example 138A (4aS)-3-benzyl-11-chloro-2,3,4,4a,5,6-hexahydro-1H-pyrazino[2,1-d][1,5]benzoxazepine The title compound was prepared as the trifluoroacetic acid salt according to the procedure outlined in Example 133A substituting 3-chloro-2-fluoro-bromobenzene for bromo-2-fluoro-4-methylbenzene followed by the procedure outlined in Example 133B. $^1$H NMR (300 MHz, DMSO-d$_6$) δ ppm 7.60 (dd, J=8.14, 1.36 Hz, 1 H), 7.50 (dd, J=8.14, 1.70 Hz, 1 H), 7.20-7.32 (m, 5 H), 7.08 (t, J=7.97 Hz, 1 H), 3.97 (t, J=6.44 Hz, 2 H), 3.36-3.51 (m, 2 H), 2.55-2.94 (m, 6 H), 1.90-2.03 (m, 1 H), 1.63-1.83 (m, 2 H); MS (APCI+) m/z 408, 410 (M+H)$^+$.

Example 138B (4aS)-11-chloro-2,3,4,4a,5,6-hexahydro-1H-pyrazino[2,1-d][1,5]benzoxazepine The title compound was prepared as the trifluoroacetic acid salt according to the procedure outlined in Example 30D substituting Example 138A for Example 30C. $^1$H NMR (300 MHz, DMSO-d$_6$) δ ppm 7.02-7.11 (m, 1 H), 6.93-7.00 (m, 2 H), 4.31-4.46 (m, 1 H), 4.11-4.24 (m, 1 H), 2.97-3.44 (m, 7 H), 1.83-2.12 (m, 2 H); MS (DCI+) m/z 239 (M+H)$^+$.

A-1256402.2

Example 139

(4aS)-11-fluoro-2,3,4,4a,5,6-hexahydro-1H-pyrazino[2,1-d][1,5]benzoxazepine

The title compound was prepared according to the procedure outlined in Example 133 substituting 2,3-difluoro-bromobenzene for bromo-2-fluoro-4-methylbenzene. $^1$H NMR (300 MHz, DMSO-d$_6$) δ ppm 6.78-7.00 (m, 3 H), 4.34-4.47 (m, 1 H), 4.12-4.22 (m, 1 H), 2.98-3.42 (m, 7 H), 1.87-2.16 (m, 2 H); MS (DCI+) m/z 223 (M+H)$^+$.

Example 140

(4aS)-9-chloro-2,3,4,4a,5,6-hexahydro-1H-pyrazino[2,1-d][1,5]-benzoxazepine

Example 140A (4aS)-3-benzyl-9-chloro-2,3,4,4a,5,6-hexahydro-1H-pyrazino[2,1-d][1,5]benzoxazepine The title compound was prepared according to the procedure outlined in Example 133A substituting 5-chloro-2-fluoro-bromobenzene for bromo-2-fluoro-4-methylbenzene followed by the procedure outlined in Example 133B. $^1$H NMR (300 MHz, DMSO-d$_6$) δ ppm 7.21-7.36 (m, 5 H), 6.94 (d, J=2.37 Hz, 1 H), 6.81-6.87 (m, 1 H), 6.75 (d, 1 H), 4.26-4.36 (m, 1 H), 3.98-4.14 (m, 1 H), 3.50-3.54 (m, 2 H), 3.04-3.22 (m, 3 H), 2.61-2.70 (m, 1 H), 2.51-2.57 (m, 1 H), 2.27-2.38 (m, 1 H), 2.15-2.25 (m, 1 H), 1.88-1.98 (m, 2 H); MS (APCI+) m/z 328 (M+H)$^+$.

Example 140B (4aS)-9-chloro-2,3,4,4a,5,6-hexahydro-1H-pyrazino[2,1-d][1,5]-benzoxazepine The title compound was prepared as the trifluoroacetic acid salt according to the procedure outlined in Example 30D substituting Example 140A for Example 30C. $^1$H NMR (300 MHz, DMSO-d$_6$) δ ppm 7.04 (d, J=2.37 Hz, 1 H), 6.88-6.99 (m, 1 H), 6.82 (d, 1 H), 4.29-4.42 (m, 1 H), 4.03-4.15 (m, 1 H), 2.96-3.41 (m, 7 H), 1.81-2.14 (m, 2 H); MS (DCI+) m/z 239 (M+H)$^+$.

Example 141

10-[(E)-2-(2-fluorophenyl)vinyl]-1,2,3,4,4a,5-hexahydropyrazino[1,2-a][1,5]benzodiazepin-6(7H)-one The title compound was prepared as the trifluoroacetic acid salt according to the procedure outlined in Example 25 substituting (E)-2-fluorostyrylboronic acid for (E)-2-(3-chlorostyryl)-4,4,5,5-tetramethyl-1,3,2-dioxaborolane. $^1$H NMR (500 MHz, DMSO-d$_6$) δ ppm 9.79 (s, 1H), 9.12-8.82 (m, 2H), 7.77 (t, J=7.8, 1H), 7.40-7.18 (m, 7H), 6.98 (d, J=8.4, 1H), 3.65-3.52 (m, 1H), 3.47-3.35 (m, 4H), 3.14-2.94 (m, 2H), 2.68 (dd, J=13.5, 7.0, 1H), 2.08 (d, J=13.5, 1H); MS (DCI+) m/z 338.2 (M+H)$^+$.

Example 142

10-{(E)-2-[2-(trifluoromethyl)phenyl]vinyl}-1,2,3,4,4a,5-hexahydropyrazino[1,2-a][1,5]benzodiazepin-6(7H)-one The title compound was prepared as the trifluoroacetic acid salt according to the procedure outlined in Example 25 substituting (E)-2-(trifluoromethyl)styrylboronic acid for (E)-2-(3-chlorostyryl)-4,4,5,5-tetramethyl-1,3,2-dioxaborolane. $^1$H NMR (500 MHz, DMSO-d$_6$) δ ppm 9.81 (s, 1H), 9.01 (br, 1H), 8.90 (br, 1H), 7.96 (d, J=8.0, 1H), 7.75 (d, J=7.9, 1H), 7.71 (t, J=7.7, 1H), 7.50 (t, J=7.7, 1H), 7.38-7.29 (m, 4H), 7.02 (d, J=8.1, 1H), 3.61 (dd, J=10.7, 7.0, 1H), 3.42-3.30 (m, 3H), 3.30-2.95 (m, 3H), 2.69 (dd, J=13.5, 7.0, 1H), 2.12-2.05 (m, 1H); MS (DCI+) m/z 388.2 (M+H)$^+$.

Example 143

10-[(E)-2-(3,5-difluorophenyl)vinyl]-1,2,3,4,4a,5-hexahydropyrazino[1,2-a][1,5]benzodiazepin-6(7H)-one The title compound was prepared as the trifluoroacetic acid salt according to the procedure outlined in Example 25 substituting (E)-2-(3,5-difluorostyryl)-4,4,5,5-tetramethyl-1,3,2-dioxaborolane for (E)-2-(3-chlorostyryl)-4,4,5,5-tetramethyl-1,3,2-dioxaborolane. $^1$H NMR (500 MHz, DMSO-d$_6$) δ ppm 9.80 (s, 1H), 9.04-8.95 (br, 2H), 7.45-7.38 (m, 1H), 7.40-7.29 (m, 4H), 7.29-7.21 (m, 1H), 7.16-7.08 (m, 1H), 6.99 (d, J=8.1, 1H), 3.59 (dd, J=10.9, 6.9, 1H), 3.45-3.33 (m, 4H), 3.14-2.95 (m, 2H), 2.68 (dd, J=13.5, 7.0, 1H), 2.12-2.05 (m, 1H); MS (DCI+) m/z 356.2 (M+H)$^+$.

Example 144

10-[2-(2-fluorophenyl)ethyl]-1,2,3,4,4a,5-hexahydropyrazino[1,2-a][1,5]benzodiazepin-6(7H)-one

Example 144A tert-butyl 10-[(E)-2-(2-fluorophenyl)vinyl]-6-oxo-1,2,4a,5,6,7-hexahydropyrazino[1,2-a][1,5]benzodiazepine-3(4H)-carboxylate The title compound was prepared according to the procedure outlined in Example 5 substituting Example 4B for Example 4 and substituting (E)-2-fluorostyrylboronic acid for phenylboronic acid. The crude material thus obtained was carried to the following step without further purification.

Example 144B

10-[2-(2-fluorophenyl)ethyl]-1,2,3,4,4a,5-hexahydropyrazino[1,2-a][1,5]benzodiazepin-6(7H)-one The title compound was prepared as the trifluoroacetic acid salt according to the procedure outlined in Example 29B substituting Example 144A for Example 29A. $^1$H NMR (500 MHz, DMSO-d$_6$) δ=9.61 (s, 1H), 9.11-8.94 (br, 2H), 7.32-7.20 (m, 2H), 7.16-7.08 (m, 2H), 6.97-6.85 (m, 3H), 4.17-3.94 (m, 1H), 3.59-3.47 (m, 1H), 3.41-3.32 (m, 2H), 3.31-3.14 (m, 2H), 3.09-2.89 (m, 4H), 2.66-2.52 (m, 1H), 2.06-1.99 (d, J=13 Hz, 1H); MS (DCI+) m/z 340.1(M+H)$^+$.

Example 145

10-[2-(3-fluorophenyl)ethyl]-1,2,3,4,4a,5-hexahydropyrazino[1,2-a][1,5]benzodiazepin-6(7H)-one

Example 145A tert-butyl 10-[(E)-2-(3-fluorophenyl)vinyl]-6-oxo-1,2,4a,5,6,7-hexahydropyrazino[1,2-a][1,5]benzodiazepine-3(4H)-carboxylate The title compound was prepared according to the procedure outlined in Example 5 substituting Example 4B for Example 4 and substituting (E)-3-fluorostyrylboronic acid for phenylboronic acid. The crude material thus obtained was carried to the following step without further purification.

Example 145B

10-[2-(3-fluorophenyl)ethyl]-1,2,3,4,4a,5-hexahydropyrazino[1,2-a][1,5]benzodiazepin-6(7H)-one The title compound was prepared as the trifluoroacetic acid salt according to the procedure outlined in Example 29B substituting Example 145A for Example 29A. $^1$H NMR (500 MHz, DMSO-d$_6$) δ ppm 9.61 (s, 1H), 9.17-8.93 (br, 2H), 7.31 (dd, J=14.3, 7.9 Hz, 1H), 7.07 (dd, J=10.9, 4.3 Hz, 2H), 7.00 (td, J=8.8, 2.5 Hz, 1H), 6.93 (dd, J=11.5, 3.4 Hz, 2H), 6.87 (d, J=7.9 Hz, 1H), 3.55-3.46 (m, 1H), 3.37 (t, J=12.3 Hz, 2H), 3.22 (dd, J=28.3, 11.7 Hz, 2H), 3.11-2.94 (m, 2H), 2.92-2.79 (m, 4H), 2.60 (dd, J=13.4, 7.1 Hz, 1H), 2.03 (d, J=13.5 Hz, 1H); MS (DCI+) m/z 340.1 (M+H)$^+$.

Example 146

10-{2-[2-(trifluoromethyl)phenyl]ethyl}-1,2,3,4,4a,5-hexahydropyrazino[1,2-a][1,5]benzodiazepin-6(7H)-one

Example 146A tert-butyl 6-oxo-10-{(E)-2-[2-(trifluoromethyl)phenyl]vinyl}-1,2,4a,5,6,7-hexahydropyrazino[1,2-a][1,5]benzodiazepine-3(4H)-carboxylate The title compound was prepared according to the procedure outlined in Example 5 substituting Example 4B for Example 4 and substituting (E)-2-(trifluoromethyl)styrylboronic acid for phenylboronic acid. The crude material thus obtained was carried to the following step without further purification.

Example 146B

10-{2-[2-(trifluoromethyl)phenyl]ethyl}-1,2,3,4,4a,5-hexahydropyrazino[1,2-a][1,5]benzodiazepin-6(7H)-one The title compound was prepared as the trifluoroacetic acid salt according to the procedure outlined in Example 29B substituting Example 146A for Example 29A. $^1$H NMR (500 MHz, DMSO-d$_6$) δ ppm 9.63 (s, 1H), 9.10-8.90 (br, 2H), 7.69 (d, J=7.8 Hz, 1H), 7.62 (t, J=7.6 Hz, 1H), 7.54 (d, J=7.7 Hz, 1H), 7.43 (t, J=7.7 Hz, 1H), 6.96 (s, 1H), 6.96-6.87 (m, 2H), 3.59-3.15 (m, 5H), 3.08-2.93 (m, 4H), 2.95-2.75 (m, 2H), 2.62 (dd, J=13.4, 7.0 Hz, 1H), 2.07-1.94 (d, J=13.4 Hz, 1H); MS (DCI+) m/z 390.2 (M+H)+.

Example 147

10-[2-(3,5-difluorophenyl)ethyl]-1,2,3,4,4a,5-hexahydropyrazino[1,2-a][1,5]benzodiazepin-6(7H)-one

Example 147A tert-butyl 10-[(E)-2-(3,5-difluorophenyl)vinyl]-6-oxo-1,2,4a,5,6,7-hexahydropyrazino[1,2-a][1,5]benzodiazepine-3(4H)-carboxylate The title compound was prepared according to the procedure outlined in Example 5 substituting Example 4B for Example 4 and substituting (E)-2-(3,5-difluorostyryl)-4,4,5,5-tetramethyl-1,3,2-dioxaborolane for phenylboronic acid. The crude material thus obtained was carried to the following step without further purification.

Example 147B

10-[2-(3,5-difluorophenyl)ethyl]-1,2,3,4,4a,5-hexahydropyrazino[1,2-a][1,5]benzodiazepin-6(7H)-one The title compound was prepared as the trifluoroacetic acid salt according to the procedure outlined in Example 29B substituting Example 147B for Example 29A. $^1$H NMR (500 MHz, DMSO-d$_6$) δ ppm 9.61 (s, 1H), 9.13-8.82 (br, 2H), 7.10-6.83 (m, 6H), 3.50 (d, J=8.8 Hz, 1H), 3.37 (t, J=11.8 Hz, 2H), 3.25 (dt, J=24.0, 6.5 Hz, 2H), 3.11-2.80 (m, 6H), 2.60 (dd, J=13.4, 7.1 Hz, 1H), 2.03 (d, J=13.5 Hz, 1H); MS (DCI+) m/z 358.2 (M+H)+.

Example 148

(4aS)-8-chloro-1,2,3,4,4a,5-hexahydropyrazino[1,2-a][1,5]benzodiazepin-6(7H)-one

Example 148A (4aS)-3-benzyl-8-chloro-1,2,3,4,4a,5-hexahydropyrazino[1,2-a][1,5]benzodiazepin-6(7H)-one Chiral separation of Example 110C via SFC (Chiralpak® AD-H, 21×250 mm, 5 nm, 10-50% methanol with 0.1% diethylamine-CO$_2$ gradient over 20 minutes at 40 mL/minute, retention time=16.2 minutes) afforded the title compound. The title compound was carried directly into Example 148B.

Example 148B (4aS)-8-chloro-1,2,3,4,4a,5-hexahydropyrazino[1,2-a][1,5]benzodiazepin-6(7H)-one The title compound was prepared as the trifluoroacetic acid salt according to the procedure outlined in Example 30D substituting Example 148A for Example 30C. $^1$H NMR (400 MHz, DMSO-d$_6$) δ ppm 7.21-7.31 (m, 2 H), 7.13-7.21 (m, 1 H), 3.54-3.66 (m, 1 H), 3.24-3.45 (m, 4 H), 2.96-3.07 (m, 2 H), 2.64 (dd, J=13.58, 7.17 Hz, 1 H), 2.08 (d, J=13.43 Hz, 1 H); MS (DCI+) m/z 252 (M+H)+.

Example 149

10-(benzyloxy)-1,2,3,4,4a,5-hexahydropyrazino[1,2-a][1,5]benzodiazepin-6(7H)-one

Example 149A 4-(benzyloxy)-2-fluoro-1-nitrobenzene (Bromomethyl)benzene (10.9 g, 63.7 mmol) and 3-fluoro-4-nitrophenol (10 g, 63.7 mmol) were added to 150 mL acetone followed by potassium carbonate (8.8 g, 63.7 mmol) and sodium iodide (9.54 g, 63.7 mmol). The reaction mixture was heated at 55° C. overnight. The resulting mixture was filtered and concentrated. The crude material was recrystallized in ethyl acetate/hexane to give the title compound. MS (DCI+) m/z 264.9 (M+NH$_4$)+.

Example 149B methyl 2-(4-benzyl-1-(5-(benzyloxy)-2-nitrophenyl)piperazin-2-yl)acetate Example 149A (10 g, 40 mmol) and Example 12C (11.6 g, 47 mmol) in acetonitrile 100 mL in the presence of potassium carbonate (11 g, 81 mmol) were heated at 60° C. for 3 days. The reaction mixture was filtered and concentrated. Purification via flash chromatography (0-60% ethyl acetate in hexane) provided the title compound. MS (ESI+) m/z 476.2 (M+H)+.

Example 149C 3-benzyl-10-(benzyloxy)-1,2,3,4,4a,5-hexahydropyrazino[1,2-a][1,5]benzodiazepin-6(7H)-one The title compound was prepared according to the procedure outlined in Example 24B substituting Example 149B for Example 24A. MS (ESI+) m/z 414.2 (M+H)+.

Example 149D 10-hydroxy-1,2,3,4,4a,5-hexahydropyrazino[1,2-a][1,5]benzodiazepin-6(7H)-one The title compound was prepared according to the procedure outlined in Example 12G substituting Example 149C for Example 12F. The crude material was used in the next step without further purification.

Example 149E tert-butyl 10-hydroxy-6-oxo-1,2,4a,5,6,7-hexahydropyrazino[1,2-a][1,5]benzodiazepine-3(4H)-carboxylate Example 149D (60 mg, 0.26 mmol) and di-tert-butyl dicarbonate (61.8 mg, 0.28 mmol) in water (0.5 mL) were stirred at 30° C. for 2 hours. Then the precipitate was isolated by centrifugation. The solid isolated was used in the next step without further purification. $^1$H NMR (500 MHz, DMSO-d$_6$) δ ppm 9.25 (s, 1H), 6.74 (d, J=8.4 Hz, 1H), 6.46 (d, J=2.4 Hz, 1H), 6.42 (dd, J=8.4, 2.5 Hz, 1H), 3.97-3.83 (m, 2H), 3.13-3.01 (m, 2H), 2.91-2.81 (m, 2H), 2.58-2.52 (m, 2H), 1.93 (d, J=13.2 Hz, 1H).

Example 149F 10-(benzyloxy)-1,2,3,4,4a,5-hexahydropyrazino[1,2-a][1,5]benzodiazepin-6(7H)-one Example 149E (25 mg, 0.075 mmol) and (bromomethyl)benzene (14 mg, 0.082 mmol) were dissolved in 1 mL acetone. To this mixture, potassium carbonate (21 mg, 0.15 mmol) and sodium iodide (11 mg, 0.075 mmol) were added. The reaction mixture was heated at 70° C. overnight. The crude material was directly loaded onto a silica gel column and purified by flash chromatography. 4 M HCl in dioxane (0.3 mL) was added to the material thus obtained and heated at 50° C. until reaction completion. The solid thus obtained was collected by filtration to give the title compound. $^1$H NMR (500 MHz, DMSO-$d_6$) δ ppm 9.50 (s, 1H), 9.28-9.22 (br, 2H), 7.48-7.30 (m, 5H), 6.89 (d, J=9.1 Hz, 1H), 6.76-6.70 (m, 2H), 5.09 (bs, 2H), 3.60-3.53 (m, 1H), 3.29-3.22 (m, 4H), 3.06-2.90 (m, 2H), 2.62 (dd, J=13.4, 7.0 Hz, 1H), 2.05-1.98 (d, J=13.5 Hz, 1H).

Example 150

7,7a,8,9,10,11-hexahydropyrazino[1,2-d]pyrido[3,2-b][1,4]diazepin-6(5H)-one

Example 150A methyl 2-(4-benzyl-1-(3-nitropyridin-2-yl)piperazin-2-yl)acetate The title compound was prepared according to the procedure outlined in Example 149B substituting 2-fluoro-3-nitropyridine for 149A. MS (DCI) m/z 371.1 (M+H)$^+$.

Example 150B 2-(1-(2-amino-3-chlorophenyl)-4-benzylpiperazin-2-yl)acetic acid The title compound was prepared according to the procedure outlined in Example 12E substituting Example 150A for Example 12D. The product was carried to the following step without further characterization.

Example 150C 2-(1-(3-aminopyridin-2-yl)-4-benzylpiperazin-2-yl)acetic acid

To Example 150B (6.41 g, 18.83 mmol) in tetrahydrofuran (40 mL) and methanol (40 mL) was added LiOH hydrate (1.185 g, 28.2 mmol) and water (10 mL). The mixture was stirred at 50° C. until reaction completion. The mixture was then concentrated and 7 mL 4 M HCl in dioxane was added. The mixture was stirred at room temperature for two hours and the solvent was evaporated. The material thus obtained was used directly in the next step.

Example 150D 9-benzyl-7,7a,8,9,10,11-hexahydropyrazino[1,2-d]pyrido[3,2-b][1,4]diazepin-6(5H)-one The title compound was prepared according to the procedure outlined in Example 12F substituting Example 150C for Example 12E to give the title compound. MS (DCI+) m/z 309.1 (M+H)$^+$.

Example 150E 7,7a,8,9,10,11-hexahydropyrazino[1,2-d]pyrido[3,2-b][1,4]diazepin-6(5H)-one The title compound was prepared according to the procedure outlined in Example 12G substituting Example 150C for Example 12F. The crude material was purified by flash chromatography eluting with a gradient of 10-50% of methanol (2 M NH$_3$ solution) in CH$_2$Cl$_2$ to afford the title compound. $^1$H NMR (300 MHz, DMSO-$d_6$) δ ppm 9.57 (bs, 1H), 8.05 (dd, J=4.8, 1.7 Hz, 1H), 7.21 (dd, J=7.6, 1.8 Hz, 1H), 6.94 (dd, J=7.6, 4.8 Hz, 1H), 3.49-3.38 (m, 2H), 2.85-2.53 (m, 6H), 2.07 (ddd, J=13.3, 3.6, 1.4 Hz, 1H); MS (DCI+) m/z 309.1 (M+H)$^+$.

Example 151

7-methyl-10-(2-phenylethyl)-1,2,3,4,4a,5-hexahydropyrazino[1,2-a][1,5]benzodiazepin-6(7H)-one

Example 151A tert-butyl 6-oxo-10-(2-phenylethyl)-1,2,4a,5,6,7-hexahydropyrazino[1,2-a][1,5]-benzodiazepine-3(4H)-carboxylate Example 29A (110 mg, 0.29 mmol) in methanol (11 mL) was added to 5% Pd—C, wet (22 mg) in a 100 mL pressure tube and stirred for 16 hour under hydrogen (30 psi) at room temperature. The mixture was filtered through a nylon membrane and concentrated. The material was used in the next step without further characterization.

Example 151B 7-methyl-10-(2-phenylethyl)-1,2,3,4,4a,5-hexahydropyrazino[1,2-a][1,5]benzodiazepin-6(7H)-one The title compound was prepared as the trifluoroacetic acid salt according to the procedure outlined in Example 77B substituting Example 151A for Example 77A and substituting iodomethane for ethyl iodide to give the title compound. $^1$H NMR (400 MHz, DMSO-$d_6$) δ ppm 9.13 (br, 2H), 7.39-6.96 (m, 4H), 6.97 (d, J=1.7 Hz, 4H), 3.65 (m, 2H), 3.45-3.32 (m, 3H), 3.30-3.12 (m, 4H), 3.11-2.80 (m, 4H), 2.60 (m, 1H), 2.09 (m, 1H), 1.59 (d, J=7.2 Hz, 1H); MS (DCI+) m/z 336.1 (M+H)$^+$.

Example 152

10-[2-(3-fluorophenyl)ethoxy]-1,2,3,4,4a,5-hexahydropyrazino[1,2-a][1,5]benzodiazepin-6(7H)-one Example 149E (20 mg, 0.06 mmol) and 2-(3-fluorophenyl)ethanol (9.3 mg, 0.066 mmol) were dissolved in 1 mL tetrahydrofuran. To this, PS-triphenylphosphine (58 mg, 0.18 mmol, 3.1 mmol/g) was added followed by di-tert-butyl azodicarboxylate (20.9 mg, 0.09 mmol). The mixture was stirred at room temperature overnight. The resulting mixture was filtered, concentrated and purified by flash chromatography (0-50% ethyl acetate in hexane). To the material thus obtained was added 0.5 mL 4 M HCl in dioxane. The reaction was stirred at 50° C. until completion. The mixture was concentrated to give the title compound as the hydrochloride salt. $^1$H NMR (500 MHz, DMSO-$d_6$) δ ppm 9.44 (br, 1H), 9.07 (br, 2H), 7.36 (dd, J=14.4, 7.9 Hz, 1H), 7.18 (t, J=8.0 Hz, 2H), 7.05 (td, J=8.8, 2.4 Hz, 1H), 6.87 (d, J=8.6 Hz, 1H), 6.70-6.54 (m, 2H), 4.26-4.08 (m, 2H), 3.59-3.47 (m, 1H), 3.30 (m, 4H), 3.11-2.85 (m, 4H), 2.60 (dd, J=13.4, 7.0 Hz, 1H), 1.97 (d, J=13.5 Hz, 1H).

Example 153

10-[(1R)-1-phenylethoxy]-1,2,3,4,4a,5-hexahydropyrazino[1,2-a][1,5]benzodiazepin-6(7H)-one The title compound was prepared as the hydrochloride salt according to the procedure outlined in Example 152 substituting (S)-1-phenylethanol for 2-(3-fluorophenyl)ethanol. $^1$H NMR (500 MHz, DMSO-$d_6$) δ ppm 9.45-9.40 (br, 1H), 9.22-9.07 (br, 2H), 7.41 (bs, 2H), 7.35 (td, J=7.6, 2.3 Hz, 2H), 7.30-7.22 (m, 1H), 6.78 (d, J=8.6 Hz, 1H), 6.65 (t, J=2.7 Hz, 1H), 6.61-6.53 (m, 1H), 5.53-5.44 (m, 1H), 3.57 (m, 2H), 3.35-3.20 (m, 2H), 3.10-2.86 (m, 3H), 2.66-2.53 (m, 1H), 2.04-1.94 (m, 1H), 1.54 (dd, J=6.3, 3.7 Hz, 3H).

Example 154

10-[(1S)-1-phenylethoxy]-1,2,3,4,4a,5-hexahydropyrazino[1,2-a][1,5]benzodiazepin-6(7H)-one The title compound was prepared as the hydrochloride salt according to the procedure outlined in Example 152 substituting (R)-1-phenylethanol for 2-(3-fluorophenyl)ethanol. $^1$H NMR (300 MHz, DMSO-$d_6$) δ ppm 9.42 (s, 1H), 9.05-8.99 (br, 2H), 7.45-7.21 (m, 5H), 6.78 (d, J=8.6 Hz, 1H), 6.65 (d, J=3.3 Hz, 1H), 6.67-6.63 (m, 1H), 5.48 (t, J=5.8 Hz, 1H), 3.50 (m, 1H), 3.32-2.95 (m, 6H), 2.60 (m, 1H), 2.02-1.93 (d, J=13.5 Hz, 1H), 1.54 (dd, J=6.3, 2.3 Hz, 3H).

Example 155

10-[(2-fluorobenzy)oxy]-1,2,3,4,4a,5-hexahydropyrazino[1,2-a][1,5]benzodiazepin-6(7H)-one The title compound was prepared as the hydrochloride salt according to the procedure outlined in Example 152 substituting (2-fluorophenyl)methanol for 2-(3-fluorophenyl)ethanol. $^1$H NMR (300 MHz, DMSO-$d_6$) δ ppm 9.50 (s, 1H), 9.00-8.94 9 (br, 2H), 7.56 (br, 1H), 7.49-7.38 (m, 1H), 7.31-7.20 (m, 2H), 6.94-6.87 (m, 1H), 6.81-6.73 (m, 2H), 5.12 (bs, 2H), 3.50 (m, 1H), 3.40-3.22 (m, 3H), 3.21-2.91 (m, 3H), 2.60 (m, 1H), 2.06-1.98 (m, 1H).

Example 156

10-[(3-fluorobenzy)oxy]-1,2,3,4,4a,5-hexahydropyrazino[1,2-a][1,5]benzodiazepin-6(7H)-one The title compound was prepared as the hydrochloride salt according to the procedure outlined in Example 152 substituting (3-fluorophenyl)methanol for 2-(3-fluorophenyl)ethanol. $^1$H NMR (300 MHz, DMSO-$d_6$) δ ppm 9.49 (s, 1H), 7.51-7.39 (m, 1H), 7.33-7.25 (m, 2H), 7.22-7.11 (m, 1H), 6.90 (d, J=8.2 Hz, 1H), 6.75 (m, 2H), 5.12 (s, 2H), 3.57 (m, 1H), 3.40-3.22 (m, 3H), 3.12-2.91 (m, 3H), 2.60 (m, 1H), 2.02 (d, J=13.0 Hz, 1H).

Example 157

10-{[2-(trifluoromethyl)benzyl]oxy}-1,2,3,4,4a,5-hexahydropyrazino[1,2-a][1,5]benzodiazepin-6(7H)-one The title compound was prepared as the hydrochloride salt according to the procedure outlined in Example 152 substituting (2-(trifluoromethyl)phenyl)methanol for 2-(3-fluorophenyl)ethanol. $^1$H NMR (300 MHz, DMSO-$d_6$) δ ppm 9.51 (s, 1H), 8.98 (br, 2H), 7.85-7.67 (m, 3H), 7.62-7.49 (m, 1H), 6.91 (d, J=9.4 Hz, 1H), 6.79-6.67 (m, 2H), 5.22 (s, 2H), 3.57-3.48 (m, 6H), 3.38-3.19 (m, 27H), 3.11-2.87 (m, 2H), 2.67-2.57 (m, 1H), 2.02 (d, J=13.1 Hz, 1H).

Example 158

10-(2-phenylethoxy)-1,2,3,4,4a,5-hexahydropyrazino[1,2-a][1,5]benzodiazepin-6(7H)-one The title compound was prepared as the hydrochloride salt according to the procedure outlined in Example 152 substituting 2-phenylethanol for 2-(3-fluorophenyl)ethanol. $^1$H NMR (300 MHz, DMSO-$d_6$) δ ppm 9.48 (s, 1H), 8.92 (br, 2H), 7.37-7.21 (m, 5H), 6.87 (d, J=8.5 Hz, 1H), 6.66 (dd, J=8.5, 2.6 Hz, 1H), 6.62 (d, J=2.6 Hz, 1H), 4.19 (td, J=6.8, 2.1 Hz, 2H), 3.57 (m, 1H), 3.30 (m, 4H), 3.02 (m, 4H), 2.61 (dd, J=13.3, 7.1 Hz, 1H), 2.05-1.96 (d, J=13 Hz, 1H); MS (ESI+) m/z 338.1 (M+H)$^+$.

Example 159

10-{[(2R)-1-phenylpropan-2-yl]oxy}-1,2,3,4,4a,5-hexahydropyrazino[1,2-a][1,5]benzodiazepin-6(7H)-one The title compound was prepared as the hydrochloride salt according to the procedure outlined in Example 152 substituting (S)-1-phenylpropan-2-ol for 2-(3-fluorophenyl)ethanol. $^1$H NMR (500 MHz, DMSO-$d_6$) δ ppm 9.47 (s, 1H), 8.98 (bs, 2H), 7.33-7.27 (m, 4H), 7.26-7.17 (m, 1H), 6.85 (dd, J=8.6, 1.9 Hz, 1H), 6.69-6.62 (m, 1H), 6.56 (t, J=2.4 Hz, 1H), 4.72-4.62 (m, 1H), 3.57 (m, 1H), 3.26-3.20 (m, 4H), 3.06-2.90 (m, 3H), 2.83 (dt, J=13.6, 5.5 Hz, 1H), 2.66-2.58 (m, 1H), 2.03-1.96 (m, 1H), 1.21 (dd, J=6.0, 2.5 Hz, 3H).

Example 160

10-{[(2S)-1-phenylpropan-2-yl]oxy}-1,2,3,4,4a,5-hexahydropyrazino[1,2-a][1,5]benzodiazepin-6(7H)-one The title compound was prepared as the hydrochloride salt according to the procedure outlined in Example 152 substituting (R)-1-phenylpropan-2-ol for 2-(3-fluorophenyl)ethanol to give the title compound. $^1$H NMR (500 MHz, DMSO-$d_6$) δ ppm 9.47 (s, 1H), 8.98 (bs, 2H), 7.33-7.27 (m, 4H), 7.26-7.17 (m, 1H), 6.85 (dd, J=8.6, 1.9 Hz, 1H), 6.69-6.62 (m, 1H), 6.56 (t, J=2.4 Hz, 1H), 4.72-4.62 (m, 1H), 3.57 (m, 3H), 3.26-3.20 (m, 2H), 3.06-2.90 (m, 3H), 2.83 (dt, J=13.6, 5.5 Hz, 1H), 2.66-2.58 (m, 1H), 2.03-1.96 (m, 1H), 1.21 (dd, J=6.0, 2.5 Hz, 3H).

Example 161

10-[(1R)-1-(2-fluorophenyl)ethoxy]-1,2,3,4,4a,5-hexahydropyrazino[1,2-a][1,5]benzodiazepin-6(7H)-one The title compound was prepared as the hydrochloride salt according to the procedure outlined in Example 152 substituting (S)-1-(2-fluorophenyl)ethanol for 2-(3-fluorophenyl)ethanol. $^1$H NMR (300 MHz, DMSO-$d_6$) δ ppm 9.44 (s, 1H), 8.96 (s, 2H), 7.52-7.14 (m, 4H), 6.80 (d, J=8.6 Hz, 1H), 6.66 (d, J=2.6 Hz, 1H), 6.59-6.49 (m, 1H), 5.68 (dd, J=6.3, 2.8 Hz, 1H), 3.49 (m, 2H), 3.25 (m, 2H), 3.04 (d, J=36.0 Hz, 3H), 2.64-2.51 (m, 1H), 1.98 (d, J=13.1 Hz, 1H), 1.58 (dd, J=6.3, 2.7 Hz, 3H); MS (ESI+) m/z 356.1 (M+H)+.

Example 162

10-[(1S)-1-(2-fluorophenyl)ethoxy]-1,2,3,4,4a,5-hexahydropyrazino[1,2-a][1,5]benzodiazepin-6(7H)-one The title compound was prepared as the hydrochloride salt according to the procedure outlined in Example 152 substituting (R)-1-(2-fluorophenyl)ethanol for 2-(3-fluorophenyl)ethanol. $^1$H NMR (300 MHz, DMSO-d$_6$) δ ppm 9.43 (s, 1H), 9.05-8.95 (m, 2H), 7.39 (m, 1H), 7.29-7.20 (m, 2H), 7.14-7.03 (m, 1H), 6.80 (dd, J=8.6, 1.2 Hz, 1H), 6.67 (d, J=2.7 Hz, 1H), 6.58 (ddd, J=8.6, 6.0, 2.6 Hz, 1H), 5.58-5.46 (m, 1H), 3.50 (m, 4H), 3.09 (m, 3H), 2.61 (m, 1H), 2.03-1.98 (m, 1H), 1.57-1.43 (m, 3H); MS (ESI+) m/z 356.1 (M+H)+.

Example 163

(4aS)-10-{[(2S)-1-phenylpropan-2-yl]oxy}-1,2,3,4,4a,5-hexahydropyrazino[1,2-a][1,5]benzodiazepin-6(7H)-one

Example 163A tert-butyl (4aS)-10-hydroxy-6-oxo-1,2,4a,5,6,7-hexahydropyrazino[1,2-a][1,5]benzodiazepine-3(4H)-carboxylate The title compound was prepared as racemic mixture according to the procedure outlined in Example 149E. The enantiomers were separated by supercritical fluid chromatography; Chiralpak® OD-H column, 21 mm id, 250 mm in length. The outlet pressure was 100 bar, oven temperature at 35° C., and mobile phase flow rate at 40 mL/minute. A linear gradient of 10-30% methanol with 0.1% diethylamine in CO$_2$ over 15 minutes was used. Retention time of the title compound was 11.8 minutes. $^1$H NMR (500 MHz, DMSO-d$_6$) δ ppm 9.25 (s, 1H), 6.74 (d, J=8.4 Hz, 1H), 6.46 (d, J=2.4 Hz, 1H), 6.42 (dd, J=8.4, 2.5 Hz, 1H), 3.97-3.83 (m, 2H), 3.13-3.01 (m, 2H), 2.91-2.81 (m, 2H), 2.58-2.52 (m, 2H), 1.93 (d, J=13.2 Hz, 1H), 1.42 (s, 9H).

Example 163B (4aS)-10-{[(2S)-1-phenylpropan-2-yl]oxy}-1,2,3,4,4a,5-hexahydropyrazino[1,2-a][1,5]benzodiazepin-6(7H)-one The title compound was prepared as the hydrochloride salt according to the procedure outlined in Example 152 substituting (R)-1-phenylpropan-2-ol for 2-(3-fluorophenyl)ethanol and substituting Example 163A for Example 149E to give the title compound. $^1$H NMR (400 MHz, DMSO-d$_6$) δ ppm 9.51 (s, 1H), 9.29 (bs, 2H), 7.29-7.16 (m, 5H), 6.85 (d, J=8.7 Hz, 1H), 6.68-6.53 (m, 1H), 6.55 (d, J=2.6 Hz, 1H), 4.68 (m, 1H), 3.57 (m, 2H), 3.37-3.19 (m, 3H), 3.06-2.76 (m, 4H), 2.60 (m, 1H), 2.01 (d, J=13 Hz, 1H), 1.21 (d, J=6.0 Hz, 3H).

Example 164

(4aS)-10-[2-(3-fluorophenyl)ethoxy]-1,2,3,4,4a,5-hexahydropyrazino[1,2-a][1,5]benzodiazepin-6(7H)-one The title compound was prepared as the hydrochloride salt according to the procedure outlined in Example 152 substituting 2-(3-fluorophenyl)ethanol for 2-(3-fluorophenyl)ethanol and substituting Example 163A for Example 149E to give the title compound. $^1$H NMR (500 MHz, DMSO-d$_6$) δ ppm 9.53-9.40 (br, 1H), 9.20-8.94 (br, 2H), 7.39-7.27 (m, 1H), 7.21-7.13 (m, 2H), 7.07-6.98 (m, 1H), 6.89-6.80 (m, 1H), 6.69-6.58 (m, 2H), 4.27-4.13 (m, 2H), 3.53-3.47 (m, 1H), 3.29-3.19 (m, 4H), 3.07-2.89 (m, 4H), 2.64-2.54 (m, 1H), 2.06-1.94 (d, J=13.0 Hz, 1H).

Example 165

(4aS)-10-{[(2R)-1-phenylpropan-2-yl]oxy}-1,2,3,4,4a,5-hexahydropyrazino[1,2-a][1,5]benzodiazepin-6(7H)-one The title compound was prepared as the hydrochloride salt according to the procedure outlined in Example 152 substituting (S)-1-phenylpropan-2-ol for 2-(3-fluorophenyl)ethanol and substituting Example 163A for Example 149E. The HCl salt thus obtained was partitioned between saturated aqueous NaHCO$_3$ solution and ethyl acetate. The organic layer was separated and concentrated. The material thus obtained was purified further by flash chromatography eluting with a gradient of 0-20% methanol (2 M NH$_3$ solution) in CH$_2$Cl$_2$ to afford the title compound. $^1$H NMR (500 MHz, DMSO-d$_6$) δ ppm 9.27 (s, 1H), 7.35-7.10 (m, 5H), 6.80 (d, J=8.6 Hz, 1H), 6.57 (dd, J=8.6, 2.6 Hz, 1H), 6.50 (d, J=2.6 Hz, 1H), 4.63 (h, J=6.1 Hz, 1H), 3.50 (m, 1H), 3.14 (dd, J=17.6, 8.8 Hz, 1H), 2.99-2.87 (m, 4H), 2.86-2.75 (m, 2H), 2.67 (ddd, J=14.9, 13.0, 7.4 Hz, 2H), 1.87 (t, J=15.8 Hz, 1H), 1.21 (d, J=6.0 Hz, 3H); MS (DCI+) m/z 352.1 (M+H)+.

Example 166

(4aR)-10-{[(2R)-1-phenylpropan-2-yl]oxy}-1,2,3,4,4a,5-hexahydropyrazino[1,2-a][1,5]benzodiazepin-6(7H)-one

Example 166A tert-butyl (4aR)-10-hydroxy-6-oxo-1,2,4a,5,6,7-hexahydropyrazino[1,2-a][1,5]benzodiazepine-3(4H)-carboxylate The title compound was prepared as a racemic mixture according to the procedure outlined in Example 149E. The enantiomers were separated by supercritical fluid chromatography; Chiralpak® OD-H column, 21 mm id, 250 mm in length. The outlet pressure was 100 bar, oven temperature at 35° C., and mobile phase flow rate at 40 mL/minute. A linear gradient of 10-30% methanol with 0.1% diethylamine in CO$_2$ over 15 minutes was used. Retention time of the title compound was 11.2 minutes. $^1$H NMR (500 MHz, DMSO-d$_6$) δ ppm 9.25 (s, 1H), 6.74 (d, J=8.4 Hz, 1H), 6.46 (d, J=2.4 Hz, 1H), 6.42 (dd, J=8.4, 2.5 Hz, 1H), 3.97-3.83 (m, 2H), 3.13-3.01 (m, 2H), 2.91-2.81 (m, 2H), 2.58-2.52 (m, 2H), 1.93 (d, J=13.2 Hz, 1H), 1.42 (s, 9H).

Example 166B (4aR)-10-{[(2R)-1-phenylpropan-2-yl]oxy}-1,2,3,4,4a,5-hexahydropyrazino[1,2-a][1,5]benzodiazepin-6(7H)-one The title compound was prepared as the hydrochloride salt according to the procedure outlined in Example 152 substituting (S)-1-phenylpropan-2-ol for 2-(3-fluorophenyl)ethanol and substituting Example 166A for Example 149E to give the title compound. $^1$H NMR (400 MHz, DMSO-d$_6$) δ ppm 9.51 (s, 1H), 9.29 (bs, 2H), 7.29-7.16 (m, 5H), 6.85 (d, J=8.7 Hz, 1H), 6.68-6.53 (m, 1H), 6.55 (d, J=2.6 Hz, 1H), 4.68 (m, 1H), 3.57 (m, 2H), 3.37-3.19 (m, 3H), 3.06-2.76 (m, 4H), 2.60 (m, 1H), 2.01 (d, J=13 Hz, 1H), 1.21 (d, J=6.0 Hz, 3H).

Example 167

(4aR)-10-{[(2S)-1-phenylpropan-2-yl]oxy}-1,2,3,4, 4a,5-hexahydropyrazino[1,2-a][1,5]benzodiazepin-6 (7H)-one The title compound was prepared as the hydrochloride salt according to the procedure outlined in Example 152 substituting (R)-1-phenylpropan-2-ol for 2-(3-fluorophenyl)ethanol and substituting Example 166A for Example 149E to give the title compound. $^1$H NMR (500 MHz, DMSO-d$_6$) δ ppm 9.27 (s, 1H), 7.35-7.10 (m, 5H), 6.80 (d, J=8.6 Hz, 1H), 6.57 (dd, J=8.6, 2.6 Hz, 1H), 6.50 (d, J=2.6 Hz, 1H), 4.63 (h, J=6.1 Hz, 1H), 3.50 (m, 1H), 3.14 (dd, J=17.6, 8.8 Hz, 1H), 2.99-2.87 (m, 4H), 2.86-2.75 (m, 2H), 2.67 (ddd, J=14.9, 13.0, 7.4 Hz, 2H), 1.87 (t, J=15.8 Hz, 1H), 1.21 (d, J=6.0 Hz, 3H); MS (DCI+) m/z 352.1 (M+H)$^+$.

Example 168

(4aS)-3-benzyl-2,3,4,4a,5,6-hexahydro-1H-pyrazino [2,1-d][1,5]-benzoxazepine

Example 168A (S)-2-(4-benzyl-1-(2-bromophenyl)piperazin-2-yl) ethanol

The title compound was prepared according to the procedure outlined in Example 133A substituting 1-bromo-2-fluorobenzene for 1-bromo-2-fluoro-4-methylbenzene to give the title compound. $^1$H NMR (300 MHz, DMSO-d$_6$) δ ppm 7.59-7.48 (m, 1H), 7.39-7.18 (m, 7H), 7.08 (dd, J=8.3, 1.4 Hz, 1H), 6.90-6.81 (m, 1H), 4.15-4.02 (m, 2H), 3.53-3.36 (m, 2H), 2.91-2.71 (m, 3H), 2.71-2.54 (m, 2H), 1.97-1.86 (m, 1H), 1.80-1.66 (m, 3H); MS (DCI+) m/z 375.1 (M+H)$^+$.

Example 168B (4aS)-3-benzyl-2,3,4,4a,5,6-hexahydro-1H-pyrazino [2,1-d][1,5]benzoxazepine The title compound was prepared according to the procedure outlined in Example 133B substituting Example 168A for Example 133A to give the title compound which was purified by flash chromatography (0-100% ethyl acetate in hexane). $^1$H NMR (500 MHz, DMSO-d$_6$) δ ppm 7.38-7.23 (m, 5H), 6.94 (dd, J=7.9, 1.5 Hz, 1H), 6.89 (td, J=7.6, 1.5 Hz, 1H), 6.83 (td, J=7.6, 1.5 Hz, 1H), 6.75 (dd, J=7.8, 1.5 Hz, 1H), 4.33 (tt, J=16.3, 8.0 Hz, 1H), 4.09 (dt, J=10.9, 4.4 Hz, 1H), 3.66-3.43 (m, 2H), 3.21-3.02 (m, 3H), 2.62 (d, J=66.9 Hz, 2H), 2.32 (d, J=60.0 Hz, 2H), 2.02-1.83 (m, 2H); MS (DCI+) m/z 295.2 (M+H)$^+$.

Example 169

(4aS)-2,3,4,4a,5,6-hexahydro-1H-pyrazino[2,1-d][1, 5]benzoxazepine

The title compound was prepared according to the procedure outlined in Example 133C substituting Example 168B for Example 133B. The crude material was purified by flash chromatography with 0-50% methanol (2 M NH$_3$ solution) in CH$_2$Cl$_2$. $^1$H NMR (400 MHz, DMSO-d$_6$) δ ppm 6.94-6.86 (m, 1H), 6.82 (ddd, J=7.7, 6.8, 2.1 Hz, 1H), 6.74 (dd, J=7.8, 1.5 Hz, 1H), 4.42-4.25 (m, 1H), 4.10 (dt, J=11.0, 4.4 Hz, 1H), 3.06-2.91 (m, 4H), 2.86 (dt, J=11.8, 3.7 Hz, 1H), 2.80-2.68 (m, 2H), 2.65-2.55 (m, 1H), 2.02-1.81 (m, 2H); MS (DCI+) m/z 205.1 (M+H)$^+$.

Example 170

(4aS)-10-(cyclopropylmethoxy)-1,2,3,4,4a,5-hexahydropyrazino[1,2-a][1,5]benzodiazepin-6(7H)-one The title compound was prepared according to the procedure outlined in Example 152 substituting cyclopropylmethanol for 2-(3-fluorophenyl)ethanol and substituting Example 163A for Example 149E. The product thus obtained was purified further by preparative HPLC to give the title compound as the trifluoroacetic acid salt. $^1$H NMR (400 MHz, DMSO-d$_6$) δ ppm 9.48 (s, 1H), 9.04 (m, 2H), 6.87 (d, J=8.8 Hz, 1H), 6.69-6.52 (m, 2H), 3.78 (t, J=8.8 Hz, 2H), 3.64-3.19 (m, 5H), 3.00 (dd, J=23.0, 10.9 Hz, 1H), 2.61 (dd, J=13.4, 7.0 Hz, 1H), 2.01 (d, J=13.4 Hz, 1H), 1.29-1.09 (m, 1H), 0.65-0.46 (m, 1H), 0.37-0.24 (m, 1H).

Example 171

(4aS)-10-[2-(pyridin-2-yl)ethoxy]-1,2,3,4,4a,5-hexahydropyrazino[1,2-a][1,5]benzodiazepin-6(7H)-one The title compound was prepared according to the procedure outlined in Example 152 substituting 2-(pyridin-2-yl)ethanol for 2-(3-fluorophenyl)ethanol and substituting Example 163A for Example 149E. The product thus obtained was purified further by preparative HPLC to give the title compound as the trifluoroacetic acid salt. $^1$H NMR (400 MHz, DMSO-d$_6$) δ ppm 9.50 (s, 1H), 9.05 (br, 2H), 8.68 (dd, J=5.2, 0.9 Hz, 1H), 8.09 (t, J=7.2 Hz, 1H), 7.68 (d, J=7.9 Hz, 1H), 7.60-7.47 (m, 1H), 6.87 (d, J=8.6 Hz, 1H), 6.69-6.55 (m, 2H), 4.45-4.27 (m, 2H), 3.58-3.45 (m, 1H), 3.42-3.18 (m, 6H), 3.12-2.88 (m, 2H), 2.60 (dd, J=13.4, 7.1 Hz, 1H), 2.01 (d, J=13.4 Hz, 1H).

Example 172

(4aS)-10-[2-(2-chlorophenyl)ethoxy]-1,2,3,4,4a,5-hexahydropyrazino[1,2-a][1,5]benzodiazepin-6(7H)-one The title compound was prepared according to the procedure outlined in Example 152 substituting 2-(2-chlorophenyl)ethanol for 2-(3-fluorophenyl)ethanol and substituting Example 163A for Example 149E. The product thus obtained was purified further by preparative HPLC to give the title compound as the trifluoroacetic acid salt. $^1$H NMR (400 MHz, DMSO-d$_6$) δ ppm 9.49 (s, 1H), 9.08 (br, 2H), 7.53-7.40 (m, 2H), 7.30 (pd, J=7.4, 1.8 Hz, 2H), 6.87 (d, J=8.6 Hz, 1H), 6.71-6.59 (m, 2H), 4.19 (tt, J=12.4, 4.4 Hz, 2H), 3.57-3.43 (m, 1H), 3.41-3.22 (m, 4H), 3.16 (t, J=6.9 Hz, 2H), 3.00 (dt, J=22.1, 10.0 Hz, 2H), 2.61 (dd, J=13.4, 7.0 Hz, 1H), 2.01 (d, J=13.5 Hz, 1H); MS (DCI+) m/z 372.1 (M+H)$^+$.

Example 173

(4aS)-10-{2-[3-(trifluoromethyl)phenyl]ethoxy}-1,2,3,4,4a,5-hexahydropyrazino[1,2-a][1,5]benzodiazepin-6(7H)-one The title compound was prepared according to the procedure outlined in Example 152 substituting 2-(3-(trifluoromethyl)phenyl)ethanol for 2-(3-fluorophenyl)ethanol and substituting Example 163A for Example 149E. The product thus obtained was purified further by preparative HPLC to give the title compound as the trifluoroacetic acid salt. $^1$H NMR (400 MHz, DMSO-$d_6$) δ ppm 9.49 (s, 1H), 9.04 (br, 2H), 7.70 (s, 1H), 7.66 (d, J=7.3 Hz, 1H), 7.62-7.49 (m, 2H), 6.87 (d, J=8.7 Hz, 1H), 6.67 (dd, J=8.6, 2.6 Hz, 1H), 6.61 (d, J=2.6 Hz, 1H), 4.23 (tt, J=12.8, 4.5 Hz, 3H), 3.57-3.46 (m, 1H), 3.35 (t, J=12.3 Hz, 2H), 3.26 (d, J=8.0 Hz, 2H), 3.14 (t, J=6.6 Hz, 2H), 3.09-2.89 (m, 2H), 2.60 (dd, J=13.4, 7.0 Hz, 1H), 2.01 (d, J=13.4 Hz, 1H); MS (DCI+) m/z 406.1 (M+H)$^+$.

The title compound was prepared according to the procedure outlined in Example 152 substituting butan-2-ol for 2-(3-fluorophenyl)ethanol and substituting Example 163A for Example 149E. The product thus obtained was purified further by preparative HPLC to give the title compound as the trifluoroacetic acid salt. $^1$H NMR (500 MHz, DMSO-$d_6$) δ ppm 9.47 (s, 1H), 9.04 (br, 2H), 6.86 (d, J=8.6 Hz, 1H), 6.63 (dt, J=9.8, 4.9 Hz, 1H), 6.60 (t, J=2.7 Hz, 1H), $^1$H NMR (500 MHz, DMSO-$d_6$) δ 4.36 (h, J=5.9 Hz, 1H), 3.61-3.50 (m, 2H), 3.30 (dt, J=22.1, 14.3 Hz, 2H), 3.00 (dd, J=22.2, 10.6 Hz, 1H), 2.63 (dd, J=13.4, 7.0 Hz, 1H), 2.01 (d, J=13.4 Hz, 1H), 1.67-1.51 (m, 1H), 1.24-1.16 (m, 1H), 0.94-0.87 (m, 1H); MS (DCI+) m/z 290.1 (M+H)$^+$.

Example 175

(4aS)-10-[2-(3-chlorophenyl)ethoxy]-1,2,3,4,4a,5-hexahydropyrazino[1,2-a][1,5]benzodiazepin-6(7H)-one The title compound was prepared according to the procedure outlined in Example 152 substituting 2-(3-chlorophenyl)ethanol for 2-(3-fluorophenyl)ethanol and substituting Example 163A for Example 149E. The product thus obtained was purified further by preparative HPLC to give the title compound as the trifluoroacetic acid salt. $^1$H NMR (500 MHz, DMSO-$d_6$) δ ppm 9.49 (s, 1H), 9.16 (br, 2H), 7.42 (s, 1H), 7.38-7.24 (m, 3H), 6.88 (d, J=8.6 Hz, 1H), 6.67-6.60 (m, 2H), 4.27-4.10 (m, 2H), 3.57-3.47 (m, 1H), 3.42-3.30 (m, 2H), 3.31-3.20 (m, 2H), 3.10-2.88 (m, 4H), 2.61 (dd, J=13.4, 7.0 Hz, 1H), 2.01 (d, J=13.4 Hz, 1H); MS (DCI+) m/z 374.1 (M+H)$^+$.

Example 176

(4aS)-10-[2-(3-methylphenyl)ethoxy]-1,2,3,4,4a,5-hexahydropyrazino[1,2-a][1,5]benzodiazepin-6(7H)-one The title compound was prepared according to the procedure outlined in Example 152 substituting 2-m-tolylethanol for 2-(3-fluorophenyl)ethanol and substituting Example 163A for Example 149E. The product thus obtained was purified further by preparative HPLC to give the title compound as the trifluoroacetic acid salt. $^1$H NMR (500 MHz, DMSO-$d_6$) δ ppm 9.49 (s, 1H), 9.24-9.01 (m, 2H), 7.20 (t, J=7.5 Hz, 1H), 7.15-7.09 (m, 2H), 7.04 (d, J=7.5 Hz, 1H), 6.87 (d, J=8.6 Hz, 1H), 6.66 (dd, J=8.6, 2.6 Hz, 1H), 6.61 (d, J=2.6 Hz, 1H), 4.22-4.11 (m, 2H), 3.57-3.47 (m, 1H), 3.34 (dd, J=29.2, 14.4 Hz, 2H), 3.27 (d, J=7.7 Hz, 2H), 3.09-2.90 (m, 4H), 2.61 (dd, J=13.4, 7.0 Hz, 1H), 2.01 (d, J=13.4 Hz, 1H); MS (DCI+) m/z 352.1 (M+H)$^+$.

Example 177

(4aS)-10-(1-phenylpropoxy)-1,2,3,4,4a,5-hexahydropyrazino[1,2-a][1,5]benzodiazepin-6(7H)-one The title compound was prepared according to the procedure outlined in Example 152 substituting 1-phenylpropan-1-ol for 2-(3-fluorophenyl)ethanol and substituting Example 163A for Example 149E. The product thus obtained was purified further by preparative HPLC to give the title compound as the trifluoroacetic acid salt. $^1$H NMR (500 MHz, DMSO-$d_6$) δ ppm 9.42 (s, 1H), 9.10-8.75 (m, 2H), 7.36 (dt, J=15.2, 4.6 Hz, 4H), 7.27-7.21 (m, 1H), 6.77-6.70 (m, 1H), 6.63 (d, J=2.6 Hz, 1H), 6.56-6.50 (m, 1H), 5.23-5.18 (m, 1H), 3.50-3.42 (m, 1H), 3.34 (d, J=11.9 Hz, 2H), 3.22 (dt, J=22.6, 10.6 Hz, 2H), 3.09-2.88 (m, 2H), 2.58 (dd, J=13.4, 7.0 Hz, 1H), 2.00-1.86 (m, 2H), 1.84-1.73 (m, 1H), 0.92 (t, J=7.3 Hz, 3H); MS (DCI+) m/z 352.1 (M+H)$^+$.

Example 178

(4aS)-10-[(1R)-1-(2,5-difluorophenyl)ethoxy]-1,2,3,4,4a,5-hexahydropyrazino[1,2-a][1,5]benzodiazepin-6(7H)-one The title compound was prepared according to the procedure outlined in Example 152 substituting (S)-1-(2,5-difluorophenyl)ethanol for 2-(3-fluorophenyl)ethanol and substituting Example 163A for Example 149E. The product thus obtained was purified further by preparative HPLC to give the title compound as the trifluoroacetic acid salt. $^1$H NMR (500 MHz, DMSO-$d_6$) δ ppm 9.48 (s, 1H), 9.01 (br, 2H), 7.34-7.24 (m, J=11.1, 7.6, 3.8 Hz, 2H), 7.21-7.12 (m, 1H), 6.83 (d, J=8.7 Hz, 1H), 6.69 (d, J=2.6 Hz, 1H), 6.60 (dd, J=8.6, 2.6 Hz, 1H), 5.67 (q, J=6.3 Hz, 1H), 3.58-3.47 (m, 1H), 3.35 (t, J=11.1 Hz, 2H), 3.26 (dd, J=17.9, 7.3 Hz, 1H), 3.12 (d, J=12.5 Hz, 1H), 3.07-2.88 (m, 2H), 2.60 (dd, J=13.4, 7.0 Hz, 1H), 1.99 (d, J=13.5 Hz, 1H), 1.58 (t, J=5.3 Hz, 3H); MS (DCI+) m/z 374.1 (M+H)$^+$.

Example 179

(4aS)-10-chloro-2,3,4,4a,5,6-hexahydro-1H-pyrazino[2,1-d][1,5]benzoxazepine

Example 179A (S)-2-(4-benzyl-1-(2-bromo-5-chlorophenyl)piperazin-2-yl)ethanol The title compound was prepared according to the procedure outlined in Example 133A substituting 1-bromo-4-chloro-2-fluorobenzene for 1-bromo-2-fluoro-4-methylbenzene. The crude material was used in the next step without further characterization.

Example 179B (4aS)-3-benzyl-10-chloro-2,3,4,4a,5,6-hexahydro-1H-pyrazino[2,1-d][1,5]benzoxazepine The title compound was prepared according to the procedure outlined in Example 133B substituting Example 179A

Example 179C (4aS)-10-chloro-2,3,4,4a,5,6-hexahydro-1H-pyrazino[2,1-d][1,5]benzoxazepine The title compound was prepared according to the procedure outlined in Example 30D substituting Example 179B for Example 30C. $^1$H NMR (400 MHz, DMSO-$d_6$) δ ppm 8.81 (br, 1H), 7.10-6.96 (m, 1H), 6.93-6.82 (m, 1H), 4.53-4.37 (m, 1H), 4.20-4.07 (m, 1H), 3.41-2.95 (m, 7H), 2.15-1.98 (m, 1H), 1.97-1.75 (m, 1H).

Example 180 cis-1,2,3,4,4a,5,6,11b-octahydro-7H-pyrido[3,4-d][2]benzazepin-7-one

Example 180A 2-(4,4,5,5-tetramethyl-[1,3,2]dioxaborolan-2-yl)-benzoic acid ethyl ester A mixture of 2-bromo-benzoic acid ethyl ester (45.8 g, 0.2 mol), potassium acetate (60 g, 0.6 mol), 4,4,5,5,4',4',5',5'-octamethyl-[2,2]bi[[1,3,2]dioxaborolanyl] (55.9 g, 0.22 mol) and dichlorobis(triphenylphosphine)palladium(II) (7.0 g, 0.02 mol) in 500 mL of N,N-dimethylformamide was stirred at 100° C. under N$_2$ overnight. After cooling and dilution with 2 L of water, the mixture was extracted with diethyl ether (500 mL) and purified by column chromatography on silica gel (petroleum ether/ethyl acetate, 50:1) to obtain the title compound.

Example 180B 4-iodo-nicotinonitrile

To a stirred solution of 2,2,6,6-tetramethyl-piperidine (42.3 g, 0.3 mol) in 2 L of tetrahydrofuran was added butyllithium (120 mL, 2.5 M, 0.3 mol) at −78° C. under N$_2$ atmosphere. The mixture was stirred for 1 hour before a solution of nicotinonitrile (26 g, 0.25 mol) in 500 mL of tetrahydrofuran was slowly added, and the resulting mixture was stirred for 0.5 hour at −78° C. Then I$_2$ (76.2 g, 0.3 mol) in 500 mL of tetrahydrofuran was added in a dropwise manner. After stirring for 2 hours, the mixture was quenched with 500 mL of ice-water. Tetrahydrofuran was removed under reduced pressure and the aqueous phase was extracted with ether. The organic phase was washed with brine, citric acid, brine, aqueous Na$_2$S$_2$O$_3$ and brine again. After being dried over Na$_2$SO$_4$, the organic phase was concentrated and purified by using column chromatography on silica gel (petroleum ether:ethyl acetate, 10:1) to obtain the title compound.

Example 180C 2-(3-cyano-pyridin-4-yl)-benzoic acid ethyl ester

A mixture of Example 180B (35.9 g, 0.156 mol), K$_2$CO$_3$ (43.1 g, 0.312 mol), dichlorobis(triphenylphosphine)palladium(II) (11.0 g, 0.016 mol) and Example 180A in 600 mL of anhydrous 1,4-dioxane was stirred at 100° C. for 12 hours. After cooling to room temperature, the mixture was diluted with 2 L of water and extracted with diethyl ether. The organic phase was washed with brine, dried and purified by column chromatography on silica gel (petroleum ether:ethyl acetate, 2:1) to obtain the title compound.

Example 180D 5,6-dihydro-7H-pyrido[3,4-d][2]benzazepin-7-one

A mixture of Example 180C (29.4 g, 0.117 mol) and Raney®-nickel (30 g) in 2 L of methanol saturated with NH$_3$ was stirred under H$_2$ (50 psi) at 50° C. for 24 hours. After cooling and removal of the catalyst, the mixture was concentrated under reduced pressure to obtain the title compound which was used without further purification.

Example 180E 3-benzyl-7-oxo-6,7-dihydro-5H-pyrido[3,4-d][2]benzazepin-3-ium bromide A mixture of Example 180D (24.6 g, 0.117 mol) and benzyl bromide (40.1 g, 0.234 mol) in 200 mL of ethanol was stirred at reflux overnight. After cooling with an ice-water bath, the solid was collected by filtration and washed with ethanol to obtain the title compound.

Example 180F 3-benzyl-1,2,3,4,5,6-hexahydro-7H-pyrido[3,4-d][2]benzazepin-7-one To a suspension of Example 180E (17.7 g, 46.4 mmol) in 200 mL of ethanol/water (4:1) at 0° C. was added NaBH$_4$ (8.9 g, 0.232 mol) portion-wise. After stirring for 0.5 hour, the mixture was quenched with 1 N HCl to pH 4-5 and concentrated under reduced pressure. The residue was dissolved in 100 mL of saturated aqueous K$_2$CO$_3$ and extracted with dichloromethane. The organic phase was washed with brine, dried and purified by column chromatography on silica gel eluting with dichloromethane/methanol (30:1) to obtain the title compound.

Example 180G tert-butyl cis-7-oxo-1,2,4,4a,5,6,7,11b-octahydro-3H-pyrido[3,4-d][2]benzazepine-3-carboxylate A mixture of Example 180F (10 g, 32.9 mmol), di-tert-butyl dicarbonate (14 g, 65 mmol) and Pd(OH)$_2$/C (4 g) was stirred in 200 mL of methanol under H$_2$ (50 psi) at 50° C. for 24 hours. The catalyst was removed by filtration, and the filtrate was concentrated under reduced pressure to obtain the crude title compound which was used without further purification.

Example 180H cis-1,2,3,4,4a,5,6,11b-octahydro-7H-pyrido[3,4-d][2]benzazepin-7-one To a suspension of Example 180G in 400 mL of diethyl ether was added 80 mL of HCl/methanol (5/V) at 25° C. The mixture was stirred overnight. The solid formed was collected and dried to obtain the title compound as the hydrochloride salt.

For further purification, the product was triturated with methanol-acetone (1:5) and then with methanol-ether (1:5). The title compound was collected by filtration and dried to provide the title compound as the hydrochloride salt. $^1$H NMR (501 MHz, DMSO-d$_6$) δ ppm 9.28-9.19 (m, 1H), 9.19-9.08 (m, 1H), 8.02 (s, 1H), 7.58-7.45 (m, 2H), 7.45-7.33 (m, 2H), 3.27 (ddd, J=12.0, 7.4, 4.1, 3H), 3.16 (dd, J=7.7, 6.4, 1H), 3.02 (dd, J=12.6, 2.1, 1H), 2.72-2.60 (m, 1H), 2.43 (s, 1H), 2.33 (dd, J=14.9, 3.2, 2H), 2.28-2.06 (m, 1H); MS (ESI+) m/z 216.9 (M+H)$^+$.

Example 181

(4aS)-10-ethoxy-1,2,3,4,4a,5-hexahydropyrazino[1,2-a][1,5]benzodiazepin-6(7H)-one Example 181A (4aS)-3-benzyl-10-ethoxy-1,2,3,4,4a,5-hexahydropyrazino[1,2-a][1,5]benzodiazepin-6(7H)-one The title compound was prepared according to the procedure outlined in Example 43A substituting 2-(1-(2-amino-5-methoxyphenyl)-4-benzylpiperazin-2-yl)acetic acid for 2-(1-(2-amino-5-ethoxyphenyl)-4-benzylpiperazin-2-yl)acetic acid 2-(1-(2-Amino-5-ethoxyphenyl)-4-benzylpiperazin-2-yl)acetic acid was prepared according the procedure outlined in Examples 12D, 12E, and 12F by substituting 2-fluoro-4-methoxy-1-nitrobenzene with 2-fluoro-4-ethoxy-1-nitrobenzene.

The enantiomers were separated by supercritical fluid chromatography using Chiralpak® AS-H, 21 mm id, 250 mm in length from Chiral Technologies, Inc. Oven temperature 35° C., pressure 100 bar, flow rate 40 mL/minute, mobile phase modifier: methanol with 0.1% diethylamine, 10-30% modifier isocratic for 20 minutes. Retention time 14.1 minutes. $^1$H NMR (500 MHz, DMSO-d$_6$) δ ppm 9.03 (s, 1H), 7.09 (d, J=6.4, 4H), 7.05-6.98 (m, 1H), 6.57 (s, 1H), 6.33 (s, 2H), 3.79-3.69 (m, 2H), 3.29 (d, J=2.3, 2H), 3.02 (t, J=8.7, 1H), 2.84 (td, J=11.3, 2.5, 1H), 2.74 (d, J=11.3, 1H), 2.57 (d, J=10.7, 1H), 2.28-2.24 (m, 2H), 1.98 (t, J=10.7, 1H), 1.87 (td, J=11.1, 2.8, 1H), 1.59 (d, J=13.2, 1H), 1.06 (t, J=7.0, 3H). MS (ESI+) m/z 352.0 (M+H)$^+$.

Example 181B (4aS)-10-ethoxy-1,2,3,4,4a,5-hexahydropyrazino[1,2-a][1,5]benzodiazepin-6(7H)-one The title compound was prepared according to the procedure outlined in Example 43B substituting Example 181A for Example 43A. The crude material was concentrated and then treated with 4 M HCl in dioxane (0.3 mL) in dichloromethane (0.2 mL) at room temperature for 10 minutes. The supernatant liquid was removed, and the grey solid obtained was further purified by silica gel chromatography (Extra-Clean™ SPE Si, Alltech®, 2 g) eluting first with 5% methanol/dichloromethane and then with 10% methanol/dichloromethane to obtain the title compound. $^1$H NMR (500 MHz, DMSO-d$_6$) δ ppm 9.48 (s, 1H), 9.30 (s, 2H), 6.87 (d, J=8.4, 1H), 6.62 (d, J=1.5, 2H), 4.12-3.93 (m, 2H), 3.64-3.53 (m, 1H), 3.37-3.26 (m, 4H), 3.07-2.91 (m, 2H), 2.61 (dd, J=13.4, 7.1, 1H), 2.01 (d, J=13.4, 1H), 1.31 (t, J=7.0, 3H). MS (ESI+) m/z 261.9 (M+H)$^+$.

Example 182

1,2,3,4,4a,5,6,7-octahydropyrazino[1,2-a][1]benzazepine

Example 182A 1,3,4,5-tetrahydro-2H-1-benzazepin-2-one

To an ice bath cooled solution of 3,4-dihydronaphthalen-1 (2H)-one (20 mL, 150 mmol) in chloroform (300 mL) was added sodium azide (14.62 g, 225 mmol) and then concentrated sulfuric acid (80 mL, 1499 mmol) was added dropwise over 30 minutes, and the mixture was stirred at room temperature for 24 hours. The biphasic solution was poured into ice, and the product was extracted twice with ethyl acetate. The organic layer was washed with water, dried over Na$_2$SO$_4$ and concentrated to give the crude product which was purified by silica gel chromatography (Analogix IntelliFlash™ 280, SF 25-120) loading with dichloromethane and eluting with 30% ethyl acetate/hexanes to obtain the title compound. $^1$H NMR (500 MHz, DMSO-d$_6$) δ ppm 9.50 (s, 1H), 7.28-7.14 (m, 2H), 7.07 (td, J=7.4, 1.2, 1H), 7.00-6.85 (m, 1H), 2.67 (t, J=6.9, 2H), 2.20-2.03 (m, 4H); MS (ESI-) m/z 160.1 (M-H)$^-$.

Example 182B 1,3,4,5-tetrahydro-2H-1-benzazepine-2-thione

To a solution of Example 182A (12.435 g, 77 mmol) in pyridine (309 mL) under nitrogen was added phosphorus pentasulfide (34.3 g, 154 mmol), and the mixture was heated at 120° C. (reflux) for 2 hours. The solvent was decanted and water was added. The product was extracted with dichloromethane, pre-absorbed onto silica gel and purified by silica gel chromatography (Analogix IntelliFlash™ 280, SF10-150) eluting with 30% ethyl acetate/hexanes to obtain the title compound. $^1$H NMR (500 MHz, DMSO-d$_6$) δ ppm 11.75 (s, 1H), 7.32-7.25 (m, 2H), 7.19 (td, J=7.5, 1.2, 1H), 7.10-7.00 (m, 1H), 2.63 (m, 4H), 2.20 (m, 2H); MS (ESI-) m/z 176.1 (M-H)$^-$.

Example 182C 2-(methylthio)-4,5-dihydro-3H-1-benzazepine

A solution of Example 182B (2.3 g, 12.97 mmol) in acetone (51.9 mL) was heated to 60° C. in and oil bath. Then potassium hydroxide (36.4 g, 649 mmol) was added followed by the dropwise addition of iodomethane (0.811 mL, 12.97 mmol). The resulting yellow slurry was stirred for 5 minutes and then the solids were collected by filtration. The solids were washed with acetone and the filtrate was concentrated to obtain the crude title compound which was used was used without purification for the next reaction.

Example 182D (2Z)-2-(nitromethylene)-2,3,4,5-tetrahydro-1H-1-benzazepine

A mixture of Example 182C (2.481 g, 12.97 mmol) and nitromethane (13.99 mL, 259 mmol) was heated with an oil bath at 120° C. for 48 hours. The nitromethane was evaporated and the crude mixture was purified by silica gel chromatography (Analogix IntelliFlash™ 280, SF25-80) eluting with 15-30% ethyl acetate/hexanes to obtain the title compound. ¹H NMR (500 MHz, DMSO-d$_6$) δ ppm 11.15 (s, 1H), 7.34-7.25 (m, 3H), 7.25-7.15 (m, 1H), 6.87 (s, 1H), 2.77-2.64 (m, 2H), 2.22 (m, 2H), 2.14 (m, 2H); MS (ESI+) m/z 205.3 (M+H)⁺.

Example 182E 1-(2,3,4,5-tetrahydro-1H-1-benzazepin-2-yl)methanamine

To a solution of Example 182D (0.643 g, 3.15 mmol) in tetrahydrofuran (31.5 mL) under argon was added dropwise lithium aluminum hydride in tetrahydrofuran (9.45 mL, 18.89 mmol), and the mixture was stirred at room temperature for 30 minutes. Water was added carefully and the mixture was extracted once with dichloromethane. The organic extract was dried over Na$_2$SO$_4$, and the solvent was evaporated to obtain the crude title compound which was used was used without purification for the next reaction. MS (ESI+) m/z 177.3 (M+H)⁺.

Example 182F 3,4,4a,5,6,7-hexahydropyrazino[1,2-a][1]benzazepine-1,2-dione

A solution of Example 182E (0.282 g, 1.600 mmol) in diethyl oxalate (1.518 mL, 11.20 mmol) was heated at 140° C. for 1 hour and then at 180° C. for 2 hours. The crude mixture was purified by silica gel chromatography (Analogix IntelliFlash™ 280, SF24-40) eluting with dichloromethane, then with 2% methanol/dichloromethane, and then with 10% methanol/dichloromethane to obtain the title compound. ¹H NMR (400 MHz, DMSO-d$_6$) δ ppm 8.66 (s, 1H), 7.37-7.17 (m, 4H), 3.91 (dd, J=12.8, 4.2, 1H), 3.49 (d, J=11.4, 1H), 3.19-3.13 (m, 1H), 2.71 (dd, J=18.6, 12.5, 1H), 2.56 (m, 1H), 2.02 (m, 2H), 1.86 (m, 1H), 1.42 (m, 1H); MS (ESI+) m/z 248.2 (M+NH$_4$)⁺.

Example 182G 1,2,3,4,4a,5,6,7-octahydropyrazino[1,2-a][1]benzazepine

To a solution of Example 182F (0.110 g, 0.478 mmol) in tetrahydrofuran (4.78 mL) was added lithium aluminum hydride solution in tetrahydrofuran (1.194 mL, 2.389 mmol), and the mixture was first stirred at room temperature for 5 minutes and then heated for 5 minutes at 80° C. Water was added carefully and the product was extracted once with dichloromethane. The organic extract was dried over Na$_2$SO$_4$ and concentrated. The crude mixture was purified by reverse phase HPLC to obtain the title compound as the trifluoroacetic acid salt. ¹H NMR (400 MHz, DMSO-d$_6$) δ ppm 8.96 (s, 1H), 8.77 (s, 1H), 7.20 m, 1H), 7.10 (m, 1H), 7.06-6.87 (m, 2H), 3.11 (m, 2H), 3.03-2.92 (m, 2H), 2.66-2.54 (m, 1H), 1.72 (m, 1H), 1.63-1.34 (m, 3H); MS (ESI+) m/z 203.4 (M+H)⁺.

Example 183

3-methyl-1,2,3,4,4a,5,6,7-octahydropyrazino[1,2-a][1]benzazepine

To a solution of Example 182 (0.046 g, 0.227 mmol) in dichloromethane (1.749 mL) was added acetic acid (0.169 mL, 2.96 mmol), formaldehyde (7.51 mg, 0.250 mmol) and MP-cyanoborohydride (0.546 g, 0.682 mmol), and the mixture was stirred at room temperature for 24 hours. The reaction mixture was filtered and the beads were washed with methanol. The filtrate was concentrated and purified by reverse phase HPLC to obtain the title compound as the trifluoroacetic acid salt. ¹H NMR (400 MHz, DMSO-d$_6$) δ ppm 9.87 (s, 1H), 7.21 m, 1H), 7.11 (m, 1H), 6.96 (m, 2H), 3.41-3.10 (m, 6H), 3.02 (m, 2H), 2.87 (s, 3H), 2.58 (m, 1H), 1.69 (m, 1H), 1.52 (m, 1H), 1.41 (m, 2H). MS (ESI+) m/z 217.2 (M+H)⁺.

Example 184

N-(7-oxo-1,2,3,4,4a,5,6,7-octahydropyrazino[1,2-a][1,4]benzodiazepin-9-yl)-3-(trifluoromethyl)benzenesulfonamide Example 184A N-(3-benzyl-7-oxo-1,2,3,4,4a,5,6,7-octahydropyrazino[1,2-a][1,4]benzodiazepin-9-yl)-3-(trifluoromethyl)benzenesulfonamide Example 184A was synthesized according to Example 47, substituting 3-(trifluoromethyl)benzene-1-sulfonyl chloride for benzenesulfonyl chloride. The material was used without further purification in Example 184B. MS (ESI+) m/z 531.38 (M+H)⁺.

Example 184B

N-(7-oxo-1,2,3,4,4a,5,6,7-octahydropyrazino[1,2-a][1,4]benzodiazepin-9-yl)-3-(trifluoromethyl)benzenesulfonamide Example 184A (0.05 g, 0.094 mmol) and ethanol (20 mL) were added to 20% Pd(OH)$_2$—C, wet (10 mg, 0.071 mmol) in a 50 mL pressure bottle and stirred for 6 hours under hydrogen at 30 psi and 50° C. The mixture was filtered through a nylon membrane. The filtrate was concentrated and the residue was suspended in dichloromethane/dioxane and treated with 4 M HCl in dioxane for 10 minutes at room temperature to yield a solid. The mixture was centrifuged, the solvent was removed, and the solid was dried. The title compound was obtained following several triturations with methanol. ¹H NMR (500 MHz, DMSO-d$_6$) δ ppm 10.37 (s, 1H), 8.86 (s, 1H), 8.26 (d, J=5.2, 1H), 8.07-7.95 (m, 3H), 7.93 (s, 1H), 7.83 (dd, J=9.3, 6.2, 2H), 7.21-7.07 (m, 2H), 6.98 (t, J=7.6, 1H), 3.29-3.09 (m, 6H), 3.03-2.97 (m, 3H); MS (ESI+) m/z 441.44 (M+H)⁺.

Example 185

10-benzyl-1,2,3,4,4a,5-hexahydropyrazino[1,2-a][1,5]benzodiazepin-6(7H)-one

The title compound was prepared as an HCl salt according to the procedure outlined in Example 53 substituting 4-benzyl-2-bromoaniline for 2-bromo-3-methyl aniline. ¹H NMR (300 MHz, DMSO-d$_6$) δ ppm 7.15-7.38 (m, 5 H), 7.01 (s, 1 H), 6.88 (s, 2 H), 3.92 (s, 2 H), 3.49-3.68 (m, 2 H), 3.16-3.43 (m, 3 H), 2.87-3.09 (m, 2 H), 2.62 (dd, J=13.48, 7.14 Hz, 1 H), 2.01 (d, J=13.48 Hz, 1 H); MS (ESI+) m/z 308 (M+H)⁺.

Example 186

(4aS)-3-benzyl-9-chloro-2,3,4,4a,5,6-hexahydro-1H-pyrazino[2,1-d][1,5]-benzoxazepine The title compound was prepared as a trifluoroacetic acid salt according to the procedure outlined in Example 133A substituting 5-chloro-2-fluoro-bromobenzene for bromo-2-fluoro-4-methylbenzene followed by the procedure outlined in Example 133B. $^1$H NMR (300 MHz, DMSO-$d_6$) δ ppm 7.21-7.36 (m, 5 H), 6.94 (d, J=2.37 Hz, 1 H), 6.81-6.87 (m, 1 H), 6.75 (d, 1 H), 4.26-4.36 (m, 1 H), 3.98-4.14 (m, 1 H), 3.50-3.54 (m, 2 H), 3.04-3.22 (m, 3 H), 2.61-2.70 (m, 1 H), 2.51-2.57 (m, 1 H), 2.27-2.38 (m, 1 H), 2.15-2.25 (m, 1 H), 1.88-1.98 (m, 2 H); MS (ESI+) m/z 328 (M+H)$^+$.

Example 187

(4aS)-9-phenyl-2,3,4,4a,5,6-hexahydro-1H-pyrazino[2,1-d][1,5]benzoxazepine

A microwave vial was charged with Example 140 (60 mg, 0.25 mmol), phenylboronic acid (30 mg, 0.25 mmol), dicyclohexyl(2',6'-dimethoxybiphenyl-2-yl)phosphine (10.3 mg, 0.025 mmol), palladium(II) acetate (2.8 mg, 0.013 mmol), $K_2CO_3$ (0.25 mL, 2M) and 1,2-dimethoxyethane (2 mL). The reaction was heated in a Biotage Initiator™ microwave (400 W) at 150° C. for 30 minutes. Purification via reverse phase HPLC afforded the title compound as a trifluoroacetic acid salt. $^1$H NMR (400 MHz, DMSO-$d_6$) δ ppm 7.57-7.66 (m, 2 H) 7.43 (t, J=7.63 Hz, 2 H) 7.32 (t, J=7.32 Hz, 1 H) 7.24 (d, J=2.14 Hz, 1 H) 7.20 (dd, J=8.24, 2.14 Hz, 1 H) 6.90 (d, J=8.24 Hz, 1 H) 4.37-4.45 (m, 1 H) 4.11-4.19 (m, 1 H) 3.32-3.48 (m, 4 H) 3.13-3.27 (m, 2 H) 3.03-3.13 (m, 1 H) 2.05-2.16 (m, 1 H) 1.90-2.01 (m, 1 H); MS (ESI+) m/z 281 (M+H)$^+$.

Example 188

(4aS)-9-chloro-3-methyl-2,3,4,4a,5,6-hexahydro-1H-pyrazino[2,1-d][1,5]benzoxazepine The title compound was prepared according to the procedure outlined in Example 78 substituting Example 140 for Example 77. $^1$H NMR (400 MHz, DMSO-$d_6$) δ ppm 7.03 (d, J=2.44 Hz, 1H), 6.97 (dd, J=8.54, 2.14 Hz, 1H), 6.84 (d, J=8.24 Hz, 1H), 4.37-4.46 (m, 1 H), 4.05-4.14 (m, 1H), 3.25-3.55 (m, 5H), 3.03-3.23 (m, 2H), 2.82-2.89 (m, 3H), 2.03-2.14 (m, 1H), 1.71-1.82 (m, 1H); MS (ESI+) m/z 253 (M+H)$^+$.

Example 189

(4aS)-9-(2-methylphenyl)-2,3,4,4a,5,6-hexahydro-1H-pyrazino [2,1-d][1,5]benzoxazepine The title compound was prepared as a trifluoroacetic acid salt according to the procedure outlined in Example 187 substituting 2-methylphenylboronic acid for phenylboronic acid. $^1$H NMR (400 MHz, DMSO-$d_6$) δ ppm 7.17-7.29 (m, 4 H), 6.93 (s, 1 H), 6.87 (s, 2 H), 4.37-4.45 (m, 1 H), 4.12-4.19 (m, 1 H), 3.28-3.45 (m, 4 H), 3.01-3.26 (m, 3 H), 2.24 (s, 3 H), 2.06-2.16 (m, 1 H), 1.91-2.01 (m, 1 H); MS (ESI+) m/z 295 (M+H)$^+$.

Example 190

(4aS)-9-(3-methylphenyl)-2,3,4,4a,5,6-hexahydro-1H-pyrazino [2,1-d][1,5]benzoxazepine The title compound was prepared as a trifluoroacetic acid salt according to the procedure outline in Example 187 substituting 3-methylphenylboronic acid for phenylboronic acid. $^1$H NMR (500 MHz, DMSO-$d_6$) δ ppm 7.40 (d, J=7.93 Hz, 1 H), 7.31 (t, J=7.63 Hz, 1 H), 7.22 (d, J=2.14 Hz, 1 H), 7.18 (dd, J=8.24, 2.14 Hz, 1 H), 7.13 (d, J=7.63 Hz, 1 H), 6.89 (d, J=8.24 Hz, 1 H), 4.37-4.44 (m, 1 H), 4.12-4.18 (m, 1 H), 3.32-3.46 (m, 4 H), 3.14-3.26 (m, 2 H), 3.03-3.12 (m, 1 H), 2.36 (s, 3 H), 2.05-2.14 (m, 1 H), 1.92-1.99 (m, 1 H); MS (ESI+) m/z 295 (M+H)$^+$.

Example 191

(4aS)-9-(4-methylphenyl)-2,3,4,4a,5,6-hexahydro-1H-pyrazino [2,1-d][1,5]benzoxazepine The title compound was prepared as a trifluoroacetic acid salt according to the procedure outline in Example 187 substituting 4-methylphenylboronic acid for phenylboronic acid. $^1$H NMR (500 MHz, DMSO-$d_6$) δ ppm 7.51 (d, J=8.24 Hz, 2 H), 7.20-7.26 (m, 3 H), 7.17 (dd, J=8.24, 2.14 Hz, 1 H), 6.88 (d, J=7.93 Hz, 1 H), 4.35-4.43 (m, 1 H), 4.11-4.17 (m, 1 H), 3.31-3.47 (m, 4 H), 3.14-3.26 (m, 2 H), 3.03-3.11 (m, 1 H), 2.33 (s, 3 H), 2.05-2.13 (m, 1 H), 1.91-2.00 (m, 1 H); MS (ESI+) m/z 295 (M+H)$^+$.

Example 192

(4aS)-9-(2-methoxyphenyl)-2,3,4,4a,5,6-hexahydro-1H-pyrazino[2,1-d][1,5]benzoxazepine The title compound was prepared as a trifluoroacetic acid salt according to the procedure outline in Example 187 substituting 2-methoxyphenylboronic acid for phenylboronic acid. $^1$H NMR (500 MHz, DMSO-$d_6$) δ ppm 7.26-7.33 (m, 2 H), 7.06-7.10 (m, 2 H), 7.05 (dd, J=8.24, 2.14 Hz, 1 H), 7.00 (t, J=7.48 Hz, 1 H), 6.84 (d, J=8.24 Hz, 1 H), 4.40-4.47 (m, 1 H), 4.11-4.17 (m, 1 H), 3.76 (s, 3 H), 3.30-3.43 (m, 4 H), 3.03-3.26 (m, 3 H), 2.07-2.16 (m, 1 H), 1.91-1.99 (m, 1 H); MS (ESI+) m/z 311 (M+H)$^+$.

Example 193

(4aS)-9-(3-methoxyphenyl)-2,3,4,4a,5,6-hexahydro-1H-pyrazino[2,1-d][1,5]benzoxazepine The title compound was prepared as a trifluoroacetic acid salt according to the procedure outline in Example 187 substituting 3-methoxyphenylboronic acid for phenylboronic acid. $^1$H NMR (500 MHz, DMSO-$d_6$) δ ppm 7.34 (t, J=7.93 Hz, 1 H), 7.16-7.24 (m, 3 H), 7.12-7.15 (m, 1 H), 6.86-6.93 (m, 2 H), 4.37-4.44 (m, 1 H), 4.12-4.18 (m, 1 H), 3.81 (s, 3 H), 3.32-3.47 (m, 4 H), 3.13-3.26 (m, 2 H), 3.03-3.12 (m, 1 H), 2.06-2.15 (m, 1 H), 1.92-2.01 (m, 1 H); MS (ESI+) m/z 311 (M+H)$^+$.

Example 194

(4aS)-9-(4-methoxyphenyl)-2,3,4,4a,5,6-hexahydro-1H-pyrazino[2,1-d][1,5]benzoxazepine The title compound was prepared as a trifluoroacetic acid salt according to the procedure outline in Example 187 substituting 4-methoxyphenylboronic acid for phenylboronic acid. $^1$H NMR (500 MHz, DMSO-$d_6$) δ ppm 7.51-7.58 (m, 2 H), 7.18 (d, J=2.44 Hz, 1 H), 7.14 (dd, J=8.24, 2.14 Hz, 1 H), 6.99 (d, J=8.85 Hz, 2 H), 6.87 (d, J=7.93 Hz, 1 H), 4.34-4.42 (m, 1 H), 4.09-4.17 (m, 1 H), 3.78 (s, 3 H) 3.32-3.47 (m, 4 H), 3.13-3.27 (m, 2 H), 3.02-3.12 (m, 1 H), 2.04-2.14 (m, 1 H), 1.91-2.00 (m, 1 H); MS (ESI+) m/z 311 (M+H)$^+$.

Example 195

(4aS)-9-[2-(methylsulfonyl)phenyl]-2,3,4,4a,5,6-hexahydro-1H-pyrazino[2,1-d][1,5]benzoxazepine The title compound was prepared as a trifluoroacetic acid salt according to the procedure outline in Example 187 substituting 2-(methylsulfonyl)phenylboronic acid for phenylboronic acid. $^1$H NMR (500 MHz, DMSO-$d_6$) δ ppm 8.07-8.10 (m, 1 H), 7.91-7.95 (m, 2 H), 7.62-7.77 (m, 3 H), 7.42-7.46 (m, 1 H), 4.44-4.51 (m, 1 H), 4.14-4.21 (m, 1 H), 3.27-3.42 (m, 4 H), 2.98-3.17 (m, 3 H), 2.74-2.78 (m, 3 H), 2.08-2.18 (m, 1 H), 1.91-1.99 (m, 1 H); MS (ESI+) m/z 359 (M+H)$^+$.

Example 196

(4aS)-9-[3-(methylsulfonyl)phenyl]-2,3,4,4a,5,6-hexahydro-1H-pyrazino[2,1-d][1,5]benzoxazepine The title compound was prepared as a trifluoroacetic acid salt according to the procedure outline in Example 187 substituting 3-(methylsulfonyl)phenylboronic acid for phenylboronic acid. $^1$H NMR (500 MHz, DMSO-$d_6$) δ ppm 8.09 (t, J=1.68 Hz, 1 H), 8.00 (d, J=7.93 Hz, 1 H), 7.87 (d, J=8.54 Hz, 1 H), 7.71 (t, J=7.78 Hz, 1 H), 7.27-7.35 (m, 2 H), 6.95 (d, J=8.24 Hz, 1 H), 4.39-4.50 (m, 1 H), 4.13-4.22 (m, 1 H), 3.34-3.49 (m, 4 H), 3.29 (s, 3 H), 3.04-3.26 (m, 3 H), 2.07-2.17 (m, 1 H), 1.92-2.02 (m, 1 H); MS (ESI+) m/z 359 (M+H)$^+$.

Example 197

1-{2-[(4aS)-2,3,4,4a,5,6-hexahydro-1H-pyrazino[2,1-d][1,5]benzoxazepin-9-yl]phenyl}ethanone The title compound was prepared as a trifluoroacetic acid salt according to the procedure outline in Example 187 substituting 2-acetylphenylboronic acid for phenylboronic acid. $^1$H NMR (400 MHz, DMSO-$d_6$) δ ppm 7.50-7.59 (m, 2 H), 6.84-6.92 (m, 3 H), 4.41-4.51 (m, 1 H), 4.11-4.21 (m, 1 H), 3.02-3.41 (m, 7 H), 2.06-2.17 (m, 4 H), 1.90-1.99 (m, 1 H); MS (ESI+) m/z 323 (M+H)$^+$.

Example 198

1-{3-[(4aS)-2,3,4,4a,5,6-hexahydro-1H-pyrazino[2,1-d][1,5]benzoxazepin-9-yl]phenyl}ethanone The title compound was prepared as a trifluoroacetic acid salt according to the procedure outline in Example 187 substituting 3-acetylphenylboronic acid for phenylboronic acid. $^1$H NMR (400 MHz, DMSO-$d_6$) δ ppm 8.12 (t, J=1.83 Hz, 1 H), 7.84-7.94 (m, 2 H), 7.59 (t, J=7.78 Hz, 1 H), 7.24-7.34 (m, 2 H), 6.94 (d, J=8.24 Hz, 1 H), 4.38-4.49 (m, 1 H), 4.13-4.22 (m, 1 H), 3.34-3.51 (m, 4 H), 3.04-3.30 (m, 3 H), 2.65 (s, 3 H), 2.06-2.19 (m, 1 H), 1.93-2.03 (m, 1 H); MS (ESI+) m/z 323 (M+H)$^+$.

Example 199

1-{4-[(4aS)-2,3,4,4a,5,6-hexahydro-1H-pyrazino[2,1-d][1,5]benzoxazepin-9-yl]phenyl}ethanone The title compound was prepared as a trifluoroacetic acid salt according to the procedure outline in Example 187 substituting 4-acetylphenylboronic acid for phenylboronic acid. $^1$H NMR (400 MHz, DMSO-$d_6$) δ ppm 8.01 (d, J=8.54 Hz, 2 H), 7.79 (d, J=8.24 Hz, 2 H), 7.28-7.36 (m, 2 H), 6.94 (d, J=8.24 Hz, 1 H), 4.39-4.50 (m, 1 H), 4.13-4.22 (m, 1 H), 3.34-3.49 (m, 4 H), 3.04-3.29 (m, 3 H), 2.60 (s, 3 H), 2.06-2.19 (m, 1 H), 1.92-2.03 (m, 1 H); MS (ESI+) m/z 323 (M+H)$^+$.

Example 200

2-[(4aS)-2,3,4,4a,5,6-hexahydro-1H-pyrazino[2,1-d][1,5]benzoxazepin-9-yl]phenol

The title compound was prepared as a trifluoroacetic acid salt according to the procedure outline in Example 187 substituting 2-hydroxyphenylboronic acid for phenylboronic acid. $^1$H NMR (300 MHz, DMSO-$d_6$) δ ppm 7.18-7.26 (m, 1 H), 7.07-7.17 (m, 3 H), 6.79-6.94 (m, 3 H), 4.36-4.48 (m, 1 H), 4.08-4.18 (m, 1 H), 2.98-3.41 (m, 7 H), 2.04-2.18 (m, 1 H), 1.86-2.00 (m, 1 H); MS (ESI+) m/z 297 (M+H)$^+$.

Example 201

3-[(4aS)-2,3,4,4a,5,6-hexahydro-1H-pyrazino[2,1-d][1,5]benzoxazepin-9-yl]phenol

The title compound was prepared as a trifluoroacetic acid salt according to the procedure outline in Example 187 substituting 3-hydroxyphenylboronic acid for phenylboronic acid. $^1$H NMR (400 MHz, DMSO-$d_6$) δ ppm 7.39-7.45 (m, 2 H), 7.12-7.15 (m, 1 H), 7.10 (dd, J=8.24, 2.14 Hz, 1 H), 6.79-6.86 (m, 3 H), 4.33-4.41 (m, 1 H), 4.09-4.16 (m, 1 H), 3.30-3.47 (m, 4 H), 3.12-3.26 (m, 2 H), 3.01-3.11 (m, 1 H), 2.02-2.14 (m, 1 H), 1.88-1.99 (m, 1 H); MS (ESI+) m/z 297 (M+H)$^+$.

Example 202

4-[(4aS)-2,3,4,4a,5,6-hexahydro-1H-pyrazino[2,1-d][1,5]benzoxazepin-9-yl]phenol

The title compound was prepared as a trifluoroacetic acid salt according to the procedure outline in Example 187 substituting 4-hydroxyphenylboronic acid for phenylboronic acid. $^1$H NMR (400 MHz, DMSO-$d_6$) δ ppm 7.11-7.24 (m, 3 H), 6.96-7.05 (m, 2 H), 6.88 (d, J=8.24 Hz, 1 H), 6.73 (dd, J=8.54, 2.14 Hz, 1 H), 4.36-4.45 (m, 1 H), 4.11-4.18 (m, 1 H), 3.31-3.46 (m, 4 H), 3.02-3.27 (m, 3 H), 2.05-2.16 (m, 1 H), 1.90-1.99 (m, 1 H); MS (ESI+) m/z 297 (M+H)$^+$.

Example 203

(4aS)-9-(2-fluorophenyl)-2,3,4,4a,5,6-hexahydro-1H-pyrazino[2,1-d][1,5]-benzoxazepine The title compound was prepared as a trifluoroacetic acid salt according to the procedure outline in Example 187 substituting 2-fluorophenylboronic acid for phenylboronic acid. $^1$H NMR (400 MHz, DMSO-$d_6$) δ ppm 7.48-7.55 (m, 1 H), 7.34-7.42 (m, 1 H), 7.24-7.32 (m, 2 H), 7.08-7.16 (m, 2 H), 6.91 (d, J=8.24 Hz, 1 H), 4.41-4.49 (m, 1 H), 4.12-4.20 (m, 1 H), 3.30-3.44 (m, 4 H), 3.02-3.26 (m, 3 H), 2.07-2.18 (m, 1 H), 1.91-2.02 (m, 1 H); MS (ESI+) m/z 299 (M+H)$^+$.

Example 204

(4aS)-9-(3-fluorophenyl)-2,3,4,4a,5,6-hexahydro-1H-pyrazino[2,1-d][1,5]benzoxazepine The title compound was prepared as a trifluoroacetic acid salt according to the procedure outline in Example 187 substituting 3-fluorophenylboronic acid for phenylboronic acid. $^1$H NMR (400 MHz, DMSO-d$_6$) δ ppm 7.41-7.53 (m, 3 H), 7.29 (d, J=2.44 Hz, 1 H), 7.25 (dd, J=8.24, 2.14 Hz, 1 H), 7.09-7.18 (m, 1 H), 6.90 (d, J=8.24 Hz, 1 H), 4.35-4.46 (m, 1 H), 4.12-4.21 (m, 1 H), 3.31-3.50 (m, 4 H), 3.00-3.27 (m, 3 H), 2.05-2.16 (m, 1 H), 1.90-2.02 (m, 1 H); MS (ESI+) m/z 299 (M+H)$^+$.

Example 205

(4aS)-9-(4-fluorophenyl)-2,3,4,4a,5,6-hexahydro-1H-pyrazino[2,1-d][1,5]benzoxazepine The title compound was prepared as a trifluoroacetic acid salt according to the procedure outline in Example 187 substituting 4-fluoroboronic acid for phenylboronic acid. $^1$H NMR (400 MHz, DMSO-d$_6$) δ ppm 7.62-7.71 (m, 2 H), 7.15-7.29 (m, 6 H), 6.89 (d, J=8.24 Hz, 1 H), 4.34-4.44 (m, 1 H), 4.09-4.20 (m, 1 H), 3.01-3.49 (m, 7 H), 2.04-2.15 (m, 1 H), 1.90-2.01 (m, 1 H); MS (ESI+) m/z 299 (M+H)$^+$.

Example 206

(4aS)-9-(pyridin-3-yl)-2,3,4,4a,5,6-hexahydro-1H-pyrazino[2,1-d][1,5]benzoxazepine The title compound was prepared as a trifluoroacetic acid salt according to the procedure outline in Example 187 substituting pyridine-3-ylboronic acid for phenylboronic acid. $^1$H NMR (400 MHz, DMSO-d$_6$) δ ppm 9.11 (d, J=1.83 Hz, 1 H), 8.73 (dd, J=5.19, 1.53 Hz, 1 H), 8.48-8.59 (m, 1 H), 7.84 (dd, J=7.93, 5.49 Hz, 1 H), 7.43 (d, J=2.14 Hz, 1 H), 7.38 (dd, J=8.39, 2.29 Hz, 1 H), 6.98 (d, J=8.24 Hz, 1 H), 4.40-4.51 (m, 1 H), 4.14-4.23 (m, 1 H), 3.32-3.51 (m, 4 H), 3.14-3.28 (m, 2 H), 3.02-3.13 (m, 1 H), 2.06-2.20 (m, 1 H), 1.90-2.04 (m, 1 H); MS (ESI+) m/z 282 (M+H)$^+$.

Example 207

(4aS)-9-(pyridin-4-yl)-2,3,4,4a,5,6-hexahydro-1H-pyrazino[2,1-d][1,5]benzoxazepine The title compound was prepared as a trifluoroacetic acid salt according to the procedure outline in Example 187 substituting pyridine-4-ylboronic acid for phenylboronic acid. $^1$H NMR (400 MHz, DMSO-d$_6$) δ ppm 8.84 (d, J=6.71 Hz, 2 H), 8.24 (d, J=7.02 Hz, 2 H), 7.54-7.64 (m, 2 H), 7.01 (d, J=8.24 Hz, 1 H), 4.49-4.60 (m, 1 H), 4.18-4.29 (m, 1 H), 3.34-3.54 (m, 4 H), 3.15-3.28 (m, 2 H), 3.03-3.15 (m, 1 H), 2.09-2.21 (m, 1 H), 1.92-2.05 (m, 1 H); MS (ESI+) m/z 282 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I):

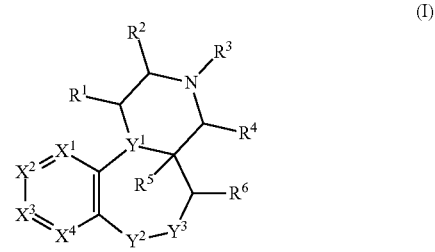

or a pharmaceutically acceptable salt thereof, wherein
$R^1$, $R^2$, $R^4$, $R^5$ and $R^6$ are independently selected from the group consisting of hydrogen, alkenyl, alkyl, haloalkyl, $G^1$, and —$(CR^{4a}R^{5a})_m$—$G^1$;
$R^{4a}$ and $R^{5a}$, at each occurrence, are each independently hydrogen, halogen, alkyl, or haloalkyl;
$G^1$, at each occurrence, is independently aryl or heteroaryl, wherein each $G^1$ is independently unsubstituted or substituted with 1, 2, 3, 4, or 5 substituents selected from the group consisting of alkyl, alkenyl, alkynyl, halogen, cyano, —$G^3$, —$NO_2$, —$OR^{1b}$, —O—$(CR^{4b}R^{5b})_m$—$G^3$, —$OC(O)R^{1b}$, —$OC(O)N(R^b)(R^{3b})$, —$SR^{1b}$, —$S(O)R^{2b}$, —$S(O)_2R^{2b}$, —$S(O)_2N(R^b)(R^{3b})$, —$C(O)R^{1b}$, —$C(O)OR^{1b}$, —$C(O)N(R^b)(R^{3b})$, —$C(OH)[(CR^{4b}R^{5b})_m$—$R^{4b}]_2$, —$N(R^b)(R^{3b})$, —$N(R^a)C(O)R^{1b}$, —$N(R^a)C(O)O(R^{1b})$, —$N(R^a)C(O)N(R^b)(R^{3b})$, —$(CR^{4b}R^{5b})_m$—$G^3$, —$(CR^{4b}R^{5b})_m$—$NO_2$, —$(CR^{4b}R^{5b})_m$—$OR^{1b}$, —$(CR^{4b}R^{5b})_m OC(O)R^{1b}$, —$(CR^{4b}R^{5b})_m$—$OC(O)N(R^b)(R^{3b})$, —$(CR^{4b}R^{5b})_m$—$SR^{1b}$, —$(CR^{4b}R^{5b})_m$—$S(O)_2R^{2b}$, —$(CR^{4b}R^{5b})_m$—$S(O)_2N(R^b)(R^{3b})$, —$(CR^{4b}R^{5b})_m$—$C(O)R^{1b}$, —$(CR^{4b}R^{5b})_m$—$C(O)$ $OR^{1b}$, —$(CR^{4b}R^{5b})_m$—$C(O)N(R^b)(R^{3b})$, —$(CR^{4b}R^{5b})_m$—$N(R^b)(R^{3b})$, —$(CR^{4b}R^{5b})_m$—$N(R^a)C(O)R^{1b}$, —$(CR^{4b}R^{5b})_m$—$N(R^a)C(O)O(R^{1b})$, —$(CR^{4b}R^{5b})_m$—$N(R^a)C(O)N(R^b)(R^{3b})$, cyanoalkyl, and haloalkyl;
$R^a$ and $R^b$, at each occurrence, are each independently hydrogen, alkyl, or haloalkyl;
$R^{1b}$ and $R^{3b}$, at each occurrence, are each independently hydrogen, alkyl, or haloalkyl;
$R^{2b}$, at each occurrence, is independently alkyl or haloalkyl;
$R^{4b}$ and $R^{5b}$, at each occurrence, are each independently hydrogen, halogen, alkyl, or haloalkyl;
m, at each occurrence, is independently 1, 2, 3, 4, or 5;
$G^3$, at each occurrence, is independently aryl or heteroaryl, wherein each $G^3$ is independently unsubstituted or substituted with 1, 2, 3, 4, or 5 substituents selected from the group consisting of alkyl, alkenyl, alkynyl, halogen, cyano, —$NO_2$, —$OR^{1b}$, —$OC(O)R^{1b}$, —$OC(O)N(R^b)(R^{3b})$, —$SR^{1b}$, —$S(O)R^{2b}$, —$S(O)_2R^{2b}$, —$S(O)_2N(R^b)(R^{3b})$, —$C(O)R^{1b}$, —$C(O)$ $OR^{1b}$, —$C(O)N(R^b)(R^{3b})$, —$N(R^b)(R^{3b})$, —$N(R^a)C(O)R^{1b}$, —$N(R^a)C(O)O(R^{1b})$, —$N(R^a)C(O)N(R^b)(R^{3b})$, —$(CR^{4b}R^{5b})_m$—$NO_2$, —$(CR^{4b}R^{5b})_m$—$OR^{1b}$, —$(CR^{4b}R^{5b})_m$—$OC(O)R^{1b}$, —$(CR^{4b}R^{5b})_m$—$OC(O)N(R^b)(R^{3b})$, —$(CR^{4b}R^{5b})_m$—$SR^{1b}$, —$(CR^{4b}R^{5b})_m$—$S(O)_2R^{2b}$, —$(CR^{4b}R^{5b})_m$—$S$ $-(O)_2N(R^b)(R^{3b})$, $-(CR^{4b}R^{5b})_m-C(O)R^{1b}$, $-(CR^{4b}R^{5b})_m-C(O)OR^{1b}$, $-(CR^{4b}R^{5b})_m-C(O)N(R^b)(R^{3b})$, $-(CR^{4b}R^{5b})_m-N(R^b)(R^{3b})(CR^{4b}R^{5b})_m-N(R^a)C(O)R^{1b}$, $-(CR^{4b}R^{5b})_m-N(R^a)C(O)O(R^{1b})$, $-(CR^{4b}R^{5b})_m-N(R^a)C(O)N(R^b)(R^{3b})$, cyanoalkyl, and haloalkyl;

$R^3$ is selected from the group consisting of hydrogen, alkyl, alkylcarbonyl, haloalkyl, $(CR^{4a}R^{5a})_m-G^1$, $C(O)-G^1$, $-S(O)_2R^7$, and $-C(O)NR^8R^9$;

$R^7$ and $R^8$ are independently selected from the group consisting of alkyl, haloalkyl, $G^1$ and $-(CR^{4a}R^{5a})_m-G^1$;

$R^9$ is selected from the group consisting of hydrogen, alkyl, and haloalkyl;

$X^1$ is $CR^{10}$;
$X^2$ is $CR^{11}$;
$X^3$ is $CR^{12}$;
$X^4$ is $CR^{13}$;

$R^{10}$, $R^{11}$, $R^{12}$, and $R^{13}$ are each independently hydrogen, alkyl, alkenyl, alkynyl, halogen, cyano, $-G^1$, $-G^2$, $-NO_2$, $-OR^1$, $-O-(CR^{4a}R^{5a})_m-G^1$, $-O-(CR^{4a}R^{5a})_m-G^2$, $-OC(O)R^{1a}$, $-OC(O)N(R^b)(R^{3a})$, $-SR^{1a}$, $-S(O)R^{2a}$, $-S(O)_2R^{2a}$, $-S(O)_2N(R^b)(R^{3a})$, $-C(O)R^{1a}$, $-C(O)OR^{1a}$, $-C(O)N(R^b)(R^{3a})$, $-N(R^b)(R^{3a})$, $-N(R^a)C(O)R^{1a}$, $-N(R^a)C(O)O(R^{1a})$, $-N(R^a)C(O)N(R^b)(R^{3a})$, $-N(R^a)S(O)_2(R^{2a})$, $-(CR^{4a}R^{5a})_m-NO_2$, $-(CR^{4a}R^{5a})_m-OR^{1a}$, $-(CR^{4a}R^{5a})_m-OC(O)R^{1a}$, $-(CR^{4a}R^{5a})_m-OC(O)N(R^b)(R^{3a})$, $-(CR^{4a}R^{5a})_m-SR^{1a}$, $-(CR^{4a}R^{5a})_m-S(O)R^{2a}$, $-(CR^{4a}R^{5a})_m-S(O)_2R^{2a}$, $-(CR^{4a}R^{5a})S(O)_2N(R^b)(R^{3a})$, $-(CR^{4a}R^{5a})_m-C(O)R^{1a}$, $-(CR^{4a}R^{5a})_m-C(O)OR^{1a}$, $-(CR^{4a}R^{5a})_m-C(O)N(R^b)(R^{3a})$, $-(CR^{4a}R^{5a})_m-N(R^b)(R^{3a})$, $-(CR^{4a}R^{5a})_m-N(R^a)C(O)R^{1a}$, $-(CR^{4a}R^{5a})_m-N(R^a)C(O)O(R^{1a})$, $-(CR^{4a}R^{5a})_m-N(R^a)C(O)N(R^b)(R^{3a})$, $-(CR^{4a}R^{5a})_m-G^1$, $-CR^{4a}=CR^{5a}-G^1$, cyanoalkyl, or haloalkyl;

wherein $R^{1a}$ and $R^{3a}$, at each occurrence, are each independently hydrogen, alkyl, haloalkyl, $G^1$, or $-(CR^{4a}R^{5a})_m-G^1$;

$R^{2a}$, at each occurrence, is independently alkyl, haloalkyl, $G^1$, or $-(CR^{4a}R^{5a})_m-G^1$;

$G^2$, at each occurrence, is independently cycloalkyl, cycloalkenyl or heterocycle, wherein each $G^2$ is independently unsubstituted or substituted with 1, 2, 3, 4, or 5 substituents selected from the group consisting of alkyl, alkenyl, halogen, cyano, $-NO_2$, $-OR^{1b}$, $S(O)_2R^{2b}$, $-C(O)OR^{1b}$, haloalkyl, and oxo;

or $R^{10}$ and $R^{11}$, or $R^{11}$ and $R^{12}$, or $R^{12}$ and $R^{13}$ taken together with the carbon atoms to which they are attached form a phenyl ring, cycloalkyl, heterocycle, or heteroaryl, wherein each phenyl ring, cycloalkyl, heterocycle and heteroaryl is independently unsubstituted or substituted with 1, 2, 3, 4, or 5 substituents selected from the group consisting of alkyl, alkenyl, alkynyl, halogen, cyano, $-G^1$, $-G^2$, $-NO_2$, $-OR^{1a}$, $-O-(CR^{4a}R^{5a})_m-G^1$, $-O-(CR^{4a}R^{5a})_m-G^2$, $-OC(O)R^{1a}$, $-OC(O)N(R^b)(R^{3a})$, $-SR^{1a}-S(O)R^{2a}$, $-S(O)_2R^{2a}$, $-S(O)_2N(R^b)(R^{3a})$, $-C(O)R^{1a}$, $-C(O)OR^{1a}$, $-C(O)N(R^b)(R^{3a})$, $-N(R^b)(R^{3a})$, $-N(R^a)C(O)R^{1a}$, $-N(R^a)C(O)O(R^{1a})$, $-N(R^a)C(O)N(R^b)(R^{3a})$, $-N(R^a)S(O)_2(R^{2a})$, $-(CR^{4a}R^{5a})_m-NO_2$, $-(CR^{4a}R^{5a})_m-OR^{1a}$, $-(CR^{4a}R^{5a})_m-OC(O)R^{1a}$, $-(CR^{4a}R^{5a})_m-OC(O)N(R^b)(R^{3a})_m-(CR^{4a}R^{5a})_m-SR^{1a}-(CR^{4a}R^{5a})_m-S(O)R^{2a}$, $-(CR^{4a}R^{5a})_m-S(O)_2R^{2a}$, $-(CR^{4a}R^{5a})_m-S(O)_2N(R^b)(R^{3a})$, $-(CR^{4a}R^{5a})_m-C(O)R^{1a}$, $-(CR^{4a}R^{5a})_m-C(O)OR^{1a}$, $-(CR^{4a}R^{5a})_m-C(O)N(R^b)(R^{3a})$, $-(CR^{4a}R^{5a})_m-N(R^b)(R^{3a})$, $-(CR^{4a}R^{5a})_m-N(R^a)C(O)R^{1a}$, $-(CR^{4a}R^{5a})_m-N(R^a)C(O)O(R^{1a})$, $-(CR^{4a}R^{5a})m N(R^a)C(O)N(R^b)(R^{3a})$, $-(CR^{4a}R^{5a})_m-G^1$, $-CR^{4a}=CR^{5a}-G^1$, cyanoalkyl, or haloalkyl;

$Y^1$ is N;
$Y^2$ is O;
$Y^3$ is $CR^{15}R^{16}$; and $R^{15}$ and $R^{16}$ are independently selected from the group consisting of hydrogen, alkyl, and haloalkyl.

2. The compound according to claim 1 of formula (Ie):

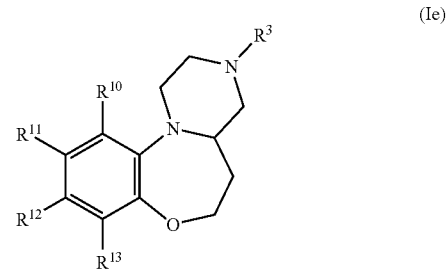

(Ie)

or a pharmaceutically acceptable salt thereof, wherein
$R^3$ is hydrogen, alkyl, alkylcarbonyl, haloalkyl, $-(CR^{4a}R^{5a})_m-G^1$, $-C(O)-G^1$, $-S(O)_2R^7$, or $-C(O)NR^8R^9$.

3. The compound according to claim 2 wherein $R^3$ is hydrogen.

4. The compound according to claim 2, wherein the compound is selected from the group consisting of:
(4aS)-3-methyl-2,3,4,4a,5,6-hexahydro-1H-pyrazino[2,1-d][1,5]benzoxazepine;
(4aS)-10-methyl-2,3,4,4a,5,6-hexahydro-1H-pyrazino[2,1-d][1,5]benzoxazepine;
(4aS)-10-methoxy-2,3,4,4a,5,6-hexahydro-1H-pyrazino[2,1-d][1,5]benzoxazepine;
(4aS)-2,3,4,4a,5,6-hexahydro-1H-pyrazino[2,1-d][1,5]benzoxazepin-10amine;
(4aS)-10-fluoro-2,3,4,4a,5,6-hexahydro-1H-pyrazino[2,1-d][1,5]benzoxazepine;
(4aS)-9-methyl-2,3,4,4a,5,6-hexahydro-1H-pyrazino[2,1-d][1,5]benzoxazepine;
(4aS)-11-chloro-2,3,4,4a,5,6-hexahydro-1H-pyrazino[2,1-d][1,5]benzoxazepine;
(4aS)-11-fluoro-2,3,4,4a,5,6-hexahydro-1H-pyrazino[2,1-d][1,5]benzoxazepine;
(4aS)-9-chloro-2,3,4,4a,5,6-hexahydro-1H-pyrazino[2,1-d][1,5]benzoxazepine;
(4aS)-3-benzyl-2,3,4,4a,5,6-hexahydro-1H-pyrazino[2,1-d][1,5]benzoxazepine;
(4aS)-2,3,4,4a,5,6-hexahydro-1H-pyrazino[2,1-d][1,5]benzoxazepine;
(4aS)-10-chloro-2,3,4,4a,5,6-hexahydro-1H-pyrazino[2,1-d][1,5]benzoxazepine;
(4aS)-3-benzyl-9-chloro-2,3,4,4a,5,6-hexahydro-1H-pyrazino[2,1-d][1,5]benzoxazepine;
(4aS)-9-phenyl-2,3,4,4a,5,6-hexahydro-1H-pyrazino[2,1-d][1,5]benzoxazepine;
(4aS)-9-chloro-3-methyl-2,3,4,4a,5,6-hexahydro-1H-pyrazino[2,1-d][1,5]benzoxazepine;
(4aS)-9-(2-methylphenyl)-2,3,4,4a,5,6-hexahydro-1H-pyrazino [2,1-d][1,5]benzoxazepine;
(4aS)-9-(3-methylphenyl)-2,3,4,4a,5,6-hexahydro-1H-pyrazino [2,1-d][1,5]benzoxazepine;

(4aS)-9-(4-methylphenyl)-2,3,4,4a,5,6-hexahydro-1H-pyrazino [2,1-d][1,5]benzoxazepine;

(4aS)-9-(2-methoxyphenyl)-2,3,4,4a,5,6-hexahydro-1H-pyrazino [2,1-d][1,5]benzoxazepine;

(4aS)-9-(3-methoxyphenyl)-2,3,4,4a,5,6-hexahydro-1H-pyrazino [2,1-d][1,5]benzoxazepine;

(4aS)-9-(4-methoxyphenyl)-2,3,4,4a,5,6-hexahydro-1H-pyrazino [2,1-d][1,5]benzoxazepine;

(4aS)-9-[2-(methylsulfonyl)phenyl]-2,3,4,4a,5,6-hexahydro-1H-pyrazino [2,1-d][1,5]benzoxazepine;

(4aS)-9-[3-(methylsulfonyl)phenyl]-2,3,4,4a,5,6-hexahydro-1H-pyrazino [2,1-d][1,5]benzoxazepine;

1-{2-[(4aS)-2,3,4,4a,5,6-hexahydro-1H-pyrazino [2,1-d][1,5]benzoxazepin-9-yl]phenyl}ethanone;

1-{3-[(4aS)-2,3,4,4a,5,6-hexahydro-1H-pyrazino [2,1-d][1,5]benzoxazepin-9-yl]phenyl}ethanone;

1-{4-[(4aS)-2,3,4,4a,5,6-hexahydro-1H-pyrazino [2,1-d][1,5]benzoxazepin-9-yl]phenyl}ethanone;

2-[(4aS)-2,3,4,4a,5,6-hexahydro-1H-pyrazino[2,1-d][1,5]benzoxazepin-9-yl]phenol;

3-[(4aS)-2,3,4,4a,5,6-hexahydro-1H-pyrazino[2,1-d][1,5]benzoxazepin-9-yl]phenol;

4-[(4aS)-2,3,4,4a,5,6-hexahydro-1H-pyrazino[2,1-d][1,5]benzoxazepin-9-yl]phenol;

(4aS)-9-(2-fluorophenyl)-2,3,4,4a,5,6-hexahydro-1H-pyrazino [2,1-d][1,5]benzoxazepine;

(4aS)-9-(3-fluorophenyl)-2,3,4,4a,5,6-hexahydro-1H-pyrazino [2,1-d][1,5]benzoxazepine;

(4aS)-9-(4-fluorophenyl)-2,3,4,4a,5,6-hexahydro-1H-pyrazino [2,1-d][1,5]benzoxazepine;

(4aS)-9-(pyridin-3-yl)-2,3,4,4a,5,6-hexahydro-1H-pyrazino [2,1-d][1,5]benzoxazepine; and (4aS)-9-(pyridin-4-yl)-2,3,4,4a,5,6-hexahydro-1H-pyrazino [2,1-d][1,5]benzoxazepine.

5. A method for treating conditions, disorders or deficits modulated by a $5\text{-HT}_{2C}$ receptor, a $5\text{-HT}_6$ receptor or both $5\text{-HT}_{2C}$ and $5\text{-HT}_6$ receptors wherein the condition, disorder or deficit is selected from the group consisting of a cognitive dysfunction, attention deficit/hyperactivity syndrome, personality disorders, affective disorders, motion or motor disorders, migraine, feeding disorders, gastrointestinal disorders, obesity, diabetes, psoriasis, or ocular hypertension comprising administration of a therapeutically effective amount of the compound of claim 1, or a pharmaceutically acceptable salt thereof.

6. A method for treating a disorder or condition modulated by the $5\text{-HT}_{2c}$ receptor selected from the group consisting of bipolar disorder, depression, anxiety, schizophrenia, cognitive deficits of schizophrenia, obsessive compulsive disorder, migraine, epilepsy, eating disorders, obesity, diabetes, sexual dysfunction/erectile dysfunction, psoriasis, pain and spinal cord injury, pain, bladder dysfunction/urinary incontinence, smoking cessation, ocular hypertension and said method comprising the step of administering to a subject in need thereof the compound of claim 1, or a pharmaceutically acceptable salt, thereof.

7. The method according to claim 6 wherein the disorder modulated by the $5\text{-HT}_{2c}$ receptor is schizophrenia or cognitive deficits of schizophrenia, said method comprising the step of administering to a subject in need thereof the compound of claim 1, or a pharmaceutically acceptable salt, thereof.

8. A method for treating a disorder modulated by the $5\text{-HT}_6$ receptor selected form the group consisting of deficits in memory and cognition and learning, age-related cognitive decline, mild cognitive impairment, attention deficit/hyperactivity syndrome, schizophrenia, cognitive deficits of schizophrenia, depression, anxiety, obsessive compulsive disorders, epilepsy, migraine, anorexia, bulimia, irritable bowel syndrome, stroke, spinal or head trauma and head injuries, and obesity, said method comprising the step of administering to a subject in need thereof the compound of claim 1, or a pharmaceutically acceptable salt thereof.

9. A pharmaceutical composition comprising a therapeutically effective amount of the compound of claim 1, or a pharmaceutically acceptable salt thereof, in combination with one or more pharmaceutically acceptable carriers.

* * * * *